United States Patent
De Brabander et al.

(10) Patent No.: US 6,936,723 B2
(45) Date of Patent: *Aug. 30, 2005

(54) SYNTHETIC SALICYLIHALAMIDES, APICULARENS AND DERIVATIVES THEREOF

(75) Inventors: Jef De Brabander, Lewisville, TX (US); Yusheng Wu, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/790,266

(22) Filed: Mar. 1, 2004

(65) Prior Publication Data

US 2004/0171672 A1 Sep. 2, 2004

Related U.S. Application Data

(63) Continuation of application No. 10/418,757, filed on Apr. 18, 2003, now Pat. No. 6,734,209, which is a continuation of application No. 09/922,372, filed on Aug. 3, 2001, now Pat. No. 6,617,348.
(60) Provisional application No. 60/222,809, filed on Aug. 4, 2000, and provisional application No. 60/252,856, filed on Nov. 22, 2000.

(51) Int. Cl.$^7$ .............................................. C07D 323/00

(52) U.S. Cl. ....................................... 549/267; 549/270

(58) Field of Search ................................. 549/267, 270

(56) References Cited

U.S. PATENT DOCUMENTS 5,936,100 A  8/1999  Fürstner et al.

FOREIGN PATENT DOCUMENTS

| WO | 9905136 | 2/1999 |
| WO | 9947523 | 9/1999 |
| WO | 0051589 | 8/2000 |

OTHER PUBLICATIONS

Boyd MR, Farina C, Belfiore P, Gagliardi S, Kim JW, Hayakawa Y, Beutler JA, McKee TC, Bowman BJ, Bowman EJ (2001). Discovery of a novel antitumor benzolactone enamide class that selectively inhibits mammalian vacuolar–type (H$^+$)–ATPases. *J. Pharmacol. Exp. Ther.* 297(1): 114–120.

Jansen R, Kunze B, Reichenbach H, Höfle G (2000). Antibiotics from gliding bacteria, LXXXVI. Apicularen A and B, cytotoxic 10–membered lactones with a novel mechanism of action from *Chondromyces* species (Myxobacteria): isolation, structure elucidation, and biosynthesis. *Eur. J. Org. Chem.* 2000:913–919.

Snider BB, Song F (2000). Synthesis of the N–((1E)–alkenyl)–(2Z,4Z)–heptadienamide side chain of salicylihalamide A and apicularens A and B. *Org. Lett.* 2(3):407–408.

Ackermann L, Fürstner A, Weskamp T, Kohl FJ, Herrmann WA (1999). Ruthenium carbene complexes with imidazolin–2–ylidene ligands allow the formation of tetra–substituted cycloalkenes by RCM. *Tet. Lett.* 40:4787–4790.

Huang J, Stevens ED, Nolan SP, Petersen JL (1999). Olefin metathesis–active ruthenium complexes bearing a nucleophilic carbene ligand. *J. Am. Chem. Soc.* 121:2674–2678.

Scholl M, Trnka TM, Morgan JP, Grubbs RH (1999). Increased ring closing metathesis activity of ruthenium–based olefin metathesis catalysts coordinated with imidazolin–2–ylidene ligands *Tet. Lett.* 40:2247–2250.

Kunze B, Jansen R, Sasse F, Höfle G, Reichenbach H (1998). Apicularens A and B, new cytostatic macrolides from *Chondromyces* species (Myxobacteria): production, physico–chemical and biological properties. *J. Antibiot. (Tokyo)* 51(12):1075–1080.

McKee TC, Galinis DL, Pannell LK, Cardellina II JH, Laasko J, Ireland CM, Murray L, Capon RJ, Boyd MR (1998). The lobatamides, novel cytotoxic macrolides from Southwestern Pacific tunicates. *J. Org. Chem.* 63:7805–7810.

Erickson KL, Beutler JA, Cardellina II JH, Boyd MR (1997). Saliclylihalamides A and B, novel cytotoxic macrolides from the marine sponge *Haliclona* sp. *J. Org. Chem.* 62:8188–8192.

Crider BP, Xie XS, Stone DK (1994). Bafilomycin inhibits proton flow through the H$^+$channel of vacuolar proton pumps. *J. Biol. Chem.* 269(26):17379–17381.

Mosmann T (1983). Rapid colorimetric assay for cellular growth and survival: application to proliferation and cytotoxicity assays. *J. Immunol. Meth.* 65(1–2):55–63.

Still WC, Kahn M, Mitra A (1978). Rapid chromatographic technique for preparative separations with moderate resolution. *J. Org. Chem.* 43:2923–2925.

*Primary Examiner*—Amelia A. Owens
(74) *Attorney, Agent, or Firm*—Foley & Lardner LLP

(57) ABSTRACT

The present invention provides compounds having improved stability over that of natural benzolactones, and a process for synthesizing these compounds. These compounds exhibit anti-cancer activity and inhibit V-ATPase activity.

17 Claims, 40 Drawing Sheets

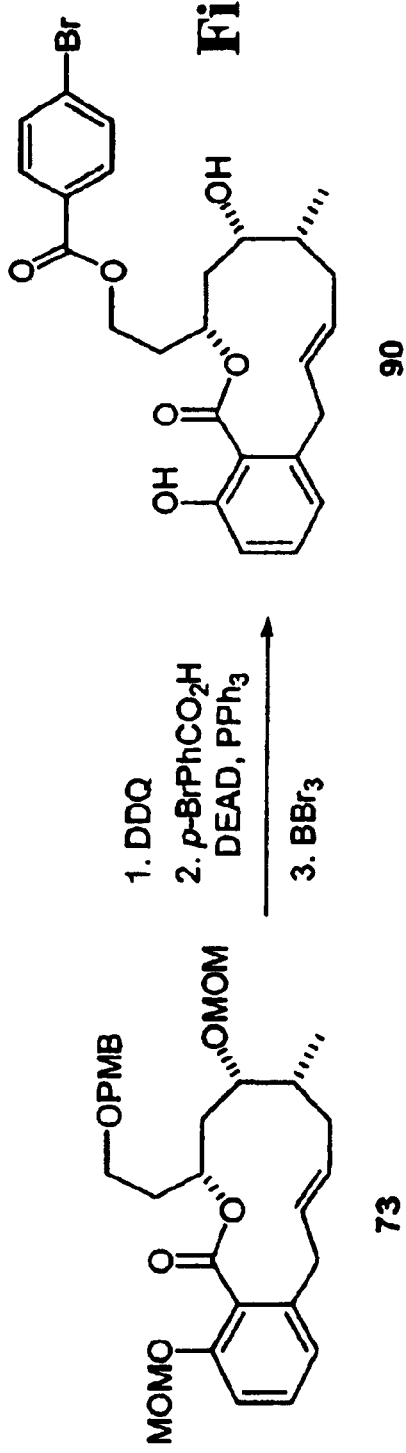
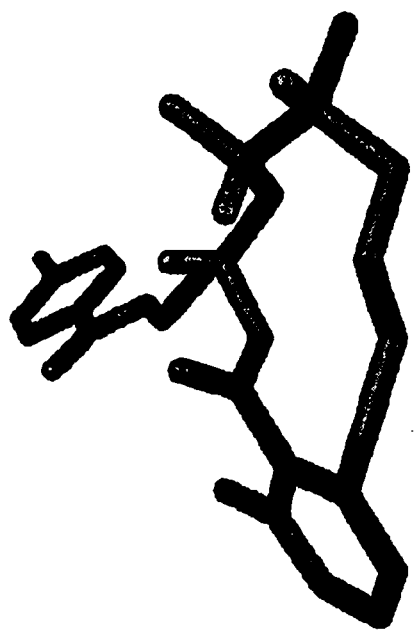
Fig. 11(a)
Fig. 11(b)

349 R = C≡C—Ph
350 R = C≡C—Bu

351 R = O(CH$_2$)$_5$Me
352 R = S(CH$_2$)$_5$Me
353 R = cholesteryloxy
354 R = farnesyloxy

SYNTHETIC SALICYLIHALAMIDES, APICULARENS AND DERIVATIVES THEREOF

CROSS REFERENCE TO RELATED APPLICATIONS

This application is a continuation application of U.S. patent application Ser. No. 10/418,757 of De Brabander et al., filed Apr. 18, 2003 now U.S. Pat. No. 6,734,209, which is a continuation of U.S. patent application Ser. No. 09/922,372 of De Brabander et al., filed Aug. 3, 2001, now issued as U.S. Pat. No. 6,617,348, which claims benefit from provisional U.S. patent application Ser. No. 60/222,809 of De Brabander et al., filed Aug. 4, 2000 and provisional U.S. Patent Application Ser. No. 60/252,856 of De Brabander et al., filed Nov. 22, 2000, the contents of which are incorporated herein by reference in their entireties.

FIELD OF THE INVENTION

The present invention relates to the organic synthesis of chemical compounds and anti-cancer pharmaceuticals, particularly macrocyclic lactones having anti-cancer activity and vacuolar ATPase inhibitory activity and methods of synthesis and use of these compounds.

BACKGROUND OF THE INVENTION

A number of biological metabolites isolated from natural sources such as sponges, tunicates, and bacteria have been found to have anti-cancer activity. These metabolites are macrocyclic lactones such as salicylihalamide and lobatamide, which appear to represent a new mechanistic class based on their cytotoxicity profiles when compared to other compounds in NCI's standard agents database. Apicularen has also been shown to be cytostatic against human cancer cell lines (Kunze et al. (1998)). Macrolides were previously known to have cytotoxic activity and some possess anti-fungal or anti-bacterial properties. The anti-cancer activity of a class of macrolides called salicylihalamide was discovered by Boyd et al., (1997) in a screen of the cytotoxic activity of extracts from a family of sponges (species Haliclona). Two novel macrolides, salicylihalamides A and B were purified from the extract and tested in the NCI 60-cell line human tumor screen. Upon screening, these compounds demonstrated a mean-graph profile that was unlike any of the known tumor profiles of known anti-tumor agents. Therefore, these compounds represent a new class of anti-tumor agents. These compounds were especially effective against human solid tumor cell lines. Solid tumors are usually the most resistant to drugs.

Various other macrocyclic lactones have been identified as having anti-tumor activity. Included are lobatamides (isolated from *Aplidium lobatum*), apicularens (isolated from *Chondromyces*), and oximidines (isolated from *Pseudomonas*). Lobatamides contain a similar enamide side chain and core structure to salicylihalamides. However, lobatamides contain an oxime methyl ether structure at the end of the enamide side chain. The NCI 60-cell line human tumor screen profile of the lobatamides correlated with the profile of salicylihalamide (McKee et al., (1998)).

Apicularen A causes a potent growth inhibition of human cancer cell lines, the induction of an apoptotic-like cell death, and the formation of mitotic spindles with multiple spindle poles and clusters of bundled actin from the cytoskeleton (Kunze et al., 1998; Jansen et al., 2000).

The NCI 60-cell line human tumor screen is a measure of the effectiveness of a compound for inhibiting or killing various human cancers. It is a set of 60 different cancer cell lines against which chemical compounds can be tested against to determine if the compound has anti-cancer activity. Each compound has an individual "fingerprint" based on effectiveness in killing each of the 60 cancer cell lines.

Fürstner et al. (U.S. Pat. No. 5,936,100) has used ring closing metathesis as a step in the synthesis of macrocyclic lactones containing one or more polar functional groups. Macrocycles of ring sizes $\geq 12$ are challenging to synthesize because the precursors tend to oligomerize.

The naturally occurring structure of salicylihalamide is unstable under certain conditions. Salicylihalamides decompose in $CDCl_3$, due to the unstable side chain (Snider and Song (2000)). The present invention provides macrocyclic lactones which exhibit improved stability over the natural compound. The present invention also includes a process for the synthesis of these compounds which is particularly flexible for making various compounds. The natural compound has not previously been synthesized and its structure was misidentified when it was purified from marine sponges of the genus *Haliclona*. Boyd et al., in PCT/US98/15011 disclosed the structure of natural salicylihalamide with a negative rotation and assigned the absolute configuration as 12R, 13S, 15R. This assignment was incorrect because the isomer with the 12R, 13S, 15R absolute configuration has a positive rotation and does not have anti-cancer activity, as proven by the inventor in the present application. Only the isomer with the 12S, 13R, 15S absolute configuration has a negative rotation and anti-cancer activity.

The present invention describes the first synthesis of (+)-and (−)-salicylihalamide A and assigns the absolute configuration of the natural product with negative rotation as 12S, 13R, 15S. It a highly efficient, trans-selective ring-closing olefin metathesis for the assembly of the benzolactone skeleton and has been readily adapted to obtain a variety of analogs.

SUMMARY OF THE INVENTION

The invention includes a method of synthesis of a broad class of cyclic benzolactones with chemotherapeutic activity which exhibit increased stability over natural benzolactones. Included in the invention are the compounds, compositions containing the compounds, methods of synthesis, and methods of treatment.

An embodiment of the invention is a composition comprising a compound of the formula:

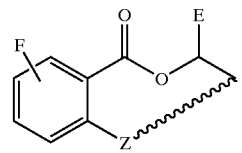

wherein E is

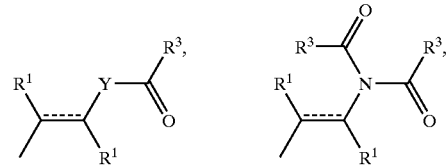

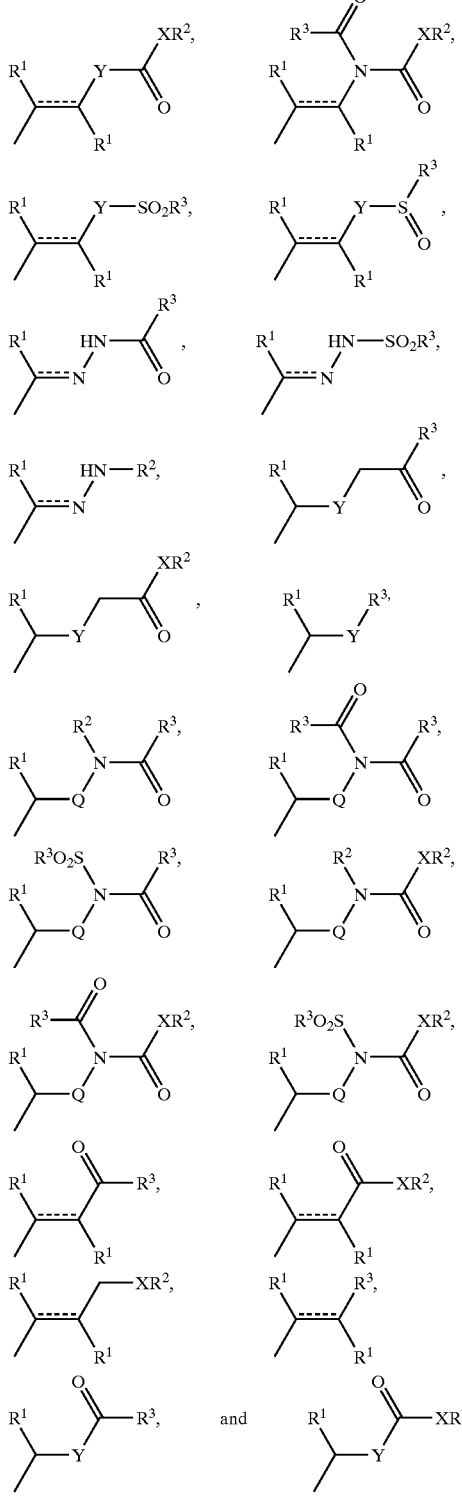

X=O, S, NR$^2$; Y=CH$_2$, O, S, NR$^2$;
Q=O, NH;
F=ortho, meta, para substituents such as halogen, CN, OR$^2$, OC(O)R$^3$, NO$_2$, OSO$_2$R$^3$, NR$^2$R$^2$, NR$^2$C(O)R$^3$, NR$^2$SO$_2$R$^3$, R$^3$;
R$^1$=H, Me;
R$^2$=R$^1$, straight chain saturated alkyl, straight chain unsaturated alkyl, branched chain alkyl, branched chain unsaturated alkyl, cycloalkyl, aryl, heteroaryl, heterocycle, CH$_2$aryl, CH$_2$heteroaryl, CH$_2$heterocycle, CHR$^1$CHR$^1$aryl, CHR$^1$CHR$^1$heteroaryl, CHR$^1$CHR$^1$heterocycle;

R$^3$=R$^2$ or CR$^1$=CR$^1$aryl, CR$^1$=CR$^1$heteroaryl, CR$^1$=CR$^1$heterocycle, C≡Caryl, C≡Cheteroaryl, C≡Cheterocycle; and Z is a contiguous linker whose presence completes an 11 to 15 membered ring. The linker can contain heteroatoms and substituents.

A further embodiment of the invention are compositions comprising compounds of the formulas:

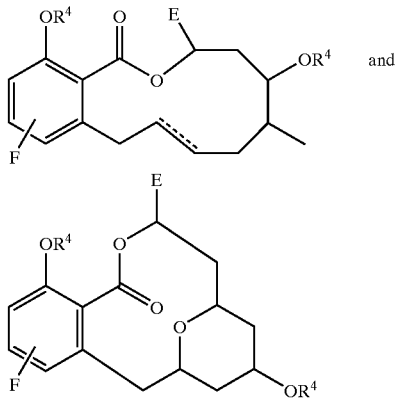

wherein E is

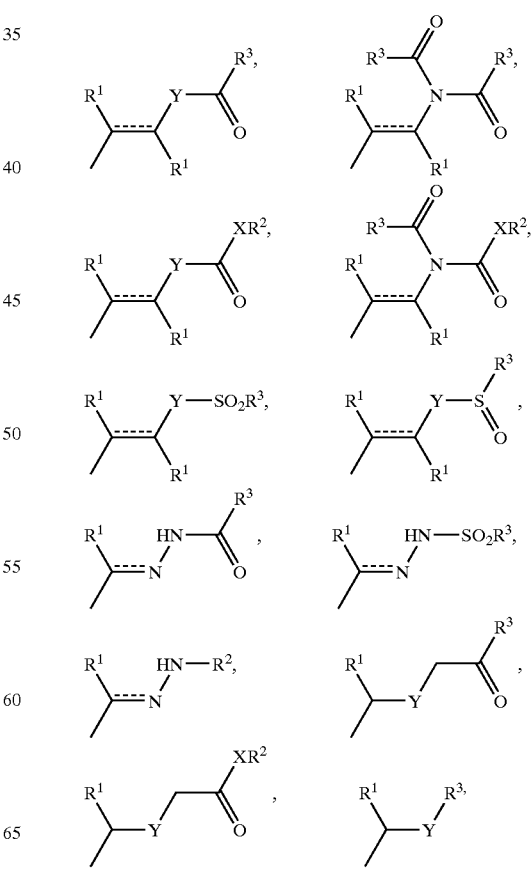

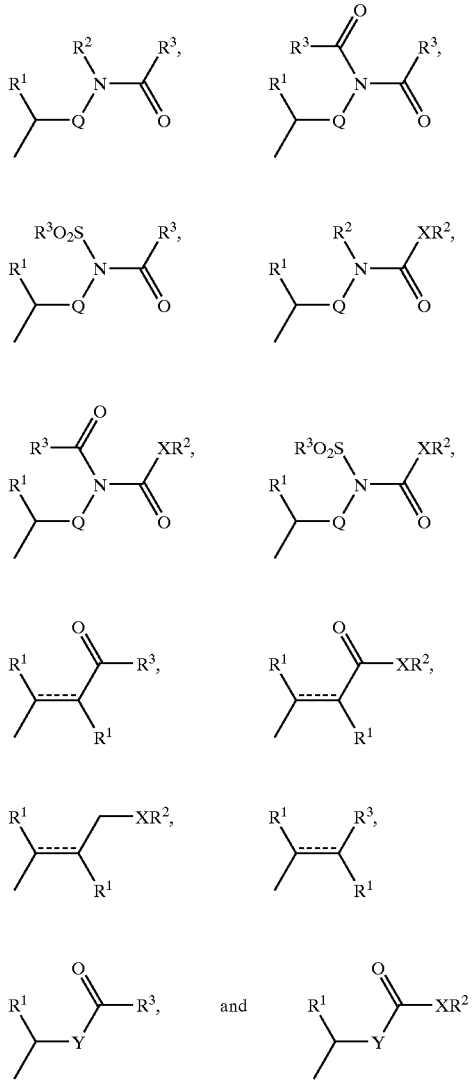

X=O, S, NR²

Y=CH₂, O, S, NR²

Q=O, NH

F=ortho, meta, para substituents such as halogen, CN, OR², OC(O)R³, NO₂, OSO₂R³, NR²R², NR²C(O)R³, NR²SO₂R³, R³

R¹=H, Me

R²=R¹, straight chain saturated alkyl, straight chain unsaturated alkyl, branched chain alkyl, branched chain unsaturated alkyl, cycloalkyl, aryl, heteroaryl, heterocycle, CH₂aryl, CH₂heteroaryl, CH₂heterocycle, CHR¹CHR¹aryl, CHR¹CHR¹heteroaryl, CHR¹CHR¹heterocycle;

R³=R² or CR¹=CR¹aryl, CR¹=CR¹heteroaryl, CR¹=CR¹heterocycle, C≡Caryl, C≡Cheteroaryl, C≡Cheterocycle; and R⁴=R¹, C(O)R³, SO₂R³, R²

Another embodiment of the invention are compositions comprising compounds of the formulas:

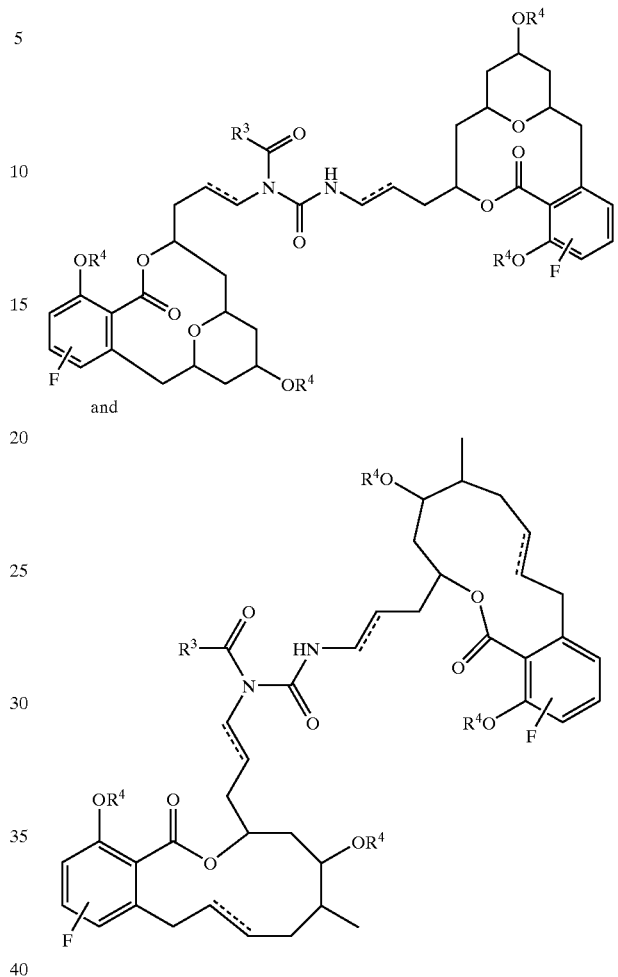

and where F=ortho, meta, para substituents such as halogen, CN, OR², OC(O)R³, NO₂, OSO₂R³, NR²R²NR² C(O)R³, NR²SO₂R³, R³;

R¹=H, Me;

R²=R¹, straight chain saturated alkyl, straight chain unsaturated alkyl, branched chain alkyl, branched chain unsaturated alkyl, cycloalkyl, aryl, heteroaryl, heterocycle, CH₂aryl, CH₂heteroaryl, CH₂heterocycle, CHR¹CHR¹aryl, CHR¹CHR¹heteroaryl, CHR¹CHR¹heterocycle;

R³=R² or CR¹=CR¹aryl, CR¹=CR¹heteroaryl, CR¹=CR¹heterocycle, C≡Caryl, C≡Cheteroaryl, C≡Cheterocycle; and

R⁴=R¹, C(O)R³, SO₂R³, R²

An embodiment of the invention is a composition wherein the compound is selected from the group consisting of:

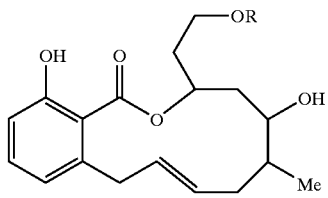

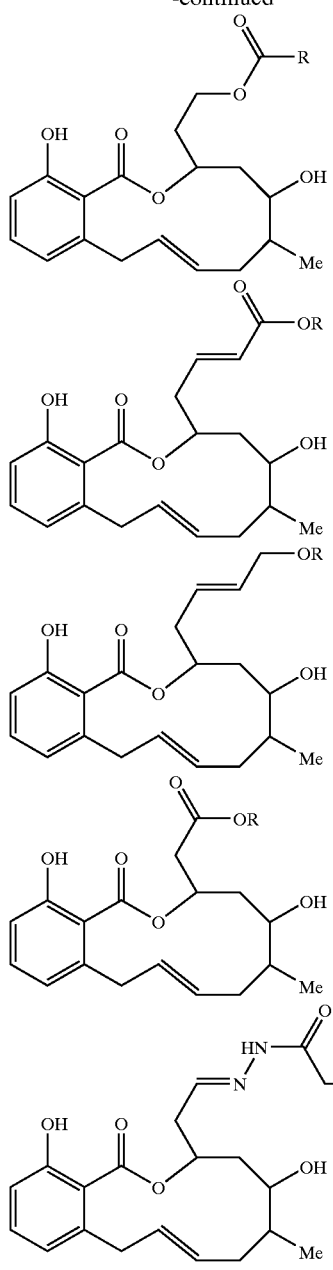

wherein R=straight chain saturated alkyl or straight chain unsaturated alkyl that is comprised of a chain of 5 to 8 carbons.

An embodiment of the invention is a composition wherein the compound is of the formula:

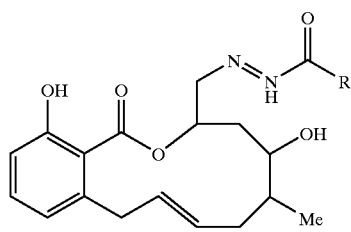

wherein R=straight chain saturated alkyl or straight chain unsaturated alkyl that is comprised of a chain of 5 to 8 carbons.

An embodiment of the invention is a composition comprising a compound of the formula:

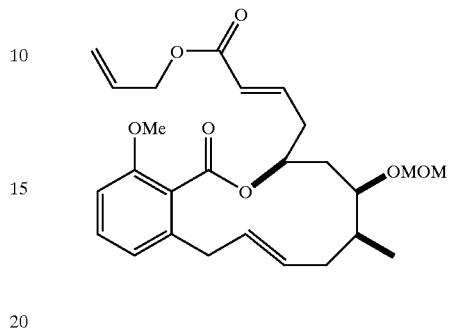

An embodiment of the invention is a composition comprising a compound of the formula:

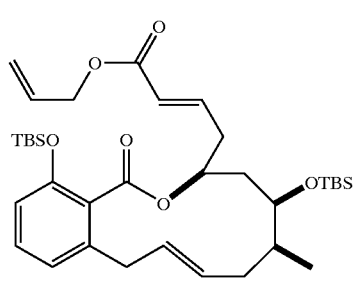

An embodiment of the invention is a composition comprising a compound of the formula:

An embodiment of the invention is a composition comprising a compound of the formula:

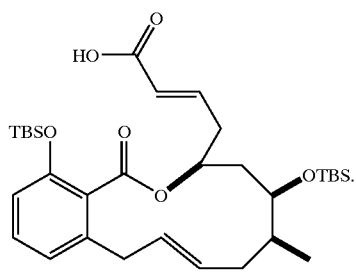

An embodiment of the invention is a composition comprising a compound of the formula:

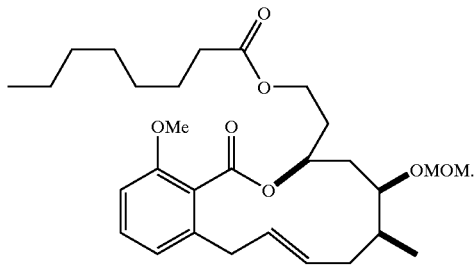

An embodiment of the invention is a composition comprising a compound of the formula:

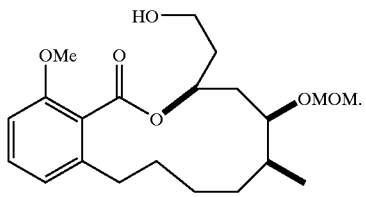

A further embodiment of the invention is the following compositions comprising compounds of the formulas: (These compounds have been tested for growth inhibitory activities against several cell lines, including human melanoma cell line SK-MEL-5 [see Example 7; Table 3], as well a inhibition against reconstituted purified Vacuolar (H+)-ATPase from bovine brain [see Example 7; Table 5]).

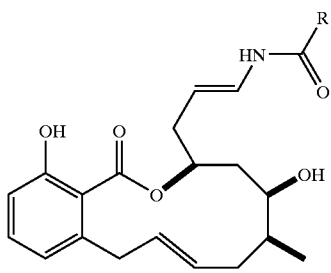

where R=Z,Z-hexadienyl; Z,E-hexadienyl; a straight chain alkyl comprising 5 to 8 carbons (e.g. —(CH2)5Me); a straight chain alcohol (e.g. —O(CH2)4Me); and a straight chain diol (e.g. —S(CH2)4Me);

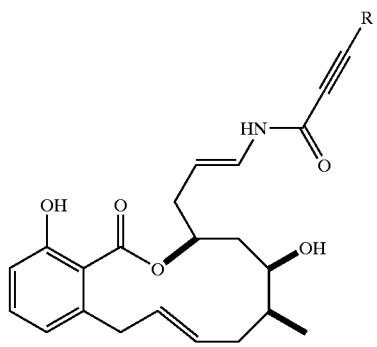

where R=Bu; Ph;

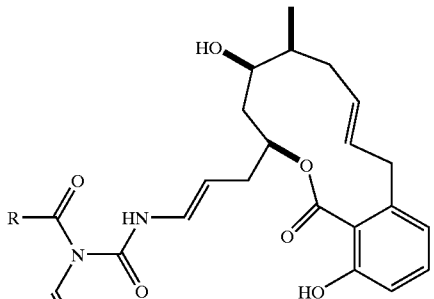

where R=Z,Z-hexadienyl; Z,E-hexadienyl; and a straight chain alkyl comprising 5 to 8 carbons (e.g. —(CH2)5Me);

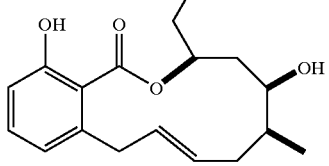

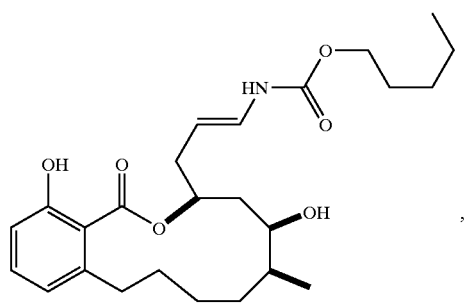

,

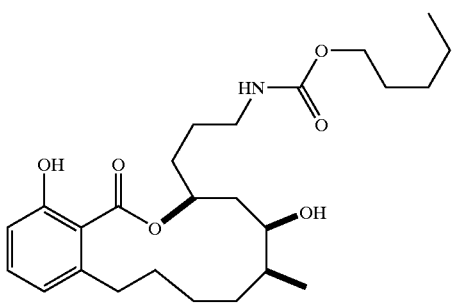

,

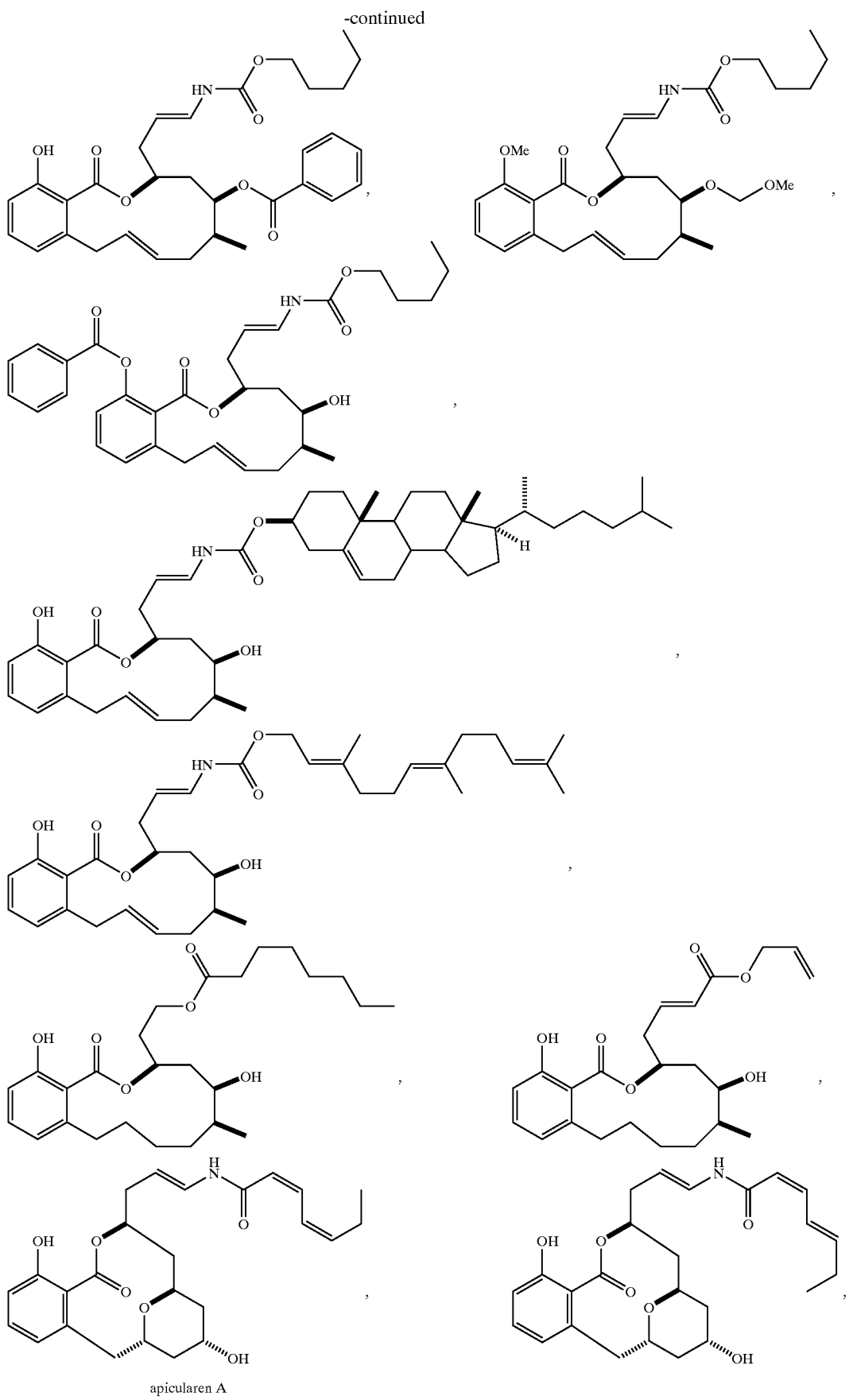

-continued
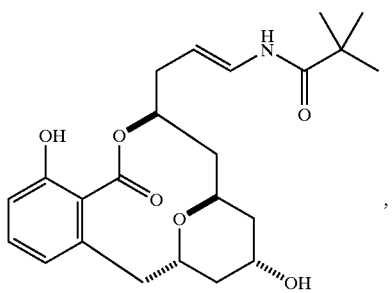
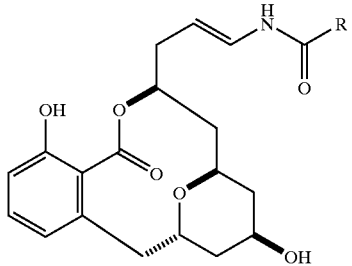
where R=a straight chain alkyl comprising 5 to 8 carbons, a straight chain alcohol, a straight chain diol, —CCBu, or —CCph.
Another embodiment of the invention is a composition wherein the compound is selected from the group consisting of:
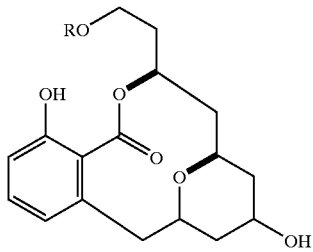
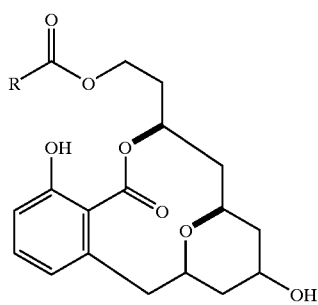
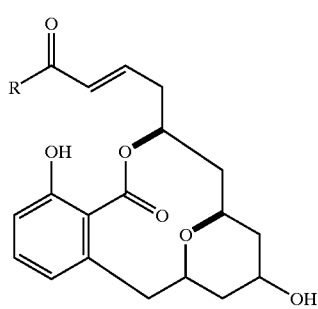
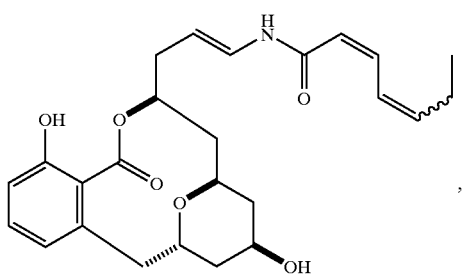, and
-continued
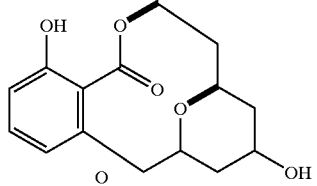
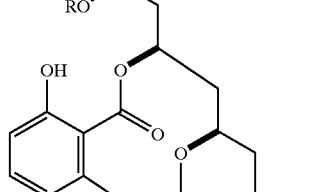
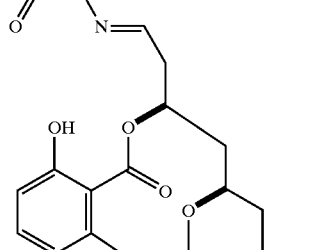
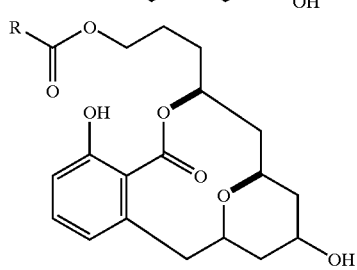

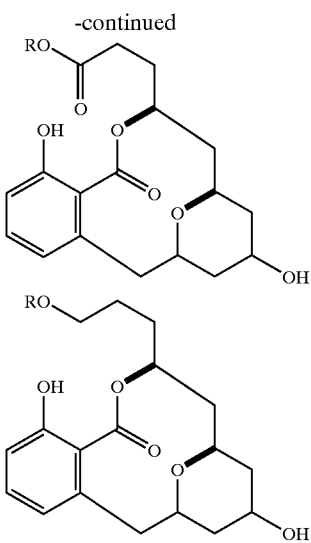

wherein R=straight chain saturated alkyl or straight chain unsaturated alkyl that is comprised of a chain of 5 to 8 carbons.

Another embodiment of the invention is a composition wherein the compound is of the formula:

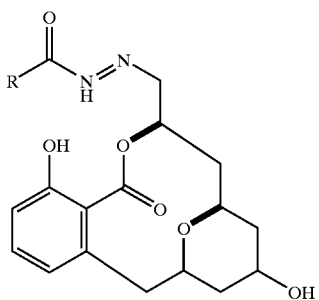

wherein R=straight chain saturated alkyl or straight chain unsaturated alkyl that is comprised of a chain of 5 to 8 carbons.

Yet another embodiment of the invention is a process for preparing a salicylihalamide comprising the steps of: a) synthesis of a benzolactone core; b) synthesis of an enamide side chain; and c) and addition of the side chain by addition of a dienyllithium (28) to the benzolactone core.

Another embodiment of the invention is a process for preparing a salicylihalamide comprising the steps of: a) synthesis of a benzolactone core; b) synthesis of a side chain; and c) and addition of the side chain to the benzolactone core.

Still another embodiment of the invention is a process for preparing an Apicularen comprising the steps of: a) synthesis of a benzolactone core: b) synthesis of an enamide side chain; and c) and addition of the side chain by addition of a dienyllithium (28) to the benzolactone core.

Another embodiment of the invention is a process for preparing an Apicularen comprising the steps of: a) synthesis of a benzolactone core: b) synthesis of a side chain; and c) and addition of the side chain to the benzolactone core.

Another embodiment of the invention is a method of treating or preventing cancer, comprising the step of administering to a patient a therapeutically effective amount of a compound of the formula:

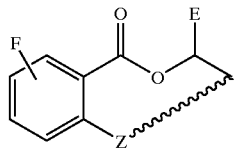

wherein E is

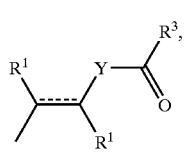 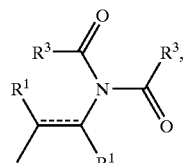

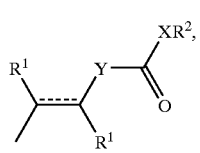 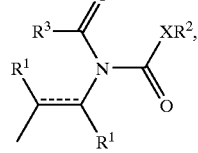

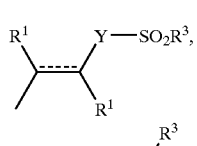 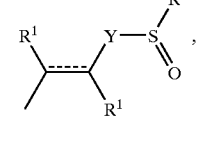

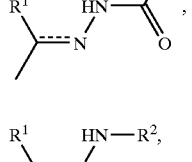 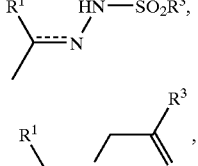

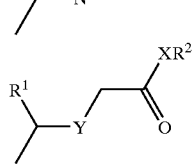 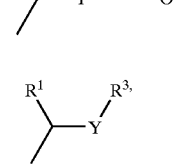

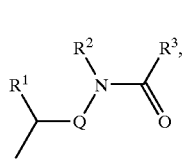 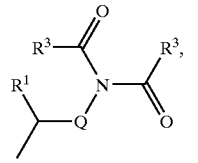

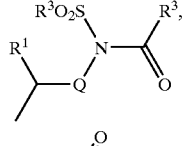 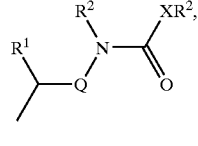

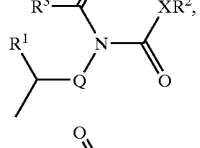 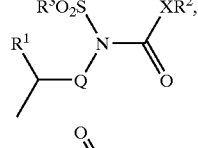

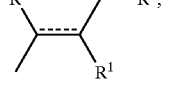

-continued

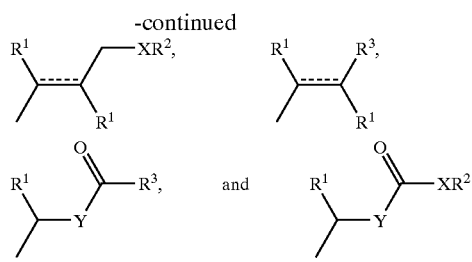

X=O, S, NR²; Y=CH₂, O, S, NR²;

Q=O, NH;

F=ortho, meta, para substituents such as halogen, CN, OR², OC(O)R³, NO₂, OSO₂R³, NR²R², NR²C(O)R³, NR²SO₂R³, R³;

R¹=H, Me;

R²=R¹, straight chain saturated alkyl, straight chain unsaturated alkyl, branched chain alkyl, branched chain unsaturated alkyl, cycloalkyl, aryl, heteroaryl, heterocycle, CH₂aryl, CH₂heteroaryl, CH₂heterocycle, CHR¹CHR¹aryl, CHR¹CHR¹heteroaryl, CHR¹CHR¹heterocycle;

R³=R² or CR¹=CR¹aryl, CR¹=CR¹heteroaryl, CR¹=CR¹heterocycle, C≡Caryl, C≡Cheteroaryl, C≡Cheterocycle; and Z is a contiguous linker whose presence completes an 11 to 15 membered ring. The linker can contain heteroatoms and substituents.

A further embodiment of the invention are compositions comprising compounds of the formulas:

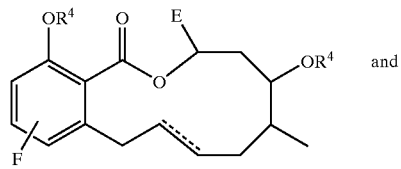

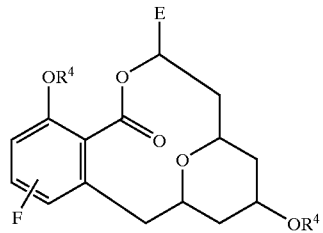

wherein E is

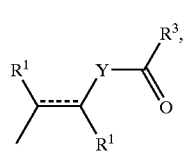 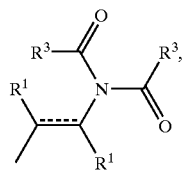

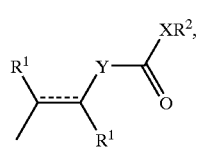 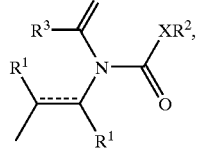

-continued

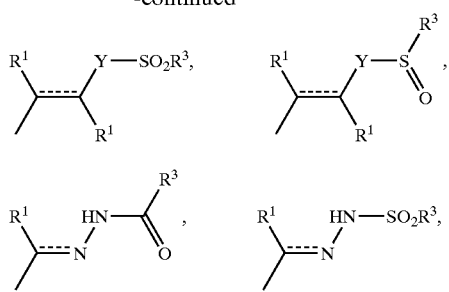

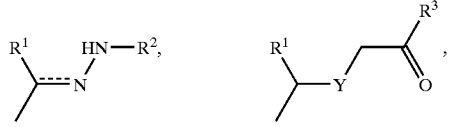

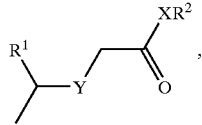 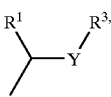

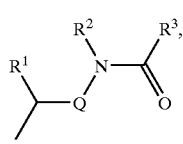 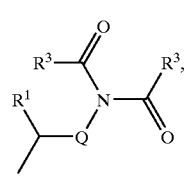

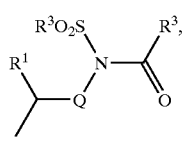 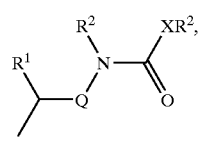

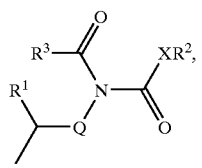 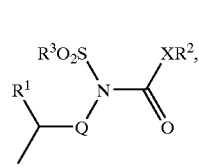

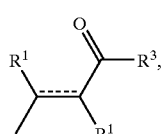 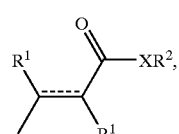

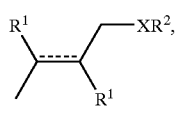 and 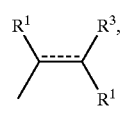

X=O, S NR²;

Y=CH₂, O, S, NR²;

Q=O, NH;

F=ortho, meta, para substituents such as halogen, CN, $OR^2$, $OC(O)R^3$, $NO_2$, $OSO_2R^3$, $NR^2R^2$, $NR^2C(O)R^3$, $NR^2SO_2R^3$, $R^3$;

R=H, Me;

$R^2=R^1$, straight chain saturated alkyl, straight chain unsaturated alkyl, branched chain alkyl, branched chain unsaturated alkyl, cycloalkyl, aryl, heteroaryl, heterocycle, $CH_2$aryl, $2CH_2$heteroaryl, $CH_2$heterocycle, $CHR^1CHR^1$aryl, $CHR^1CHR^1$heteroaryl, $CHR^1CHR^1$heterocycle $R^3=R^2$ or $CR^1=CR^1$aryl, $CR^1=CR^1$heteroaryl, $CR^1=CR^1$heterocycle, $C\equiv C$aryl, $C\equiv C$heteroaryl, $C\equiv C$heterocycle; and $R^4=R^1$, $C(O)R^3$, $SO_2R^3$, $R^2$.

Another embodiment of the invention are compositions comprising compounds of the formulas:

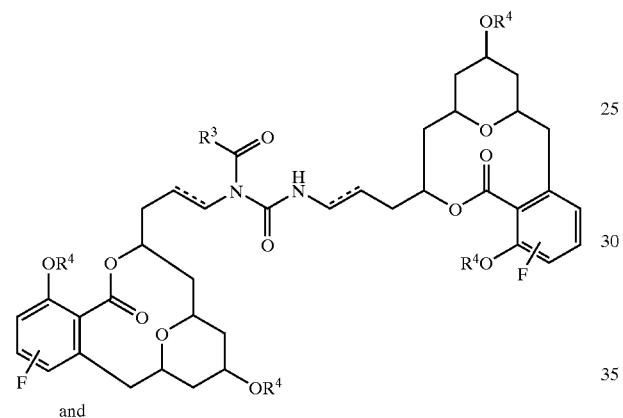

and

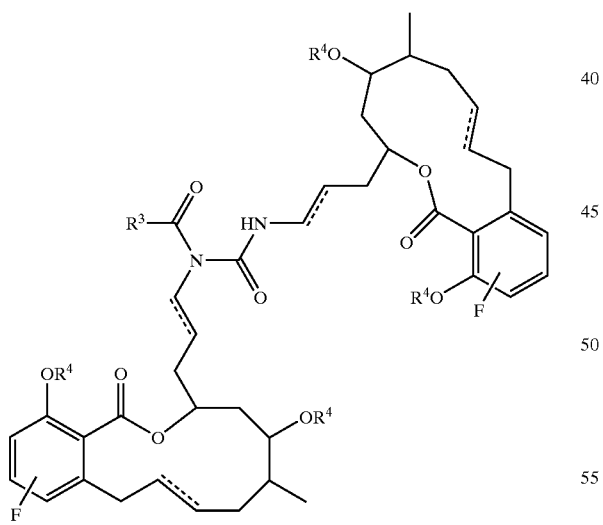

where F=ortho, meta, para substituents such as halogen, CN, $OR^2$, $OC(O)R^3$, $NO_2$, $OSO_2R^3$, $NR^2R^2$, $NR^2C(O)R^3$, $NR^2SO_2R^3$, $R^3$;

$R^1$=H, Me;

$R^2=R^1$, straight chain saturated alkyl, straight chain unsaturated alkyl, branched chain alkyl, branched chain unsaturated alkyl, cycloalkyl, aryl, heteroaryl, heterocycle, $CH_2$aryl, $CH_2$heteroaryl, $CH_2$heterocycle, $CHR^1CHR^1$aryl, $CHR^1CHR^1$heteroaryl, $CHR^1CHR^1$heterocycle;

$R^3=R^2$ or $CR^1=CR^1$aryl, $CR^1=CR^1$heteroaryl, $CR^1=CR^1$heterocycle, $C\equiv C$aryl, $C\equiv C$heteroaryl, $C\equiv C$heterocycle; and $R^4=R^1$, $C(O)R^3$, $SO_2R^3$, $R^2$;

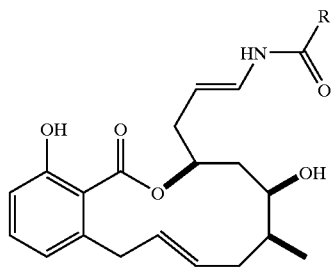

where R=Z,Z-hexadienyl; Z,E-hexadienyl; a straight chain alkyl comprising 5 to 8 carbons, a straight chain alcohol or a straight chain diol.

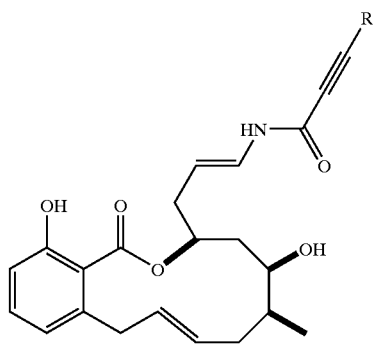

where R=Bu; Ph;

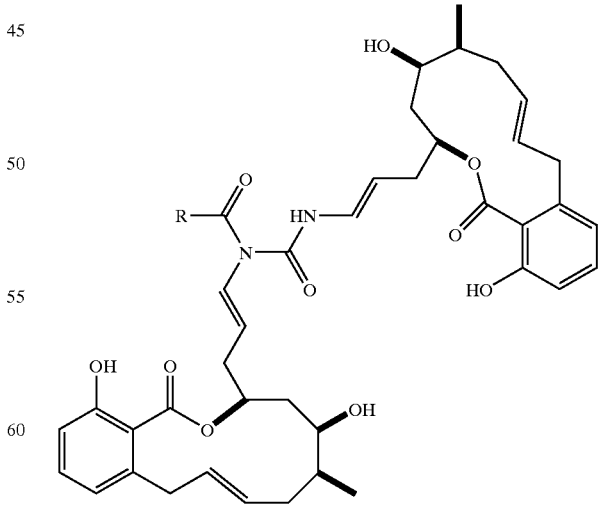

where R=Z,Z-hexadienyl; Z,E-hexadienyl; and a straight chain alkyl comprising 5 to 8 carbons;

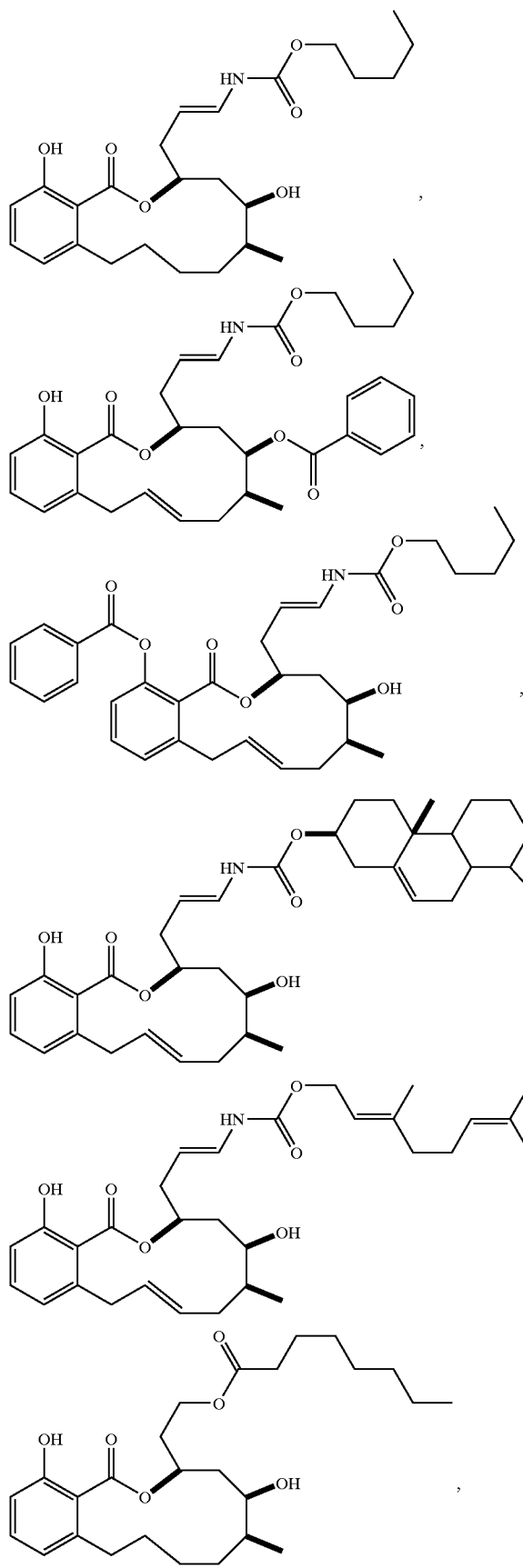
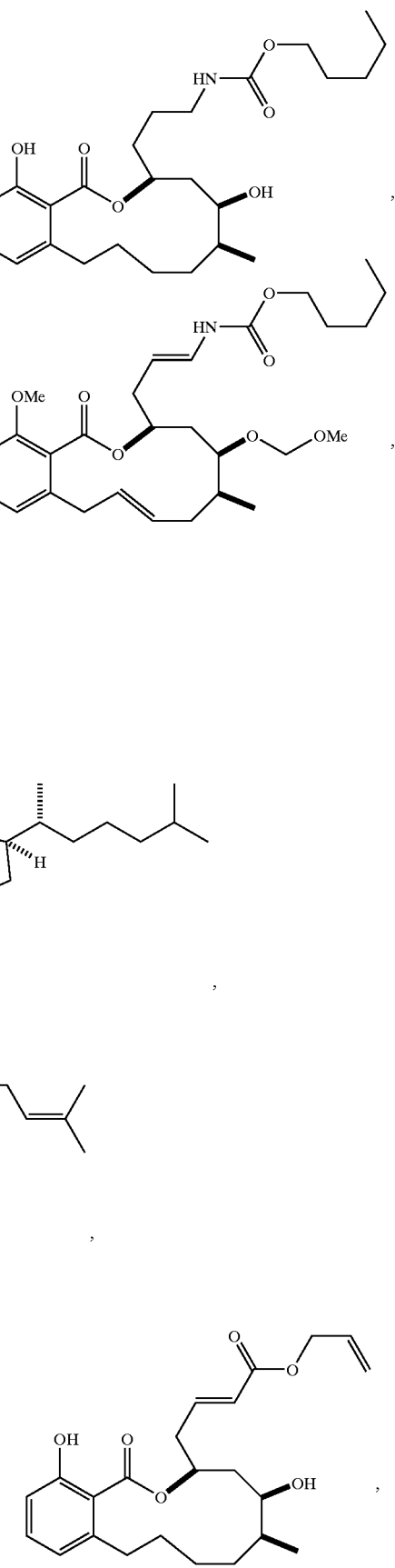

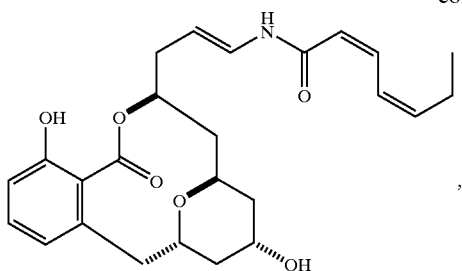

apicularen A

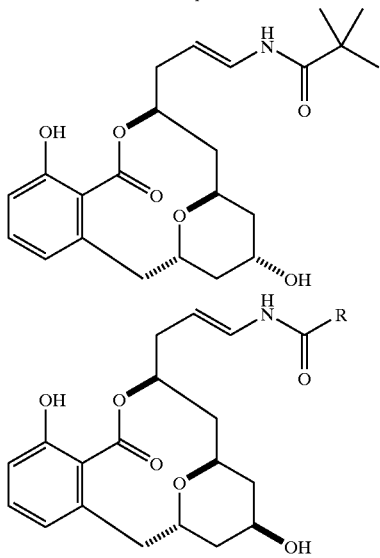

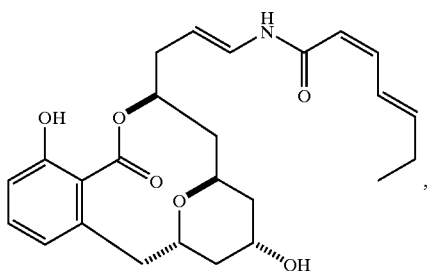

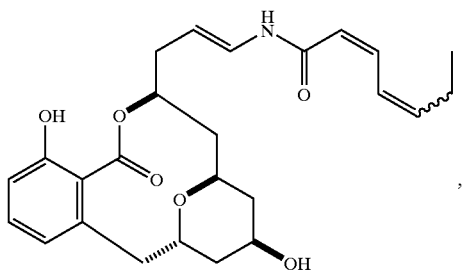

where R=a straight chain alkyl comprising 5 to 8 carbons (e.g. —(CH2)5Me), a straight chain alcohol (e.g. —O(CH2)4Me), a straight chain diol (e.g. —S(CH2)4Me), —CCBu, or —CCph.

An embodiment of the invention is a method of treating or preventing cancer, comprising the step of administering to a patient a therapeutically effective amount of a compound of the formula selected from the group consisting of:

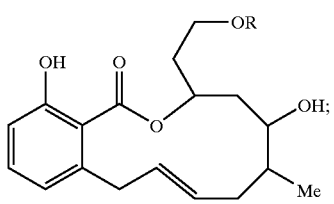

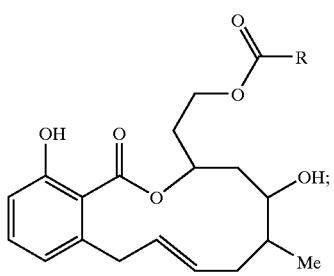

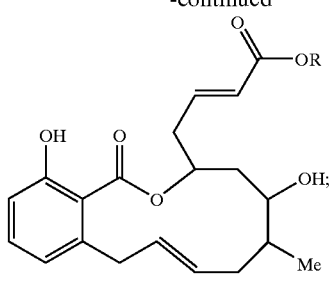

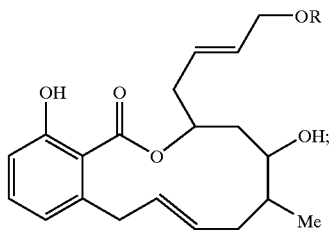

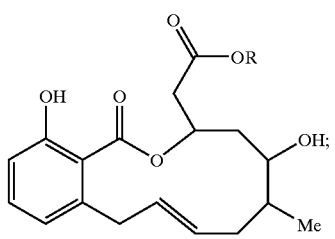

-continued and

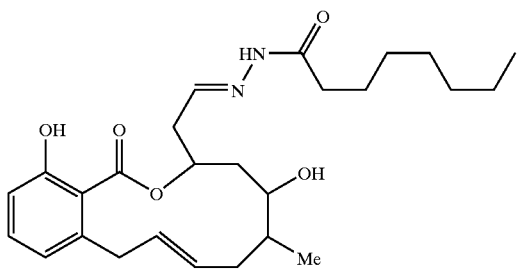

wherein R=straight chain saturated alkyl or straight chain unsaturated alkyl that is comprised of a chain of 5 to 8 carbons.

An embodiment of the invention is a method of treating or preventing cancer, comprising the step of administering to a patient a therapeutically effective amount of a compound of the formula:

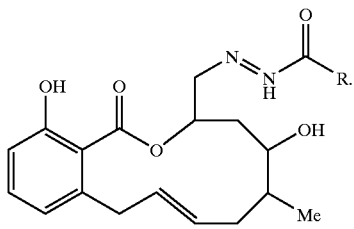

An embodiment of the invention is a method of treating or preventing cancer, comprising the step of administering to a patient a therapeutically effective amount of a compound of the formula:

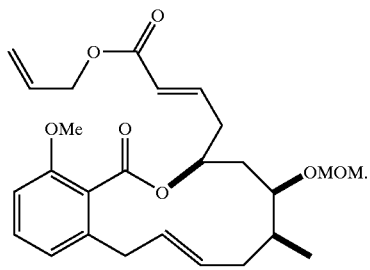

An embodiment of the invention is a method of treating or preventing cancer, comprising the step of administering to a patient a therapeutically effective amount of a compound of the formula:

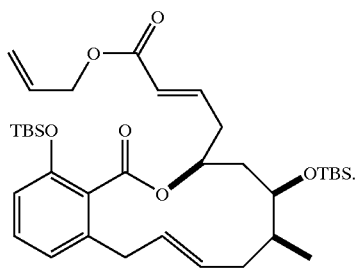

An embodiment of the invention is a method of treating or preventing cancer, comprising the step of administering to a patient a therapeutically effective amount of a compound of the formula:

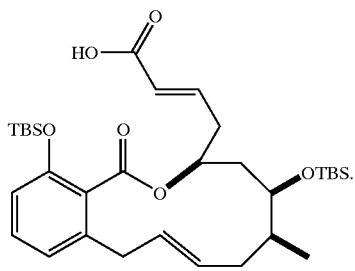

An embodiment of the invention is a method of treating or preventing cancer, comprising the step of administering to a patient a therapeutically effective amount of a compound of the formula:

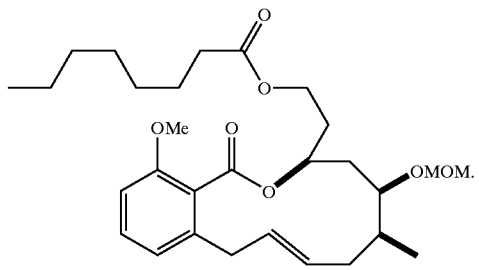

An embodiment of the invention is a method of treating or preventing cancer, comprising the step of administering to a patient a therapeutically effective amount of a compound of the formula:

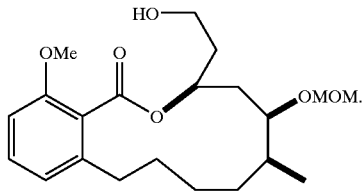

An embodiment of the invention is a method of treating or preventing cancer, comprising the step of administering to a patient a therapeutically effective amount of a compound of the formula selected from the group consisting of:

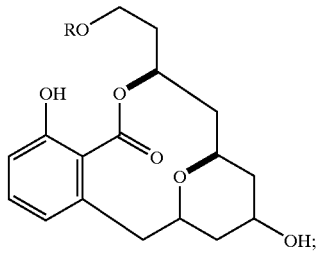

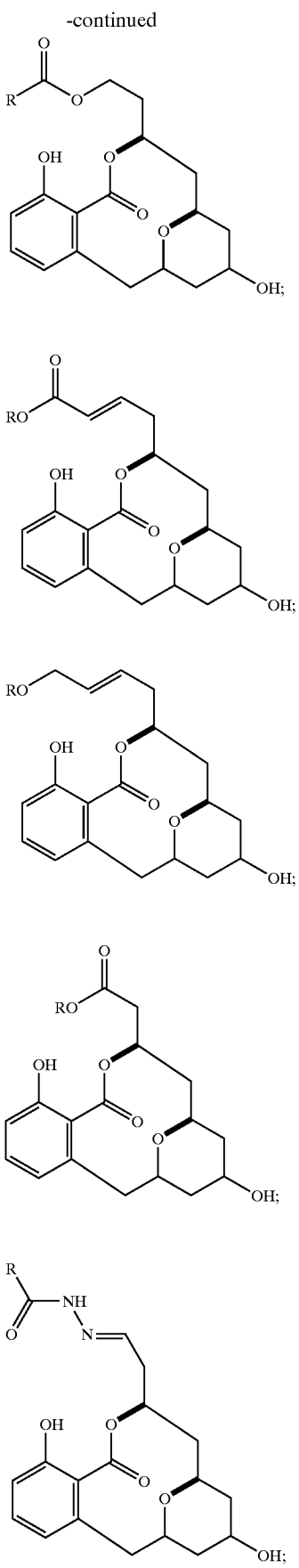

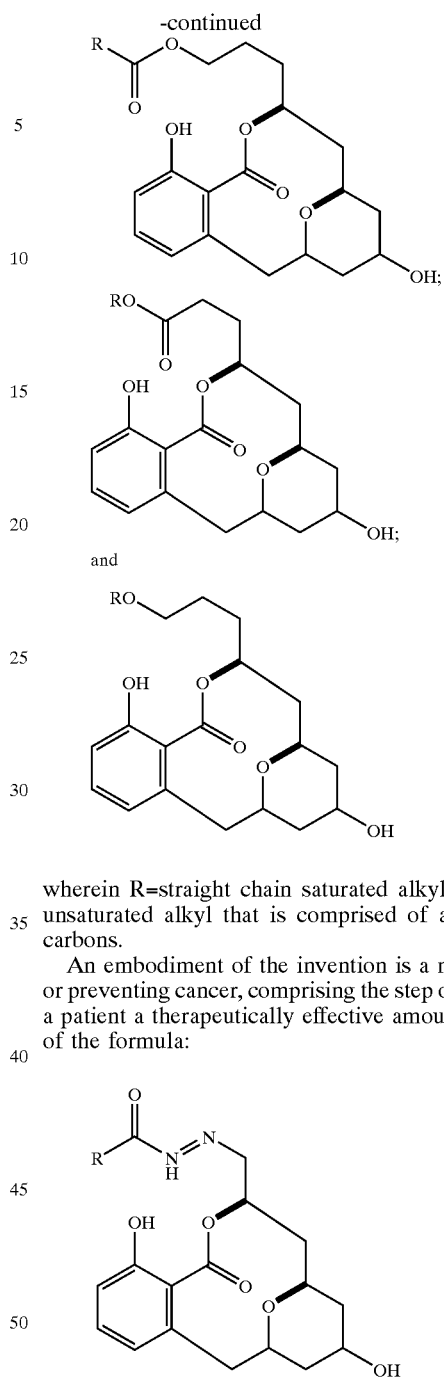

wherein R=straight chain saturated alkyl or straight chain unsaturated alkyl that is comprised of a chain of 5 to 8 carbons.

An embodiment of the invention is a method of treating or preventing cancer, comprising the step of administering to a patient a therapeutically effective amount of a compound of the formula:

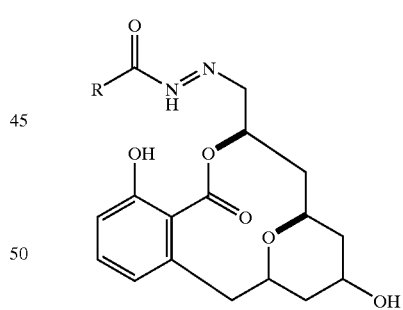

wherein R=straight chain saturated alkyl or straight chain unsaturated alkyl that is comprised of a chain of 5 to 8 carbons.

An embodiment of the invention is a method for treating cancer comprising the step of contacting a tumor cell within a subject with a macrocyclic lactone of the present invention under conditions permitting the uptake of said macrocyclic lactone by said tumor cell. The tumor cell may be derived from a tissue selected from the group consisting of brain, lung, liver, spleen, kidney, lymph node, small intestine, blood, pancreas, colon, stomach, breast, endometrium, prostate, testicle, ovary, skin, head, and neck, esophagus, and bone marrow. In a further embodiment, the subject is human. In another embodiment, the macrocyclic lactone is contained within a liposome. In yet another embodiment, the macrocyclic lactone is administered intratumorally, in the tumor vasculature, local to the tumor, regional to the tumor, or systemically. In a further embodiment, the method comprises administering a second chemotherapuetic agent to said subject. In a further embodiment, the second chemotherapeutic agent may be cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, famesyl-protein transferase inhibitors, transplatinum, 5-fluorouracil, vincristin, vinblastin and methotrexate or any analog or derivative variant of the foregoing. In another embodiment, the method further comprises administering radiation to said subject. In another embodiment, the radiation is delivered local to a cancer site. In yet another embodiment, the radiation is whole body radiation. The radiation may be γ-rays, X-rays, accelerated protons, microwave radiation, UV radiation or the directed delivery of radioisotopes to tumor cells. In another embodiment, the method further comprises administering an anticancer gene to said subject. In an embodiment of the invention, the anticancer gene is a tumor suppressor. In another embodiment of the invention, the anticancer gene is an inhibitor of apoptosis. In another embodiment of the invention, the anticancer gene is an oncogene antisense construct.

It is a further embodiment of the present invention to provide a method for inhibiting vacuolar ATPase (V-ATPase) proton-pumping activity. The method comprises contacting V-ATPase with the compounds of the present invention in an amount sufficient to inhibit the ATPase proton-pumping activity of the V-ATPase. Inhibition of the V-ATPase proton pumping activity by the compounds of the present invention is useful, inter alia, for the treatment and prevention of cancer and osteoporosis.

An embodiment of the invention is a method for altering the phenotype of a tumor cell comprising the step of contacting the cell with a macrocyclic lactone of the present invention, under conditions permitting the uptake of said macrocyclic lactone by said tumor cell. The tumor cell may be derived from a tissue selected from the group consisting of brain, lung, liver, spleen, kidney, lymph node, small intestine, blood, pancreas, colon, stomach, breast, endometrium, prostate, testicle, ovary, skin, head, and neck, esophagus, and bone marrow. In an embodiment of the invention, the phenotype is selected from the group consisting of proliferation, migration, contact inhibition, soft agar growth, cell cycling, invasiveness, tumorigenesis, and metastatic potential. In another embodiment of the invention, the macrocyclic lactone may be contained within a liposome.

Another embodiment of the invention is a method of treating a subject with cancer comprising the step of administering to said subject a macrocyclic lactone of the present invention under conditions permitting the uptake of said macrocyclic lactone by said cancer cell. In an embodiment of the invention, the subject is human.

Another embodiment of the invention is a method of suppressing growth of a tumor cell comprising contacting said cell with a macrocyclic lactone of the present invention, under conditions permitting the uptake of said macrocyclic lactone by said tumor cell. In another embodiment, the macrocyclic lactone is contained within a liposome.

Another embodiment of the invention is a method of regulating cell growth and proliferation in normal and malignant cells, comprising the step of administering, to an individual in need of said. treatment, a therapeutically effective amount of a compound of the present invention.

Another embodiment of the present invention is a method of inhibiting growth of proliferating cells comprising the step of administering, to the proliferating cells, a therapeutically effective amount of a compound of the present invention.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF SUMMARY OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 11. Synthesis of p-bromobenzoate derivative of salicylihalamide and x-ray structure of p-bromobenzoate derivative of salicylihalamide FIG. 12. Synthesis bis-olefins 328a,b FIG. 13. Ring closing metathesis synthesis of benzolactones 329a,b and 330a,b FIG. 14. Synthesis of acylazide 338

DETAILED DESCRIPTION OF THE INVENTION

Figure 1:
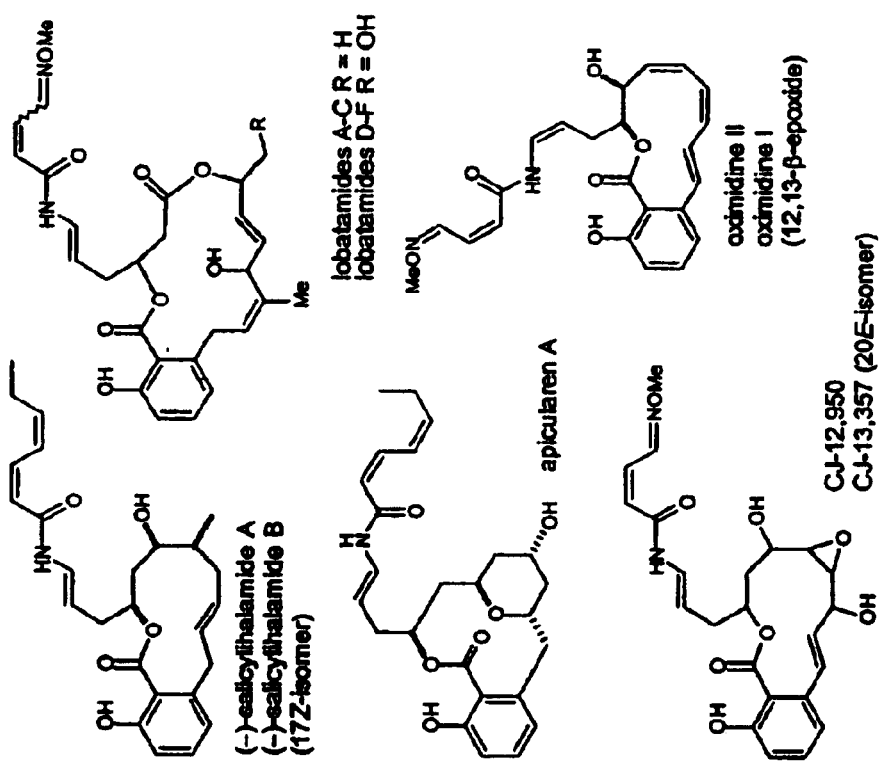
FIG. 1. Natural Salicylihalamides

Natural products that elicit a specific and unique biological response in mammalian cells represent valuable tools to identify, study, and target possible new gene products. In this context, the recent isolation of salicylihalamides A and B from the marine sponge *Haliclona* sp. is noteworthy. Pattern-recognition analysis of their unique differential NCI 60-cell mean-graph screening profiles suggests that the salicylihalamides belong to a potentially new mechanistic class of antitumor compounds. Since their discovery in 1997, an emerging class of novel active metabolites have been isolated that structurally relate to the salicylihalamides by virtue of an unprecedented highly unsaturated enamide appended on a macrocyclic benzolactone; These include the mechanistically related lobatamides, the potent cytostatic apicularens, selective inhibitors of oncogene-transformed cells (oximidines), as well as compounds that induce low density lipoprotein (LDL) receptor gene expression. However, the natural forms of these compounds are unstable under certain conditions. The opportunity to develop novel chemistry as well as accessing variants with increased stability, prompted the inventor to undertake the total synthesis of a modified salicylihalamide and modified apicularens. Included is a flexible synthetic strategy, which can be readily adapted to gain access to structural variants, as well as other members of this intriguing class of anti-tumor compounds.

The inventor has accomplished the first synthesis of both (=)- and (−)-salicylihalamide A. The synthesis utilizes a highly efficient, trans-selective ring-closing olefin metathesis for the assembly of the benzolactone skeleton and can be readily adapted to obtain a variety of analogs. The inventor synthesized the compound of the structure disclosed in Boyd et al., (PCT/US98/15011) and found that the optical rotation of synthetic salicylihalamide A (87) was ([α]$_D$=+20, c, MeOH). The inventor found that this form did not possess anti-cancer activity. The (+) form was still inactive at 20 μM whereas natural salicylihalamide ((−) form) is active at 10 nM when tested against SK-MEL-28 cells. This cell line is one of the cell lines in the NCI 60 cell line screen. The inventor then accomplished the first synthesis of (−)-salicylihalamide A. It had a negative optical rotation like that of natural salicylihalamide A [α]$_D$=−35, c 0.7, MeOH) (Erickson et al., 1997). Salicylihalamide A with an (−) optical rotation does possess anti-cancer activity as does natural salicylihalamide, whereas salicylihalamide with a (+) optical rotation does not have chemotherapeutic activity.

The inventor has determined the absolute configuration of synthetic salicylihalamide (87), suggesting that the absolute configuration of natural salicylihalamide A was misassigned and has to be corrected to the one represented by structure 89. The ultimate proof for this assignment came from a crystallographic analysis of a p-bromobenzoate derivative of salicylihalamide 90, prepared from 73 in a manner similar to the synthesis of 74. This structure is shown in FIG. 11. Comparison between synthetic salicylihalamide and natural salicylihalamide show the compounds to be identical in all respects (NMR, mass spectroscopy, IR, TLC (2 solvent systems: 50% ethylacetate in hexanes and 5% methanol in dichloromethane), and HPLC retention times(co-elute on a normal phase silica gel, 5 micron column under 2 different solvent conditions: 3% isopropanol in hexanes and 7% isopropanol in hexanes)) except for their rotations. The synthesis of the absolute configuration has also been accomplished by the inventor. See Examples 7 and 8.

Figure 4:
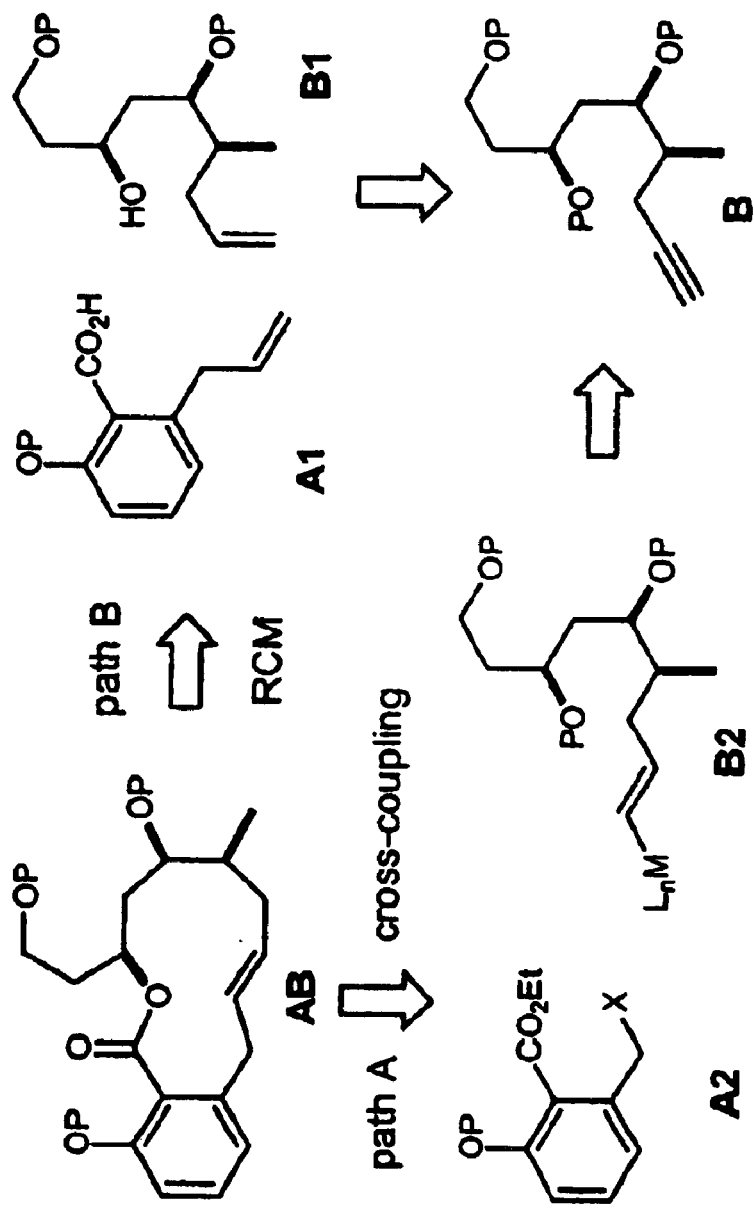
FIG. 4. Two general approaches to the synthesis of the benzolactone core of salicylihalamide.
Figure 5:
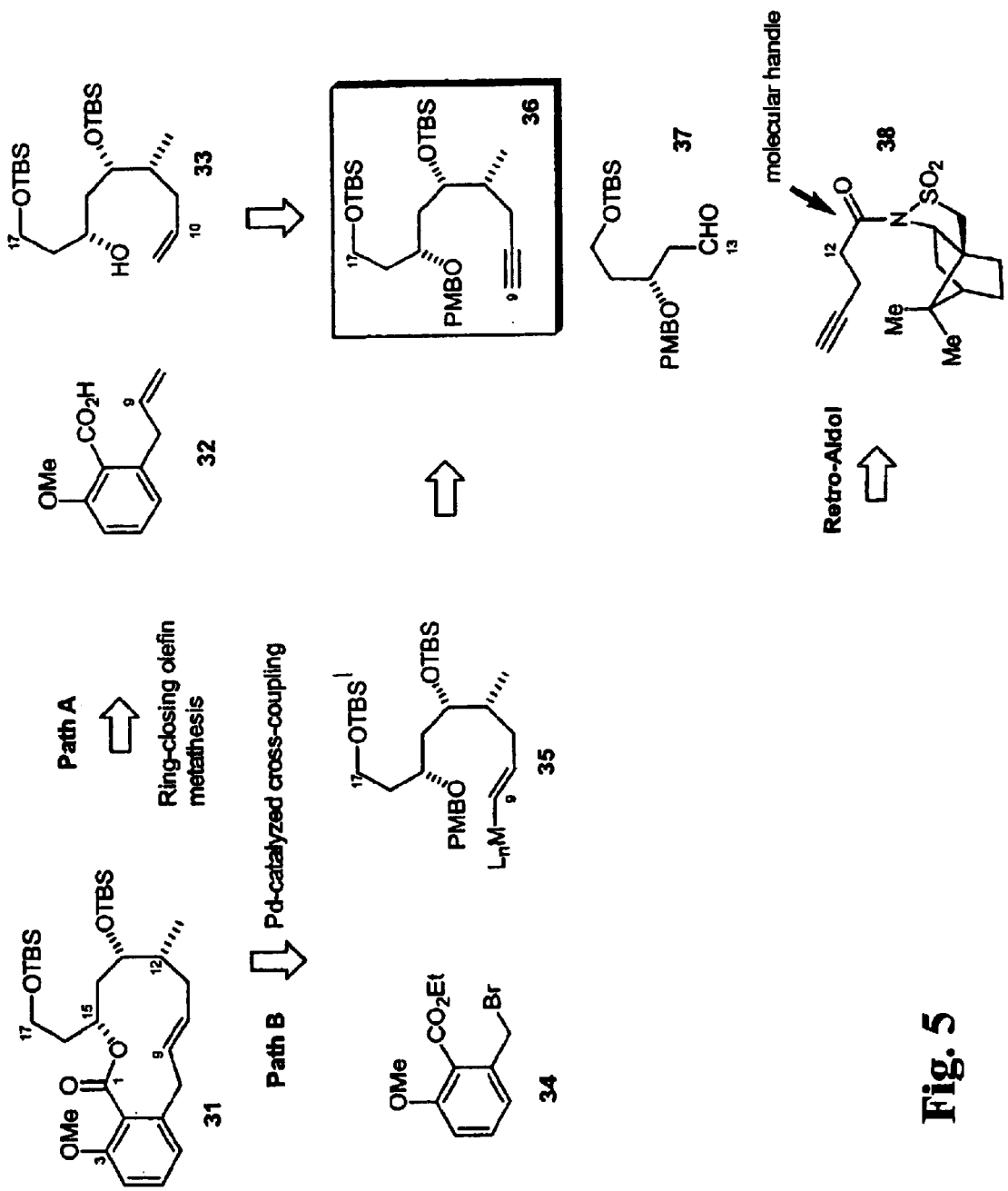
FIG. 5. Two specific approaches to the synthesis of the benzolactone core of salicylihalamide.
Figure 6:
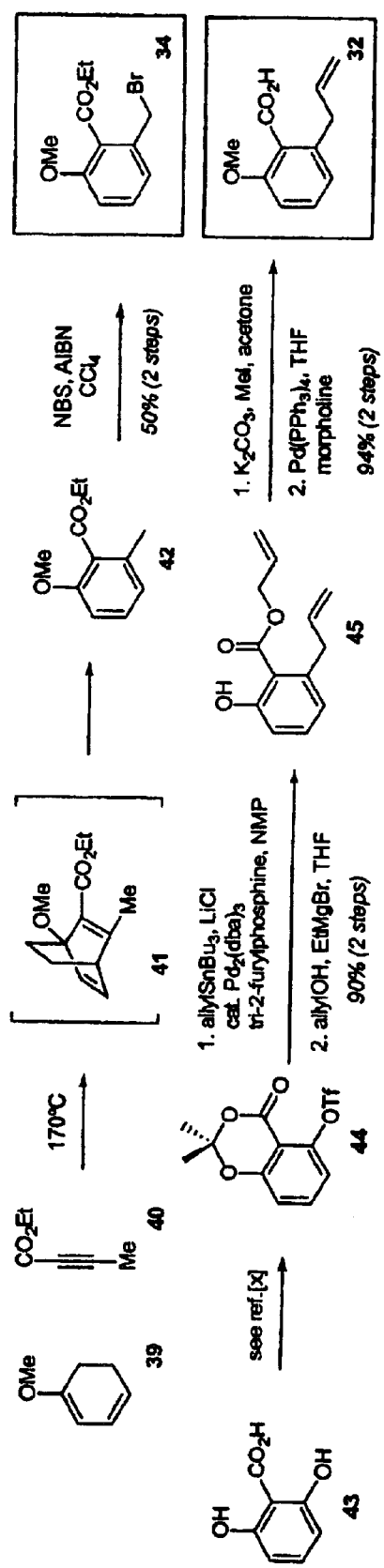
FIG. 6. Synthesis of benzylic bromide 34 and synthesis of benzoic acid derivative 32
Figure 7:
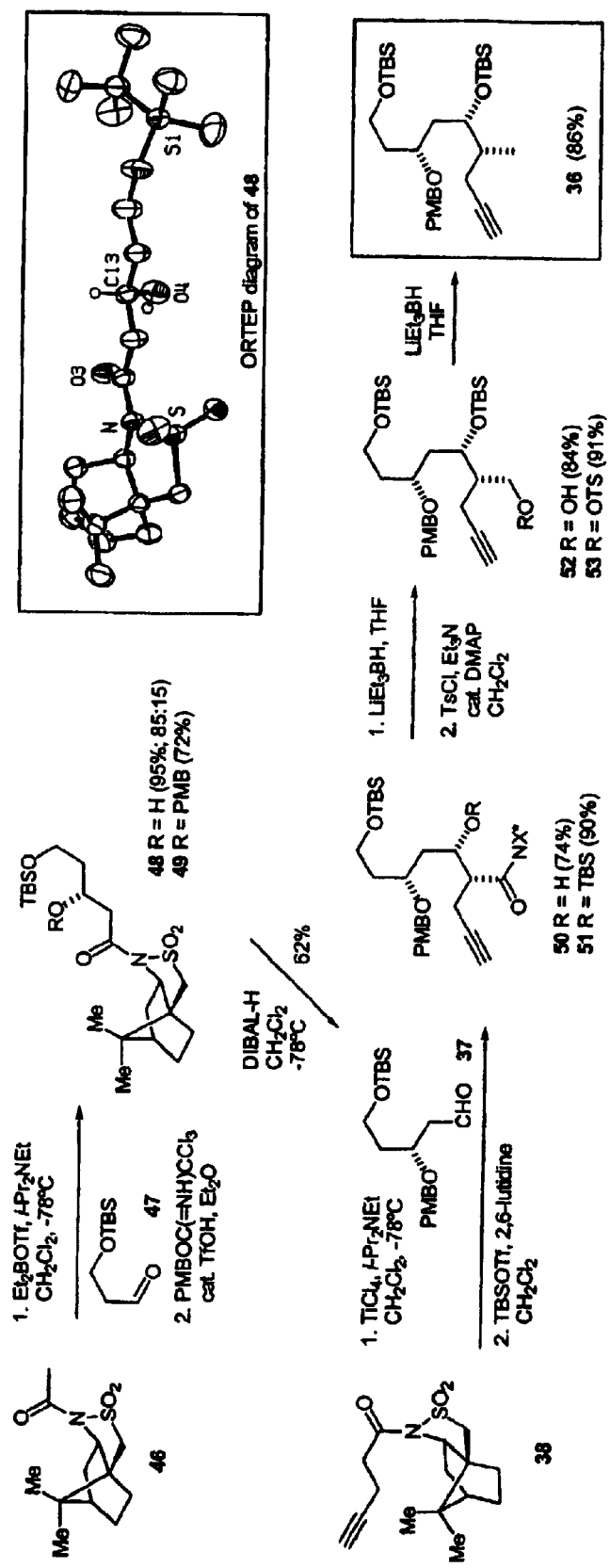
FIG. 7. Synthesis of alkyne 36

The present invention also provides for methods/processes of synthesis of the compounds of the present invention which include two equally active routes for its assembly (FIG. 4). One route features an esterification/intramolecular olefin metathesis sequence (RCM) to form the C9–C10 bond and offers the advantage of operational simplicity combined with functional group tolerance (A1+B1 gives AB; Path A; FIG. 4). Despite the robustness of the RCM in carbon-carbon bond formation, it can only be implemented successfully for the synthesis of salicylihalamides if concomitant sterocontrol for the desired E-isomer can be exerted. As detailed in full below (Examples 7 and 8), the inventor has identified a highly E-selective RCM avenue to salicylihalamide A. An alternative route involves cross coupling of a sterodefined E-alkenyl organometallic fragment B2 with a bensyl halide A2 and is envisioned to join the C8–C9 bond with control and maintenance of olefin geometry (Path B; FIG. 4). Importantly, both strategies converge to a common alkyne precursor B, adding flexibility to the synthesis. The symbol P in FIG. 4 represents a generic symbol for a hydroxy protecting group.

For example, the present invention provides for a process for preparing an Apicularen comprising:

a) synthesis of an Apicularen benzolactone core; and c) addition of a side chain to the Apicularen benzolactone core.

In addition, the present invention provides for a process for preparing a salicylihalamide comprising:

a) synthesis of a salicylihalamide benzolactone core; and b) addition of a side chain to the salicylihalamide benzolactone core.

In a preferred embodiment, the process for preparing a salicylihalamide comprises:

(a) synthesizing the compounds of formula:

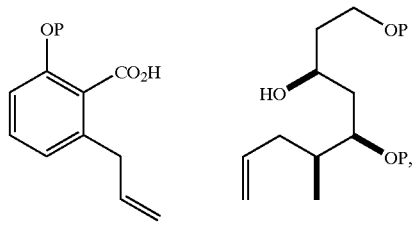

and (b) producing from the compounds of step (a), via an ring-closing metathesis, the compound of formula:

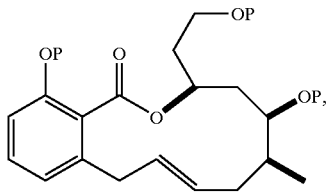

wherein P=a hydroxyl protecting group

The process may further comprise:

(i) modifying the compounds of step (a) as follows:

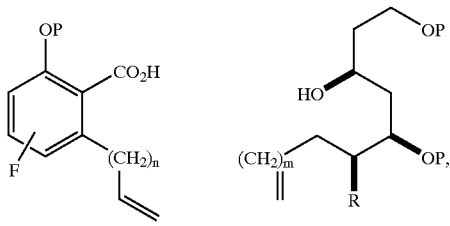

Wherein n=0, 1, 2, or 3 and m=1, 2, or 3; R=alkyl; and F=functionality as defined in claim 1; and (ii) Producing from the compounds in step (a), as defined in step (b) of above, the compounds of formula:

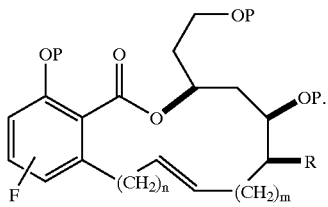

In a further preferred embodiment, the process for preparing a salicylihalamide comprises:

(a) synthesizing the compound of formula:

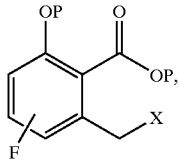

wherein X=I, Br, Cl, OSO2Aryl; F=functionality as defined in claim 1; and P=a hydroxyl protecting group;

(b) synthesizing the compound of formula:

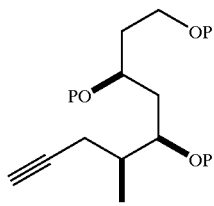

(c) synthesizing from the compound of step (b), via a hydrometallation, the compound of formula:

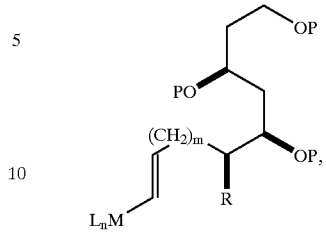

wherein m=1, 2, or 3; R=alkyl; P=a hydroxyl protecting group and $L_nM$ is a ligated metal center with M=B, Zn, Zr, Pd, Cu, Li, Sn; and (d) producing from the compounds of step (a) and (c), via metal-catalyzed cross coupling, the compound of formula:

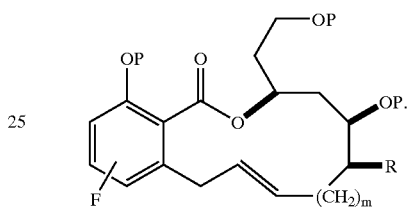

In addition to their use as anti-tumor agents, compounds of the present invention have potential for treatment of osteoporosis, a condition in which bone resorption is increased resulting in weakening of bone. The compounds can be administered alone or in combination with other treatments for osteoporosis. Other treatments for osteoporosis may include, but are not limited to calcium supplements, estrogen replacement for women, and treatment with bisphosphonates or growth factors. The pharmaceutical compositions containing the compounds of the present invention are administered in the manner as described herein.

Figure 9:
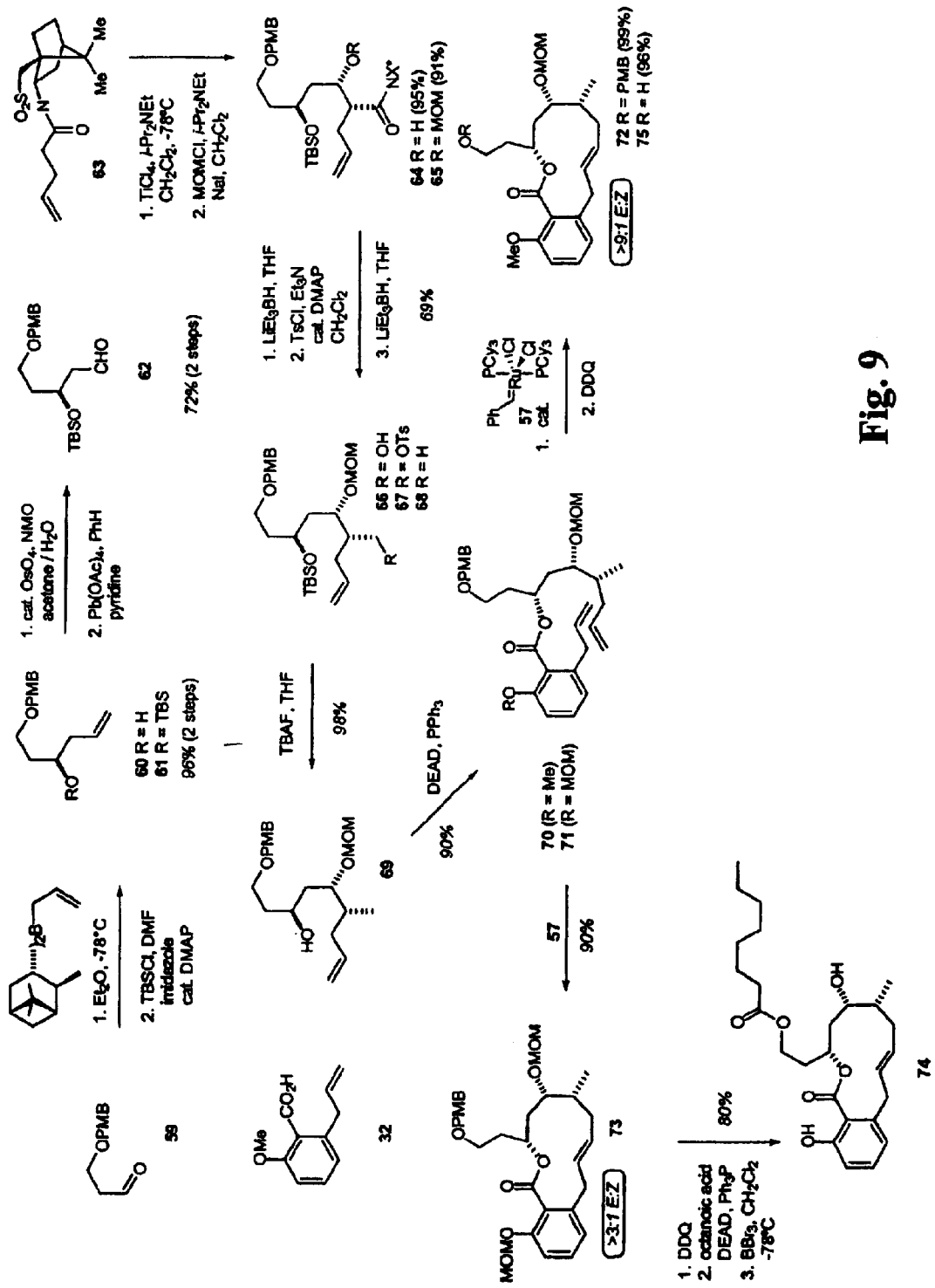
FIG. 9. Fully optimized synthesis of benzolactone 74
Figure 22:
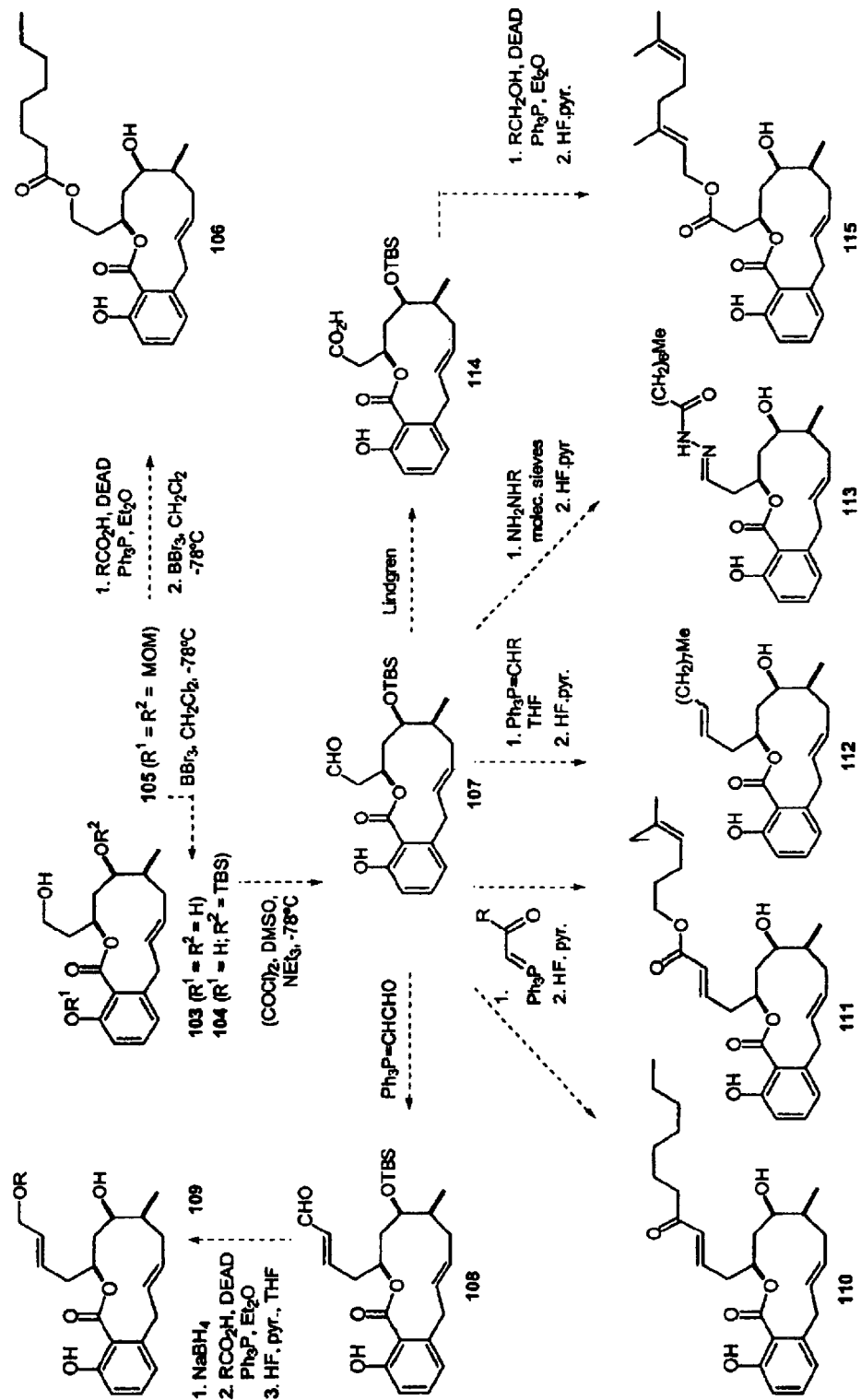
FIG. 22. Methods to build a library of synthetic salicylihalamides from common intermediates FIG. 23. Elaborations of side chain-modified congeners of salicylihalamide FIG. 24. Synthesis of apicularen and analogs FIG. 25. $^1$H NMR spectra of 301a/301c FIG. 26. ¹H NMR spectra of 87
FIG. 27. ¹H NMR spectra of C22-E isomer of 87
FIG. 28. ¹H NMR spectra of 334b
FIG. 29. ¹H NMR spectra of 335b
FIG. 30. ¹H NMR spectra of 336
FIG. 31. ¹H NMR spectra of 337
FIG. 32. ¹H NMR spectra of 343
FIG. 33. ¹H NMR spectra of 344
FIG. 34. ¹H NMR spectra of 346
FIG. 35. ¹H NMR spectra of 345
FIG. 36. ¹H NMR spectra of 351
FIG. 37. ¹H NMR spectra of 355
FIG. 38. ¹H NMR spectra of 356
FIG. 39. ¹H NMR spectra of 361
FIG. 40. ¹H NMR spectra of 362

Salicylihalamide A exhibits a unique differential cytotoxicity profile in the NCI 60-cell line human tumor assay and represents a novel mechanistic class of antitumor compounds. However, the inherent lability of the enamide side-chain has compromised the development of salicylihalamide-based probe reagents for biochemical analysis. The inventor has synthesized stable functional substitutes of the side-chain. Lobatamides A–F and salicylihalamide A–B are active and gave similar "signatures" in the NCI cancer panel. The inventor realized that the nature of the constituent atoms of the side-chain terminus could be varied (alkylidene vs. methyloxime). Also, the stereochemical nature of the side-chain is unimportant, indicating a non-specific contact, if any, with a putative biological receptor. The inventor has "mutated" the enamide without compromising function. FIG. 22 outlines methods to build a small library of synthetic "salicylihalamides" from common intermediates 105 (ent-73, FIG. 9) and 107.

Compounds represented by (ent-74, FIG. 9) are accessible from 105 via Mitsunobu esterification with a variety of carboxylic acids followed by deprotection (BBr$_3$). Aldehyde 107 is the central handle for olefination chemistry (stabilized and non-stabilized yields) and N-acyl hydrazone formation. Compounds 110-113 are representative examples of a larger group of compounds that could be made by varying the R-group in the reagents. Variations on the theme include geranyl ester 115 and allyl esters 109.

This method of synthesis is being used to provide new anti-cancer compounds. See also Examples 7 and 8. The inventor will use a cell-based cytotoxicity assay to establish structure-activity relationships. Initial hits will be sent to the National Cancer Institute for COMPARE-analysis in the NCI 60-cell line screen. Internal screening against a broad range of primary human lung cancer cell lines will be carried out. The compounds of the present invention have also been tested for their ability to inhibit the growth of tumor cells, including SK-MEL-5, H1299, J2009, H358, J2058, H175 and H1264. See Table 3 and Table 4 and Example 7 below.

Compounds may also be tested for activity in the yeast *Saccharomyces cervisiae*. Yeast-based screening methods are fast and would allow for the identification of salicylihalamide's target via genetic approaches, but only if a yeast homologue exists. Moreover, the complete genome of Saccharomyces cervisiae is sequenced and gene-chips are available as powerful tools to look at expression patterns in response to drugs. One of the traditional drawbacks lies in the fact that yeast is relatively impermeable to small-molecule drugs and becomes resistant by overproduction of multidrug resistance pumps. To alleviate potential problems, Δerg6 mutant strains, displaying reduced multi-drug resistance and more permeability to drugs due to more fluid membranes, will be used.

The compounds of the present invention can inhibit V-ATPase proton-pumping activity. The V-ATPase proton-pumping inhibitory activity of the compounds of the present invention may be tested as described in Example 7 below (Table 5).

Therefore, the present invention provides a method for inhibiting the proton-pumping activity of V-ATPase by contacting V-ATPase, either in vitro or in vivo with the compounds of the present invention. Inhibition of the proton-pumping activity of V-ATPase is useful, inter alia, for the treatment and prevention of cancer and osteoporosis. Salicylihalamide A has been shown to inhibit V-ATPase activity in crude membrane preparations of mammalian V-ATPases. See Boyd, M. R. et al., *J Pharmacol. Exp. Ther.* 297, 114–120 (2001); see also, PCT publication WO 00/51589 of Boyd et al. V-ATPase is composed of an ATPase domain and a proton translocating membraneous channel. The present invention demonstrates, through the use of a purified V-ATPase assay, that the mode of inhibition is through the blocking of the proton-pumping activity (or proton translocation, also known as pore blocking) of V-ATPase and not through its ATP hydrolysis activity. The present invention also demonstrates that the compounds of the present invention bind to the trans-membraneous proton channel domain of V-ATPase and not to the ATPase domain. See Crider, Xie and Stone, *J. Biol. Chem.* 269:17379–17381 (1994) for the experimental procedure for binding. This was shown by incubating select compounds of the present invention with the domains independently and showing that 70% of the channel activity was inhibited at 1 nM of the compound while there was virtually no interference with ATPase activity at the same concentration. See Example 7 and Table 5 below. See also Bill. Crider, Xie and Stone, *J Biol. Chem.* 269:17379–17381 (1994).

Figure 23:
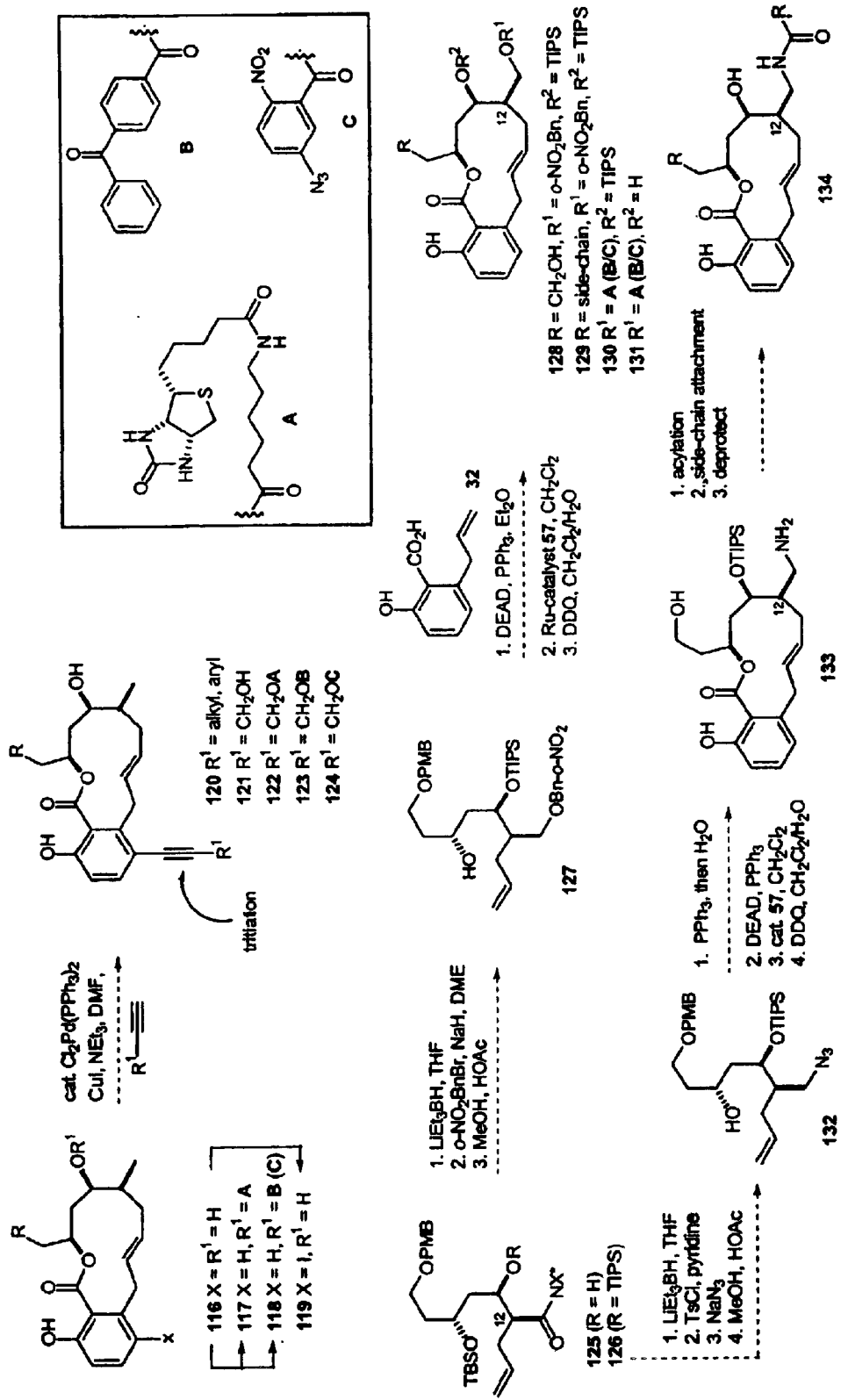
Figure 24:
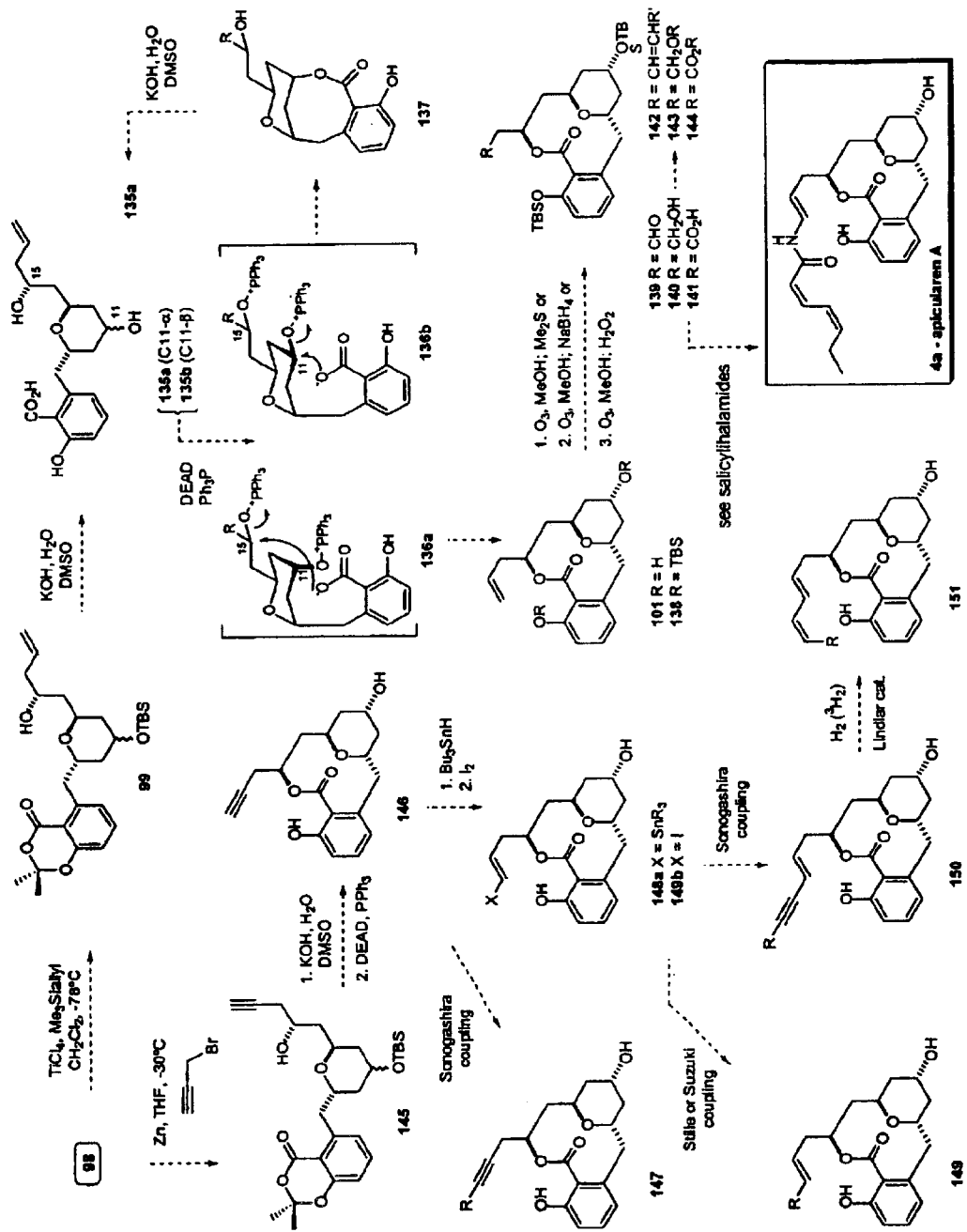

Probe reagents for biochemical analysis may be developed by modifying selected positions without compromising function. FIG. 23 outlines some elaborations of side chain-modified congeners. The exact nature of this side-chain (designated as R in FIG. 23) is contingent on the screening results. In addition, Example 7 below describes other chain modifications.

It is possible to attach probes to, or substitute for, the side-chain. Biotinylation allows cellular localization studies, affinity chromatography and ligand-based gel blotting analysis to be carried out using avidin conjugates. Treatment of alcohol 116 with N-(+)-biotinyl-6-aminocaproic acid N-hydroxysuccinimide ester will give biotinylated compound 117. The corresponding probes for photoaffinity-labeling studies, 118 ($R^1$=B or C) can be obtained via acylation with 4-benzoylbenzoic acid N-hydroxysuccinimide ester or 4-azidobenzoic acid N-hydroxysuccinimide ester, respectively. If these materials are inactivated by the proposed modifications, iodophenol 119 may be used as the starting material for derivatizations emanating from the aromatic ring. Iodophenol 119 can be prepared from 116 ($I_2$). Selectivity for the para-position is usually observed. Substituting a chloramine T/$Na^{125}I$ reagent combination for iodine is a method to synthesize radiochemicals. Sonogashira coupling of iodophenol 119 with propargyl alcohol provides a handle (121) for introducing biotin (→122) or photolabels (→123/124) using the same acylating agents as described above. Radiochemicals are accessible via tritiation (Lindlar, $^3H_2$). Alkyne libraries (120) can be prepared using Sonogashira cross-coupling chemistry.

The inventor designed a C12-carboxamide as a synthon for the C12-methyl substituent (FIG. 4). To synthesize salicylihalamide analogs and probes otherwise not accessible, the C13-OH in 125 (ent-64) will be masked as triisopropylsilylether 126, followed by reduction of the carboxamide ($LiEt_3BH$). The resulting primary alcohol can be converted to a coupling partner having a latent C12-hydroxymethyl substituent (121). Care must be taken to introduce the base-sensitive o-$NO_2$-benzylether. A nitroveratrylether is also a viable alternative. Mitsunobu inversion (acid 32), treatment with Grubbs' ruthenium carbene complex 57 and oxidative deprotection (DDQ) will provide cyclized material 128. In close analogy to the manipulations described for 104, a suitable side-chain (with respect to biological activity), identified through the studies described in FIG. 22, will be introduced (→129) followed by photo-deprotection of the nitrobenzylether (350 nm, MeOH). At this point, the hydroxymethyl substituent serves its purpose as a handle for obtaining probe reagents 131 (acylation with N-hydroxysuccinimide esters as above, followed by desylilation of 130). Finally, similar probes containing an amide linkage (134) can be constructed from azide 132 using similar chemistry.

Figure 10:
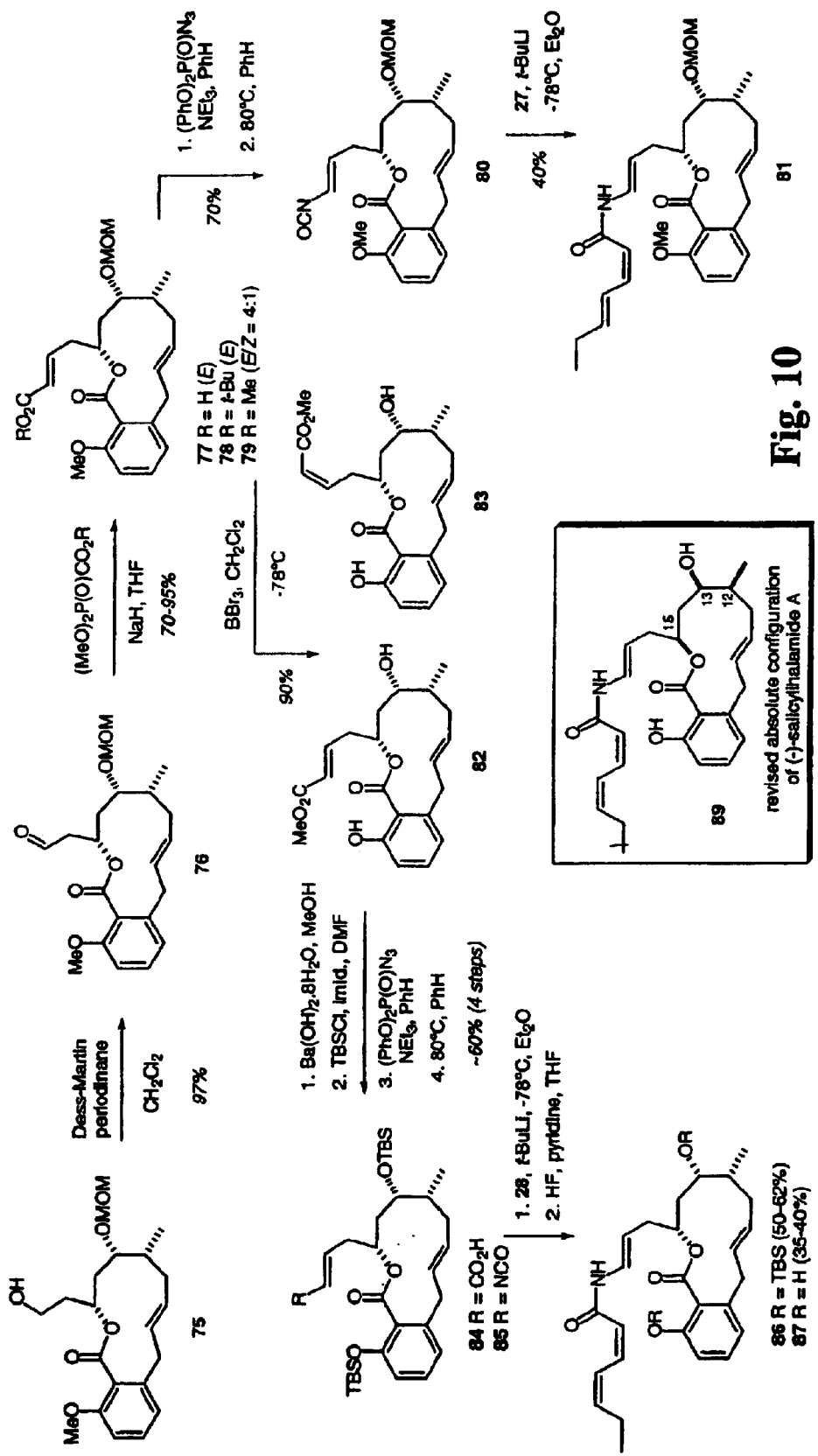
FIG. 10. Introduction of the side chain and final deprotection
Figure 12:
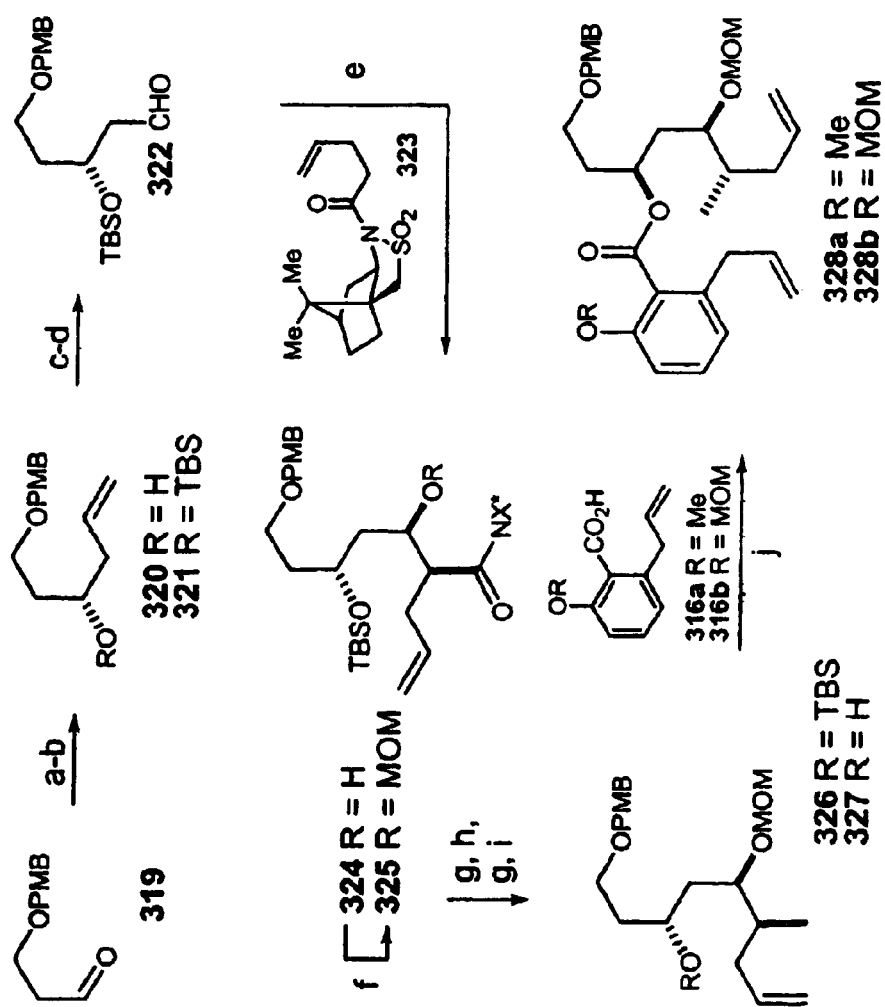

The inventor has also succeeded in the first and only total synthesis of Apicularen A and a variety of analogs. The synthetic sequence is outlined in FIGS. 20 and 43. For a description, see Example 4. The initial lactonization approach of the inventor required the natural configuration at the C15 hydroxyl-bearing center (15S) in a 1,3-syn relationship with C13. A reagent-controlled mismatched allylation (double diastereodifferentiation) was used for its formation. The inventor knew from work on salicylihalamides that ortho-alkoxy benzoates behave as poor electrophiles in esterification (lactonization) chemistry. Utilizing an intramolecular Mitsunobu inversion as the key ring-formning step could solve both problems. The substrate for this reaction would require an inverted C15 alcohol in a 1,3-anti relationship with respect to C13. The intrinsic facial bias of β-alkoxyaldehydes favors such a relationship in their addition products. Based on numerous precedents, aldehyde 98 would be expected to yield anti-homoallyl alcohol 99 with good stereocontrol by a chelation-controlled ($TiCl_4$) addition of allyltrimethylsilane. Alternatively, the corresponding addition of allenylzinc (prepared in situ from propargylbromide and Zn) would yield stereoselectively anti-homopropargyl alcohol 145. Basic hydrolysis of benzo [1,3]dioxinone 99 will release the carboxylic acid and the C11 hydroxyl functionalities simultaneously. A few scenarios can be envisioned for the subsequent Mitsunobu ring-closure (135→101/102). The accepted mechanism for the Mitsunobu inversion involves activation of the alcohol to a leaving group ($RCH_2OP^+Ph_3$). The epimeric diol mixture 135a–b would be expected to give intermediates 136a and 136b. Both intermediates could react at C15 (with inversion) to give epimeric benzolactones 101 and 102, respectively, but the possibility of a competitive cyclization involving a C11 activated hydroxy group has to be considered. However, only the undesired epimeric intermediate 136b would be expected to participate—136a can not reach the TTS required for an intramolecular $SN_2$ displacement— resulting in the formation of bridged lactone 137. Saponification of this material ultimately leads to a net recycling of undesired 135b to 135a. Truncated apicularen 101 will be manipulated in multiple ways to generate the natural product as well as a variety of side-chain modified analogs. For example, the ozone adduct of silyl-protected derivative 138 ($O_3$, −78° C.) will be decomposed to aldehyde 139 ($Me_2S$), alcohol 140 ($NaBH_4$) and carboxylic acid 141 ($H_2O_2$), respectively. Apicularen A (4a) will be accessed from aldehyde 139 via a sequence similar to the one successfully employed for the synthesis of salicylihalamide A (FIG. 10). Furthermore, compounds 139–141 are functionally equivalent to their corresponding salicylihalamide counterparts 104, 107 and 114 (FIG. 22), and will be processed in similar ways to deliver side chain-modified apicularen mimics 142–144 (apicularens of general structure 142 are accessible directly from 101 by intermolecular olefin metathesis).

Finally, alkyne 146 will be prepared from 145 in a manner similar to the one outlined for 101. The terminal alkyne provides the ideal handle for a Sonogashira cross-coupling to prepare apicularen-based analogs 147. In addition, the derived stannane 148a and/or vinyliodide 148b will extend the range of cross-coupling reactions to the synthesis of 149 (R=aryl, 1-alkenyl) and enynes 150. Catalytic hydrogenation of compounds containing a triple bond will provide Z-alkenes (e.g. 151), potentially radiolabeled ($^3H_2$, Lindlar cat.).

Examples 7 and 8 below further describe a preferred embodiment of the present invention.

In the present invention, all structural modifications that are useful as modifications to salicylihalamides are also useful as modifications to apicularens and other macrocyclic lactones.

X-ray crystallography is the study of the molecular structure of crystalline compounds through X-ray DIFFRACTION techniques. When an X-ray beam bombards a crystal, the atomic structure of the crystal causes the beam to scatter in a specific pattern. This phenomenon, known as X-ray diffraction, occurs when the wavelength of the X rays and the distances between atoms in the crystal are of similar magnitude. X-ray crystallography provides information on the positions of individual atoms in the crystal, the distances between atoms, the angles of the atomic bonds, and other features of molecular geometry. X-ray crystallography is also used to determine the structure of proteins, nucleic acids, and other substances, such as small molecules (http://www.encyclopedia.com/articles/14056.html (Jun. 7, 2000)).

Mass spectrometers use the difference in mass-to-charge ratio (m/e) of ionized atoms or molecules to separate them from each other. Mass spectrometry is therefore useful for quantitation of atoms or molecules and also for determining chemical and structural information about molecules. Molecules have distinctive fragmentation patterns that provide structural information to identify structural components. The general operation of a mass spectrometer is: create gas-phase ions, separate the ions in space or time based on their mass-to-charge ratio, and measure the quantity of ions of each mass-to-charge ratio (http://www.scimedia.com/chemed/ms/ms-intro.htm(Jun. 7, 2000)).

The temperature used for synthesis is, except where stated to be different, in a range from about −78° C. to about 125° C., preferably 0° C. to 90° C.

The term "salicylihalamide derivative" as used herein refers to those structures having a benzolactone core of the same conformation as salicylihalamide. Examples are:

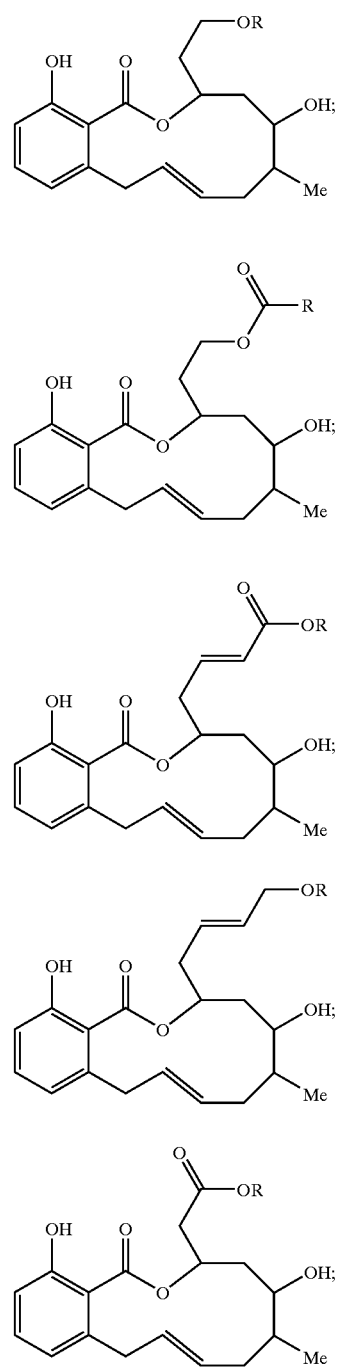

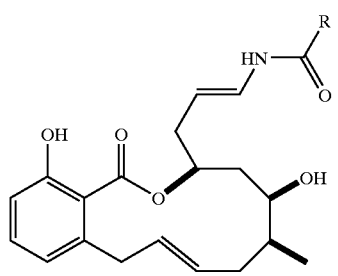
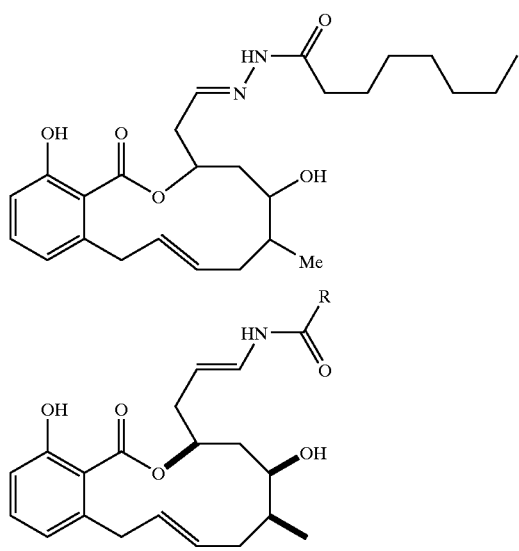
where R=a straight chain alkyl comprising 5 to 8 carbons (e.g. —(CH2)5Me), a straight chain alcohol (e.g. —O(CH2)4Me) or a straight chain diol (e.g. —S(CH2)4Me);
where R=Bu or Ph;
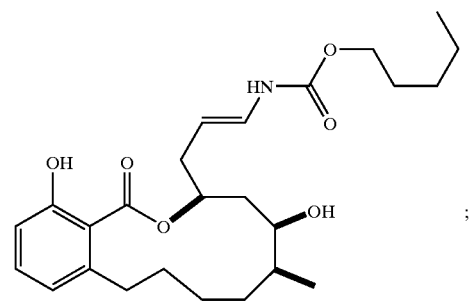
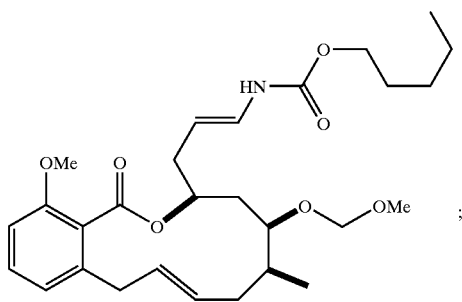
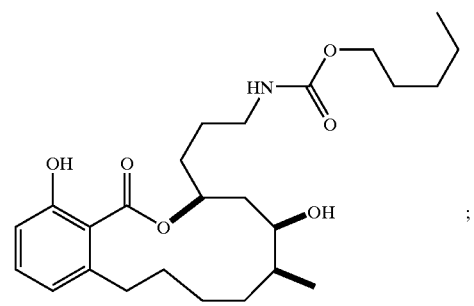
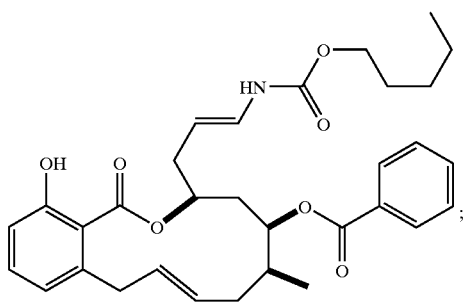
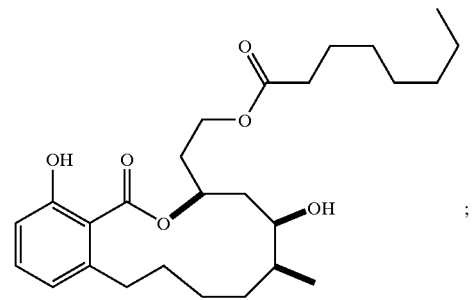
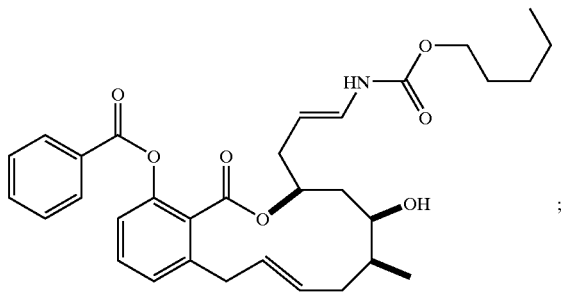

-continued
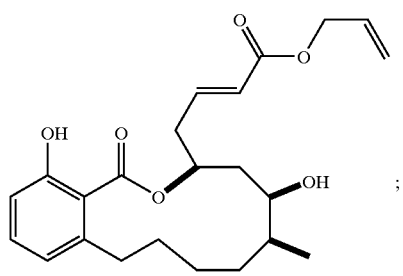
;
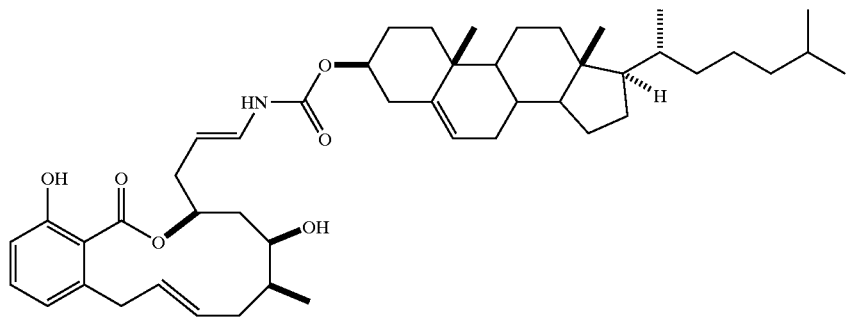
;
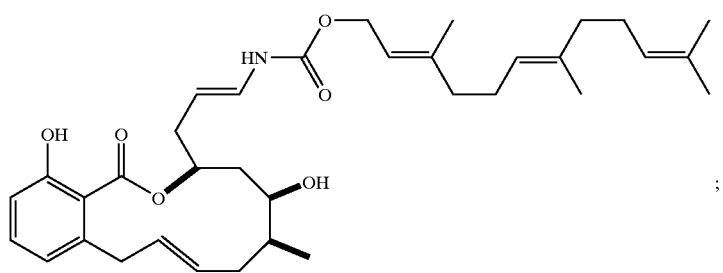
; and
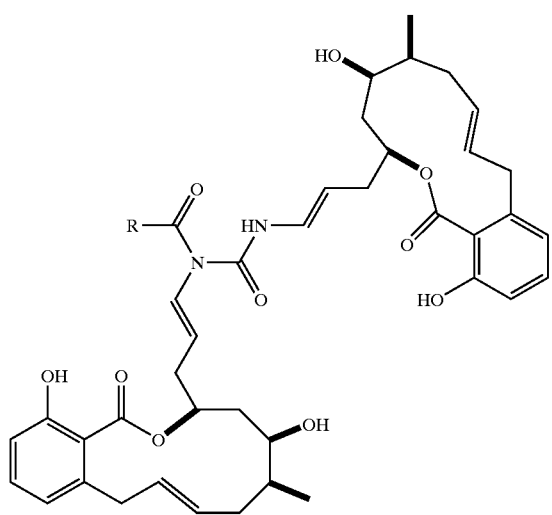

where R=Z,Z-hexadienyl, Z,E-hexadienyl or a straight chain alkyl comprising 5 to 8 carbons (e.g. —(CH2)5Me).

The term "apicularen derivative" as used herein refers to those structures having a benzolactone core of the same conformation as apicularen. Examples are:

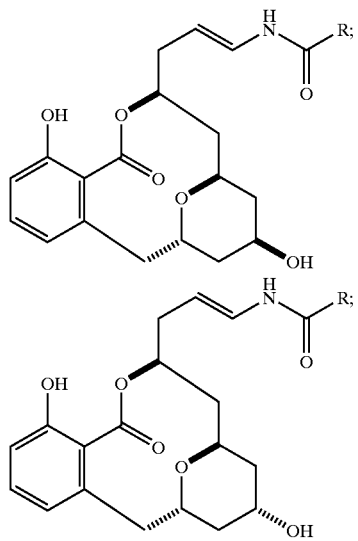

where R=a straight chain alkyl comprising 5 to 8 carbons (e.g. —(CH2)5Me), a straight chain alcohol (e.g. —O(CH2)4Me) or a straight chain diol (e.g. —S(CH2)4Me);

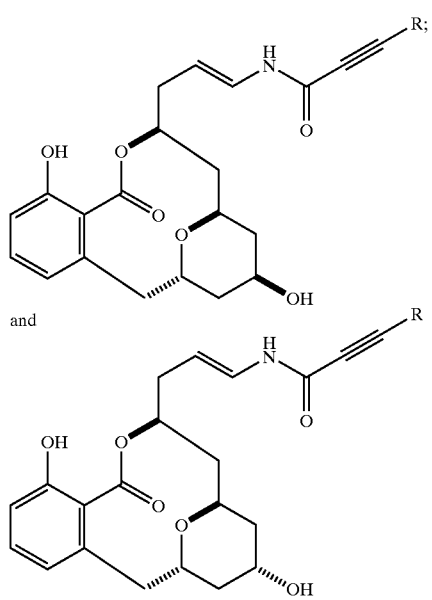

and

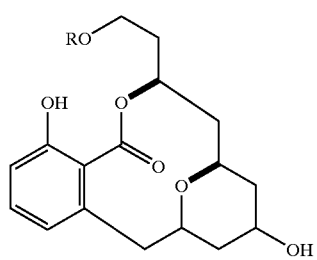

where R=Bu or Ph.

-continued

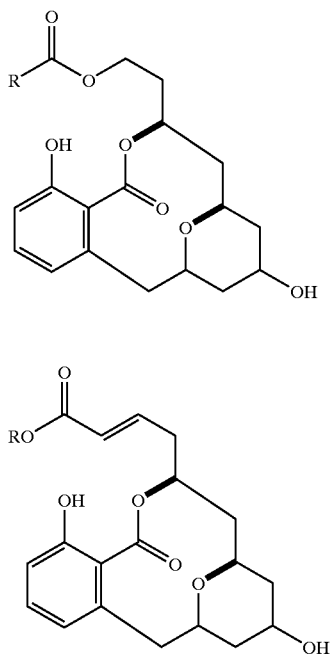

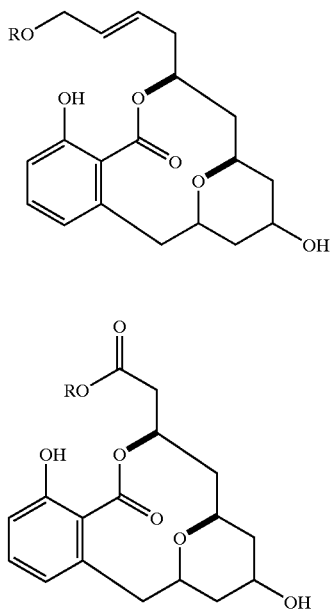

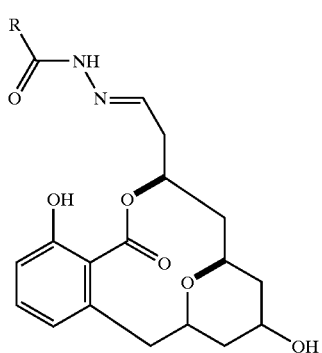

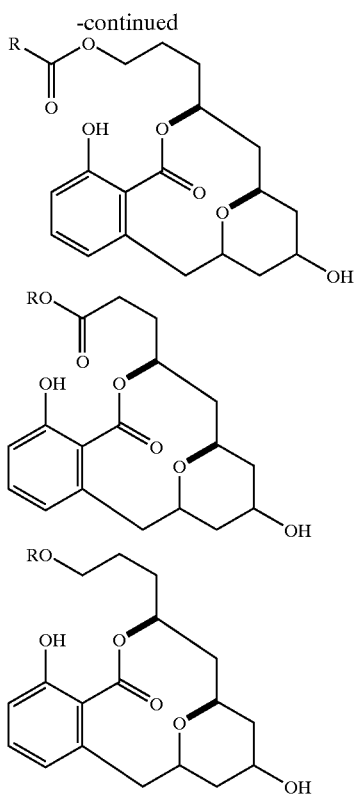

The present invention also provides for physiological compositions comprising the compounds of the present invention. Aqueous physiological compositions of the present invention comprise an effective amount of a macrocyclic lactone of the present invention or pharmaceutically acceptable salt thereof, dissolved and/or dispersed in a pharmaceutically acceptable carrier and/or aqueous medium.

The phrases "physiologically, pharmaceutically and/or pharmacologically acceptable" refer to molecular entities and/or compositions that do not produce an adverse, allergic and/or other untoward reaction when administered to an animal.

As used herein, "physiologically and/or pharmaceutically acceptable carrier" includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated. Supplementary active ingredients can also be incorporated into the compositions. For human administration, preparations should meet sterility, pyrogenicity, general safety and/or purity standards as required by FDA Office of Biologics standards.

The biological material should be extensively dialyzed to remove undesired small molecular weight molecules and/or lyophilized for more ready formulation into a desired vehicle, where appropriate. The active compounds may generally be formulated for parenteral administration, e.g., formulated for injection via the intravenous, intramuscular, sub-cutaneous, intralesional, and/or even intraperitoneal routes. The preparation of aqueous compositions that contain a therapeutically effective amount of the macrocyclic lactones of the invention or pharmaceutically acceptable salts thereof as an active component and/or ingredient will be known to those of skill in the art in light of the present disclosure. Typically, such compositions can be prepared as injectables, either as liquid solutions and/or suspensions; solid forms suitable for using to prepare solutions and/or suspensions upon the addition of a liquid prior to injection can also be prepared; and/or the preparations can also be emulsified.

The pharmaceutical forms suitable for injectable use include sterile aqueous solutions and/or dispersions; formulations including sesame oil, peanut oil and/or aqueous propylene glycol; and/or sterile powders for the extemporaneous preparation of sterile injectable solutions and/or dispersions. In all cases the form must be sterile and/or must be fluid to the extent that easy syringability exists. It must be stable under the conditions of manufacture and/or storage and/or must be preserved against the contaminating action of microorganisms, such as bacteria and/or fungi.

Solutions of the active compounds as free base and/or pharmacologically acceptable salts can be prepared in water suitably mixed with a surfactant, such as hydroxypropylcellulose. Dispersions can also be prepared in glycerol, liquid polyethylene glycols, and/or mixtures thereof and/or in oils. Under ordinary conditions of storage and/or use, these preparations contain a preservative to prevent the growth of microorganisms.

Macrocyclic lactones of the present invention can be formulated into a composition in a neutral and/or salt form. Pharmaceutically acceptable salts, include the acid addition salts and/or which are formed with inorganic acids such as, for example, hydrochloric and/or phosphoric acids, and/or such organic acids as acetic, oxalic, tartaric, mandelic, and/or the like.

The carrier can also be a solvent and/or dispersion medium containing, for example, water, ethanol, polyol (for example, glycerol, propylene glycol, and/or liquid polyethylene glycol, and/or the like), suitable mixtures thereof, and/or vegetable oils. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and/or antifungal agents, for example, parabens, chlorobutanol, phenol, sorbic acid, thimerosal, and/or the like. In many cases, it will be preferable to include isotonic agents, for example, sugars and/or sodium chloride. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the required other ingredients from those enumerated above. In the case of sterile powders for the preparation of sterile injectable solutions, the preferred methods of preparation are vacuum-drying and/or freeze-drying techniques which yield a powder of the active ingredient plus any additional desired ingredient from a previously sterile-filtered solution thereof. The preparation of more, and/or highly, concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and/or in such amount as is therapeutically effective. The formulations are easily administered in a variety of dosage forms, such as the type of injectable solutions described above, but drug release capsules and/or the like can also be employed.

For parenteral administration in an aqueous solution, for example, the solution should be suitably buffered if necessary and/or the liquid diluent first rendered isotonic with sufficient saline and/or glucose. These particular aqueous solutions are especially suitable for intravenous, intramuscular, subcutaneous and/or intraperitoneal administration. In this connection, sterile aqueous media which can be employed will be known to those of skill in the art in light of the present disclosure. For example, one dosage could be dissolved in 1 ml of isotonic NaCl solution and/or either added to 1000 ml of hypodermoclysis fluid and/or injected at the proposed site of infusion, (see for example, "Remington's Pharmaceutical Sciences" 15th Edition, pages 1035–1038 and/or 1570–1580). Some variation in dosage will necessarily occur depending on the condition of the subject being treated. The person responsible for administration will, in any event, determine the appropriate dose for the individual subject.

The macrocyclic lactones of the present invention may be formulated within a therapeutic mixture to comprise about 0.0001 to 1.0 milligrams, and/or about 0.001 to 0.1 milligrams, and/or about 0.1 to 1.0 and/or even about 10 milligrams per dose and/or so. Multiple doses can also be administered.

Various routes of administration are contemplated for various tumor types. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the macrocyclic lactone. A tumor bed may be treated prior to, during or after resection. Following resection, one could deliver the macrocyclic lactone by a catheter left in place following surgery. One may utilize the tumor vasculature to introduce the macrocyclic lactone into the tumor by injecting a supporting vein or artery. A more distal blood supply route also may be utilized.

In addition to the compounds formulated for parenteral administration, such as intravenous and/or intramuscular injection, other pharmaceutically acceptable forms include, e.g., tablets and/or other solids for oral administration; liposomal formulations; time release capsules; and/or any other form currently used, including cremes.

One may also use nasal solutions and/or sprays, aerosols and/or inhalants in the present invention. Nasal solutions are usually aqueous solutions designed to be administered to the nasal passages in drops and/or sprays. Nasal solutions are prepared so that they are similar in many respects to nasal secretions, so that normal ciliary action is maintained. Thus, the aqueous nasal solutions usually are isotonic and/or slightly buffered to maintain a pH of 5.5 to 6.5. In addition, antimicrobial preservatives, similar to those used in ophthalmic preparations, and/or appropriate drug stabilizers, if required, may be included in the formulation. Various commercial nasal preparations are known and/or include, for example, antibiotics and/or antihistamines and/or are used for asthma prophylaxis.

Additional formulations which are suitable for other modes of administration include vaginal suppositories and/or pessaries. A rectal pessary and/or suppository may also be used. Suppositories are solid dosage forms of various weights and/or shapes, usually medicated, for insertion into the rectum, vagina and/or the urethra. After insertion, suppositories soften, melt and/or dissolve in the cavity fluids. In general, for suppositories, traditional binders and/or carriers may include, for example, polyalkylene glycols and/or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and/or the like. These compositions take the form of solutions, suspensions, tablets, pills, capsules, sustained release formulations and/or powders. In certain defined embodiments, oral pharmaceutical compositions will comprise an inert diluent and/or assimilable edible carrier, and/or they may be enclosed in hard and/or soft shell gelatin capsule, and/or they may be compressed into tablets, and/or they may be incorporated directly with the food of the diet. For oral therapeutic administration, the active compounds may be incorporated with excipients and/or used in the form of ingestible tablets, buccal tables, troches, capsules, elixirs, suspensions, syrups, wafers, and/or the like. Such compositions and/or preparations should contain at least 0.1% of active compound. The percentage of the compositions and/or preparations may, of course, be varied and/or may conveniently be between about 2 to about 75% of the weight of the unit, and/or preferably between 25–60%. The amount of active compounds in such therapeutically useful compositions is such that a suitable dosage will be obtained.

The tablets, troches, pills, capsules and/or the like may also contain the following: a binder, as gum tragacanth, acacia, cornstarch, and/or gelatin; excipients, such as dicalcium phosphate; a disintegrating agent, such as corn starch, potato starch, alginic acid and/or the like; a lubricant, such as magnesium stearate; and/or a sweetening agent, such as sucrose, lactose and/or saccharin may be added and/or a flavoring agent, such as peppermint, oil of wintergreen, and/or cherry flavoring. When the dosage unit form is a capsule, it may contain, in addition to materials of the above type, a liquid carrier. Various other materials may be present as coatings and/or to otherwise modify the physical form of the dosage unit. For instance, tablets, pills, and/or capsules may be coated with shellac, sugar and/or both. A syrup of elixir may contain the active compounds sucrose as a sweetening agent methyl and/or propylparabens as preservatives, a dye and/or flavoring, such as cherry and/or orange flavor.

In certain embodiments of the present invention, the use of lipid formulations and/or nanocapsules is contemplated for the introduction of the macrocyclic lactones of the present invention or pharmaceutically acceptable salts thereof into host cells. Lipid formulations and nonocapsules may be prepared by methods well known in the art.

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

In the alternative, liposomes can be prepared in accordance with other known laboratory procedures: the method of Bangham et al. (1965), the contents of which are incorporated herein by reference; the method of Gregoriadis, as described in DRUG CARRIERS IN BIOLOGY AND MEDICINE, G. Gregoriadis ed. (1979) pp. 287–341, the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

A physiological composition comprising the liposomes will usually include a sterile, pharmaceutically acceptable carrier or diluent, such as water or saline solution.

The present invention also provides kits comprising the macrocyclic lactones of the present invention or pharmaceutically acceptable salts thereof. Such kits will generally contain, in suitable container means, a pharmaceutically acceptable formulation of the macrocyclic lactones of the present invention in a pharmaceutically acceptable formulation.

The container means will generally include at least one vial, test tube, flask, bottle, syringe and/or other container means, into which the macrocyclic lactones of the present invention formulation are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the ultimate the macrocyclic lactones of the present invention or pharmaceutically acceptable salts thereof within the body of an animal. Such an instrument may be a syringe, pipette, forceps, and/or any such medically approved delivery vehicle.

In order to increase the effectiveness of the macrocyclic lactones of the present invention, it may be desirable to combine these compositions with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the macrocylic lactones and other agent(s) at the same time. This may be achieved by contacting the cell with a single composition or pharmacological formulation that includes both agents, or by contacting the cell with two distinct compositions or formulations, at the same or different time, wherein one composition includes the macrocyclic lactone and the other includes the second agent(s).

Cancer therapies may include a variety of combination therapies with both chemical and radiation based treatments. Combination chemotherapies may include, for example, macrocylic lactones, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, famesyl-protein tansferase inhibitors, transplatinum, 5-fluorouracil, vincristin, vinblastin and methotrexate, or any analog or derivative variant of the foregoing.

The compounds may also be used together with immunotherapy. Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In yet another embodiment, the compounds of the present invention may be combined with gene therapy in which a therapeutic polynucleotide is administered before, after, or at the same time as the macrocyclic lactone of the present invention. Delivery of a vector encoding one of the following gene products will have a combined anti-hyperproliferative effect on target tissues. In the following sections, genes which can be used in gene therapy in conjunction with administration of the macrocyclic lactones will be described. For example, the compounds may be administered together with an expression construct comprising a tumor suppressor gene, such as, but not limited to, the p53 and p16 gene.

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC, the Bcl-2 protein family genes, and ICE-like protease genes.

Furthermore, the compouns of the present invention may be used in combination with surgery.

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adehesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the chemotherapeutic abililties of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Installation of the Enamide Side Chain

The macrocyclic salicylates of the invention may be decorated with one of two classes of an unsaturated side chain connected via a common enamide linkage. This acid and base sensitive construct was introduced at a late stage in the synthesis (FIG. 1). The inventor felt that the addition of an alkenyllithium 20a or 20b to a stereodefined E- or Z-alkenyl isocyanate 19 would offer the distinct advantage of mild reaction conditions and control of stereochemistry. Isocyanate 19 was derived from the corresponding $\alpha,\beta$-unsaturated carboxylic acid (acyl azide formation/Curtius rearrangement), in turn accessible from a C17 aldehyde 22 via Horner-Wadsworth-Emmons homologation. FIG. 4 shows an example of side chain synthesis.

The required alkenyllithium fragment for the synthesis of both salicylihalamides and apicularens was derived from the corresponding 1Z, 3Z-hexadienyl halide via transmetalation with t-butyllithium. Beginning with a Sonagashira coupling of Z-1-bromobutene (23) with trimethylsilylacetylene, enyne 24 was obtained in 93% yield. Exchange of the silyl group with iodine or bromine (NIS or NBS) was accomplished in the presence of $AgNO_3$. Although bromide 26 was isolated as a pure Z-compound, the corresponding iodide 25 had succumbed to partial isomerization of the double bond (Z:E=4:1). This ratio was reversed during the subsequent reduction (i. $Cy_2BH$, ii. HOAc) of the triple bond in 25 whereas only partial isomerization had occurred during the corresponding reduction of bromide 26 (28, Z:E=4:1). The subsequent transmetalation/isocyanate addition not only proceeded without further isomerizations, but effected the crucial key-transformation to obtain N-(E-styryl)-heptadienamide 30 in high yields.

Example 2

Salicylihalamides: Exploration of Fragment Synthesis and Couipling Protocols

It was then necessary to synthesize the benzolactone core of the salicylihalamides. A connectivity analysis pointed to two equally attractive routes for its assembly (31, FIG. 4). The first one featured an esterification/intramolecular olefin metathesis sequence to form the C9–C10 bond and offered the advantage of operational simplicity combined with functional group tolerance (Path A). However, the efficiency as well as stereoselectivity (E vs Z) for medium to large ring-forming metatheses are substrate dependent. Alternatively, a Pd(0)-catalyzed cross coupling of a stereo-defined E-alkenyl organometallic fragment 35 with benzylic bromide 34 joined the C8–C9 bond with maintenance of olefin geometry (Path B). Importantly, both strategies converged to a common alkyne precursor 36, adding flexibility to the synthesis. There is versatility in the available options for synthesizing fragment 36 but a particular C12–C13 aldol bond construction was singled out from the outset for the following reasons: (1) absolute and relative stereochemistry can be controlled by the use of camphorsultam auxiliaries, and (2) a functionalized C12-substituent (carboxylate or hydroxymethyl) may prove useful as an additional handle from which to develop molecular probes for mode-of-action studies.

Although related to salicylic acid, fragments 32 and 34 are not be easily obtained from a salicylic acid precursor. To access benzylic bromide, a de novo synthesis from non-aromatic precursors was performed. Indeed, by stirring a mixture of 1-methoxy-1,3-cyclohexadiene (39) with ethyl propiolate (40) at 170° C., a Diels-Alder reaction takes place (41), which is followed by a pericyclic extrusion of ethylene yielding benzoate 42. A radical bromination completes the synthesis of benzylic bromide 34 in 50% yield for the two step sequence. On the other hand, derivative 32 was obtained from 2,6-dihydroxybenzoic acid (43). After preparation of the known aryl triflate 44, a Stille coupling with allyltributylstannane introduced the ortho-allyl substituent in 95% yield. Treatment of this material with the magnesium salt of allyl alcohol induced a transesterification with concomitant release of acetone (→45). Finally, protection of the phenol and palladium-catalyzed deprotection of the allyl ester provided benzoic acid derivative 32. This sequence is critical to avoid conjugation of the double bond.

The synthesis of alkyne 36 starts from readily available aldehyde 47, prepared in two steps from 1,3-propanediol (i. NaH, THF, t-BuMe$_2$SiCl; ii. (COCl)$_2$, DMSO, NEt$_3$, CH$_2$Cl$_2$, −78° C.). Aldol reaction of aldehyde 47 with the borylenolate derived from 2-N-acetylbornanesultam 46 gave a separable mixture of two aldol products, 48 and its epimer, in an 85:15 ratio. An X-ray crystallographic analysis of 48 revealed its absolute configuration. Aldehyde 37, obtained via a one step reduction of protected aldol derivative 49, was subjected to a stereoselective syn-aldol reaction with the titanium enolate derived from (2)-N-(4-pentynoyl) bornanesultam 38. Only a single diastereomer could be detected by $^1$H NMR-analysis of the crude reaction mixture. Protection followed by reduction (LiEt$_3$BH) of the N-acyl sulfonamide 51 delivered primary alcohol 52. Tosylate formation and another reduction (LiEt$_3$BH) completed the synthesis of fragment 36 (78%, 2 steps).

Figure 8:
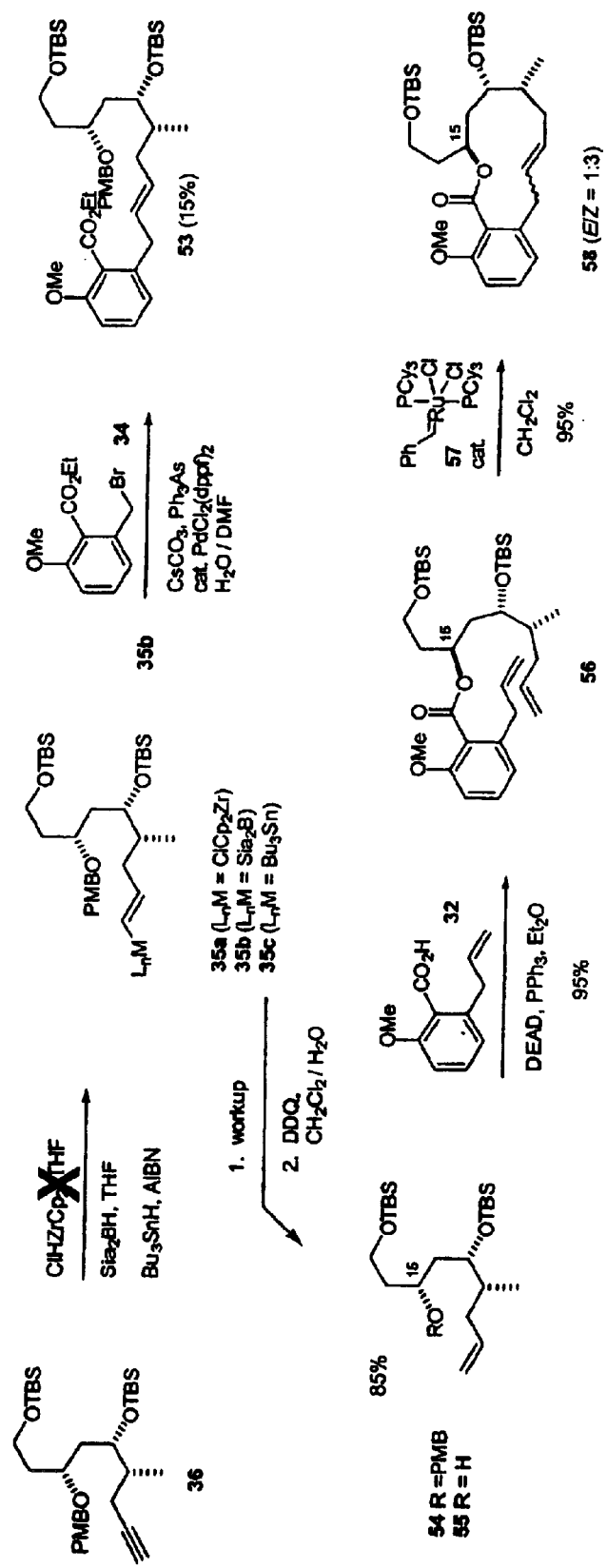
FIG. 8. Synthesis of benzolactone 58

The assembly of the alkyne 36 with the aryl sector was then achieved (FIG. 8). In one of two approaches, this involved a hydrometallation of the triple bond, followed by cross coupling with benzylic bromide 34 (path B, FIG. 4). In this context, zirconocene 35a (Ml$_n$=ClCp$_2$Zr) was considered the most appealing nucleophilic coupling partner. Stereodefined 1-(E)-alkenylzirconocenes are readily accessible via a functional group tolerant hydrozirconation and engage in cross-coupling chemistry with a variety of benzyl halides. The use of in situ prepared ClHZrCp$_2$ (LiEt$_3$BH, Cl$_2$ZrCp$_2$) was critical for obtaining reproducible results. As demonstrated in Table 1, these conditions proved to be general for a variety of alkyne/benzyl halide combinations including the cross coupling with benzyl bromide 34 (entry 6), properly substituted for the synthesis of salicylihalamides. Attempts to obtain zirconocene 35a via hydrozirconation of alkyne 36 were unsuccessful (FIG. 8). In contrast, alkyne 36 did undergo smooth hydrostannylation (Bu$_3$SnH, AIBN, toluene) as a prelude to an alternative Stille coupling with benzylic bromide 34. The corresponding vinylstannane 35c was extremely prone to protodestannylation, yielding terminal alkene 54 upon workup. The desired coupling product 53 could be obtained in a single case via Suzuki crosscoupling in 15% yield. Again, the culprit seemed to be an inefficient hydrometallation as starting alkyne 36 accounted for the remaining mass balance. It is not known why this particular alkyne resists hydrozirconation or hydroboration. Possibly, the particular combination of protecting groups and stereochemistry of 36 could render the alkyne sterically inaccessible to the bulky hydrometallating agents. Clearly, salicylihalamides and variants might still be accessible using this procedure if modified C9–C17 alkyne fragments prove to be better substrates for hydrometallation chemistry.

A ring-closing olefin metathesis path to salicylihalamides was explored. The p-methoxybenzyl protecting group of alkene 54 was oxidatively deprotected (DDQ). The inventor experienced difficulties in the attempts to acylate the resulting alcohol 55 with an acylating agent derived from benzoic acid derivative 32. The C15 epimer of bis-olefin 56 could not be obtained. This was suspected to be due to increased electron density (o-MeO-substituent) at the electrophilic carbonyl center. Indeed, a reactivity umpolung provided by a Mitsunobu esterification (carboxylic acid 32 acting as the nucleophile) was essential and delivered bis-olefin 56 in over 90% yield. Ironically, this material is useless for the synthesis of salicylihalamides due to the inverted configuration at C15 (a consequence of the Mitsunobu inversion). The inventor tested the ability of Grubbs' ruthenium carbene catalyst 57 to effect an intramolecular ring-closing olefin metathesis. Benzolactone 58 was closed in essentially quantitative yield using this approach. A separable mixture of isomers resulted with the Z-isomer predominating (3:1). This is in contrast to the excellent E-selectivity observed in the correctly configured diastereomeric series reminiscent of the natural product (vide infra).

TABLE 1

Pd-Ctalyzed cross-coupling of vinylzirconocenes with benzylic halides

| Entry | Alkyne | ArCH$_2$X | Product | Yld (%) |
|---|---|---|---|---|
| 1 | ≡—(CH$_2$)$_4$Me | BnCl | 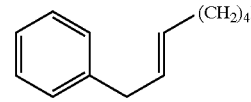 | 65 |
| 2 | | BnBr | | 68 |
| 3 | | p-MeO-BnBr | 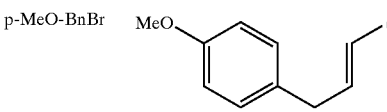 | 78 |
| 4 | | o-Br-BnBr | 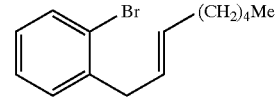 | 82 |
| 5 | | o-Br, p-F-BnBr | 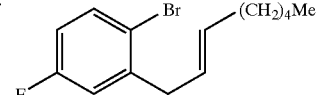 | 72 |

TABLE 1-continued

Pd-Ctalyzed cross-coupling of vinylzirconocenes with benzylic halides

| Entry | Alkyne | ArCH$_2$X | Product | Yld (%) |
|---|---|---|---|---|
| 6 | | 34 | [structure: MeO, CO$_2$Et, (CH$_2$)$_4$Me substituted arene with allyl chain] | 63 |
| 7 | ≡—Ph | BnBr | [cinnamyl-Ph product] | 65 |
| 8 | ≡—Ph | o-Br-BnBr | [o-Br cinnamyl-Ph product] | 72 |
| 9 | ≡—CH$_2$OBn | BnCl | [PhCH$_2$CH=CHCH$_2$OBn] | 73 |
| 10 | | BnBr | | 75 |
| 11 | ≡—CH(OBn)(CH$_2$)$_4$Me | BnCl | [PhCH$_2$CH=CHCH(OBn)(CH$_2$)$_4$Me] | 71 |
| 12 | | BnBr | | 67 |
| 13 | ≡—(CH$_2$)$_3$Cl | BnCl | [PhCH$_2$CH=CH(CH$_2$)$_3$Cl] | 72 |
| 14 | | BnBr | | 76 |
| 15 | ≡—CH$_2$CH$_2$CN | BnBr | [PhCH$_2$CH=CHCH$_2$CH$_2$CN] | 53 |
| 16 | ≡—(CH$_2$)$_3$OTBS | BnCl | [PhCH$_2$CH=CH(CH$_2$)$_3$OTBS] | 73 |

≡—R-FG  $\xrightarrow[\text{THF}]{\text{Cl}_2\text{ZrCp}_2 \text{ LiEt}_3\text{BH}}$  ClCp$_2$Zr—CH=CH—R-FG

+

FG—C$_6$H$_4$—CH$_2$—X $\downarrow$ 5 mol % Pd(PPh$_3$)$_4$

FG—C$_6$H$_4$—CH$_2$—CH=CH—R-FG

Example 3

Salicylihalamides: Total Synthesis of Enantiomer with Positive Rotation (Structure Proposed by Boyd et al. in PCT/US98/15011)

A procedure delivering gram quantities of benzolactone 75 is presented in FIG. 8. The inventor opted for an enantioselective allylation of aldehyde 59 to set absolute stereochemistry at C15. The corresponding homoallyl alcohol 60, obtained in 96% yield, was protected followed by oxidative double bond-cleavage (72% yield, 3 steps). Treatment of the corresponding aldehyde 62 with the in situ prepared Z(O)-titanium enolate derived from (2R)-N-(4- pentenoyl)bornanesultam 63 produced exclusively one diastereomeric aldol product 64 in 95% yield. Protection (→65), carboxamide reduction (→68) and fluoride-assisted liberation of the C15 alcohol (→69) proceeded with high overall yields (61%, 5 steps). Treatment of alcohol 69 with carboxylic acid 32 under Mitsunobu conditions (EtO$_2$CN=NCO$_2$Et, PPh$_3$) yielded bis-olefin 70 (98%), setting the stage for the key intramolecular ring-closing olefin metathesis. In contrast to bis-olefin 56 (vide supra), exposure of 70 to a catalytic amount of Grubbs' ruthenium carbene complex 57 preferentially produced the desired E-isomer 72 with selectivity of 9–10:1 (E:Z). Metathesis of the closely related bis-olefin 71 to the corresponding benzolactone 73 under identical conditions was far less selective (E/Z=3:1). The inventor has achieved an extremely efficient synthesis of the lactone core of salicylihalamides, delivering gram quantities of primary alcohols 74 or 75 (obtained from 72/73 by oxidative deprotection with DDQ) in 35% overall yield from aldehyde 59 (13 steps). Derivative 74, designed as a side-chain analog of salicylihalamide (1a), provided crystals suitable for X-ray diffraction studies, confirming the assigned structure and stereochemistry (FIG. 11b). Interestingly, the solid-state conformation of the macrolactone 74 differs significantly from the more bowl-like topography found in the solution structure of salicylihalamide A.

Figure 2:
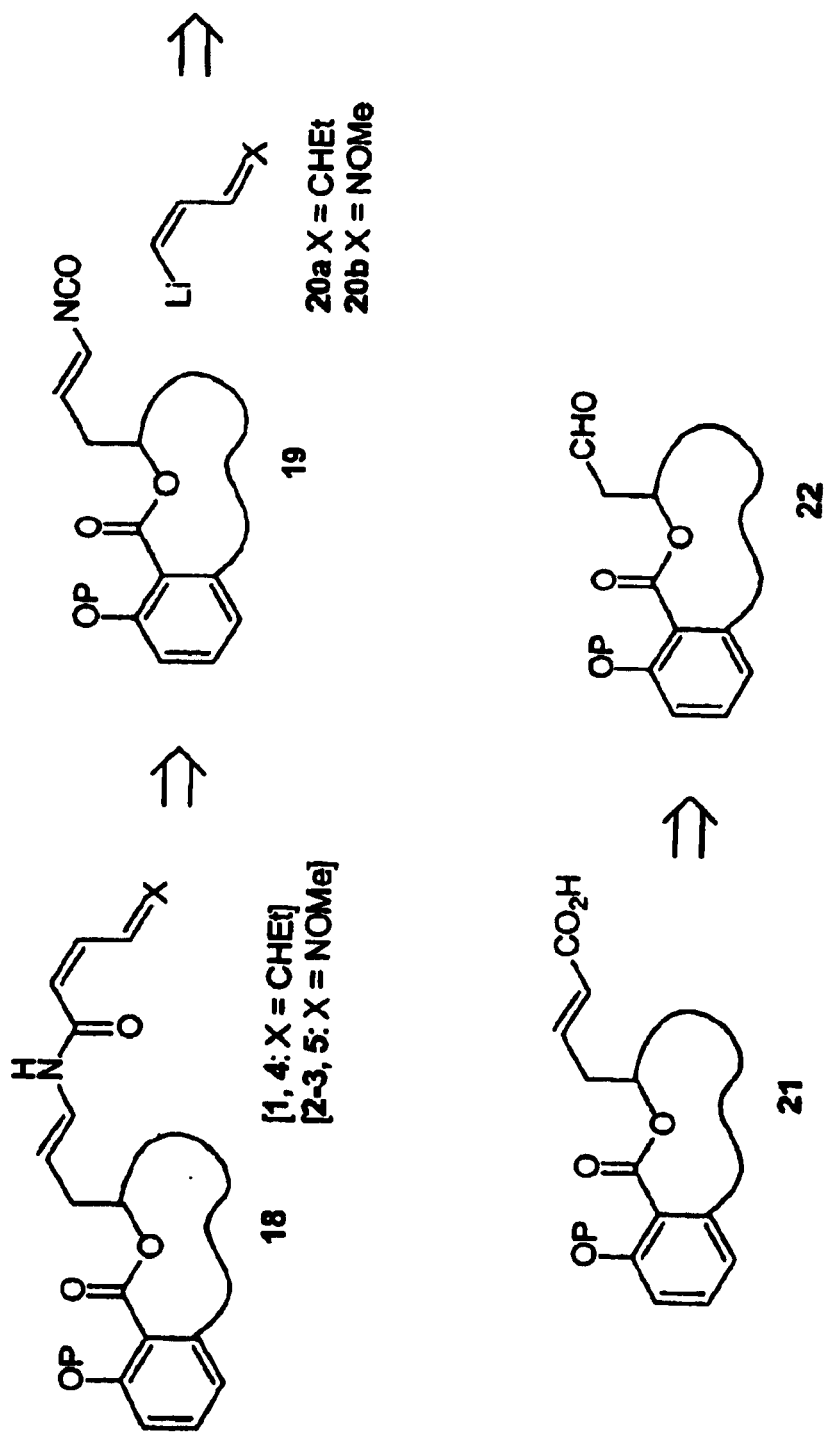
FIG. 2. Strategy for introduction of side chain
Figure 3:
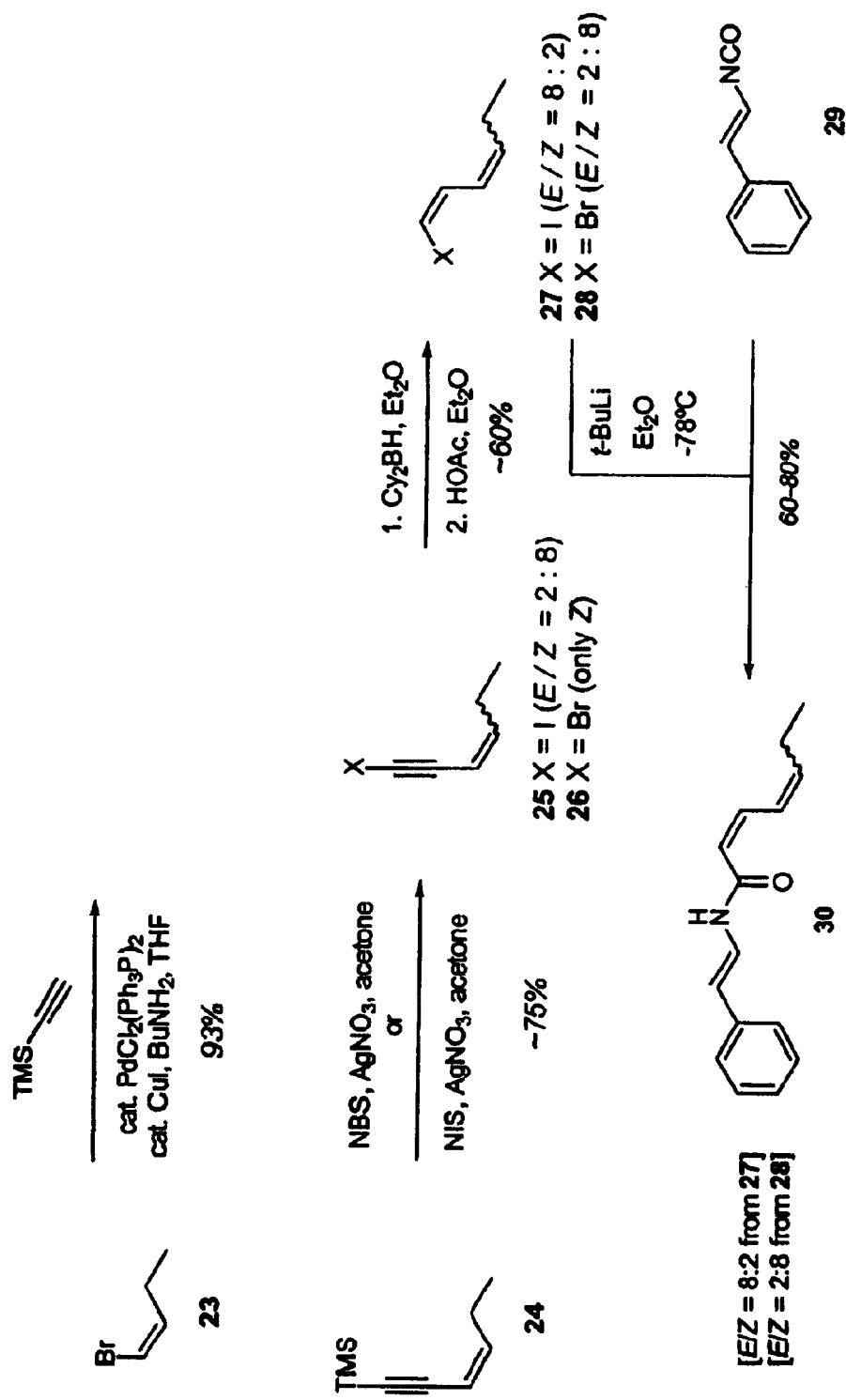
FIG. 3. System of side chain synthesis

All that remained to complete the total synthesis was the introduction of the side-chain followed by final deprotection. Alcohol 75 was oxidized to aldehyde 76 with Dess-Martin periodinane (DMP) in 93% yield (FIG. 10). Moving forward, aldehyde 76 had to be homologated to α,β-unsaturated carboxylic acid 77. This was achieved with excellent trans-selectivity by a Homer-Wadsworth-Emmons homologation with trimethylsilyl dimethylphosphonoacetate followed by a slightly acidic aqueous workup. Following acylazide formation (diphenylphosphoryl azide, NEt$_3$) and Curtius rearrangement (benzene, 80° C.), isocyanate 80 was obtained as a chromatographically pure compound. The dienamide side-chain was then installed. Incorporation proceeded smoothly via the addition of hexadienyllithium (27, t-BuLi; see FIG. 2) to a cold (−78° C.) solution of isocyanate 80. All attempts to remove the protecting groups uniformly met with failure, leading to decomposition. To circumvent this problem, the inventor used a protecting group interconversion at an earlier stage. Carboxylic acid 77 and t-butylester 78 were not viable options, yielding intractable mixtures of unidentified materials under the reaction conditions required to remove the protecting groups (BBr$_3$, CH$_2$Cl$_2$, −78° C.). In contrast, BBr$_3$ cleanly removed both methyl and MOM-ether protecting groups of methylester 79 (obtained from 76 as an inseparable mixture of E/Z-isomers), after which the corresponding E- and Z-methylesters 82 and 83 could be separated. Note that 83 is a useful intermediate for the synthesis of salicylihalamide B (1b). Hydrolysis (Ba(OH)$_2$.8H$_2$O) of the major trans-methylester 82 was followed by complete silylation (TBSCl, DMF, imidazole). Upon workup, silylester hydrolysis had occurred and the corresponding acid 84 was converted to 86 via addition of Z,Z-dienyllithium (28, t-BuLi) to isocyanate 85. The total synthesis was completed by deprotection of the silylether protecting groups with a 1:1 complex of HFpyridine in THF, affording synthetic salicylihalamide A (1) in x % yield. This material was identical in all respects ($^1$H and $^{13}$C NMR, IR, UV, MS) to natural salicylihalamide A. However, the optical rotation ([α]$_D$=+20, c , MeOH) of synthetic salicylihalamide A (87) was of opposite sign to the one recorded for natural salicylihalamide A ([α]$_D$=−35, c 0.7, MeOH).

The absolute configuration of natural salicylihalamide A (1a) was originally misassigned in Boyd et al., 1997. The correct configuration is represented by structure 89. The ultimate proof for this assignment came from a crystallographic analysis of a p-bromobenzoate derivative of salicylihalamide 90, prepared from 73 in a manner similar to the synthesis of 74. The structure is shown in FIG. 11(a). The inventor synthesized (+)-salicylihalamide A and found that it did not have chemotherapeutic activity. (−)-salicylihalamide A does have chemotherapeutic activity. The (+) form was still inactive at 20 gM whereas natural salicylihalamide ((−) form) is active at 10 nM when tested against SK-MEL-28 cells. This cell line is one of the cell lines in the NCI 60 cell line screen.

The inventor has accomplished the first synthesis of salicylihalamide A. The approach features a highly efficient, trans-selective ring-closing olefin metathesis for the assembly of the benzolactone skeleton and installation of a dienamide side-chain.

Example 4

Apicularens: Synthesis of the Macrocyclic Fragment

Figure 20:
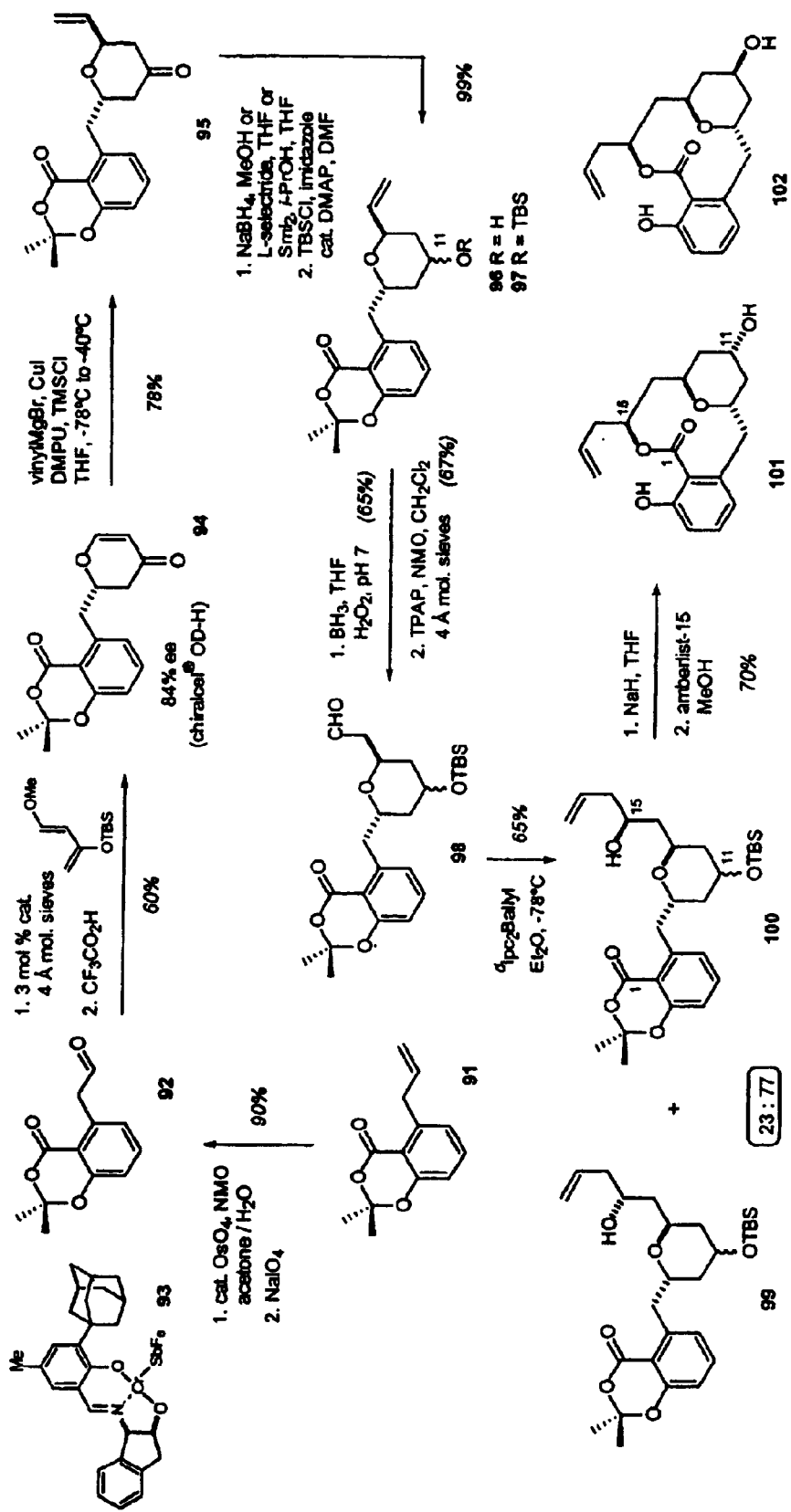
FIG. 20. Synthesis of Apicularen benzolactone core
Figure 21:
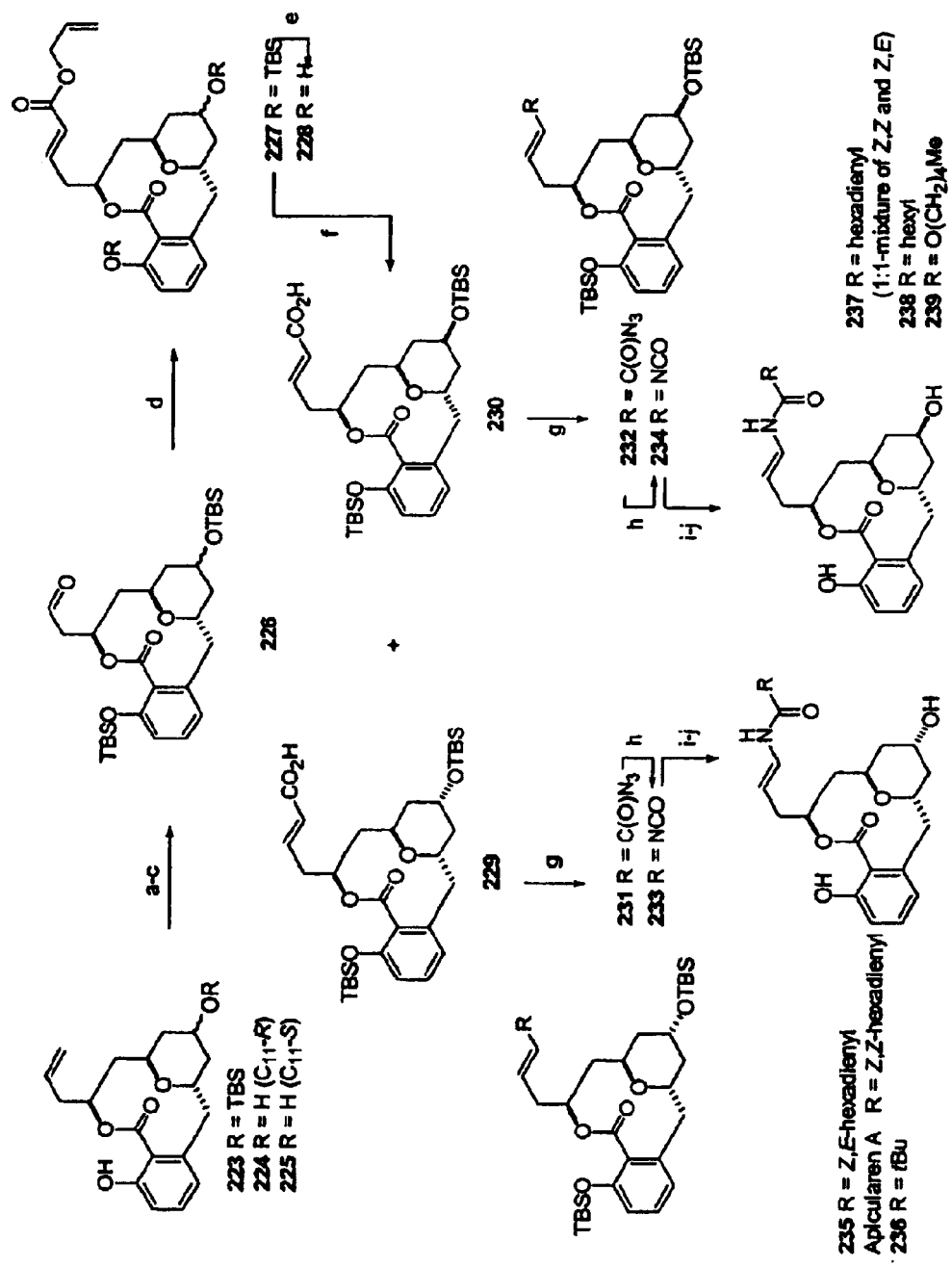
FIG. 21. Synthesis of apicularen A and analogs.

The inventor has synthesized apicularen A (4a) by the process shown in FIG. 20. Dihydropyranone 94 was considered a useful intermediate from which to build the tetrahydropyranyl ring present in apicularens. The most straightforward approach for its assembly constitutes an enantioselective hetero-Diels-Alder reaction of aldehyde 92 with Danishefsky's diene (1-methoxy-3-(trimethylsilyloxy) butadiene). The ease of catalyst synthesis and high enantioselectivities observed was the reason for using chromium complex 93 for the hetero-Diels-Alder reaction of Danishefsky's diene with aldehyde 92, obtained via oxidative cleavage of alkene 91 (an intermediate of the salicylihalamide synthesis). Dihydropyranone 94 was obtained in 60% yield after treatment of the Diels-Alder adducts with trifluoroacetic acid. The enantiomeric excess was determined by chiral HPLC-analysis (CHIRALCEL® OD-H; 84%ee). Copper(I)-catalyzed conjugate addition of vinylmagnesium bromide to this material gave exclusively the 2,6-trans substituted tetrahydropyranone 95. The next step involved stereoselective ketone reduction and a variety of agents are known that selectively deliver hydride from the pseudoaxial (e.g. NaBH$_4$ or SmI$_2$) or pseudoequatorial (L-SELECTRIDE®) position. None of these conditions were successful however, and an inseparable epimeric mixture of alcohols 96 was obtained in all cases. The corresponding ketone most likely exists as an equilibrium mixture of two equally populated conformers. Such a situation would provide an epimeric mixture if both conformers react with comparable rates, even with highly selective reducing agents. This problem could be solved by delaying the reduction until after the macrocyclization provided that this will reduce the conformational flexibility of the tetrahydropyranone ring. In the meantime, the epimeric mixture was silylated followed by hydroboration (BH$_3$, THF; H$_2$O$_2$) of alkene 97 and oxidation of the resulting primary alcohol with TPAP (tetrapropylammonium perruthenate). Completion of the macrocyclic portion of the apicularens entailed an allylation/lactonization sequence. A low selectivity was observed during the reaction of aldehyde 98 with Brown's allyldiisopinocampheylborane, delivering a 77:23 mixture of diasteromeric homoallyl alcohols 99 and 100 (65%). This was not completely unexpected given the intrinsic facial bias of β-alkoxy aldehydes for 1,3-anti addition products. Moreover, 8% of enantiomeric aldehyde 98 was present and would be expected to give product enantiomeric to 99, further lowering the syn/anti selectivity but increasing the enantiomeric purity of 100. Treatment of the desired major diastereomer 100 (mixture of C11 epimers) with NaH effected the crucial lactonization in 70% yield. After silylether removal, epimeric (C11) alcohols 101 and 102 could be separated by chromatography. The chemical shift values and coupling constants of protons H3 through H15 (400 MHz NMR) of 101 are nearly identical to the values reported for apicularen A.

Example 5

Apicularens: Total Synthesis of Apicularen A and Analogs

Figure 13:
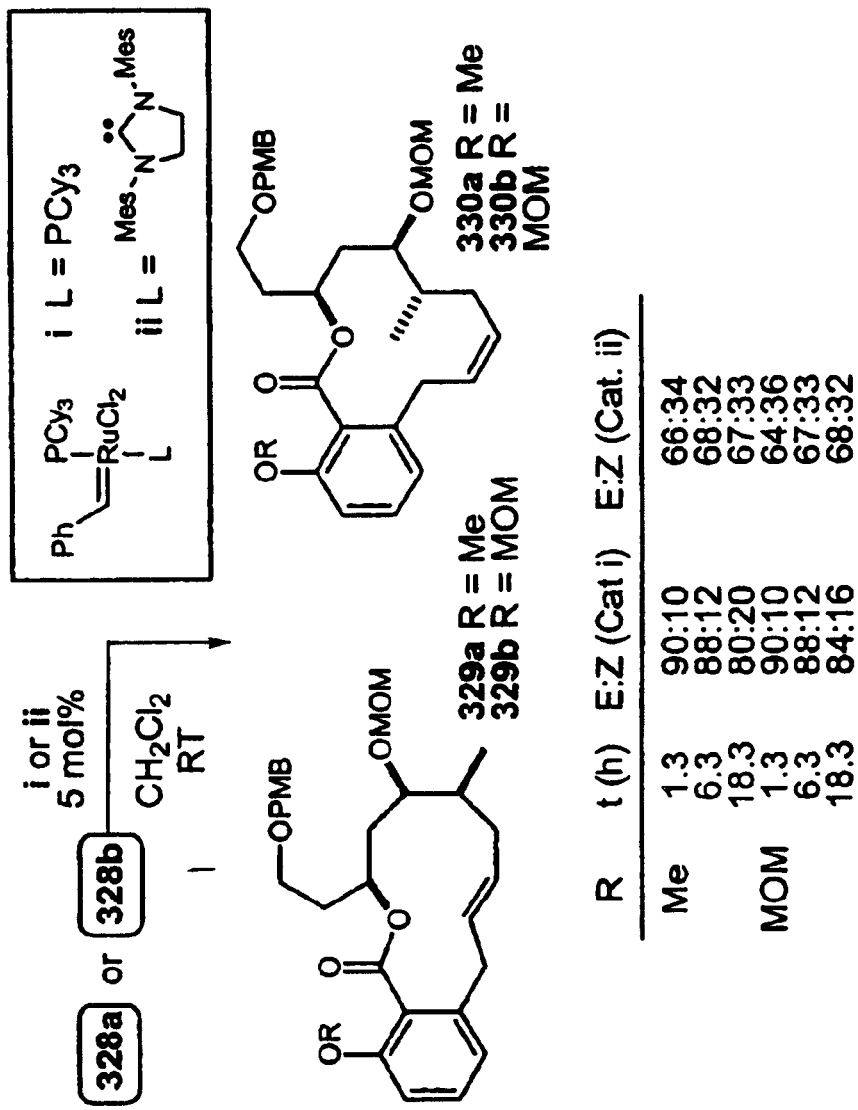
Figure 14:
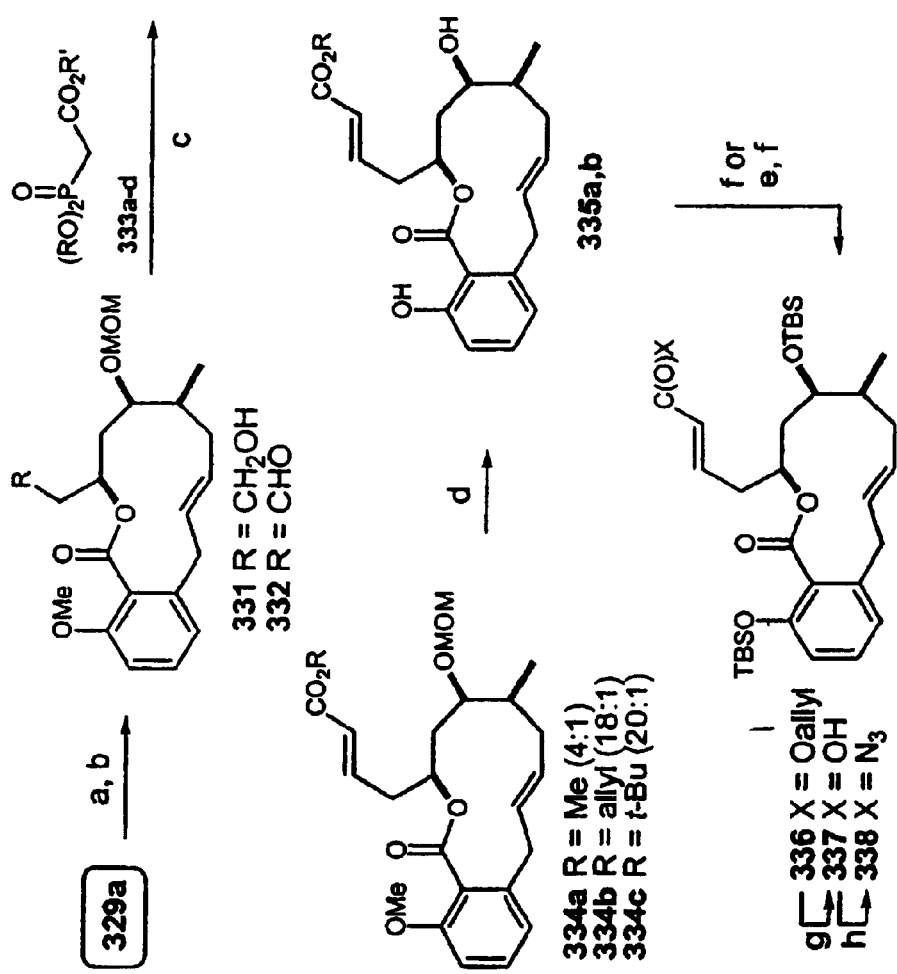
Figure 15:
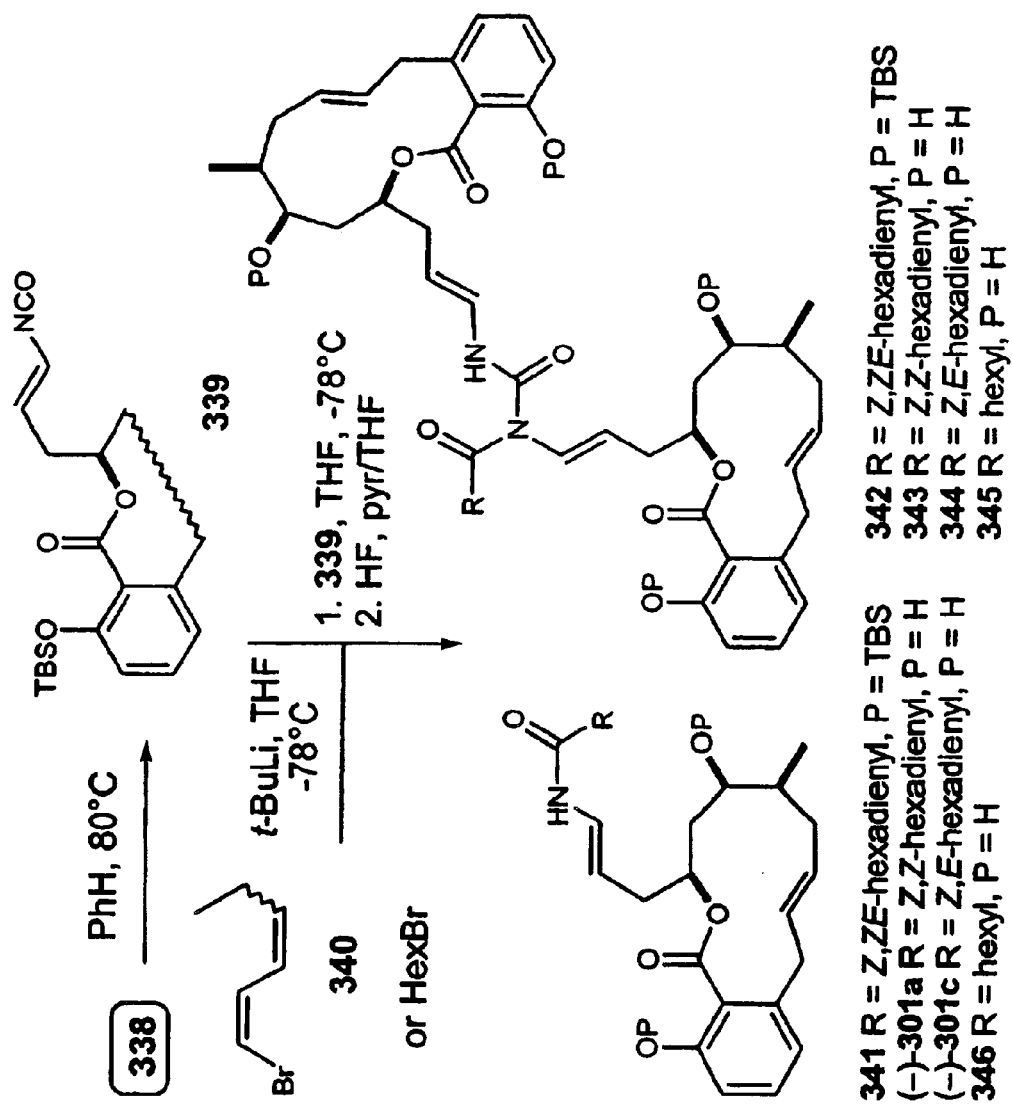
FIG. 15. Synthesis of salicylihalamides 301a/301c and analogs 343–346.
Figure 16:
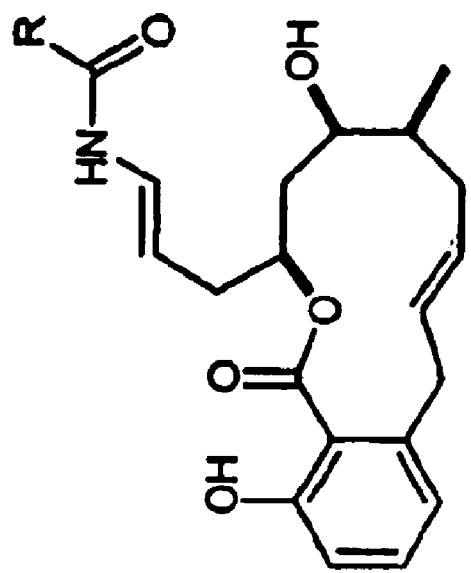
FIG. 16. Synthesis of salicylihalamide analogs 349–354
Figure 25:
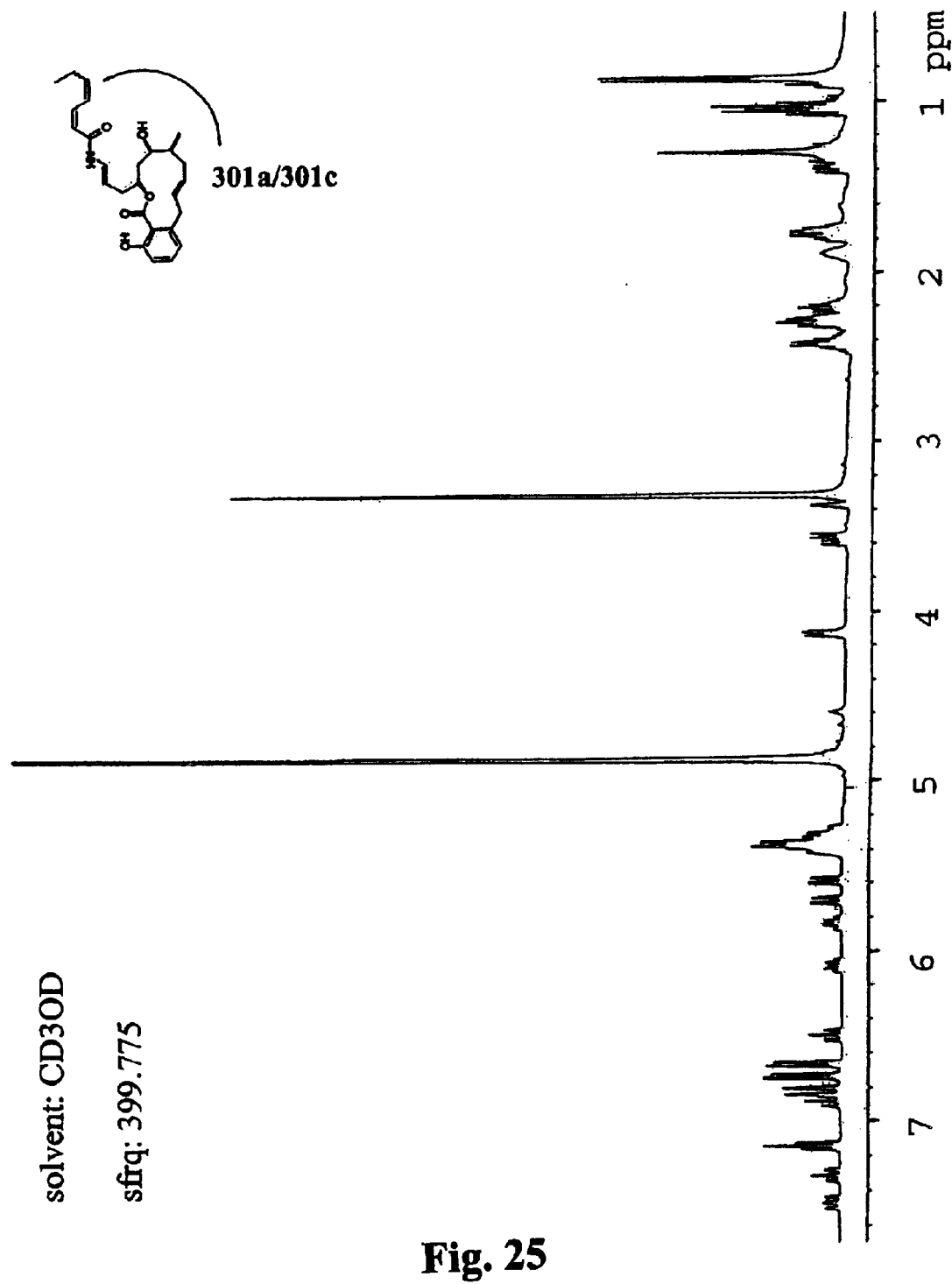
Figure 26:
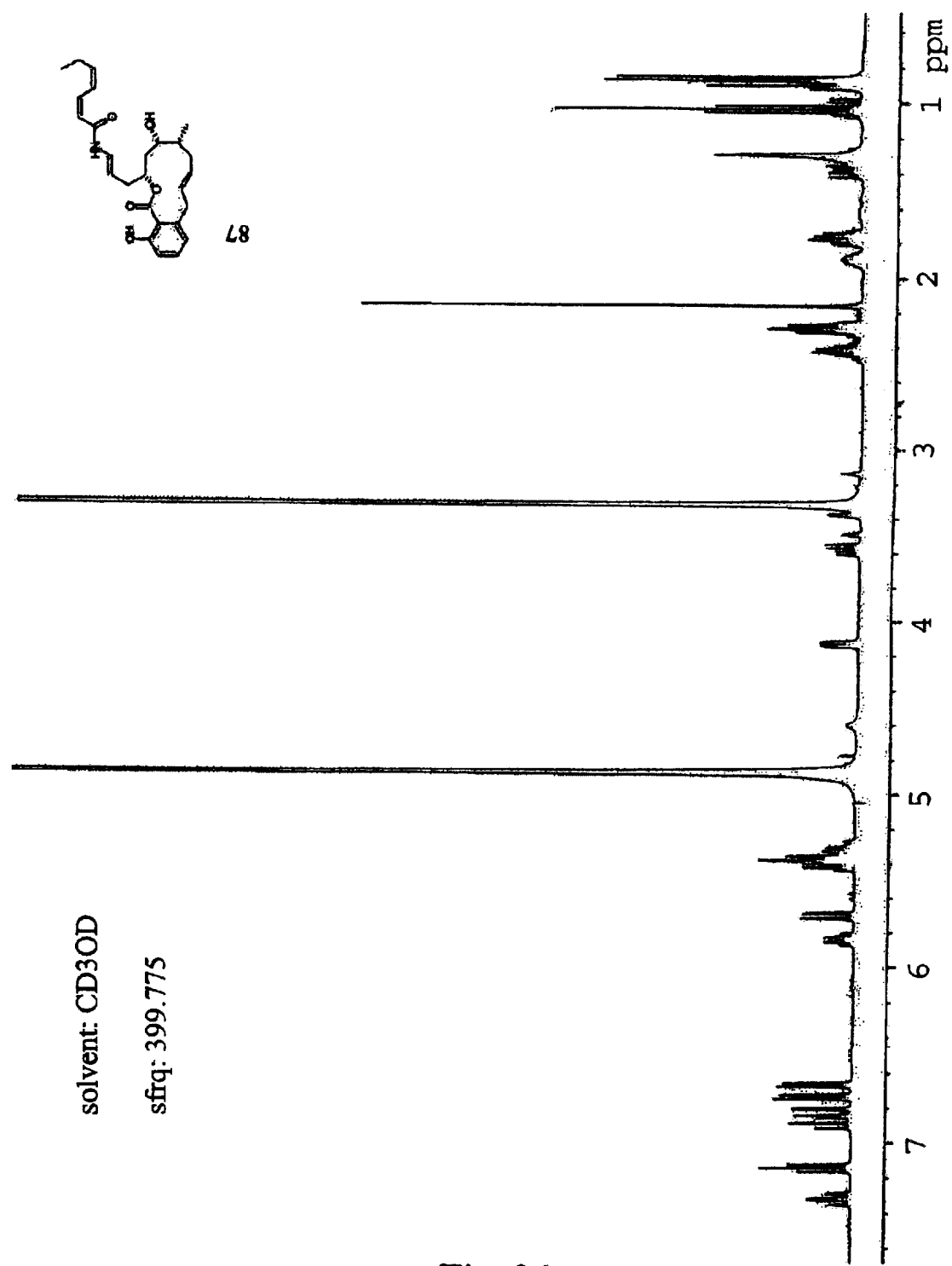

The transformation of compounds 101 and 102 [which correspond to 224 and 225 of FIG. 25, respectively] into apicularen A and a variety of analogs is shown in FIG. 25 and follows the general procedures disclosed for the installation of the side chains of salicylihalamide A and analogs (see FIG. 13–15 and Examples 7 and 8).

TABLE 2

$^1$H NMR data of apicularen A and macrocycle 101 [D$_6$]acetone

| | apicularen A | 101 |
|---|---|---|
| H | δ (m, J in Hz) | δ (m, J in Hz) |
| 8a | 3.34 (dd, 9.7/14.8) | 3.34 (dd, 9.6/15.2) |
| 8b | 2.44 (dd, 1.8/14.8) | 2.45 (dd, 1.6/15.2) |
| 9 | 3.87 (dddd, 1.7/4.8/8.2/9.7) | 3.88 (dddd, 1.2/4.8/8.0/10.0) |
| 10a | 1.93 (ddd, 4.2/4.8/12.8) | 1.93 (ddd, 4.8/4.8/12.8) |
| 10b | 1.48 (ddd, 8.5/8.8/12.8) | 1.49 (ddd, 8.4/8.4/12.8) |
| 11 | 3.98 (dddd, 4.1/5.1/7.6/8.8) | 3.99 (ddddd, 4.0/4.1/5.1/7.6/8.8) |
| 12a | 1.68 (ddd, 5.1/7.1/12.8) | 1.68 (ddd, 5.2/7.2/12.8) |
| 12b | 1.52 (ddd, 4.8/7.6/12.8) | 1.52 (ddd, 4.4/7.2/12.8) |
| 13 | 4.25 (dddd, 2.2/4.8/7.1/10.8) | 4.26 (dddd, 2.0/5.0/7.0/10.8) |
| 14a | 1.83 (ddd, 10.8/10.9/14.7) | 1.83 (ddd, 10.8/10.8/14.4) |
| 14b | 1.57 (ddd, 2.2/2.3/14.7) | 1.58 (ddd, 2.0/2.4/14.4) |
| 15 | 5.42 (dddd, 2.3/6.3/6.3/10.9) | 5.48 (dddd, 2.4/5.6/5.6/10.0) |

Example 6

Anti-cancer Activity of Synthetic Salicylihalamides

The anti-cancer activity of the synthesized (+)- and (−)-salicylihalamide-A compounds of the present invention (compounds 78 in FIG. 10 and 301a/301c in FIG. 14.) was indistinguishable. In contrast, sythetic (+)-salicylihalamide A (compound 87 in FIG. 9), the compound with the absolute configuration proposed by Boyd et al., wsa completerly inactive inthe same NCI 60-cell line screen. Salicylihalamide derivatives, showing increased stability over natural salicylihalamide, were tested in the NCI 60 cell-line screen. This screen is an art recognized model. Prior to assay, synthesized compounds were stored in dimethylsulfoxide at −70° C. Five different test concentrations of each compound were prepared by diluting the stock solution into complete medium. Sample concentrations were 2× the final concentration and range from $10^{-6}$ and $10^{-10}$ molar. An aliquot of each concentration of each compound was added to separate microtiter wells containing the respective cell lines in culture medium. The plates were incubated for 48 hours at 37° C. with 5% $CO_2$ and 100% humidity. Adherent cells were fixed by addition of cold 50% trichloracetic acid and incubation at 4° C. for 60 minutes. Suspended cells were fixed to the bottom of the well by addition of 80% trichloracetic acid. The supernatant was removed from each well and then each well was washed with deionized water and allowed to dry. Sulforhodamine B solution was added to each well and allowed to incubate for 10 minutes at room temperature. Unbound sulforhodamine B was removed by washing with 1% acetic acid. The wells were allowed to dry. Bound sulforhodamine B was solubilized using 10 mM Tris base and the optical density at 515 nanometers was determined. The synthesized salicylihalamide derivatives exhibited anticancer activity profiles.

A 1:1 mixture of salicylihalamide A (1) and C22-E isomer 211 [3,5d-g] was indistinguishable, within the limits of experimental error, from natural salicylihalamide A based on comparative testing in the National Cancer Institute 60-Cell Screen.

Example 7

Overall Synthesis Scheme of Synthetic Salicylihalamides

Compounds 328a and 328b (FIG. 11) were prepared as described for the corresponding enantiomers 70 and 71 (FIG. 8) by using enantiomeric starting materials. Thus the enantiomers of the 1pc2Ballyl reagent and compound 63 (see structure 323 in FIG. 11) were used to prepare the 328a and 328b (FIG. 11). The lack of a stereopredictive model for the formation of large rings via RCM is exemplified by our results with the metathetical ring closure of substrates 328a,b. See FIG. 11. Whereas the diastereomeric substrate 312c gave the Z-olefin 318Z (vide supra, Scheme 4) as the major isomer, 328b fortuitously produced the E-benzolactone 329a with an impressive selectivity of 10:1 when subjected to similar reaction conditions. To confuse the issue even more, an initial single experiment with the corresponding phenolic MOM ether 328b fuimished benzolactones 329b and 330b with an eroded selectivity of 3:1 upon exposure to catalyst i. FIG. 11. In principle, RCM is a reversible reaction but due to the shorter lifetime (thermal instability) of "first generation" Ru-alkylidene catalysts (e.g. i) and less efficient reaction with 1,2-disubstituted olefins (reaction products), kinetic product ratios can be expected.

In light of the above, a detailed study of the RCM of 328a,b with Ru-alkylidene pre-catalysts i and ii was conducted. See FIG. 13. N-Heterocyclic carbene ligated ruthenium alkylidene catalysts have been independently reported by three groups, cf.: (a) Huang, J.; Stevens, E. D.; Nolan, S. P.; Petersen, J. L. *J Am. Chem. Soc.* 1999, 121, 2674–2678. (b) Scholl, M.; Trnka, T. M.; Morgan, J. P.; Grubbs, R. H. *Tetrahedron Lett.* 1999, 40, 2247–2250. (c) Ackermann, L.; Fürstner, A.; Weskamp, T.; Kohl, F. J.; Herrmann, W. A. *Tetrahedron Lett.* 1999, 40, 4787–4790.

It is clear from these results that both catalysts are equally efficient in performing the desired transformation, albeit with different degrees of E/Z-selectivity. Also, both differentially protected substrates 328a,b gave identical E/Z-ratios under identical reaction conditions. Whereas the pre-catalyst i provided a 9:1 (E:Z) ratio with only a slight erosion of selectivity over time, pre-catalyst ii produced a lower 67:33 ratio, which remains constant over time. From these results, we conclude that RCM with catalyst i kinetically induces the formation of the desired E-isomers 329a,b with relatively high selectivity. The ratio observed with catalyst ii is deemed to be a thermodynamic one based on the following observations: (1) the ratio doesn't change over time, (2) an identical product ratio is observed for the formation of benzolactones 329–330 from both our precursors (328a,b), and (3) upon resubmission of either geometrically pure 329a or 330a to the same reaction conditions, an identical 67:33 mixture of 329a:330a was formed.

Having secured a viable sequence to the benzolactone core of salicylihalamide A, we turned our attention to the installation of the acylated enamine side chain. Towards this end, the p-methoxybenzyl ether in 329a (or 329b) was oxidatively removed (DDQ) and the resulting alcohol 331a was oxidized with Dess-Martin periodinane (FIG. 13). Engagement of the resulting aldehyde 332 in a Horner-Wadsworth-Emmons (HWE) homologation with trimethyl phosphonoacetate provided methyl ester 334a as an inseparable mixture of E/Z-isomers in a ratio of 4:1. After removal of the ether protecting groups with BBr$_3$, the corresponding E-methyl ester was separated by flash chromatography, hydrolyzed (Ba(OH)$_2$.8H$_2$O) and extensively silylated with excess TBSCl to deliver carboxylic acid 337. The overall yield for the transformation of 332 to 337 was a disappointing 20–30%. Therefore, a series of optimization experiments were performed that quickly led to the use of allyl diethylphosphonoacetate, delivering allyl ester 334b with 18:1 selectivity for the E-isomer. Subsequent deprotection, bis-silylation and Pd-catalyzed removal of the allyl ester improved the overall yield of 337 dramatically (75% from aldehyde 332). Transformation into acylazide 338 ((PhO)$_2$P (O)N$_3$, NEt$_3$, PhMe) preceded a Curtius rearrangement induced by heat (PhH, 80° C., 6 h). Although the corresponding vinylic isocyanate 339 was stable to chromatographic purification, it was usually engaged in the next reaction without purification. See FIG. 15.

FIG. 15 shows that final carbon-carbon bond formation proceeded smoothly via the addition of hexadienyllithium, prepared in situ from bromide 340 via metal-halogen exchange (t-BuLi, Et$_2$O), to a −78° C. solution of isocyanate 339. Compound 341 was obtained as an inseparable mixture of 22-Z and 22-E isomers together with a chromatographically (silicagel) more mobile fraction containing a mixture of E/Z-dimeric compounds 342. Careful fluoride-assisted desilylation was best performed with a buffered solution of commercially available HF-pyridine in THF/pyridine. At this point, geometrical isomers 301a/301c and 343/344 could be separated by semi-preparative HPLC.

Figure 27:
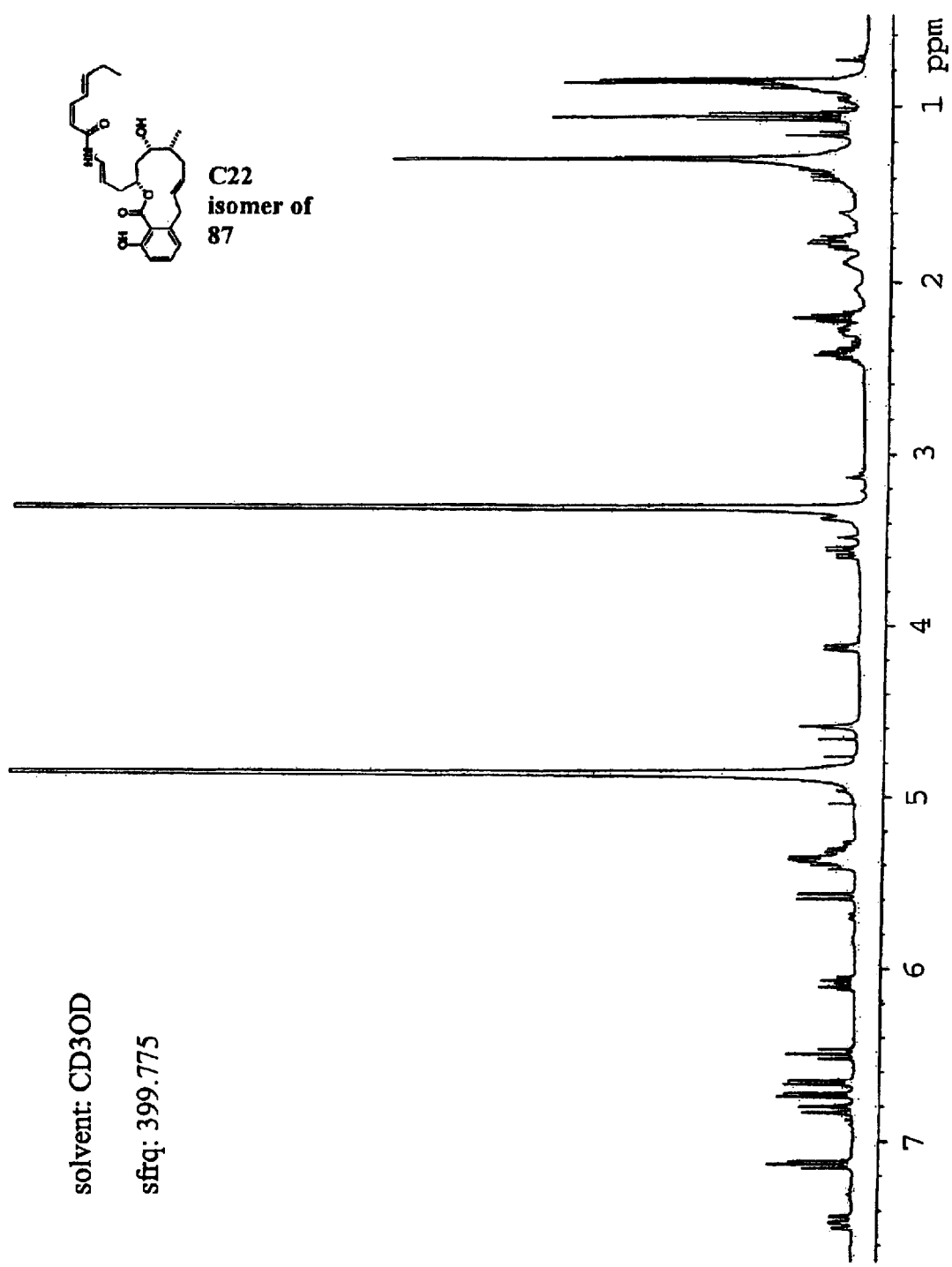
Figure 28:
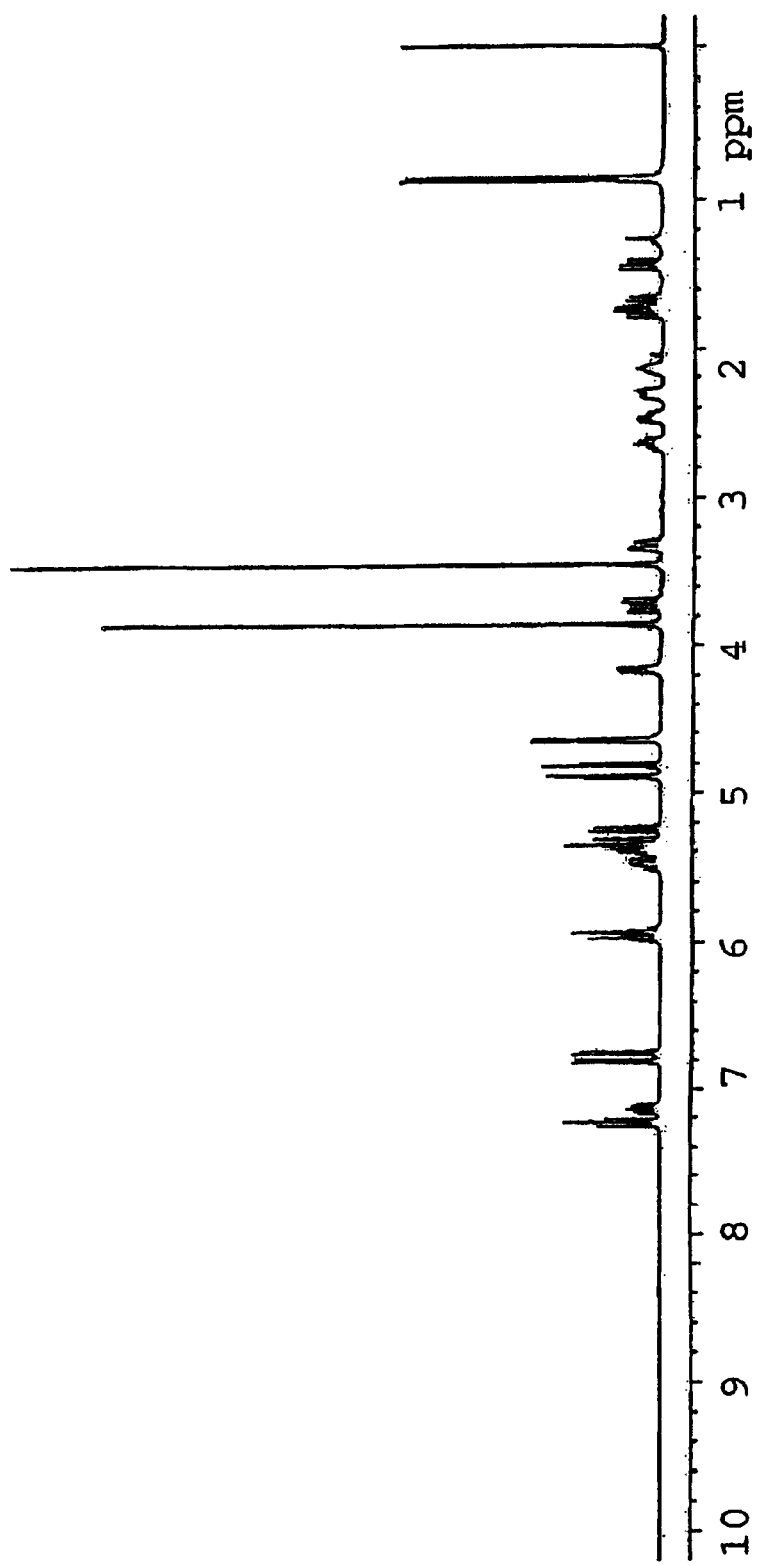
Figure 29:
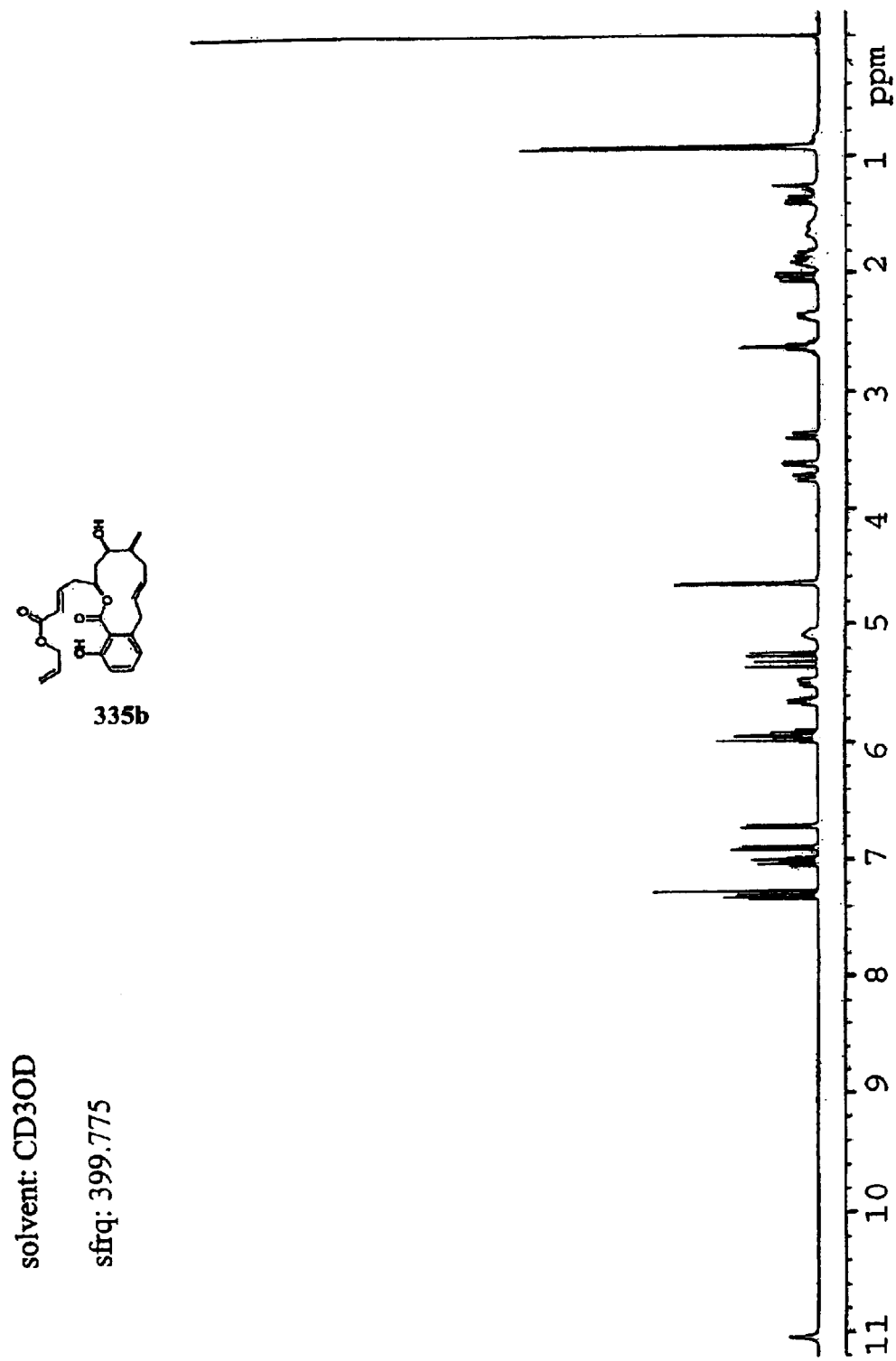
Figure 30:
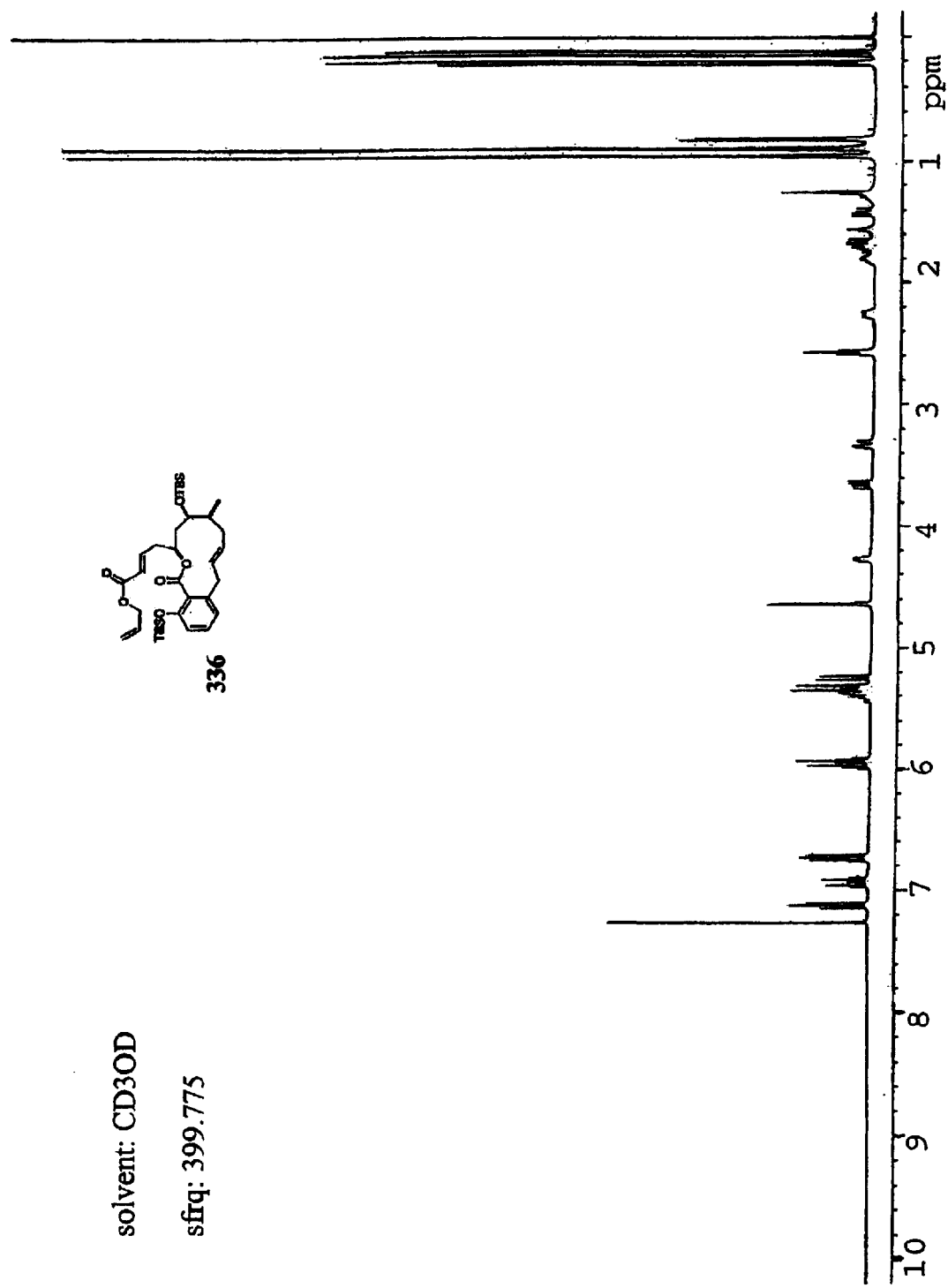
Figure 31:
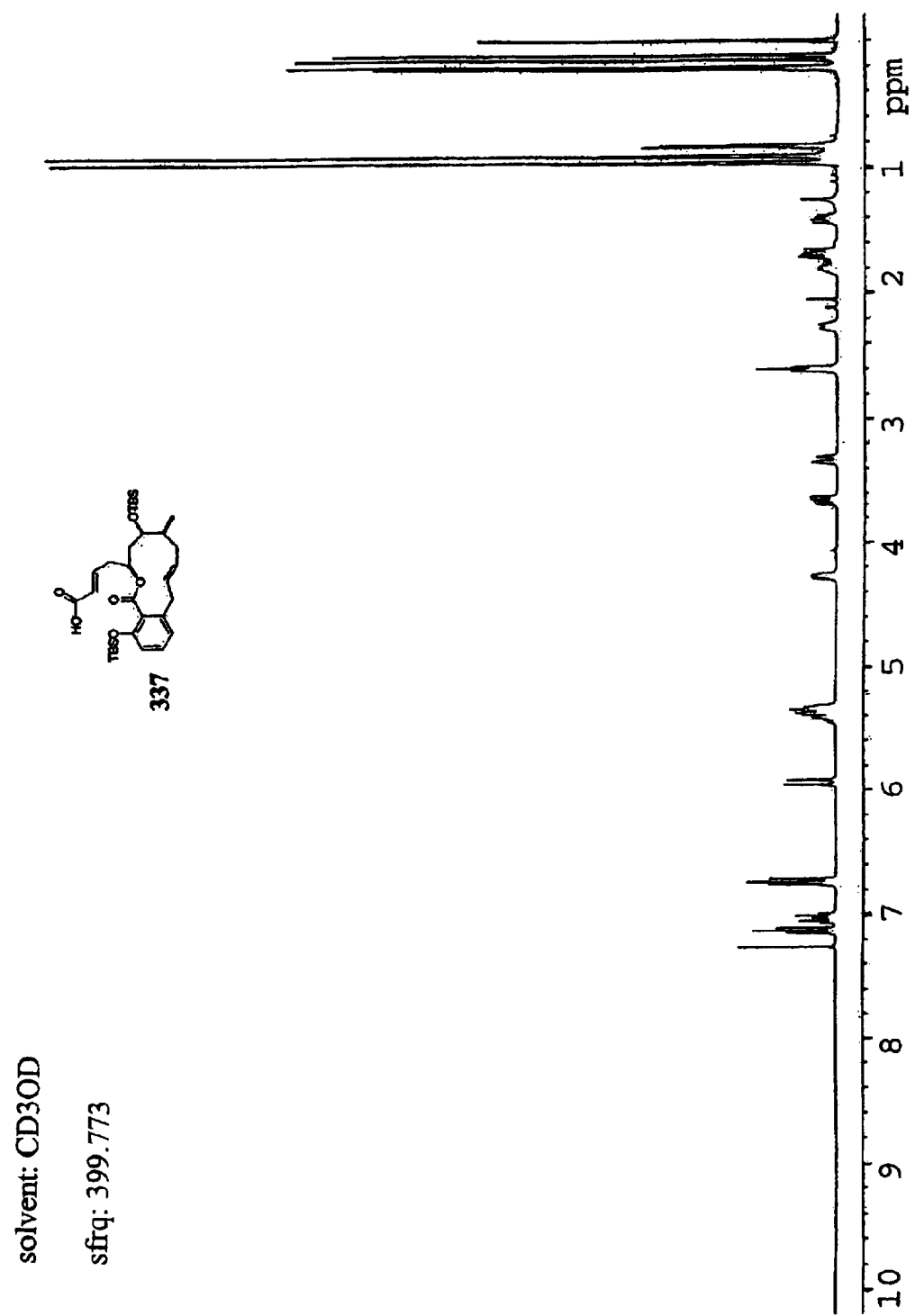
Figure 32:
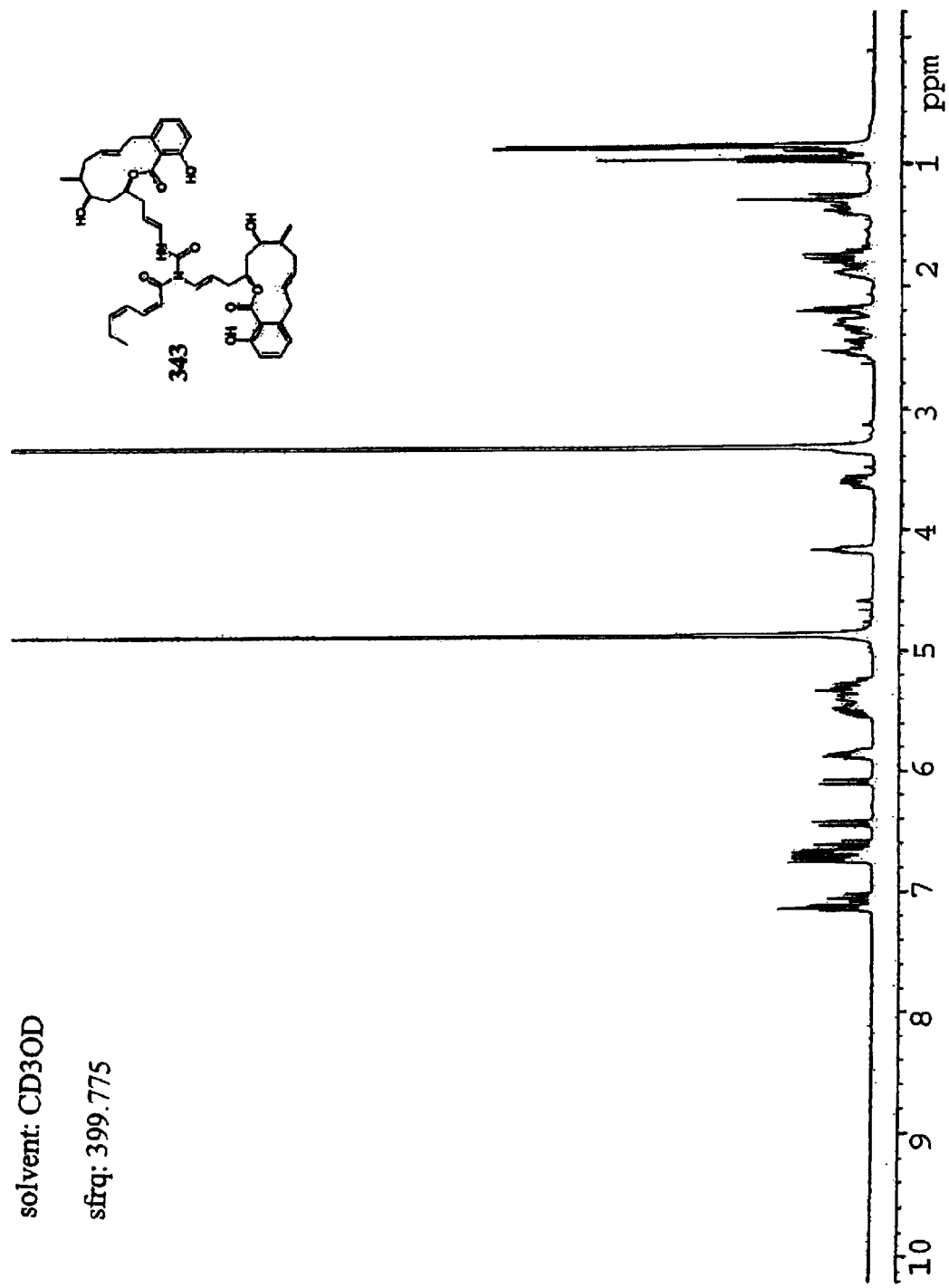
Figure 33:
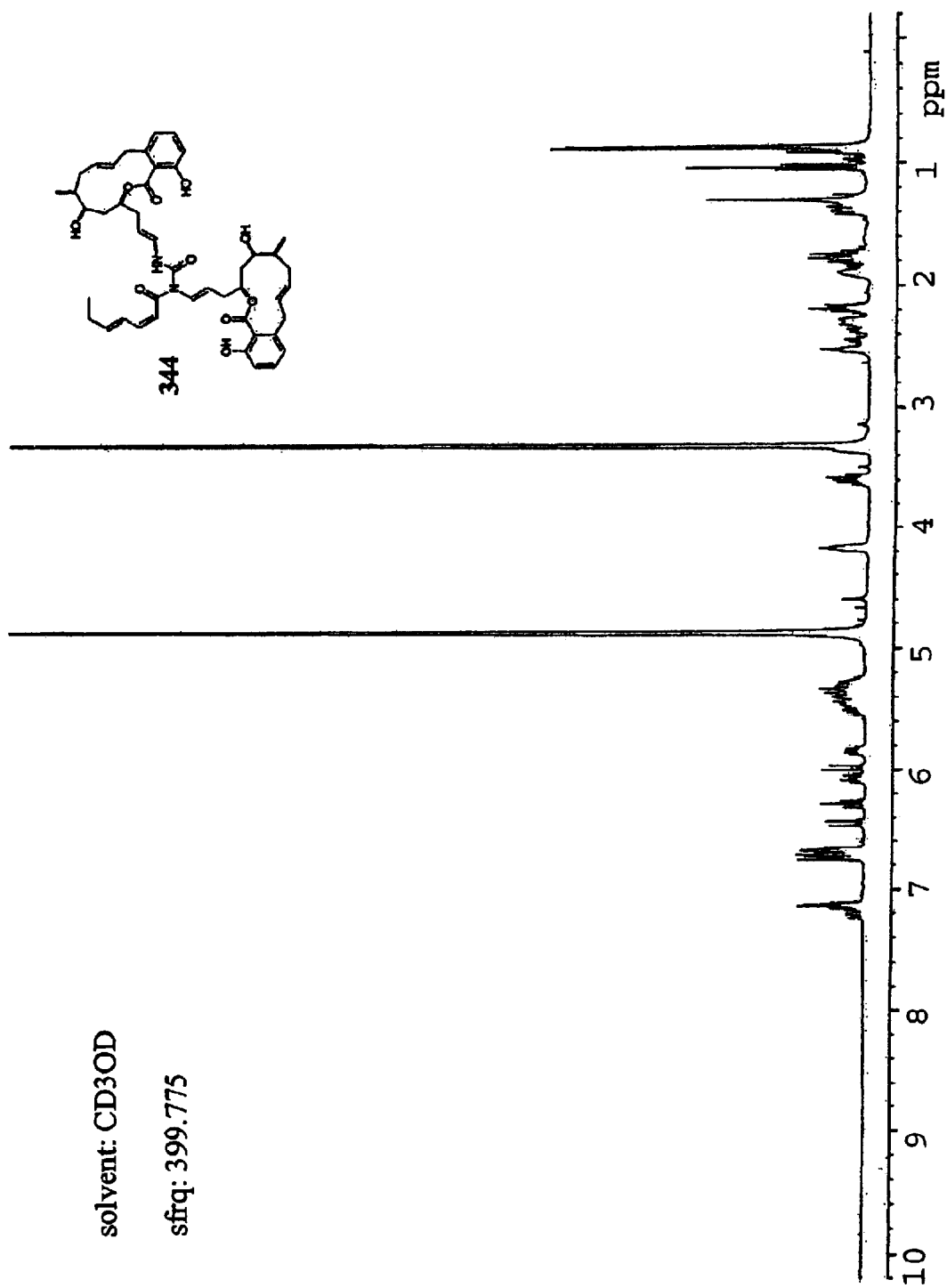
Figure 34:
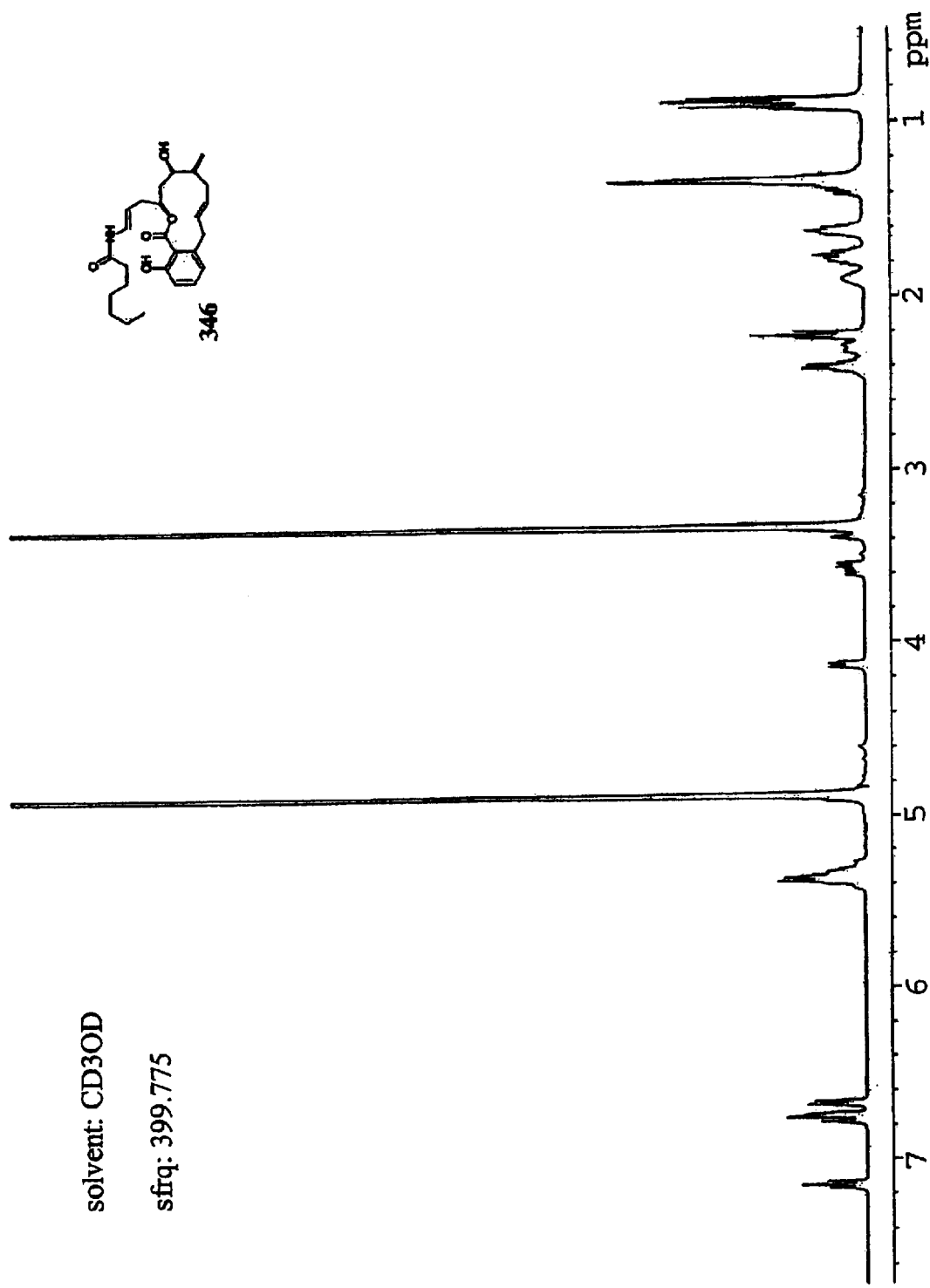
Figure 35:
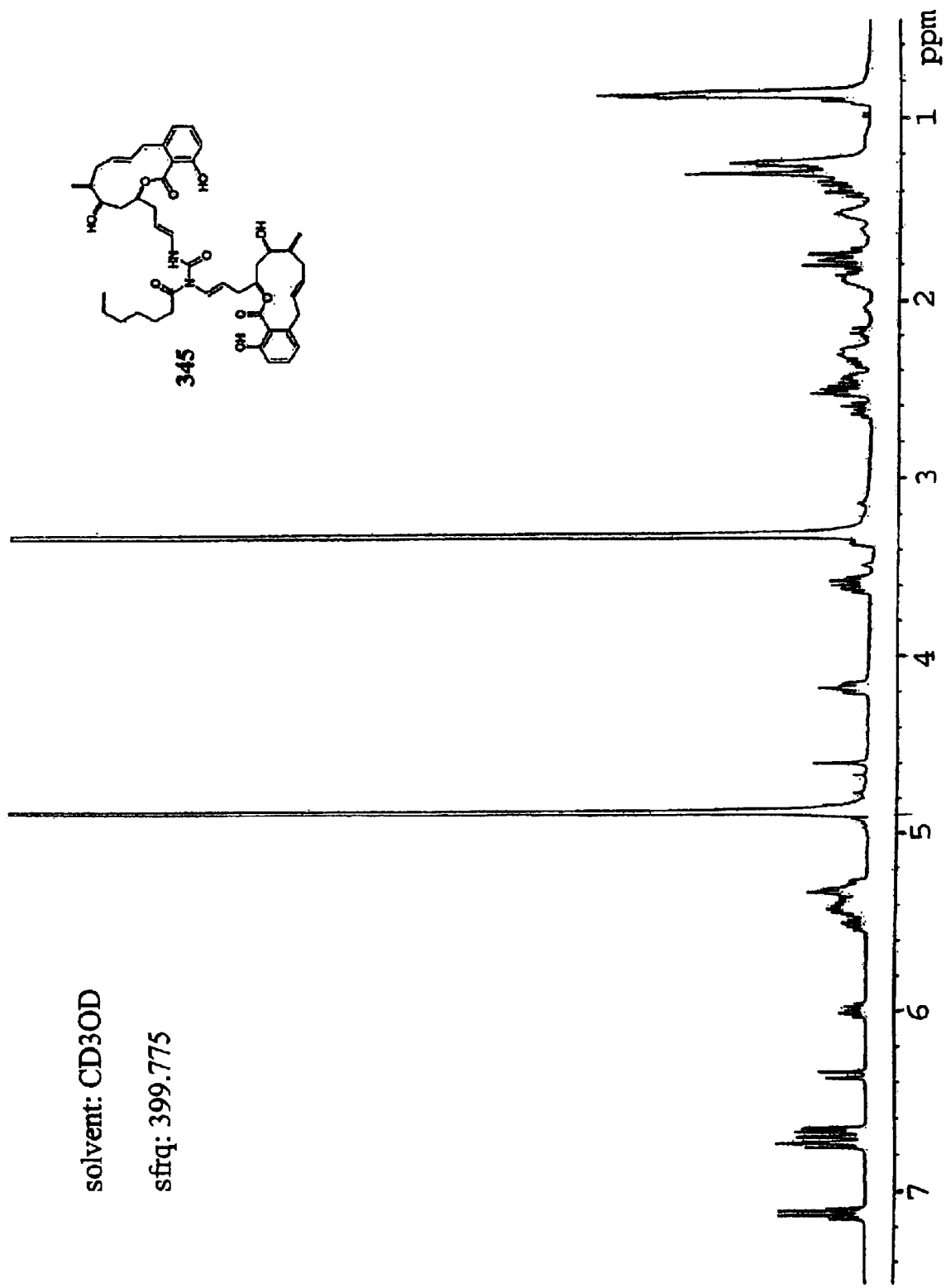
Figure 36:
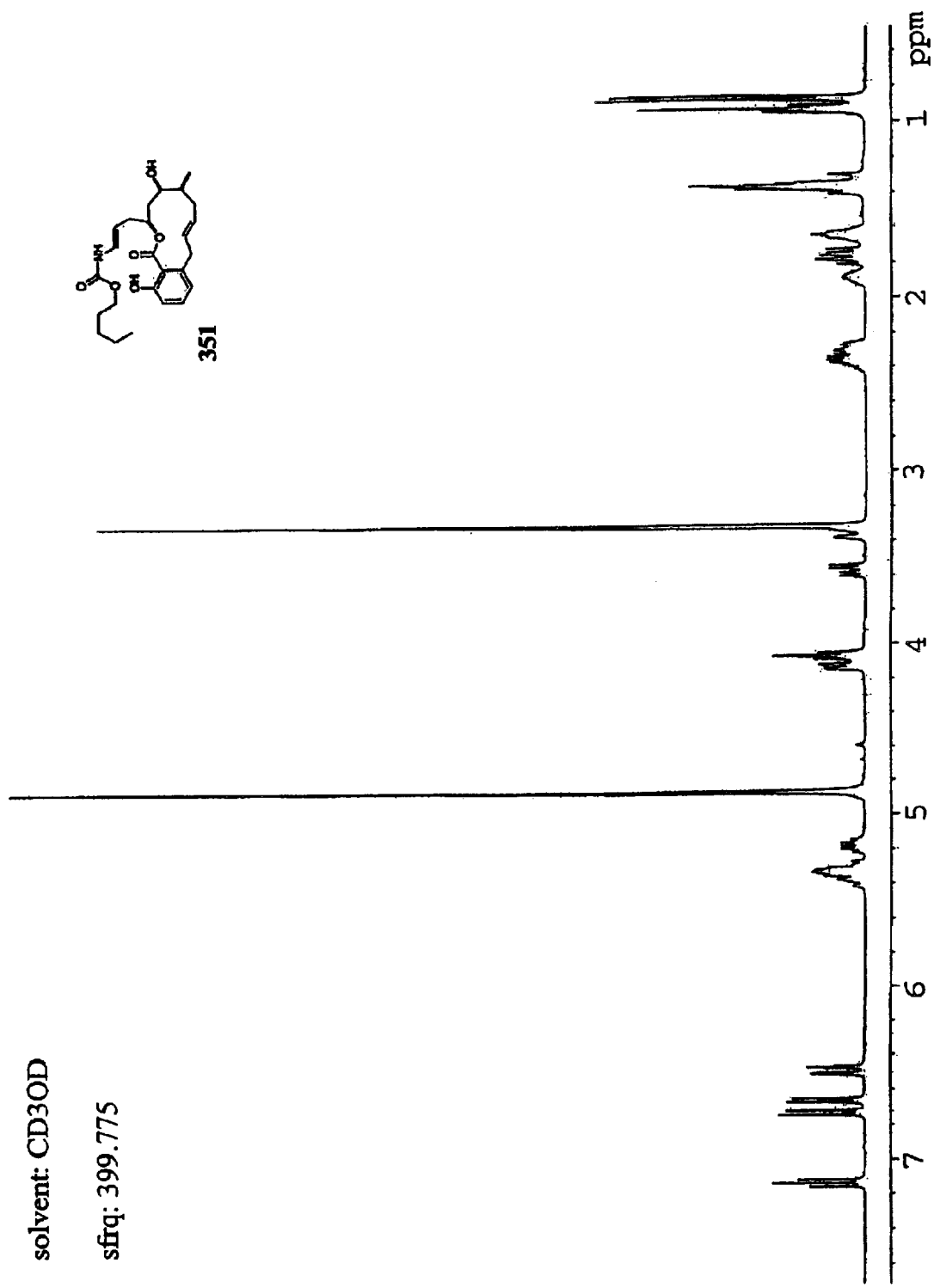
Figure 37:
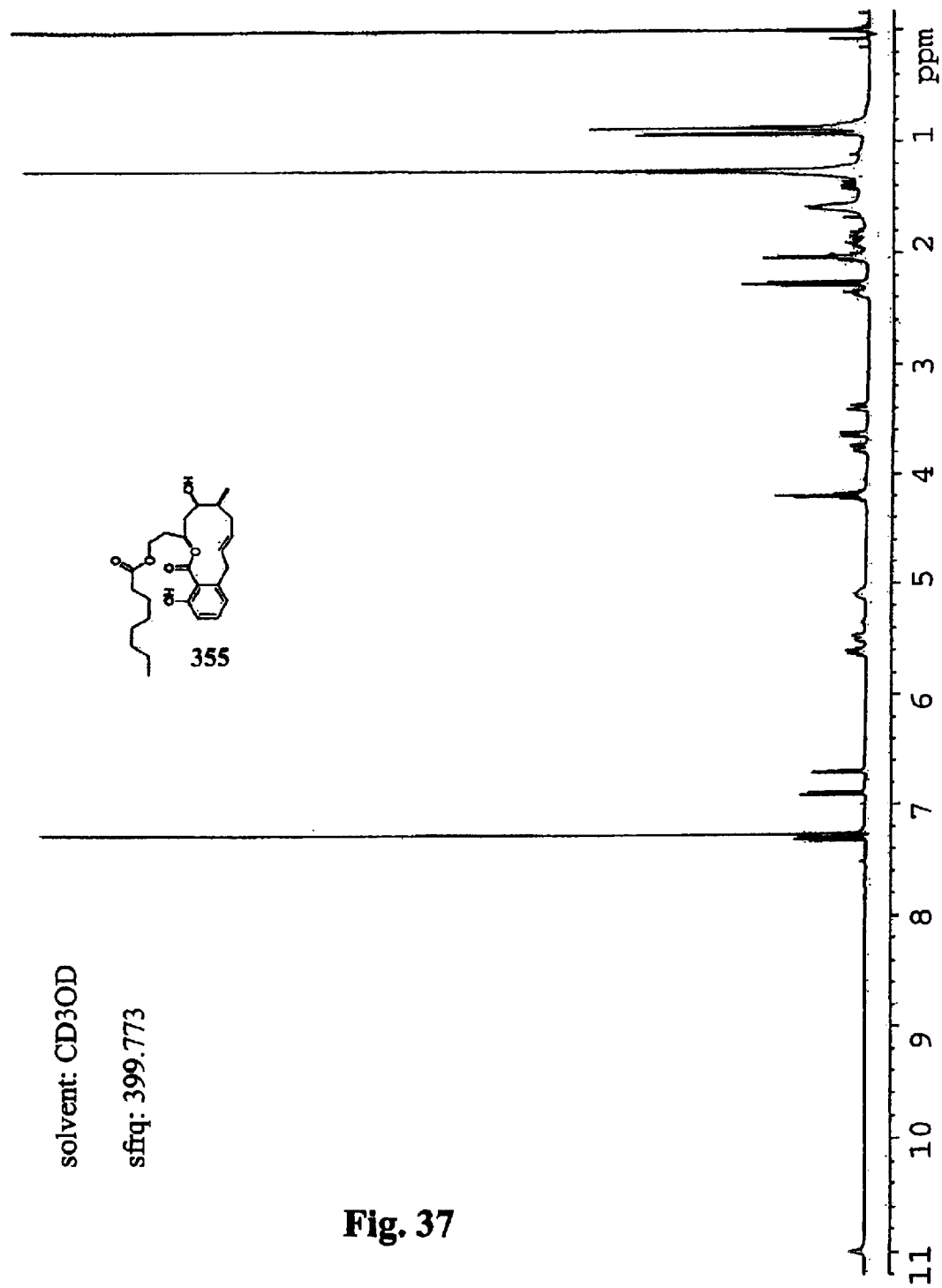
Figure 38:
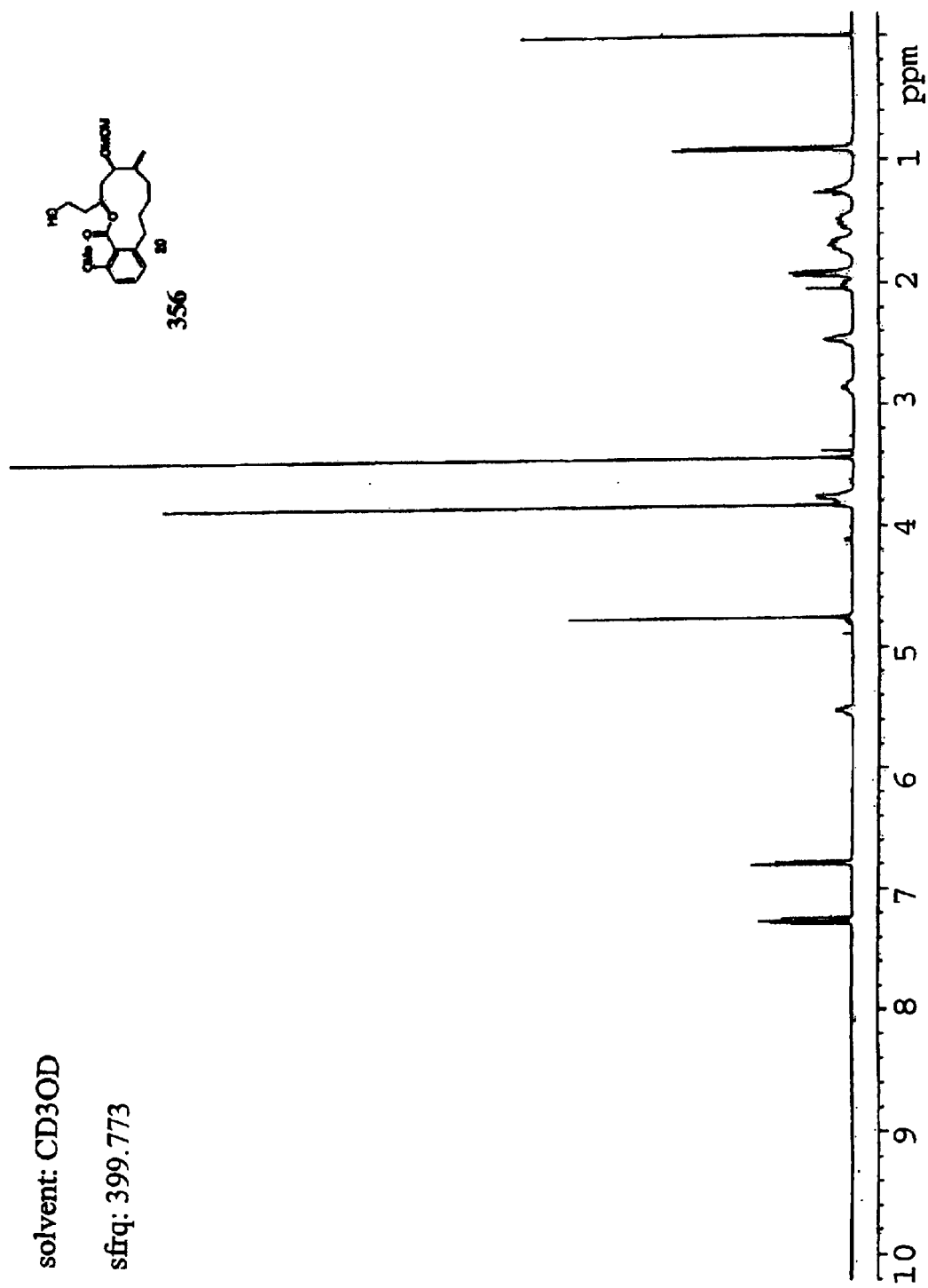
Figure 39:
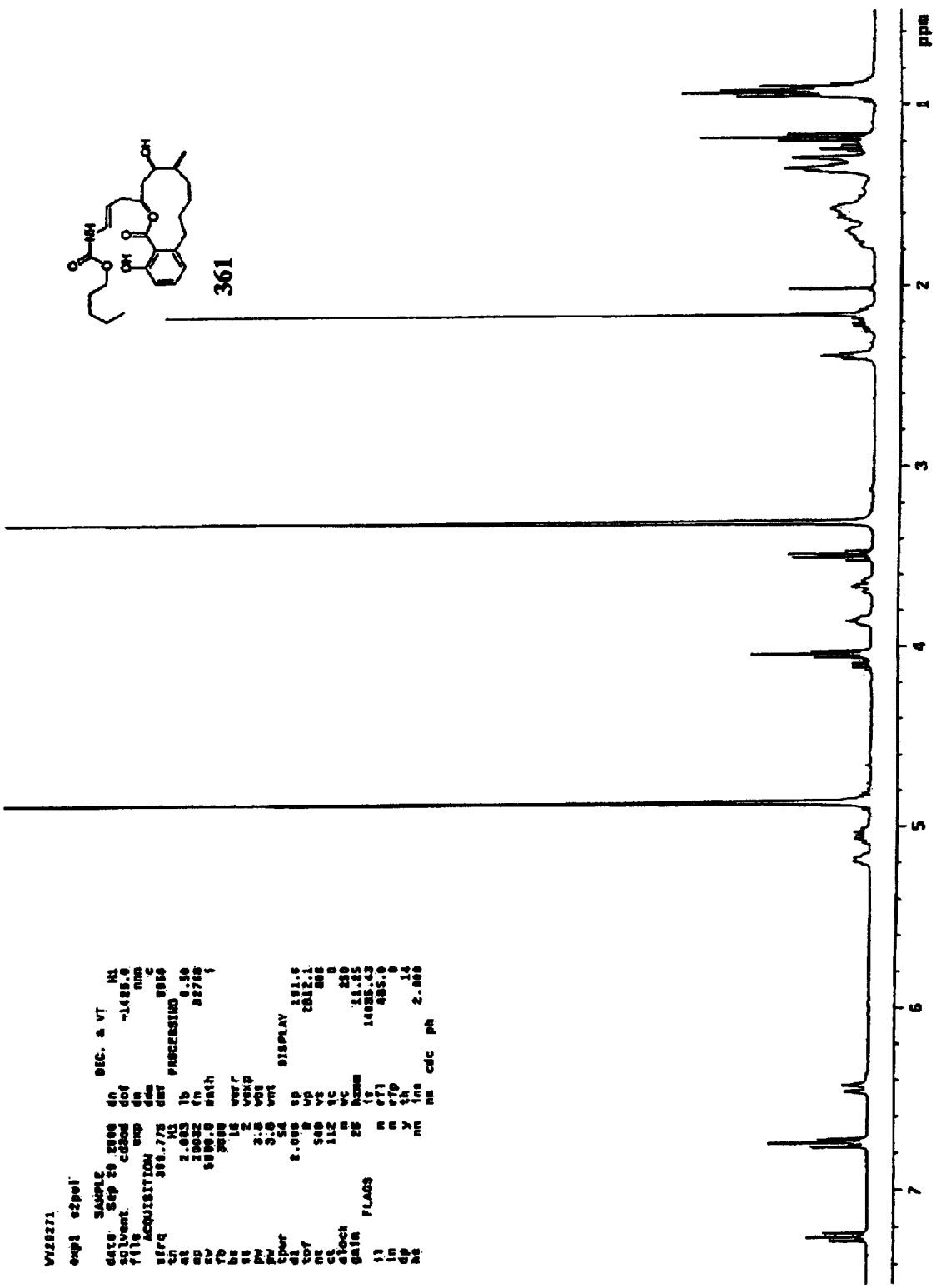
Figure 40:
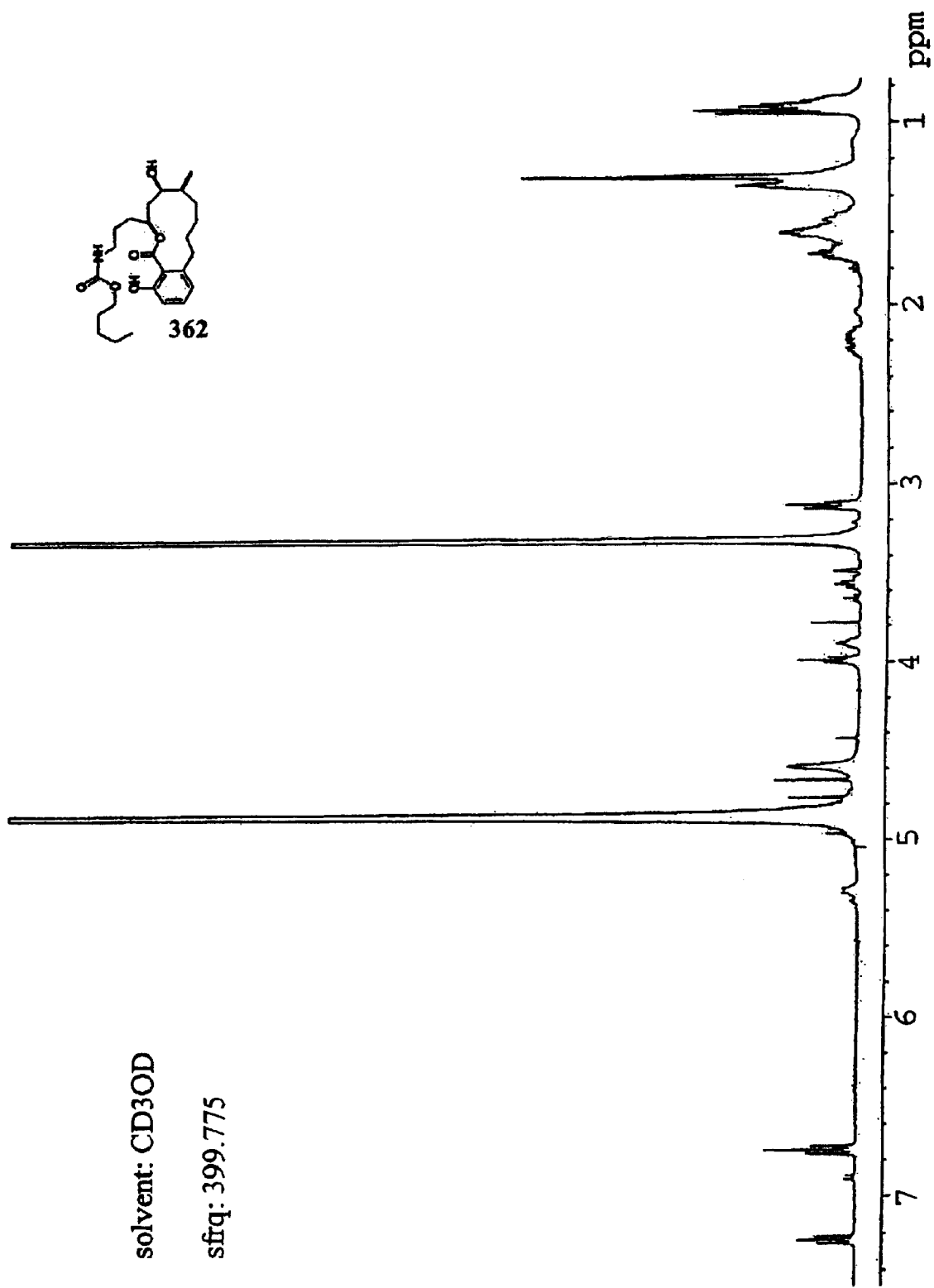

In contrast to the current study, we had initially synthesized ent-301a based on the absolute configuration reported for the natural product. Although this synthetic material was found to be identical to natural salicylihalamide A according to NMR ([D$_6$]benzene and [D$_4$]methanol), IR, UV, and co-elution on HPLC (2 different solvent systems), and TLC (3 different solvent systems), the signs of the optical rotations of synthetic ent-301a ([α]$^{23}_D$=+20.8; c=0.12; MeOH) and the natural product (reported: [α]$^{23}_D$=−35; c=0.7; MeOH), were opposite. Moreover, synthetic ent-301a was devoid of growth inhibitory activity when screened against the NCI 60-cell line panel. At this point we had the fortune that p-bromobenzoate derivative 348 provided crystals suitable for X-ray diffraction studies, confirming the absolute configuration of our synthetic lactones (FIGS. 11(a) & (b)). Based on all the available evidence, the absolute configuration of natural (−)-salicylihalamide A was assigned to be as drawn in 301a. Unequivocal proof for the absolute stereochemistry of natural salicylihalamide ultimately came from biological characterization of synthetic 301a, which provided a differential cytotoxicity profile undistinguishable from the natural product in the NCI-60 cell line panel. It is noted that careful examination of the $^1$H-NMR spectra of natural salicylihalamide A indicates the presence of a minor contaminant with an identical spectroscopic signature to our synthetic Z,E-isomer 1c (see FIG. 25 and FIG. 27). This contaminant could be a natural isomer of salicylihalamide A, or the result of isomerization during the isolation/purification procedure.

Structural variants with a suitable reporter were then orchestrated towards side-chain modifications, emanating from a common, naturally configured isocyanate 339, now accessible in 20 steps (longest linear sequence) and 21–25% overall yield. Thus, compound 346 and the corresponding dimer 345 were prepared by addition of hexyllithium (instead of hexadienyllithium) to isocyanate 339 followed by final deprotection (FIG. 15). An inverse addition of isocyanate 339 to a cold solution (−78° C.) of organolithium nucleophiles was next explored in order to suppress dimer formation. Indeed, preparation of alkynoyl enamine derivatives 349/350 followed this procedure, and no trace of dimer formation was detected (FIG. 15). Alternatively, carbamates or thiocarbamates 351–354 are obtained in an operationally simplified procedure by heating the acylazide 338 in the presence of the appropriate alcohol or thiol (FIG. 15).

A cell-based assay looking for growth inhibition of the SK-MEL 5 human melanoma cell line was performed. Side chain modified analogs 343–346 and 349–352 all retain cytostatic and cytotoxic properties at similar concentrations than the parent compound. See Table 3 below.

TABLE 3

Growth inhibitory properties of selected compounds against the human melanoma cell line SK-MEL-5[a]

| Compound | GI$_{50}$ (μM) | Compound | GI$_{50}$ (μM) | Compound | GI$_{50}$ (μM) |
|---|---|---|---|---|---|
| 30a/1c | 0.03 | 335b | >20 | 343 | 0.04 |
| 344 | 0.1 | 345 | 0.6 | 346 | 0.38 |
| 349 | 0.3 | 350 | 0.3 | 351 | 0.5 |
| 352 | 0.45 | 353 | >20 | 354 | 1.5 |
| 355 | >20 | 361 | 8 | 362 | >20 |
| 365 | >20 | 366 | 1.0 | 367 | >20 |
| Apicularen A | 0.006 | 235 | 0.06 | 236 | 0.9 |
| 237 | 0.45 | 238 | 7.5 | 239 | 0.5 |

[a]Growth was determined 2 days after the addition of the compounds by the MTT assay (Mosmann, T. J. Immunol. Methods 1983, 65, 55–63). The GI$_{50}$ values (drug concentrations required to inhibit growth by 50%) were calculated based on triplicate assays at 4 different concentrations of the drug.

In addition, the ability of compounds 323a/c and 343 to inhibit growth of a number of tumor cell lines was tested and compared to TAXOL's ability to inhibit growth of these tumor cell lines. The data are indicated below in Table 4.

TABLE 4

| Cell line | GI$_{50}$ (nM) 323a/c | GI$_{50}$ (nM) 343 | GI$_{50}$ (nM) TAXOL |
|---|---|---|---|
| H1299 | 3.2 | 5.0 | 5.0 |
| H2009 | 2.0 | 1.6 | 5.0 |
| H358 | 1.6 | 10.0 | 5.0 |
| H2058 | 3.2 | 6.3 | 5.0 |
| H175 | 0.2 | 0.2 | 5.0 |
| H1264 | 31.6 | 31.6 | 5.0 |

TABLE 4-continued

| Cell line | GI₅₀ (nM) 323a/c | GI₅₀ (nM) 343 | GI₅₀ (nM) TAXOL |
|---|---|---|---|

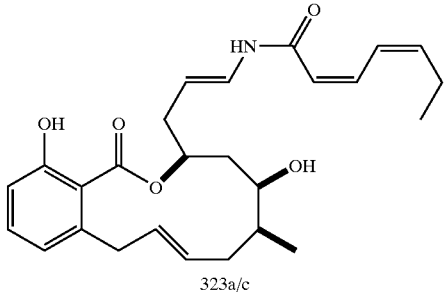

323a/c

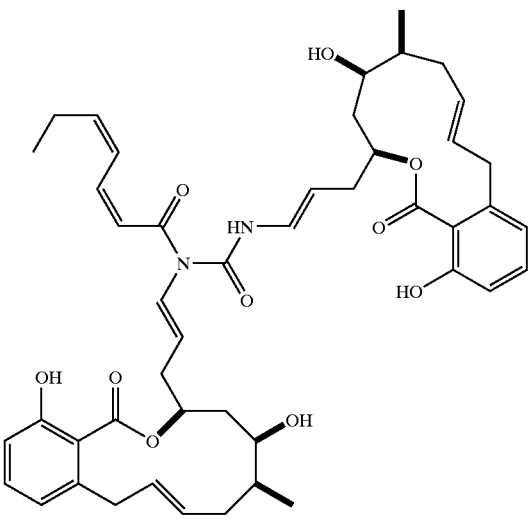

343

This indicates that the dienamide is not acting as a Michael acceptor for biological relevant nucleophiles (346, 351–352) and that substantial sterically demanding modifications can be accommodated without abrogating biological activity (343–345). The Vacuolar ATPase was identified as a putative target of salicylihalamide A It has subsequently been confirmed that the potent V-ATPase inhibitory activity of our synthetic salicylihalamides (see Table 5 below) and identified the membrane spanning Vo proton channel as the binding site for salicylihalamide A. The data of Table 5 was acquired using a purified system. Others in the art typically use crude membrane preparations to assay V-ATPase activity. Such a crude assay does not necessarily reflect V-ATPase specific activity.

TABLE 5

Inhibition of purified reconstituted V-ATPase from bovine brain[a]

| Compound | IC₅₀ (nM) | Compound | IC₅₀ (nM) | Compound | IC₅₀ (nM) |
|---|---|---|---|---|---|
| 301a/301c | 0.34 | 335b | 230 | 343 | 0.37 |
| 344 | 1.2 | 345 | 3.0 | 346 | 0.8 |
| 349 | 0.75 | 350 | 1.0 | 351 | 0.2 |
| 352 | 1.8 | 353 | >1,800 | 354 | >2,500 |

TABLE 5-continued

Inhibition of purified reconstituted V-ATPase from bovine brain[a]

| Compound | IC₅₀ (nM) | Compound | IC₅₀ (nM) | Compound | IC₅₀ (nM) |
|---|---|---|---|---|---|
| 355 | >1,000 | 361 | 9.3 | 362 | 75.7 |
| 365 | ND | 366 | 300 | 367 | 180 |
| Apicularen A | <1.0 | (+)- | 270 | Bafilomycin A | 3.1 |

[a]IC₅₀'s were measured according to: Xie X-S, Tsai SJ, Stone DK (1988) Proton pump in clathrin-coated vesicles. Methods in Enzymology 157, 634–646. See also Crider, Xie and Stone, J. Biol. Chem. 269: 17379–17381 (1994).

In light of this, we prepared analogs 353/354 incorporating a lipophilic cholesteryl or farnesyl anchor hoping to target these derivatives to the membrane (FIG. 15).

Figure 17:
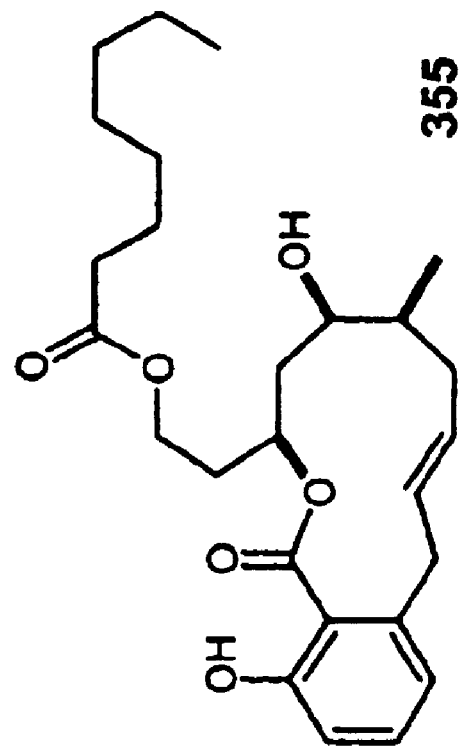
FIG. 17. Synthesis of octanoate 355

Side chain modified analogs that lack salicylihalamide's characteristic N-acyl enamine fuinctionality are attractive candidates for the following reasons: (1) they are expected to confer increased acid stability; (2) they can potentially be prepared via shorter sequences; and (3) they would answer an important question related to the functional role of the N-acyl enamine moiety. Octanoate 355, a compound with identical chain length and similar hydrophobicity than salicylihalamide, is representative of this class of compounds and was prepared from alcohol 331 via a Mitsunobu esterification followed by deprotection (FIG. 17). However, both octanoate 355 and allyl ester 335b (FIG. 13) were completely inactive in the cell-based assay and 2–3 orders of magnitude less potent than salicylihalamide in the in vitro V-ATPase assay.

At this point, we became entertained with the possibility that salicylihalamides could form a covalent complex with a putative binding protein through capture of an activated N-acyliminium ion by a nucleophilic amino acid residue (FIG. 17), which could explain the loss of biological activity for derivatives 355/335b.

Figure 18:
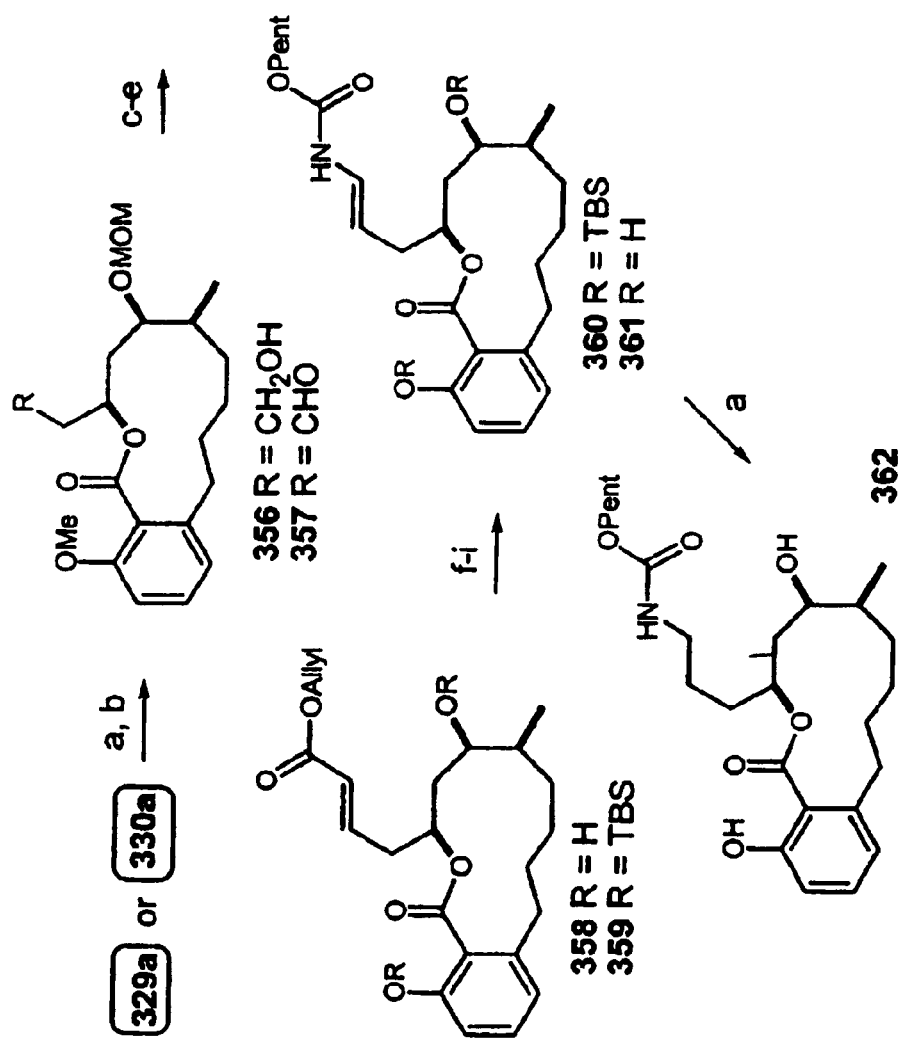
FIG. 18. Synthesis of a fully saturated salicylihalamide derivative 362

A minimally perturbed probe to test this hypothesis was envisioned to arise from a simple saturation of the enamine double bond of biologically active salicylihalamide derivative 351. However, direct hydrogenation of 351 also saturated the endocyclic double bond to produce 362 (FIG. 18). Because there was no obvious short solution to this chemoselectivity problem, a control reagent 361 was prepared as a probe to investigate independently the effect of endocyclic double bond saturation on biological activity (FIG. 18). Our point of departure entailed a hydrogenation of 329a or 330a with concomitant removal of the p-methoxybenzyl (PMB) ether. Subsequent conversion of 356 to 361 took full advantage of the chemistry outlined for the preparation of 351 without complication. Hydrogenation of this material also yielded the fully saturated salicylihalamide derivative 362. In vivo, N-carbamoyl enamine derivative 361 retained a significant, although attenuated, level of growth inhibitory activity whereas the enamine to amine permutation (361→362) completely abolished antiproliferative potential. In the in vitro V-ATPase assay, inhibition of proton pumping also decreases in the order 351 (IC₅₀ 0.2 nM)>361 (IC₅₀ 9.3 nM)>362 (IC₅₀ 75.7 nM). See Table 3 above. Because it was demonstrated that salicylihalamide is a reversible inhibitor of V-ATPase, it is likely that other factors, perhaps increased conformational flexibility, are responsible for the decreased biological activity of 362 (and to a lesser extend for 361).

Figure 19:
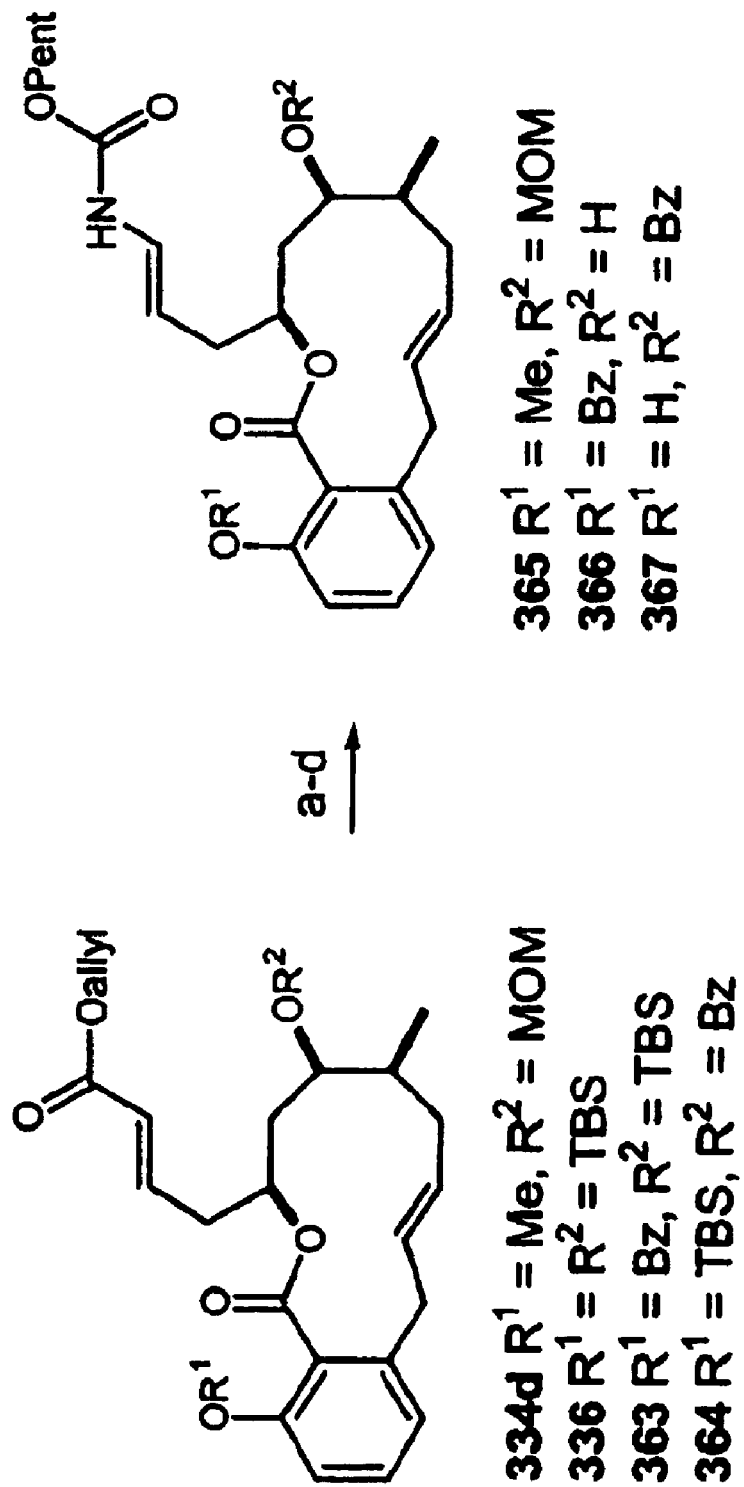
FIG. 19. Synthesis of bis- and mono-protected forms of salicylihalamide derivatives 365–367

It became apparent from these studies that a photoactivatable salicylihalamide reagent had to be developed in order to map the salicylihalamide binding site on V-ATPase in molecular detail. Although the potent in vivo and in vitro biological activity of salicylihalamide-based dimers 343–345 points to a potential site for attachment, the phenolic and secondary hydroxyls were also investigated as a handle for derivatization (Scheme 10). Staring with bis-TBS derivative 336, selective deprotection of the phenolic (TBAF, THF, 0° C., 91%) or secondary TBS ether (aq. HCl, 91%) was followed by benzoylation to furnish benzoates 363 (%) and 364 (50%) respectively. Together with compound 334d, these materials were independently elaborated to bis- and mono-protected forms of salicylihalamide derivative 351, namely compounds 365–367. See FIG. 19. For the V-ATPase activity of 365–367 see Table 5 above

Example 8

Experimental Procedures for the Synthesis of Synthetic Salicylihalalmides and Characterization Data:

I. General Techniques

Unless noted otherwise, commercially available materials were used without further purification. All solvents used were of HPLC- or ACS-grade. Solvents used for moisture sensitive operations were distilled from drying agents under a nitrogen atmosphere: $Et_2O$ and THF from sodium benzophenone ketyl; benzene and toluene from sodium; $CH_2Cl_2$, $CH_3CN$, $NEt_3$ and pyridine from $CaH_2$.

All moisture sensitive reactions were carried out under a nitrogen atmosphere with magnetic stirring. Flash chromatography (FC) was performed using E Merck silicagel 60 (240–400 mesh) according to the protocol of Still, Kahn, and Mitra (J. Org. Chem. 1978, 43, 2923). Thin Layer chromatography was performed using precoated plates purchased from E. Merck (silicagel 60 PF254, 0.25 mm) that were visualized using a $KMnO_4$ or Ce(IV) stain.

Nuclear magnetic resonance (R) spectra were recorded in $CDCl_3$, unless otherwise specified, on either a Varian Inova-400 or Mercury-300 spectrometer at operating frequencies of 400/300 MHz ($^1H$ NMR) or 100/60 MHz ($^{13}C$ NMR). Chemical shifts ($\delta$) are given in ppm relative to residual solvent (usually chloroform; $\delta$ 7.27 for $^1H$ NMR or $\delta$ 77.25 for proton decoupled $^{13}C$ NMR), and coupling constants (J) in Hz. Multiplicity is tabulated as s for singlet, d for doublet, t for triplet, q for quadruplet, and m for multiplet, whereby the prefix app is applied in cases where the true multiplicity is unresolved, and br when the signal in question is broadened.

Infrared spectra were recorded on a Perkin-Elmer 1000 series FTIR with wavenumbers expressed in $cm^{-1}$ using samples prepared as thin films between salt plates. High-resolution mass spectra (HRMS) were recorded at the NIH regional mass spectrometry facility at the University of Washington, St. Louis, Mo. Combustion analyses were performed by. Optical rotations were measured at 20° C. on a Perkin-Elmer 241 MC polarimeter.

II. Experimental Procedure

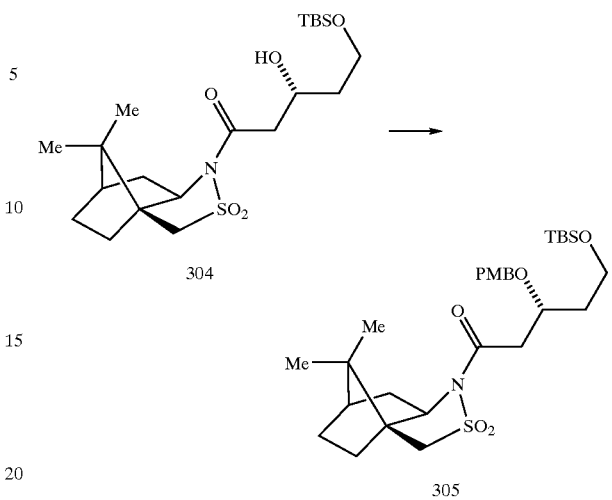

To a stirred solution of alcohol 304 (3.71 g, 8.57 mmol) in $Et_2O$ (60 mL) was added p-methoxybenzyltrichloroacetimidate (4.3 g, 17.14 mmol) followed by trifluoromethanesulfonic acid (2.3 µL, 0.026 mmol) and the mixture was stirred for 2 h at rt. The mixture was quenched with aqueous sat. $NaHCO_3$ and extracted with $Et_2O$ (3×). The combined organic layers were washed (brine), dried ($Na_2SO_4$) and concentrated. Purification by FC yielded 3.4 g (72%) of p-methoxybenzyl ether 305 as a colorless oil. 305: $[\alpha]_D$=-32.8 ($CHCl_3$, c 1.18); IR 2956, 2857, 1697, 1613, 1514, 1331, 1250, 1136, 1096, 836, 777 $cm^{-1}$; $^1H$ NMR (400 MHz, $CDCl_3$) $\delta$ 7.26 (2H, d, J=8.4 Hz), 6.85 (2H, d, J=8.4 Hz), 4.55 (1H, d, J=10.8 Hz), 4.43 (1H, d, J=10.8 Hz), 4.17–4.11 (1H, m), 3.88 (1H, app.t, J=6.4 Hz), 3.79 (3H, s), 3.70 (2H, app.t, J=6.4 Hz), 3.50 (1H, d, J=13.6 Hz), 3.43 (1H, d, J=13.6 Hz), 3.02 (1H, dd, J=6.4, 16.0 Hz), 2.98 (1H, dd, J=6.4, 16.0 Hz), 2.05–2.12 (2H, m), 1.75–1.96 (5H, m), 1.32–1.43 (2H, m), 1.14 (3H, s), 0.96 (3H, s), 0.89 (9H, s), 0.04 (6H, s); $^{13}C$ NMR (75 MHz, $CDCl_3$) $\delta$ 169.9, 159.2, 130.9, 129.5, 113.8, 72.9, 71.4, 65.3, 59.6, 55.4, 53.1, 48.5, 47.9, 44.8, 41.2, 38.7, 38.0, 33.0, 26.6, 21.0, 20.0, 18.4, -5.1, -5.2; MS (CI) 550 ([M-OMe]$^+$, 2), 121 (100). HRMS Calcd for $C_{29}H_{48}NO_6SSi$ (MH$^+$): 566.2972. Found: 566.2956.

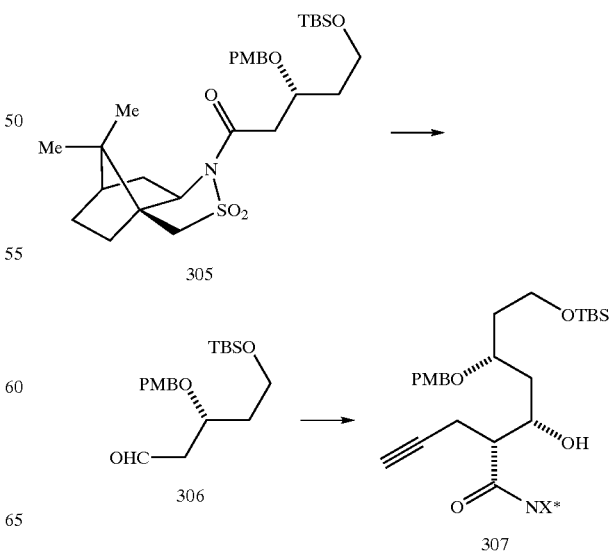

To a −78° C. solution of p-methoxybenzyl ether 305 (2.4 g, 4.34 mmol) in CH$_2$Cl$_2$ (40 mL) was added dropwise DIBAL-H (1.0 M in CH$_2$Cl$_2$, 5.2 mL). After stirring for 1 h at −78° C., MeOH (2 mL) was added and stirring was continued for 5 min after which the cooling bath was removed and solid NaSO$_4$·10H$_2$O was added portionwise. After stirring for 1 h at rt, the solid was removed by filtration and washed several times with EtOAc. The filtrate was concentrated and the residue partially purified to remove most of the bornanesultam auxiliary. The crude aldehyde 306 (~1 g) was used in the next step without further purification.

To a stirred solution of (2R)-N-(4'-pentynoyl)bornanesultam (950 mg, 3.22 mmol) in CH$_2$Cl$_2$ (20 mL) at −78° C. was added TiCl$_4$ (343 μL, 3.13 mL) and i-Pr$_2$NEt (0.56 mL, 3.22 mmol). After stirring for 1 h at the same temperature, a solution of aldehyde 306 (~1 g) in CH$_2$Cl$_2$ (2 mL) was added. After stirring for 2 h at −78° C., aqueous sat. NH$_4$Cl was added and an extraction was performed with EtOAc (3×). The combined organic layers were washed (brine), dried (Na$_2$SO$_4$) and concentrated. The residue was purified by FC (15% EtOAc/hexanes) yielding 1.33 g (74%) of aldol product 307 as a white foam. 307: [α]$_D$=−54.7 (CHCl$_3$, c 1.39); IR 3480, 2956, 2857, 1694, 1613, 1514, 1334, 1250, 1095, 836, 777 cm$^{-1}$; $^1$H NMR (400 MHz, CDCl$_3$) δ 7.25 (2H, d, J=8.4 Hz), 6.84 (2H, d, J=8.4 Hz), 4.49 (1H, d, J=10.8 Hz), 4.45 (1H, d, J=10.8 Hz), 4.26–4.32 (1H, m), 3.70–393 (2H, m), 3.78 (3H, s), 3.62–3.73 (2H, m), 3.52 (1H, d, J=2.4 Hz), 3.50 (1H, d, J=13.6 Hz), 3.42 (1H, d, J=13.6 Hz), 3.24 (1H, ddd, J=4.8, 7.2, 7.2 Hz), 2.84 (1H, ddd, J=2.8, 7.2, 17.2 Hz), 2.70 (1H, ddd, J=2.4, 4.8, 17.2 Hz), 2.10–2.17 (1H, m), 2.04 (1H, dd, J=7.6, 14.0 Hz), 1.96 (1H, app.t, J=2.4 Hz), 1.84–1.94 (5H, m), 1.69–1.78 (1H, m), 1.63 (1H, ddd, J=2.0, 6.4, 14.4 Hz), 1.30–1.42 (2H, m), 1.19 (3H, s), 0.95 (3H, s), 0.88 (9H, s), 0.03 (6H, s); $^{13}$C NMR (75 MHz, CDCl$_3$) δ 172.7, 159.3, 130.6, 129.6, 113.9, 80.5, 74.3, 71.2, 71.0, 67.2, 65.2, 59.6, 55.3, 53.3, 49.5, 48.4, 47.9, 44.7, 38.5, 37.5, 36.8, 32.9, 26.6, 26.1, 20.9, 20.0, 18.4, 18.3, −5.2; MS (CI) 648 [MH]$^+$, 632, 590, 121 (100). HRMS Calcd for C$_{34}$H$_{54}$NO$_7$SSi (MH$^+$): 648.3390. Found: 648.3368.

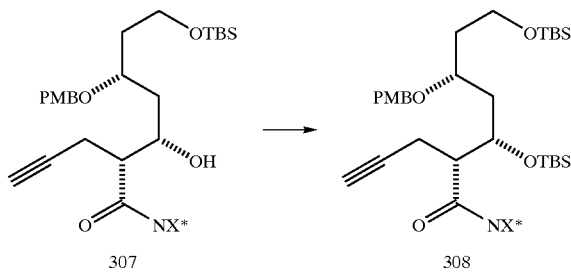

307 308

To a solution of 307 (1.27 g, 1.96 mmol) in CH$_2$Cl$_2$ (10 mL) was added at −10° C. 2,6-lutidine (0.342 mL, 2.94 mmol), followed by TBSOTf (0.496 mL, 2.16 mmol). The solution was stirred for 2 h at −10° C. and 2 h at rt followed by quenching with aqueous sat NH$_4$Cl. The aqueous layer was extracted with EtOAc (3×) and the combined organics were washed (brine), dried (Na$_2$SO$_4$) and concentrated. The residue was purified by FC (10% EtOAc/hexanes) to give 1.33 g of silylether 308 as a colorless oil (90%). 308: [α]$_D$=−36.5 (CHCl$_3$, c 0.54); IR 2956, 2857, 1700, 1613, 1515, 1332, 1250, 1100, 837, 777 cm$^{-1}$; $^1$H NMR (400 MHz, CDCl$_3$) δ 7.33 (2H, d, J=8.8 Hz), 6.85 (2H, d, J=8.8 Hz), 4.47 (2H, s), 4.37 (1H, dd, J=5.6, 11.6 Hz), 3.88 (1H, dd, J=5.2, 7.6 Hz), 3.79 (3H, s), 3.65–3.75 (3H, m), 3.49 (1H, d, J=13.6 Hz), 3.41 (1H, d, J=13.6 Hz), 3.37–3.42 (1H, m), 2.80 (1H, ddd, J=2.4, 8.4, 16.8 Hz), 2.61 (1H, ddd, J=2.4, 3.6, 16.8 Hz), 2.15–2.22 (1H, m), 2.07 (1H, dd, J=8.0, 14.0 Hz), 1.93 (1H, t, J=2.4 Hz), 1.77–1.92 (6H, m), 1.67 (1H, ddd, J=4.4, 6.4, 14.8 Hz), 1.30–1.44 (2H, m), 1.20 (3H, s), 0.96 (3H, s), 0.91 (9H, s), 0.89 (9H, s), 0.07 (3H, s), 0.06 (9H, s); 13C NMR (75 MHz, CDCl$_3$) δ 171.2, 159.0, 131.4, 129.4, 113.7, 81.6, 72.8, 70.6, 69.6, 68.8, 65.4, 59.9, 55.3, 53.3, 50.2, 48.5, 47.9, 44.6, 42.2, 38.5, 37.7, 32.8, 26.6, 26.20, 26.17, 20.8, 20.1, 18.5, 18.3, 18.0, −4.0, −4.1, −5.1; MS (CI) 762 [MH]$^+$, 713, 704, 514, 121 (100). HRMS Calcd for C$_{40}$H$_{68}$NO$_7$SSi$_2$ (MH$^+$): 762.4255. Found: 762.4246.

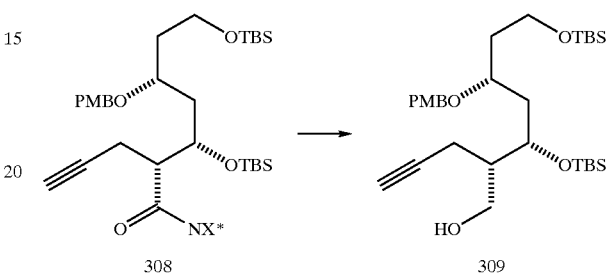

308 309

To a solution of silylether 308 (1.32 g, 1.73 mmol) in THF (60 mL) was added LiEt$_3$BH (1.0 M solution in THF, 10.4 mL) at −78° C. After stirring for 2 h at −78° C. and 5 h at −40° C., aqueous NaOH (2.0N, 30 mL) was added and the mixture was allowed to reach rt. Extraction (EtOAc, 3×), washing (brine), drying (Na$_2$SO$_4$) and concentration gave a residue that was purified by FC (10% EtOAc/hexanes). Alcohol 309 was obtained as a colorless oil (0.8 g, 84%). 309: [α]$_D$=−10.4 (CHCl$_3$, c 1.01); IR 3500, 2955, 2930, 2858, 1614, 1515, 1251, 1094, 837, 776 cm$^{-1}$; $^1$H NMR (400 MHz, CDCl$_3$) δ 7.29 (2H, d, J=8.8 Hz), 6.87 (2H, d, J=8.8 Hz), 4.54 (1H, d, J=11.2 Hz), 4.41 (1H, d, J=11.2 Hz), 4.16–4.21 (1H, m), 3.81 (3H, s), 3.65–3.80 (5H, m), 2.52 (1H, app.t, J=5.6 Hz), 2.13–2.19 (2H, m), 2.02–2.09 (1H, m), 1.99 (1H, app.t, J=2.4 Hz), 1.69–1.90 (3H, m), 1.61 (1H, ddd, J=3.2, 7.6, 14.0 Hz), 0.91 (9H, s), 0.90 (9H, s), 0.07 (6H, s), 0.066 (6H, s); $^{13}$C NMR (75 MHz, CDCl$_3$) δ 159.3, 131.1, 129.3, 113.9, 83.1, 73.4, 71.3, 70.3, 69.8, 63.6, 59.7, 55.5, 45.3, 38.8, 37.7, 26.18, 26.1, 18.5, 18.2, 17.1, −4.1, −5.1; MS (CI) 551 ([MH]$^+$, 4), 493, 121 (100). HRMS Calcd for C$_{30}$H$_{55}$O$_5$Si$_2$ (MH$^+$): 551.3588. Found: 551.3576.

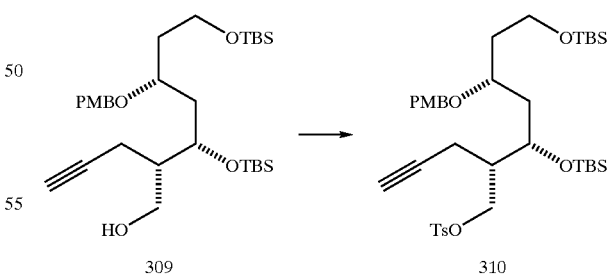

309 310

To a solution of alcohol 309 (0.78 g, 1.42 mmol) in CH$_2$Cl$_2$ (15 mL) was added Et$_3$N (0.4 mL), DMAP (50 mg) and TsCl (0.407 g, 2.13 mmol). The mixture was stirred at rt for 16 h, diluted with Et$_2$O, washed (aq. NaHCO$_3$), dried (Na$_2$SO$_4$) and concentrated. The residue was purified by FC (5% EtOAc/hexanes) to yield 0.909 g (91%) of tosylate 310 as a colorless oil. 310: [α]$_D$=−6.3 (CHCl$_3$, c 0.27); IR 2955, 2930, 2857, 1613, 1514, 1363, 1250, 1178, 1098,837,777 cm$^{-1}$; $^1$H NMR (400 MHz, CDCl$_3$), δ 7.81 (2H, d, J=8.4 Hz), 7.35 (2H, d, J=8.4 Hz), 7.29 (2H, d, J=8.8 Hz), 6.89 (2H, d, J=8.8 Hz), 4.52 (1H, d, J=11.2 Hz), 4.39 (1H, d, J=11.2 Hz), 4.06–4.19 (3H, m), 3.83 (3H, s), 3.63–3.77 (3H, m), 2.47 (3H, s), 2.30 (1H, ddd, J=2.8, 7.2, 17.2 Hz), 2.21 (1H, ddd, J=2.8, 7.2, 17.2 Hz), 2.09–2.16 (1H, m), 1.93 (1H, t, J=2.8 Hz), 1.78–1.87 (1H, m), 1.66–1.75 (2H, m), 1.44 (1H, ddd, J=3.2, 7.6, 14.0 Hz), 0.93 (9H, s), 0.82 (9H, s), 0.09 (3H, s), 0.085 (3H, s), 0.04 (3H, s), 0.001 (3H, s); $^{13}$C NMR (75 MHz, CDCl$_3$) δ 159.2, 144.9, 133.0, 131.0, 130.0, 129.3, 128.2, 113.9, 81.9, 73.3, 70.4, 70.2, 69.6, 68.6, 59.6, 55.5, 43.5, 39.1, 37.6, 26.2, 26.0, 21.8, 18.5, 18.1, 16.3, −4.1, −4.4, −5.11, −5.13; MS (CI) 705 [MH]$^+$, 647, 568, 355, 121 (100). HRMS Calcd for C$_{37}$H$_{61}$NO$_7$SSi$_2$ (MH$^+$): 705.3677. Found: 705.3663.

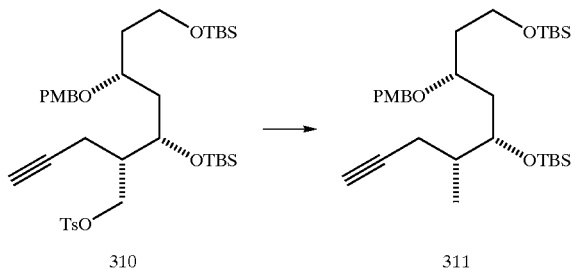

To a solution of tosylate 310 (0.9 g, 1.28 mmol) in THF (13 mL) was added LiEt$_3$BH (1.0 M solution in THF, 6.4 mL) at −0° C. After stirring for 16 h at rt, aqueous NaOH (5%, 5 mL) was added. Extraction (Et$_2$O, 3×), washing (brine), drying (Na$_2$SO$_4$) and concentration gave a residue that was purified by FC (2% EtOAc/hexanes). Compound 311 was obtained as a colorless oil (0.59 g, 86%). 311: [α]$_D$=−9.1 (CHCl$_3$, c 1.06); IR 2955, 2930, 2858, 1614, 1515, 1472, 1250, 1095, 836, 775 cm$^{-1}$; $^1$H NMR (400 MHz, CDCl$_3$) δ 7.30 (2H, d, J=8.8 Hz), 6.88 (2H, d, J=8.8 Hz), 4.53 (1H, d, J=11.2 Hz), 4.43 (1H, d, J=11.2 Hz), 3.98 (1H, app.dt, J=3.2, 8.0 Hz), 3.81 (3H, s), 3.66–3.78 (3H, m), 2.19 (1H, ddd, J=2.8, 6.8, 16.8 Hz), 2.07 (1H, ddd, J=2.8, 8.4, 16.8 Hz), 1.96 (1H, t, J=2.8 Hz), 1.86–1.93 (1H, m), 1.83 (1H, app.ddt, J=6.0, 6.0, 12.0 Hz), 1.74 (1H, app.ddt, J=8.4, 8.4, 12.0 Hz), 1.64 (1H, ddd, J=4.0, 8.8, 14.0 Hz), 1.50 (1H, ddd, J=4.0, 8.0, 14.0 Hz), 0.99 (3H, d, J=6.8 Hz), 0.92 (9H, s), 0.90 (9H, s), 0.08 (3H, s), 0.07 (6H, s), 0.06 (3H, s); $^{13}$C NMR (75 MHz, CDCl$_3$) δ 159.2, 131.3, 129.3, 113.9, 83.9, 73.5, 72.1, 70.5, 69.2, 59.8, 55.5, 55.4, 38.7, 38.5, 38.0, 26.2, 21.6, 18.5, 18.3, 14.9, −4.03, −4.04, −5.09, −5.1; MS (CI) 535 ([MH]$^+$, 6), 534 (7), 533 (6), 519 (2), 121 (100). HRMS Calcd for C$_{30}$H$_{55}$O$_4$Si$_2$ (MH$^+$): 535.3639. Found: 535.3548.

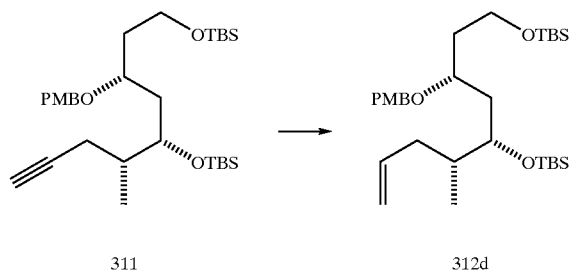

312d: [α]$_D$=−10.7 (CHCl$_3$, c 0.3); IR 2960, 2926, 2860, 1517, 1250, 1090, 833, 777 cm$^{-1}$; $^1$H NMR (400 MHz, CDCl$_3$) δ 7.25 (2H, d, J=8.8 Hz), 6.87 (2H, d, J=8.8 Hz), 5.69–5.82 (1H, m), 4.95–5.02 (2H, m), 4.50 (1H, d, J=10.8 Hz), 4.40 (1H, d, J=10.8 Hz), 3.87 (1H, ddd, J=3.2, 3.2, 8.8 Hz), 3.80 (3H, s), 3.60–3.79 (3H, m), 2.05 (1H, ddd, J=6.4, 6.4, 14.0 Hz), 1.64–1.89 (4H, m), 1.62 (1H, ddd, J=2.8, 8.8, 14.0 Hz), 1.46 (1H, ddd, J=3.6, 8.8, 14.0 Hz), 0.90 (9H, s), 0.88 (9H, s), 0.86 (3H, d, J=7.2 Hz), 0.06 (3H, s), 0.05 (3H, s), 0.03 (3H, s), 0.026 (3H, s); $^{13}$C NMR (75 MHz, CDCl$_3$) δ 159.2, 138.0, 131.5, 129.2, 115.8, 113.9, 73.8, 72.5, 70.6, 59.9, 55.5, 39.1, 38.1, 38.0, 37.4, 26.2, 18.5, 18.3, 14.2, −3.9, −4.1, −5.08, −5.10. HRMS Calcd for C$_{30}$H$_{56}$O$_4$Si$_2$Li (MLi$^+$): 543.3877. Found: 543.3875.

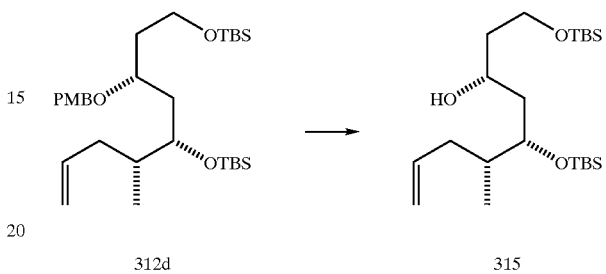

315: [α]$_D$=−23.7 (CHCl$_3$, c 0.6); IR 3528, 2956, 2930, 2858, 1472, 1256, 1084, 836, 775 cm$^{-1}$; $^1$H NMR (400 MHz, CDCl$_3$) δ 5.77 (1H, dddd, J=6.8, 6.8, 10.4, 16.8 Hz), 4.96–5.03 (2H, m), 3.96–4.04 (1H, m), 3.75–3.91 (3H, m), 3.33 (1H, d, J=2.0 Hz), 2.12–2.20 (1H, m), 1.57–1.84 (4H, m), 1.42–1.52 (2H, m), 0.90 (18H, s), 0.85 (3H, d, J=6.4 Hz), 0.10 (3H, s), 0.07 (9H, s); $^{13}$C NMR (75 MHz, CDCl$_3$) δ 137.9, 115.8, 72.8, 68.0, 62.4, 39.8, 39.2, 39.0, 37.9, 26.2, 26.1, 18.4, 18.3, 14.1, −4.2, −4.3, −5.26, −5.34. HRMS Calcd for C$_{22}$H$_{49}$O$_3$Si$_2$ (MH$^+$): 417.3220. Found: 417.3238.

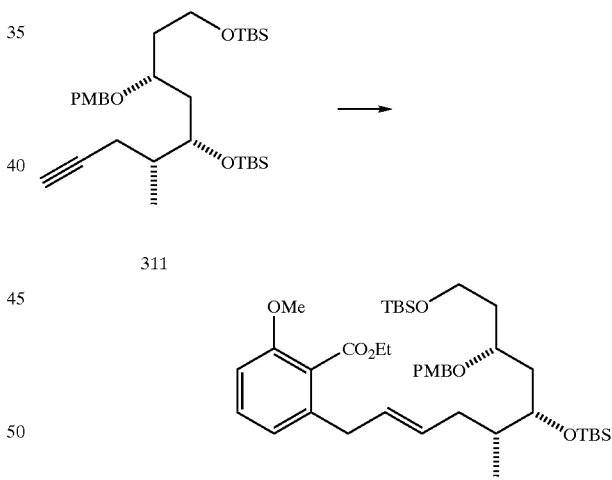

314: HRMS Calcd for C$_{41}$H$_{68}$O$_7$Si$_2$Li (MLi$^+$): 735.4664. Found: 735.4635.

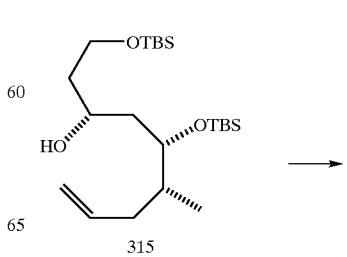

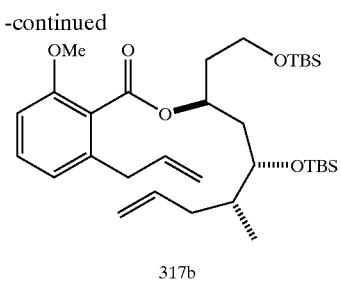

317b

317b: [α]$_D$=−8.5 (CHCl$_3$, c 0.33); IR 2957, 2930, 2857, 1728, 1586, 1471, 1258, 1068, 836, 774 cm$^{-1}$; $^1$H NMR (400 MHz, CDCl$_3$) δ 7.27 (1H, dd, J=7.6, 8.0 Hz), 6.82 (1H, d, J=7.6 Hz), 6.77 (1H, d, J=8.0 Hz), 5.92 (1H, dddd, J=6.8, 6.8, 9.6, 17.6 Hz), 5.78 (1H, dddd, J=7.2, 7.2, 10.4, 17.7 Hz), 5.31–5.38 (1H, m), 4.96–5.09 (4H, m), 3.81 (3H, s), 3.69–3.80 (3H, m), 3.33–3.37 (2H, m), 2.12–2.20 (1H, m), 1.74–2.00 (6H, m), 0.91 (3H, d, J=7.2 Hz), 0.902 (9H, s), 0.897 (9H, s), 0.06 (3H, s), 0.06 (6H, s), 0.05 (3H, s), 0.04 (3H, s); $^{13}$C NMR (75 MHz, CDCl$_3$) δ 167.7, 156.5, 138.4, 138.0, 136.5, 130.4, 124.4, 121.7, 116.7, 115.8, 109.0, 72.6, 71.0, 59.9, 56.0, 38.1, 37.9, 37.6, 37.5, 36.4, 26.15, 26.12, 18.5, 16.3, 15.5, −4.1, −4.2, −5.09, −5.13. HRMS Calcd for C$_{33}$H$_{58}$O$_5$Si$_2$Li (MLi$^+$): 597.3983. Found: 597.3985.

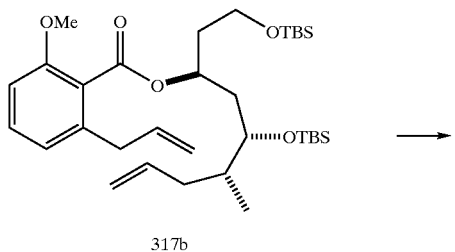

317b

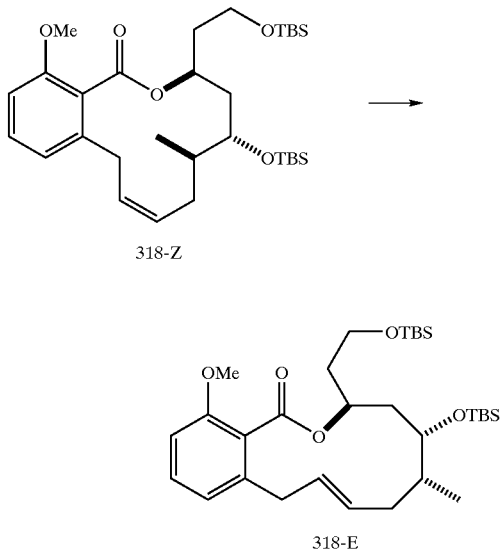

318-Z

318-E

To a solution of ester 317b (13.5 g, 0.0203 mmol) in CH$_2$Cl$_2$ (1 mL) was added at rt a solution of Cl$_2$[(Cy)$_3$P]$_3$Ru=CHPh (3.3 mg, 0.00406 mmol) in CH$_2$Cl$_2$ (5 mL) over a 3 h period via syringe pump. After evaporation of the solvent, the residue was purified by FC (2% EtOAc/hexanes) to give 2.2 mg of E-benzolactone 318-E (19%) and 9.4 mg of Z-benzolactone 318-Z (81%). 318-Z: [α]$_D$=−81.1 (CHCl$_3$, c 0.47); IR 2928, 2856, 1718, 1588, 1471, 1283, 1255, 1082, 834, 772 cm$^{-1}$; $^1$H NMR (400 MHz, CDCl$_3$) δ 7.29 (1H, t, J=8.0 Hz), 6.88 (1H, d, J=8.0 Hz), 7.76 (1H, d, J=8.0 Hz), 5.37–5.46 (1H, m), 5.28–5.35 (2H, m), 3.92–3.97 (1H, m), 3.80 (3H, s), 3.59–3.79 (3H, m), 3.03 (1H, br d, J=14.4 Hz), 2.20–2.38 (2H, m), 1.98–2.08 (1H, m), 1.74–1.88 (3H, m), 1.52–1.59 (1H, m), 0.91 (3H, d, J=7.2 Hz), 0.90 (9H, s), 0.87 (9H, s), 0.06 (3H, s), 0.05 (3H, s), 0.04 (3H, s), 0.03 (3H, s); $^{13}$C NMR (75 MHz, CDCl$_3$) δ 168.6, 156.2, 139.3, 130.5, 129.9, 128.4, 124.6, 121.9, 108.5, 77.4, 72.0, 60.4, 55.8, 39.9, 36.7, 31.8, 29.9, 26.2, 26.1, 18.4, 18.3, −3.4, −4.0, −5.1. HRMS Calcd for C$_{31}$H$_{55}$O$_5$Si$_2$ (MH$^+$): 563.3588. Found: 563.3572. 318-E: [α]$_D$=−11.8 (CHCl$_3$, C 0.11); IR $^1$H NMR (400 MHz, CDCl$_3$) 7.25 (1H, dd, J=8.4, 8.0 Hz), 6.80 (1H, d, J=8.4 Hz), 6.78 (1H, d, J=8.0 Hz), 5.42–5.54 (1H, m), 5.40 (1H, ddd, J=2.8, 8.0, 15.2 Hz), 5.23–5.28 (1H, m), 3.88 (1H, dd, J=6.0, 6.0 Hz), 3.80 (3H, s), 3.79–3.84 (1H, m), 3.68–3.75 (2H, s), 3.14 (1H, br d, J=15.2 Hz), 2.39–2.46 (1H, m), 2.20–2.30 (1H, m), 1.95–2.04 (1H, m), 1.76–1.90 (3H, m), 1.52–1.60 (1H, m), 0.93 (3H, d, J=7.2 Hz), 0.91 (9H, s), 0.88 (9H, s), 0.073 (3H, s), 0.068 (3H, s), 0.04 (3H, s), 0.02 (3H, s); $^{13}$C NMR (75 MHz, CDCl$_3$) δ 168.7, 156.8, 140.2, 130.5, 128.5, 124.5, 122.7, 109.4, 77.4, 71.8, 60.3, 55.8, 38.5, 37.2, 36.3, 29.9, 26.2, 26.1, 18.5, 18.3, −3.8, −4.0, −5.0.

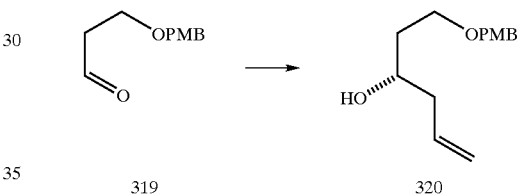

319    320

B-methoxy diisopinocampheylborane (13.7 g; 43.25 mmol) was dissolved in Et$_2$O (80 mL), cooled to −78° C., followed by the dropwise addition of allylmagnesium bromide (1.0M in Et$_2$O, 41.7 mL). After stirring for 20 min at −78° C. and warming to rt over a 1.5 h period, a precipitate formed (magnesium salts) and an additional 150 mL of Et$_2$O was added. The precipitate was filtered under inert atmosphere and washed with Et$_2$O (50 mL). The filtrate was cooled to −78° C. and a solution of aldehyde 319 (6.0 g, 30.89 mmol) in Et$_2$O (40 mL) was added dropwise. After stirring for 4 h at the same temperature, the mixture was treated with aqueous NaOH (2.0 N, 25 mL) and allowed to come to rt. Aqueous H$_2$O$_2$ (30%, 28 mL) was slowly added and stirring was continued overnight. The aqueous layer was extracted with Et$_2$O (3×) and the combined organics dried over MgSO$_4$ and concentrated in vacuo. FC (5% 10% 20% EtOAc/hexanes) afforded 6.0 g (25.4 mmol, 82%) of allyl alcohol 320. 320: [α]$_D$=−3.9 (c 1.02, CHCl$_3$); IR 3445, 2936, 2863, 1613, 1514, 1248, 1090, 1034 cm$^{-1}$; $^1$H NMR (400 MHz, CDCl$_3$) δ 7.25 (2H, d, J=8.8 Hz), 6.87 (2H, d, J=8.8 Hz), 5.83 (1H, dddd, J=7.2, 7.2, 10.2, 17.0 Hz), 5.10 (1H, br d, J=17.0), 5.09 (1H, br d, J=10.2 Hz), 4.45 (2H, s), 3.82–3.89 (1H, m), 3.80 (3H, s), 3.68 (1H, app.dt, J=5.6, 9.6 Hz), 3.61 (1H, ddd, J=5.6, 7.2, 9.6 Hz), 2.90 (1H, br s), 2.40 (2H, br app.t, J=7.0 Hz), 1.72–1.77 (2H, m); $^{13}$C NMR (75 MHz, CDCl$_3$) δ 159.3, 135.0, 130.1, 129.4, 117.6, 114.0, 73.2, 70.7, 68.9, 55.5, 42.2, 36.1; HRMS Calcd for C$_{14}$H$_{21}$O$_3$ (MH$^+$): 237.1491. Found: 237.1495.

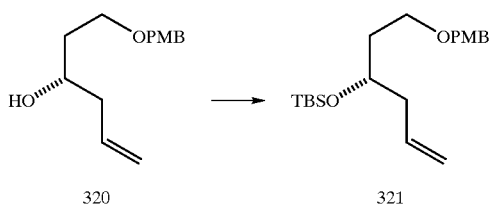

To a solution of allyl alcohol 320 (12 g, 50.78 mmol), imidazole (10.48 g, 152.34 mmol) and DMAP (200 mg) in DMF (200 mL) was added tert.butyldimethylsilyl chloride (23.4 g, 152.34 mmol). After stirring for 16 h at rt, the mixture was poured into water, extracted with $Et_2O$ (3×), and the combined organics washed with brine, dried over $MgSO_4$ and concentrated in vacuo. FC (2% EtOAc/hexanes) yields 16.7 g of silylether 321 (94%) as an oil. 321: $[α]_D$=14.8 (c 1.51, $CHCl_3$); IR 2929, 2856, 1612, 1514, 1248, 1093, 1040, 835, 774 $cm^{-1}$; $^1H$ NMR (400 MHz, $CDCl_3$) δ 7.25 (2H, d, J=8.8 Hz), 6.87 (2H, d, J=8.8 Hz), 5.75–5.86 (1H, m), 5.00–5.05 (2H, m), 4.44 (1H, d, J=11.6 Hz), 4.38 (1H, d, J=11.6 Hz), 3.86–3.91 (1H, m), 3.80 (3H, s), 3.50 (2H, app.t, J=6.4 Hz), 2.16–2.28 (2H, m), 1.64–1.81 (2H, m), 0.88 (9H, s), 0.05 (3H, s), 0.04 (3H, s); $^{13}C$ NMR (75 MHz, $CDCl_3$) δ 159.2, 135.1, 130.8, 129.4, 117.1, 113.9, 72.8, 69.2, 67.0, 55.5, 42.6, 37.0, 26.2, 18.4, −4.0, −4.3; MS (CI) 309 ($[M-C_3H_5]^+$, 8), 121 (100). Anal. Calcd for $C_{20}H_{34}O_3Si$: C, 68.52; H, 9.78. Found: C, 68.77; H, 9.78.

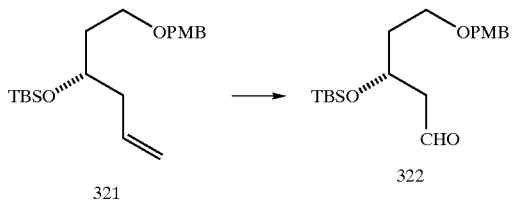

To a stirred solution of silylether 321 (22.2 g, 57.0 mmol) in acetone (220 mL) at 0° C. was added N-methyl-morpholine-N-oxide (50% wt in water, 16.0 g, 68 mmol) followed by $OsO_4$ (0.1 M in t-BuOH, 5.7 mL). The yellow solution was stirred for 4 h at 0° C. and 12 h at rt followed by concentration in vacuo. The residue was partitioned between EtOAc (200 mL) and brine (350 mL) to which aqueous HCl (1.0 N, 55 mL) and $Na_2S_2O_3$ (10.0 g) were added. Extraction of the aqueous layer with EtOAc (3×), drying of the combined organics over $MgSO_4$ and concentration in vacuo, afforded an oil which was purified by FC (30%→50% EtOAc/hexanes) afforded 21 g of a mixture of diol diastereomers which was used in the next step without further purification.

To a solution of the diol mixture (21 g, 54.6 mmol) in $CH_2Cl_2$ (300 mL) was added at 0° C. silicagel-supported $NaIO_4$ (11.3 g, 0.582 mmol/g silicagel). After stirring for 2 h at rt, the mixture was filtered, concentrated and purified by FC (10% EtOAc/hexanes) to give 18.0 g of aldehyde 322 (53.04 mmol, 97%). 322: $[α]_D$=5.6 (c 2.38, $CHCl_3$); IR 2955, 2930, 2857, 1726, 1613, 1514, 1250, 1096, 1037, 837, 777 $cm^{-1}$; $^1H$ NMR (400 MHz, $CDCl_3$) δ 9.79 (1H, app.t, J=2.4 Hz), 7.25 (2H, d, J=9.2 Hz), 6.88 (2H, d, J=9.2 Hz), 4.43 (1H, d, J=11.2 Hz), 4.38 (1H, d, J=11.2 Hz), 4.37 (1H, app.dt, J=6.0, 6.0 Hz), 3.81 (3H, s), 3.51 (2H, app.t, J=6.0 Hz), 2.58 (1H, ddd, J=2.0, 5.6, 16.0 Hz), 2.51 (1H, ddd, J=2.8, 5.6, 16.0 Hz), 1.77–1.90 (2H, m), 0.86 (9H, s), 0.07 (3H, s), 0.06 (3H, s); $^{13}C$ NMR (75 MHz, $CDCl_3$) δ 202.1, 159.2, 130.4, 129.4, 113.9, 72.9, 66.2, 65.9, 55.5, 51.3, 37.9, 26.0, 18.3, −4.27, −4.32; HRMS Calcd for $C_{19}H_{33}O_4Si$ ($MH^+$): 353.2148. Found: 353.2165.

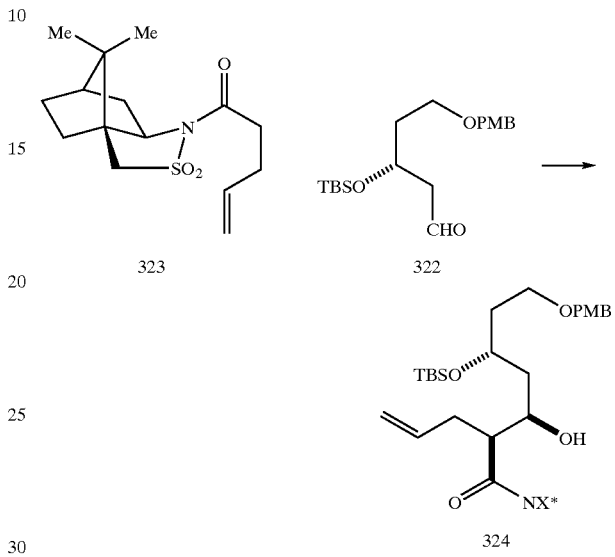

To a solution of N-(4-pentenyl)-bornanesultam 323 (18.3 g, 61.27 mmol) in $CH_2Cl_2$ (240 mL) was added at −78° C. $TiCl_4$ (6.44 mL, 58.71 mmol), followed by the dropwise addition of $^iPr_2NEt$ (11.2 mL, 63.82 mmol). The deep red solution was stirred for 1 h at −78° C. and a solution of aldehyde 322 (18.0 g, 51.06 mmol) in $CH_2Cl_2$ (60 mL) was added dropwise. Stirring was continued for 2 h at the same temperature and the mixture was quenched by the addition of phosphate buffer (pH 7.0, 150 mL), saturated aqueous $NaHCO_3$ (150 mL) and $H_2O$. The aqueous layer was extracted with $CH_2Cl_2$ (3×) and the combined organics were dried over $MgSO_4$ and concentrated in vacuo. The residue was purified by FC (15% EtOAc/hexanes) to give 30.4 g of aldol product 324 (46.8 mmol, 92%). 324: $[α]_D$=45.9 (c 2.56, $CHCl_3$); IR 3515, 2956, 2856, 1689, 1613, 1514, 1335, 1249, 1134, 1095, 1038, 836, 776 $cm^{-1}$; $^1H$ NMR (400 MHz, $CDCl_3$) δ 7.25 (2H, d, J=8.8 Hz), 6.87 (2H, d, J=8.8 Hz), 5.79–5.90 (1H, m), 5.08 (1H, br d, J=17.2 Hz), 4.97 (1H, br d, J=10.0 Hz), 4.42 (1H, d, J=12 Hz), 4.38 (1H, d, J=12.0 Hz), 4.02–4.11 (2H, m), 3.85 (1H, app.t, J=6.4 Hz), 3.80 (3H, s), 3.51 (2H, app.t, J=6.4 Hz), 3.49 (1H, d, J=13.6 Hz), 3.40 (1H, d, J=13.6 Hz), 3.27 (1H, d, J=1.6 Hz), 3.21 (1H, app.dt, J=6.0, 8.0 Hz), 2.50–2.60 (2H, m), 1.99–2.05 (2H, m), 1.72–1.94 (6H, m), 1.59 (1H, ddd, J=2.0, 6.4, 14.4 Hz), 1.30–1.39 (2H, m), 1.15 (3H, s), 0.96 (3H, s), 0.87 (9H, s), 0.09 (3H, s), 0.07 (3H, s); $^{13}C$ NMR (75 MHz, $CDCl_3$) δ 174.4, 159.1, 135.2, 130.8, 129.3, 117.5, 113.9, 72.8, 69.5, 69.4, 66.7, 65.5, 55.5, 53.5, 50.6, 48.3, 47.9, 44.9, 41.8, 38.7, 37.2, 33.6, 33.2, 26.7, 26.2, 21.2, 20.3, 18.3, −4.2. Anal. Calcd for $C_{34}H_{55}NO_7SSi$: C, 62.83; H, 8.53; N, 2.16. Found: C, 63.07; H, 8.67; N, 2.89.

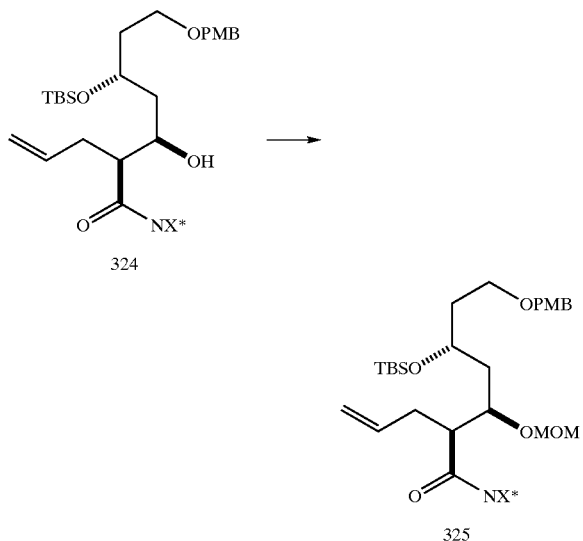

To a suspension of NaI (7.46 g, 49.23 mmol) in DME (45 mL) was added chloromethyl methyl ether (4.67 mL, 61.54 mmol). After stirring for 15 min at rt a solution of aldol 324 (8.0 g, 12.31 mmol) in DME (65 mL) was added followed by $^i$Pr$_2$NEt (11.87 mL, 67.7 mL) and stirring was continued for 12 h at reflux. The mixture was quenched by the addition of saturated aqueous NaHCO$_3$ (60 mL) and water (250 mL). The aqueous layer was extracted with Et$_2$O (4×), the coinbined organics washed with HCl (1.0 M), and brine and dried over MgSO$_4$. After concentration in vacuo, the residue was purified by FC (10% EtOAc/hexanes) to give 7.8 g of MOM-ether 325 (11.2, 91%). 325: $[\alpha]_D$=75.3 (c 3.91, CHCl$_3$); IR 2956, 2856, 1691, 1613, 1514, 1334, 1249, 1134, 1098, 1030, 837, 775 cm$^{-1}$; $^1$H NMR (400 MHz, CDCl$_3$) δ 7.25 (2H, d, J=8.0 Hz), 6.85 (2H, d, J=8.0 Hz), 5.77–5.88 (1H, m), 5.06 (1H, d, J=16.4 Hz), 4.96 (1H, d, J=10.0 Hz), 4.66 (1H, d, J=7.2 Hz), 4.61 (1H, d, J=7.2 Hz), 4.42 (1H, d, J=7.2 Hz), 4.38 (1H, d, J=7.2 Hz), 3.98 (1H, m), 3.85 (1H, dd, J=12.8, 6.0 Hz), 3.78–3.83 (1H, m), 3.80 (3H, s), 3.54 (2H, app.t, J=6.4 Hz), 3.47 (1H, d, J=14.0 Hz), 3.40 (1H, d, J=14.0 Hz), 3.28–3.34 (1H, m), 3.32 (3H, s), 2.44–2.56 (2H, m), 1.80–2.06 (7H, m), 1.58–1.70 (2H, m), 1.24–1.38 (2H, m), 1.14 (3H, s), 0.95 (3H, s), 0.87 (9H, s), 0.08 (3H, s), 0.04 (3H, s); $^{13}$C NMR (75 MHz, CDCl$_3$) δ 172.9, 159.0, 135.1, 131.0, 129.3, 117.5, 113.8, 97.3, 75.9, 72.6, 67.02, 66.98, 65.6, 56.5, 55.5, 53.5, 50.2, 48.2, 47.9, 44.9, 42.9, 38.7, 36.3, 35.0, 33.2, 26.7, 26.2, 21.2, 20.3, 18.4, −3.9, −4.5. HRMS Calcd for C$_{36}$H$_{59}$NO$_8$SSiLi (MLi$^+$): 700.3891. Found: 700.3879.

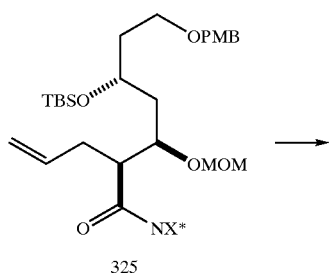

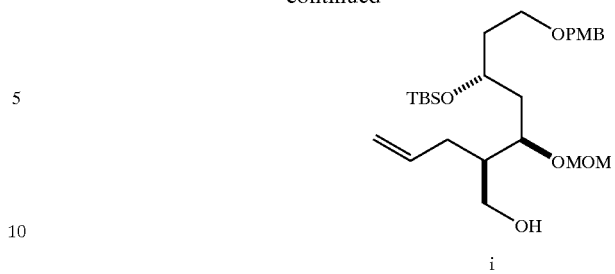

To a solution of MOM-ether 325 (5.2 g, 7.49 mmol) in THF (80 mL) at −78° C. was added dropwise LiEt$_3$BH (1.0 M in THF, 37.5 mL). The mixture was allowed to come to rt and stirring was continued for 3 h. The reaction was quenched by the addition of aqueous NaOH (2.0 N, 50 mL) and water (400 mL). The aqueous layer was extracted with Et$_2$O (3×), washed with HCl (1.0 N) and brine, and dried over MgSO$_4$. The resulting residue was purified by FC (20% EtOAc/hexanes) to give 3.3 g of alcohol i (6.84 mmol, 91%). i: $[\alpha]_D$=8.7 (c 1.0, CHCl$_3$); IR 3468, 2953, 2930, 2857, 1613, 1514, 1250, 1094, 1037, 836, 776 cm1; $^1$H NMR (400 MHz, CDCl$_3$), δ 7.24 (2H, d, J=8.4 Hz), 6.86 (2H, d, J=8.4 Hz), 5.71–5.81 (1H, m), 5.03 (1H, br d, J=16.8 Hz), 5.00 (1H, br d, J=9.5 Hz), 4.64 (1H, d, J=6.8 Hz), 4.60 (1H, d, J=6.8 Hz), 4.42 (1H, d, J=11.6 Hz), 4.38 (1H, d, J=11.6 Hz), 3.94–4.00 (1H, m), 3.80–3.85 (1H, m), 3.79 (3H, s), 3.57–3.69 (2H, m), 3.52 (2H, app.t, J=6.4 Hz), 3.35 (3H, s), 2.75 (1H, br s), 1.91–2.06 (3H, m), 1.60–1.90 (4H, m), 0.88 (9H, s), 0.07 (3H, s), 0.05 (3H, s); $^{13}$C NMR (75 MHz, CDCl$_3$) δ 159.1, 136.8, 130.7, 129.4, 116.5, 113.8, 96.4, 76.9, 72.9, 67.0, 66.7, 63.6, 56.3, 55.5, 42.9, 38.9, 37.0, 31.9, 26.2, 18.3, −4.0, −4.3. Anal. Calcd for C$_{26}$H$_{46}$O$_6$Si: C, 64.69; H, 9.60. Found: C, 64.66; H, 10.04.

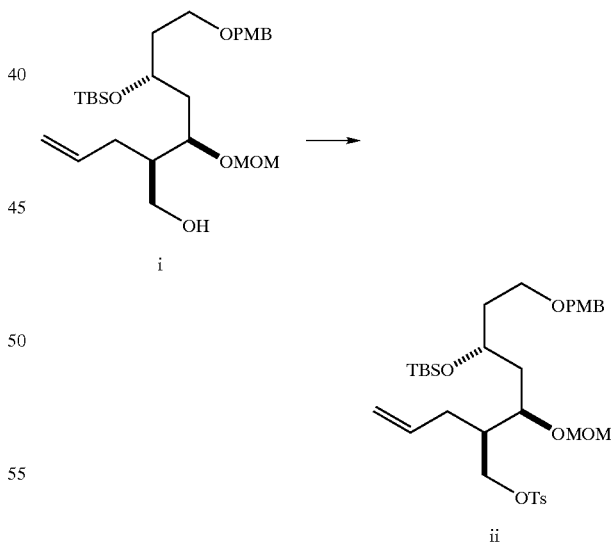

A solution of alcohol i (2.0 g, 4.14 mmol), TsCl (3.99 g, 20.7 mmol), DMAP (100 mg) and NEt$_3$ (3.46 mL, 24.86 mmol) in CH$_2$Cl$_2$ (40 mL) was stirred at rt for 16 h and at 35° C. for 5 h. The mixture was poured into water, extracted with Et$_2$O (3×) and the combined organics washed with water and brine. After drying over MgSO$_4$ and concentration in vacuo, the residue was purified by FC (10%→15% EtOAc/hexanes) to give 2.4 g of tosylate ii (3.77, 91%). ii:

[α]$_D$=17.3 (c 1.2, CHCl$_3$); IR 2953, 2930, 2856, 1613, 1514, 1464, 1365, 1249, 1190, 1178, 1097, 1037, 836, 776 cm$^{-1}$; $^1$H NMR (400 MHz, CDCl$_3$) δ 7.79 (2H, d, J=8.4 Hz), 7.34 (2H, d, J=8.4 Hz), 7.24 (2H, d, J=8.8 Hz), 6.87 (2H, d, J=8.8 Hz), 5.60–5.70 (1H, m), 4.95–5.01 (2H, m), 4.50 (2H, s), 4.42 (1H, d, J=11.2 Hz), 4.38 (1H, d, J=11.2 Hz), 4.10 (1H, dd, J=6.0, 9.6 Hz), 4.01 (1H, dd, J=5.6, 9.6 Hz), 3.88–3.94 (1H, m), 3.81 (3H, s), 3.67–3.71 (1H, m), 3.50 (2H, app.t, J=6.0 Hz), 3.25 (3H, s), 2.45 (3H, s), 2.04–2.10 (2H, m), 1.98–2.04 (1H, m), 1.76–1.84 (1H, m), 1.59–1.68 (3H, m), 0.87 (9H, s), 0.03 (3H, s), 0.01 (3H, s); $^{13}$C NMR (75 MHz, CDCl$_3$) δ 159.1, 144.7, 135.7, 133.0, 130.6, 129.8, 129.3, 128.0, 117.1, 113.7, 96.3, 74.8, 72.7, 69.9, 66.9, 66.6, 55.9, 55.4, 41.4, 39.1, 36.8, 31.2, 26.1, 21.8, 18.2, −4.1, −4.4. Anal. Calcd for C$_{33}$H$_{52}$O$_8$SSi: C, 62.23; H, 8.23. Found: C, 60.34; H, 7.75.

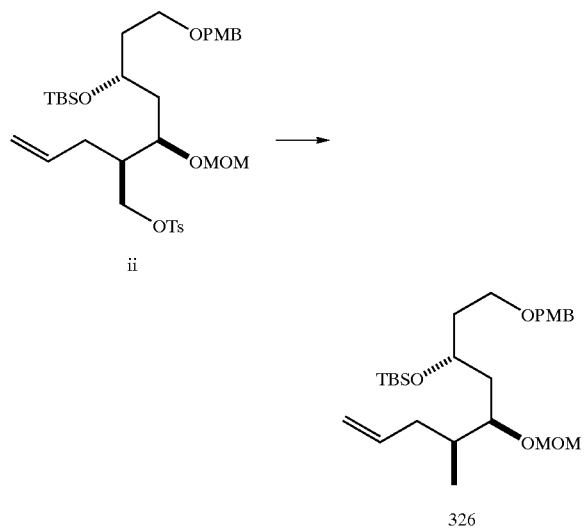

ii

To a stirred solution of tosylate ii (2.3 g, 3.61 mmol) in THF (70 mL) was added at 0° C. LiEt$_3$BH (1.0 M in THF, 14.4 mL). After stirring for 18 h at rt, aqueous NaOH (2.0 N, 12 mL) and water (400 mL) were added and an extraction was performed with Et$_2$O (3×). The combined organics were dried over MgSO$_4$, concentrated in vacuo and the residue purified by FC (5% EtOAc/hexanes) to give 1.55 g of 326 (3.32 mmol, 92%) as an oil. 326: [α]$_D$=34.8 (c 2.45, CHCl$_3$); IR 2955, 2930, 2856, 1613, 1514, 1249, 1096, 1038, 836, 775 cm$^{-1}$; $^1$H NMR (400 MHz, CDCl$_3$) δ 7.25 (2H, d, J=8.4 Hz), 6.86 (2H, d, J=8.4 Hz), 5.69–5.79 (1H, m), 4.99 (1H, br d, J=17.6 Hz), 4.98 (1H, br d, J=9.6 Hz), 4.62 (1H, d, J=6.8 Hz), 4.57 (1H, d, J=6.8 Hz), 4.43 (1H, d, J=11.2 Hz), 4.38 (1H, d, J=11.2 Hz), 3.96–4.02 (1H, m), 3.80 (3H, s), 3.49–3.55 (3H, m), 3.33 (3H, s), 2.01–2.10 (1H, m), 1.80–1.93 (3H, m), 1.61–1.70 (2H, m), 1.51 (1H, ddd, J=2.8, 8.4, 13.6 Hz), 0.88 (9H, s), 0.87 (3H, d, J=5.2 Hz), 0.06 (3H, s), 0.04 (3H, s); $^{13}$C NMR (75 MHz, CDCl$_3$) δ 159.1, 137.4, 130.8, 129.3, 116.0, 113.8, 95.9, 78.2, 72.8, 67.3, 66.9, 56.0, 55.4, 38.3, 37.5, 36.8, 36.1, 26.2, 18.3, 14.4, −4.0, −4.4. Anal. Calcd for C$_{26}$H$_{46}$O$_5$Si: C, 66.91; H, 9.93. Found: C, 66.52; H, 10.35.

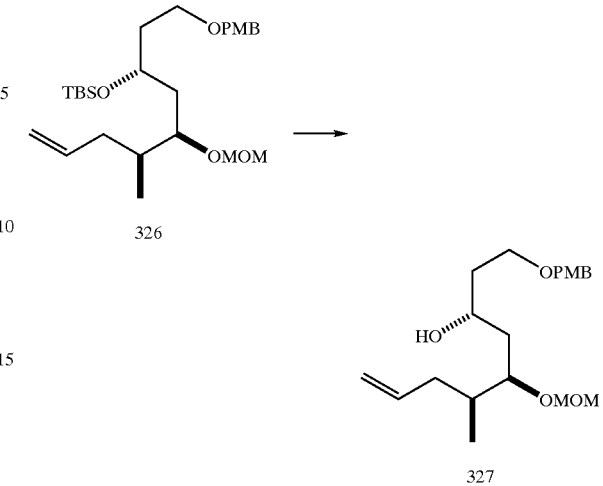

To a solution of silylether 326 (1.49 g, 3.19 mmol) in THF (10 mL) was added Bu$_4$NF (1.0 M in THF, 19.1 mL). After stirring for 12 h at rt, the mixture was quenched with water (150 mL). The aqueous layer was extracted with Et$_2$O (3×) and the combined organics were dried over MgSO$_4$ and concentrated in vacuo. The residue was purified by FC (25% EtOAc/hexanes) to give 1.1 g of alcohol 327 (3.12 mmol, 98%). 327: [α]$_D$=33.12 (c 2.6, CHCl$_3$); IR 3494, 2934, 1613, 1514, 1248, 1095, 1036 cm$^{-1}$; $^1$H NMR (400 MHz, CDCl$_3$) δ 7.26 (2H, d, J=8.4 Hz), 6.87 (2H, d, J=8.4 Hz), 5.69–5.80 (1H, m), 5.00 (1H, br d, J=15.6 Hz), 4.99 (1H, br d, J=10.8 Hz), 4.71 (1H, d, J=6.8 Hz), 4.63 (1H, d, J=6.8 Hz), 4.45 (2H, s), 3.91–3.98 (1H, m), 3.80 (3H, s), 3.56–3.70 (3H, m), 3.53 (1H, d, J=1.6 Hz), 3.39 (3H, s), 2.00–2.06 (1H, m), 1.81–1.96 (2H, m), 1.59–1.80 (3H, m), 1.53 (1H, app.dt, J=3.6, 14.4 Hz), 0.89 (3H, d, J=6.8 Hz); $^{13}$C NMR (75 MHz, CDCl$_3$) δ 159.2, 137.1, 130.4, 129.4, 116.1, 113.9, 95.7, 80.7, 73.0, 69.6, 68.0, 56.2, 55.5, 37.7, 37.2, 36.7, 35.7, 14.1. Anal. Calcd for C$_{20}$H$_{32}$O$_5$: C, 68.15; H, 9.15. Found: C, 68.30; H, 9.47.

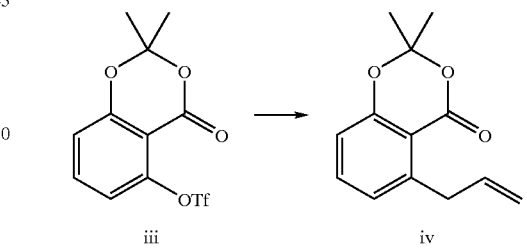

iii                                            iv

To a stirred suspension of 2,2-dimethyl-5-(trifluoromethanesulfonyl)-benzo[1,3]dioxin-4-one (iii) (2.0 g, 6.13 mmol), anhydrous LiCl (0.8 g, 18.4 mmol), Pd$_2$(dba)$_3$ (112 mg, 0.12 mmol), and tri-(2-furyl)phosphine (115 mg, 0.49 mmol) in 4-methyl-2-pyrrolidinone (10 mL) was added allyltributyltin (2.35 mL, 7.36 mmol). After stirring for 48 h at rt, saturated aqueous KF (20 mL) was added and an extraction was performed with Et$_2$O (3×). The combined organics were dried over MgSO$_4$, concentrated in vacuo and the residue was purified by FC (4% EtOAc/hexanes) to give 1.3 g of 5-allyl-2,2-dimethyl-benzo[1,3]dioxin-4-one (iv) which was slightly impure.

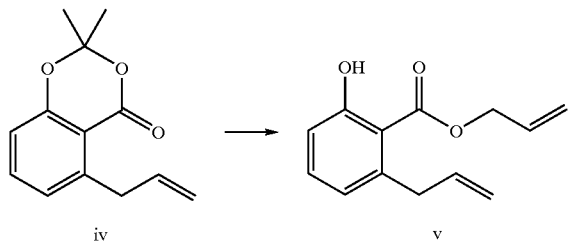

To a stirred solution of allyl alcohol (2.25 mL, 32.8 mL) in THF (10 mL) was added dropwise EtMgBr (1.0M in THF, 29.8 mmol) at 0° C. After stirring for 15 min at rt, a solution of 5-allyl-2,2-dimethyl-benzo[1,3]dioxin-4-one (iv) (1.3 g, 5.96 mmol) in THF (5 mL) was added and stirring was continued for 5 h at rt and 2.5 h at 60° C. Diethyl ether (50 mL) was added and the mixture was poured into saturated aqueous NH$_4$Cl (20 mL) and water (50 mL). An extraction was performed with Et$_2$O (3×) and the combined organics were dried over MgSO$_4$ and concentrated in vacuo. The residue was purified by FC (2% Et$_2$O/pentane) to give 1.2 g of allyl 6-allyl-2-hydroxybenzoate (v) (90%) as a colorless oil. v: IR 2918, 2850, 1663, 1607, 1450, 1248, 1219,909,733 cm$^{-1}$; $^1$H NMR (400 MHz, CDCl$_3$) δ 7.33 (1H, app.t, J=7.3 Hz), 6.88 (1H, br d, J=7.3 Hz), 6.75 (1H, d, J=7.3 Hz), 5.92–6.09 (2H, m), 5.43 (1H, br d, J=14.0 Hz), 5.33 (1H, br d, J=8.3 Hz), 5.02 (1H, br d, J=10.0 Hz), 4.96 (1H, br d, J=16.5 Hz), 4.86 (2H, br d, J=6.7 Hz), 3.70 (2H, d, J=5.9 Hz); $^{13}$C NMR (75 MHz, CDCl$_3$) o 171.0, 162.8, 143.0, 137.7, 134.6, 131.5, 122.6, 119.8, 116.3, 115.6, 112.2, 66.7, 40.6; MS (El) 218 (M$^+$, 10), 177 (24), 159 (100).

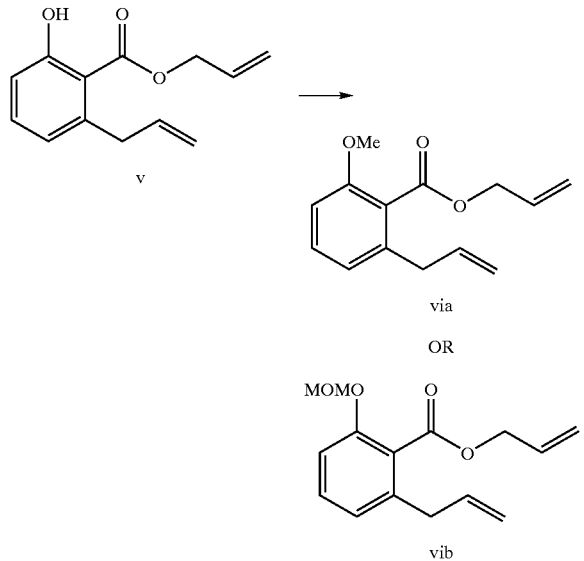

To a solution of allyl 6-allyl-2-hydroxybenzoate (v) (1.2 g, 5.5 mmol) in acetone (12 mL) was added K$_2$CO$_3$ (0.84 g, 6.05 mmol) and MeI (1.04 mL, 16.5 mmol) and the mixture was stirred for 40 h at rt. After filtration of the mixture through a short plug of silicagel, the filtrate was concentrated in vacuo and the residue purified by FC (3% Et$_2$O/pentane) to give 1.25 of allyl 6-allyl-2-methoxybenzoate (via) (98%) as a colorless oil. via: IR 2918, 2850, 1733, 1715, 1585, 1363, 1244, 1223,914,733 cm$^{-1}$; $^1$H NMR (400 MHz, CDCl$_3$) o 7.29 (1H, app:t, J=8.0 Hz), 6.83 (1H, d, J=7.6 Hz), 6.79 (1H, d, J=8.4 Hz), 5.97–6.06 (1H, m), 5.86–5.96 (1H, m), 5.42 (1H, br d, J=17.2 Hz), 5.28 (1H, br d, J=10.4 Hz), 5.05 (1H, br d, J=16.8 Hz), 5.04 (1H, br d, J=10.0 Hz), 4.82 (2H, br d, J=6.0 Hz), 3.82 (3H, s), 3.36 (2H, d, J=6.8 Hz); $^{13}$C NMR (75 MHz, CDCl$_3$) δ 167.8, 156.6, 138.7, 136.4, 132.1, 130.6, 123.6, 121.8, 118.8, 116.5, 109.2, 66.0, 56.1, 37.9; MS (El) 232 (M$^+$, 18), 191 (28), 175 (34), (147 (50), 132 (100), 115 (58). Anal. Calcd for C$_{14}$H$_{16}$O$_3$: C, 72.39; H, 6.94. Found: C, 72.10; H, 6.87. vib (MOM): IR 2956, 2928, 2853, 1732, 1636, 1589, 1466, 1256, 1153, 1031, 919 cm$^{-1}$; $^1$H NMR (400 MHz, CDCl$_3$) δ 7.26 (1H, dd, J=7.6, 8.4 Hz), 7.01 (1H, d, J=7.6 Hz), 6.88 (1H, d, J=8.4 Hz), 6.01 (1H, ddt, J=5.6, 10.0, 17.2 Hz), 5.90 (1H, ddt, J=6.8, 10.4, 16.8 Hz), 5.42 (1H, br d, J=17.2 Hz), 5.28 (1H, br d, J=10.0 Hz), 5.17 (2H, s), 5.06 (1H, br d, J=16.8 Hz), 5.05 (1H, br d, J=10.4 Hz), 4.81 (2H, d, J=5.6 Hz), 3.46 (3H, s), 3.37 (2H, d, J=6.8 Hz); $^{13}$C NMR (75 MHz, CDCl$_3$) δ 167.8, 154.2, 138.8, 136.5, 132.2, 130.7, 124.7, 123.0, 118.9, 116.6, 112.9, 94.9, 66.0, 56.4, 37.8. HRMS Calcd for C$_{15}$H18O$_4$Li (MLi$^+$): 269.1365. Found: 269.1371.

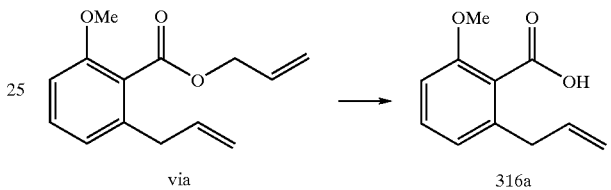

To a stirred solution of allyl 6-allyl-2-methoxybenzoate (via) (1.01 g, 4.35 mmol) and Pd(Ph$_3$)$_4$ in THF (10 mL) was added morpholine (3.5 mL, 43.5 mmol). After stirring for 1 h at rt, the mixture was concentrated in vacuo and the residue purified by FC (2% MeOH/CH$_2$Cl$_2$ containing 0.3% AcOH) to give 0.8 g of benzoic acid derivative 316a (96%). 316a: IR 2919, 2850, 1713, 1586, 1470, 1264, 910, 733 cm$^{-1}$; $^1$H NMR (400 MHz, CDCl$_3$) δ 7.34 (1H, app.t, J=8.0 Hz), 6.89 (1H, d, J=7.6 Hz), 6.85 (1H, d, J=8.4 Hz), 5.92–6.02 (1H, m), 5.06–5.12 (2H, m), 3.90 (3H, s), 3.55 (2H, d, J=6.8 Hz); $^{13}$C NMR (100 MHz, CDCl$_3$) δ 172.1, 156.9, 140.1, 136.6, 131.3, 122.5, 122.0, 116.5, 109.4, 56.4, 38.3; MS (El) 192 (M$^+$, 52), 177 (100). HRMS Calcd for C$_{11}$H$_{13}$O$_3$ (MH$^+$): 193.0865. Found: 193.0864. 316b: HRMS Calcd for C$_{12}$H$_{15}$O$_4$ (MH$^+$): 223.0970. Found: 223.0972.

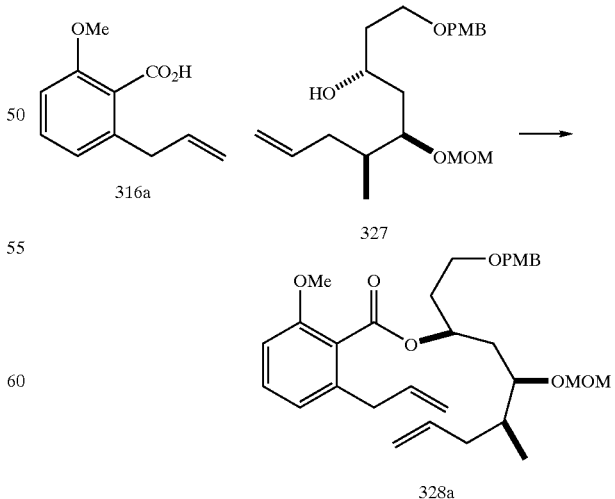

To a stirred solution of alcohol 327 (795 mg, 2.255 mmol), acid 316a (650 mg, 3.38 mmol) and PPh$_3$ (azeotropically dried with benzene, 956 mg, 3.61 mmol) in Et$_2$O (35 mL) was added diethylazodicarboxylate (DEAD, 0.57 mL, 3.61 mmol). After stirring for 12 h at rt and 4 h at reflux, the mixture was partitioned between water (200 mL) and Et$_2$O (100 mL). The aqueous layer was extracted with Et$_2$O (2×) and the combined organics dried over MgSO$_4$ and concentrated in vacuo. The residue was purified by FC (10% EtOAc/hexanes) to afford 1.04 g of ester 328a (1.97 mmol, 88%). 328a: $[\alpha]_D$=−2.44 (c 1.80, CHCl$_3$); IR 2932, 1725, 1585, 1514, 1470, 1266, 1247, 1099, 1071, 1037, 915 cm$^{-1}$; $^1$H NMR (400 MHz, CDCl$_3$) δ 7.28 (1H, app.t, J=7.6 Hz), 7.27 (2H, d, J=8.4 Hz), 6.86 (2H, d, J=8.4 Hz), 6.82 (1H, d, J=7.6 Hz), 6.77 (1H, d, J=8.8 Hz), 5.87–5.97 (1H, m), 5.69–5.79 (1H, m), 5.40–5.47 (1H, m), 5.05 (1H, br d, J=9.0 Hz), 5.03 (1H, br d, J=17.0 Hz), 4.96 (1H, br d, J=18.0 Hz), 4.91 (1H, br d, J=10.4 Hz), 4.73 (1H, d, J=6.8 Hz), 4.71 (1H, d, J=6.8 Hz), 4.47 (1H, d, J=11.6 Hz), 4.42 (1H, d, J=11.6 Hz), 3.80 (3H, s), 3.79 (3H, s), 3.70 (1H, app.quint, J=4.0 Hz), 3.55–3.65 (2H, m), 3.40 (3H, s), 3.35 (2H, d, J=6.8 Hz), 1.97–2.11 (3H, m), 1.87–1.97 (1H, m), 1.77–1.87 (1H, m), 1.66–1.78 (2H, m), 0.90 (3H, d, J=6.8 Hz); $^{13}$C NMR (75 MHz, CDCl$_3$) δ 167.9, 159.2, 156.3, 138.2, 137.2, 136.5, 130.6, 130.3, 129.3, 124.2, 121.7, 116.5, 116.0, 113.9, 108.8, 97.2, 78.5, 72.9, 70.9, 66.7, 56.0, 55.8, 55.5, 37.9, 37.5, 36.8, 35.6, 35.5, 14.0. Anal. Calcd for C$_{31}$H$_{42}$O$_7$: C, 70.70; H, 8.04. Found: C, 70.62; H, 8.32. ent-328b (MOM): $[\alpha]_D$=−3.2 (c 1.50, CHCl$_3$); IR 2932, 1726, 1585, 1513, 1465, 1249, 1095, 1035 cm$^{-1}$; $^1$H NMR (400 MHz, CDCl$_3$) δ 7.23–7.29 (3H, m), 7.03 (1H, d, J=8.0 Hz), 6.85–6.89 (3H, m), 5.93 (1H, dddd, J=6.0, 6.0, 10.4, 16.8 Hz), 5.72 (1H, dddd, J=7.2, 7.2, 10.0, 16.8 Hz), 5.40–5.47 (1H, m), 5.18 (1H, d, J=6.8 Hz), 5.13 (1H, d, J=6.8 Hz), 5.02–5.09 (2H, m), 4.95 (1H, br d, J=16.8 Hz), 4.92 (1H, br d, J=10.4 Hz), 4.73 (1H, d, J=6.8 Hz), 4.70 (1H, d, J=6.8 Hz), 4.47 (1H, d, J=11.6 Hz), 4.42 (1H, d, J=11.6 Hz), 3.80 (3H, s), 3.55–370 (3H, m), 3.44 (3H, s), 3.40 (3H, s), 3.36 (2H, d, J=6.0 Hz), 1.70–2.12 (7H, m), 0.89 (3H, d, J=6.8 Hz); $^{13}$C NMR (75 MHz, CDCl$_3$) δ 167.9, 159.3, 154.0, 138.3, 137.3, 136.5, 130.7, 130.3, 129.4, 125.1, 122.8, 116.7, 116.1, 113.9, 112.4, 97.0, 94.6, 78.4, 72.9, 71.0, 66.6, 56.2, 55.9, 55.4, 37.8, 37.4, 36.7, 35.5, 35.3, 13.9. HRMS Calcd for C$_{32}$H$_{44}$O$_8$Li (MLi$^+$): 563.3196. Found: 563.3202.

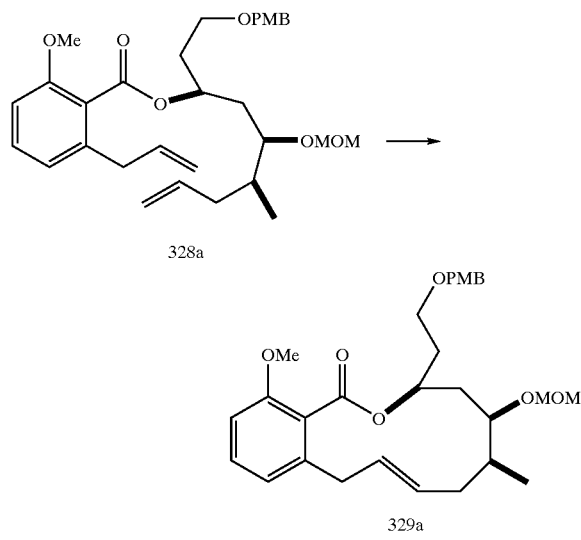

328a

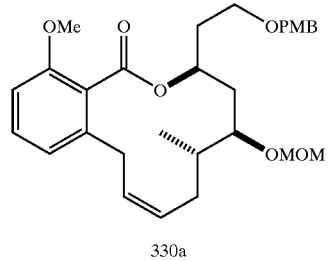

330a

To a flask charged with degassed CH$_2$Cl$_2$ (180 mL) was added simultaneously a solution of Cl$_2$[(Cy)$_3$P]$_3$Ru=CHPh (141 mg, 0.17 mmol) in CH$_2$Cl$_2$ (30 mL) and a solution of ester 328a (0.6 g, 1.14 mmol) in CH$_2$Cl$_2$ (50 mL) over a 4 h period via addition funnels. After the addition was complete, the solvent was evaporated and the residue purified by FC (15% EtOAc/hexanes) to give 465 mg of benzolactone 329a (0.93 mmol, 81%) and 46 mg of the corresponding Z-isomer 330a (0.092 mmol, 8%). 329a: $[\alpha]_D$=−49.5 (c 1.30, CHCl$_3$); IR 2955, 2931, 2840, 1724, 1613, 1585, 1514, 1468, 1275, 1249, 1098, 1071, 1040 cm$^{-1}$; $^1$H NMR (400 MHz, CDCl$_3$) δ 7.27 (2H, d, J=8.4 Hz), 7.22 (1H, app.t, J=8.0 Hz), 6.86 (2H, d, J=8.4 Hz), 6.78 (1H, d, J=8.0 Hz), 6.76 (1H, d, J=8.0 Hz), 5.44–5.53 (2H, m), 5.34 (1H, br dd, J=9.2, 15.2 Hz), 4.88 (1H, d, J=6.8 Hz), 4.79 (1H, d, J=6.8 Hz), 4.47 (2H, s), 4.15 (1H, dd, J=3.6, 9.2 Hz), 3.79 (3H, s), 3.72 (1H, dd, J=9.6, 16.4 Hz), 3.71 (3H, s), 3.65 (2H, app.t, J=6.8 Hz), 3.43 (3H, s), 3.32 (1H, br d, J=16.4 Hz), 2.30 (1H, br d, J=14.0 Hz), 2.07–2.18 (1H, m), 2.02 (1H, app.ddt, J=6.8, 9.2, 14.4 Hz), 1.91 (1H, dddd, J=4.0, 7.2, 7.2, 14.4 Hz), 1.76 (1H, dd, J=8.8, 15.2 Hz), 1.71 (1H, app.td, J=11.6, 14.0 Hz), 1.45 (1H, dd, J=9.2, 15.2 Hz), 0.86 (3H, d, J=6.8 Hz); $^{13}$C NMR (75 MHz, CDCl$_3$) δ 168.3, 159.1, 156.5, 139.2, 131.5, 130.8, 130.1, 129.2, 128.6, 124.7, 123.0, 113.9, 109.3, 97.0, 79.4, 72.8, 72.5, 66.9, 55.8, 55.6, 55.5, 38.04, 38.0, 36.7, 36.0, 34.3, 13.7; HRMS Calcd for C$_{29}$H$_{39}$O$_7$ (MH$^+$): 499.2696. Found: 499.2697. 330a: $[\alpha]_D$=−25.0 (c 0.6, CHCl$_3$); IR 2932, 1729, 1613, 1598, 1514, 1469, 1250, 1115, 1065, 1038 cm$^{-1}$; $^1$H NMR (400 MHz, CDCl$_3$) o 7.29 (1H, app.t, J=7.6 Hz), 7.27 (2H, d, J=8.8 Hz), 6.85 (2H, d, J=8.8 Hz), 6.82 (1H, d, J=6.4 Hz), 6.82 (1H, d, J=8.4 Hz), 5.53 (1H, app.dt, J=3.6, 9.6 Hz), 5.30–5.37 (2H, m), 4.78 (1H, d, J=6.8 Hz), 4.72 (1H, d, J=6.8 Hz), 4.46 (1H, d, J=11.2 Hz), 4.38 (1H, d, J=11.2 Hz), 3.97 (1H, dd, J=8.0, 15.2 Hz), 3.74–3.84 (1H, m), 3.80 (3H, s), 3.76 (3H, s), 3.50–3.58 (2H, m), 3.39 (3H, s), 3.03 (1H, br d, J=14.0 Hz), 1.85–2.18 (6H, m), 1.54–1.60 (1H, m), 0.93 (3H, d, J=6.4 Hz); $^{13}$C NMR (75 MHz, CDCl$_3$) δ 166.9, 159.1, 157.1, 140.1, 130.8, 130.7, 129.4, 129.3, 128.8, 123.7, 122.8, 113.8, 109.5, 97.4, 77.9, 73.0, 72.0, 66.8, 56.1, 55.8, 55.5, 36.7, 36.6, 35.8, 32.8, 32.2, 13.8. ent-329b/ent-330b (MOM): $^1$H NMR (400 MHz, CDCl$_3$), major isomer only, δ 7.26 (2H, d, J=8.4 Hz), 7.20 (1H, dd, J=8.4, 7.6 Hz), 7.03 (1H, d, J=8.4 Hz), 6.87 (2H, d, J=8.4 Hz), 6.80 (1H, d, J=7.6 Hz), 5.44–5.56 (2H, m), 5.34 (1H, br dd, J=9.2, 15.6 Hz), 5.06 (2H, s), 4.88 (1H, d, J=6.8 Hz), 4.79 (1H, d, J=6.8 Hz), 4.46 (2H, s), 4.13 (1H, dd, J=3.2, 9.2 Hz), 3.72 (1H, dd, J=8.8, 16.0 Hz), 3.66 (2H, app.t, J=6.8 Hz), 3.43 (3H, s), 3.39 (3H, s), 3.32 (1H, br d, J=16.0 Hz), 2.30 (1H, br d, J=14.0 Hz), 2.07–2.19 (1H, m), 1.86–2.06 (2H, m), 1.76 (1H, dd, J=8.8, 15.2 Hz), 1.70 (1H, ddd, J=11.6, 11.6, 14.0 Hz), 1.47 (1H, dd, J=9.6, 15.2 Hz), 0.87 (3H, d, J=7.2 Hz [minor Z-isomer at 0.93]). HRMS Calcd for C$_{30}$H$_{40}$O$_8$Li (MLi$^+$): 535.2883. Found: 535.2876.

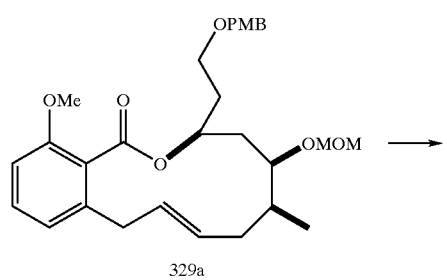

329a

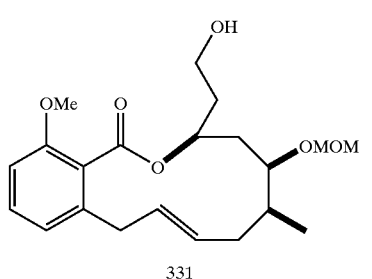

331

To a solution of benzolactone 329a (0.85 g, 1.70 mmol) in CH$_2$Cl$_2$ (35 mL) and water (1.7 mL) was added DDQ (472 mg, 2.04 mmol). After stirring for 1.5 h at rt, the yellow slurry was poured into saturated aqueous NaHCO$_3$ (10 mL) and water (100 mL) and an extraction was performed with EtOAc (4×). The combined organic layers were dried over MgSO$_4$ and concentrated in vacuo. The residue was purified by FC (50% EtOAc/hexanes) to give 617 mg of alcohol 331 (1.63 mmol, 96%). 331: $[\alpha]_D$=−50.4 (c 1.21, CHCl$_3$); IR 3440, 2955, 1723, 1584, 1469, 1275, 1039 cm$^{-1}$; $^1$H NMR (400 MHz, CDCl$_3$) δ 7.24 (1H, app.t, J=8.0 Hz), 6.81 (1H, d, J=8.4 Hz), 6.78 (1H, d, J=7.6 Hz), 5.45–5.54 (2H, m), 5.35 (1H, dddd, J=2.0, 2.0, 9.6, 15.6 Hz), 4.89 (1H, d, J=6.8 Hz), 4.82 (1H, d, J=6.8 Hz), 4.17 (1H, dd, J=3.6, 8.8 Hz), 3.82 (3H, s), 3.69–3.87 (3H, m), 3.46 (3H, s), 3.33 (1H, dddd, J=2.0, 2.0, 4.4, 16.4 Hz), 2.43 (1H, br s), 2.31 (1H, br d, J=14.0 Hz), 2.09–2.19 (1H, m), 1.80–1.98 (2H, m), 1.79 (1H, dd, J=8.0, 15.6 Hz), 1.72 (1H, app.td, J=11.6, 14.0 Hz), 1.45 (1H, dd, J=9.2, 15.6 Hz), 0.87 (3H, d, J=6.8 Hz); $^{13}$C NMR (75 MHz, CDCl$_3$) δ 168.3, 156.2, 139.3, 131.6, 130.2, 128.4, 124.4, 123.3, 109.4, 97.2, 79.7, 73.2, 59.6, 55.9, 55.8, 39.2, 38.0, 36.2, 34.3, 13.7; HRMS Calcd for C$_{21}$H$_{31}$O$_6$ (MH$^+$): 379.2121. Found: 379.2120. ent- (MOM): HRMS Calcd for C$_{22}$H$_{32}$O$_7$Li (MLi$^+$): 415.2308. Found: 415.2323.

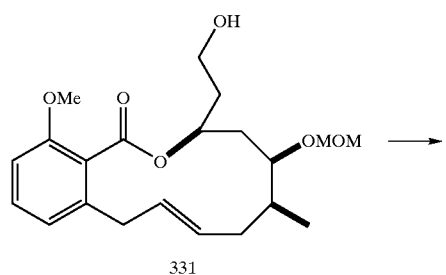

331

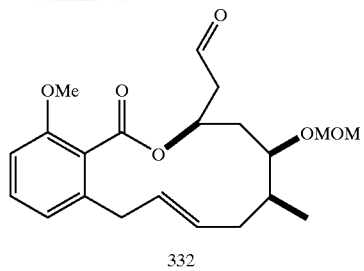

332

To a solution of alcohol 331 (337 mg, 0.89 mmol) in CH$_2$Cl$_2$ (30 mL) was added Dess-Martin periodinane (0.94 g, 2.23 mmol). After stirring at rt for 3 h, saturated aqueous NaHCO$_3$ (5 mL) and water (100 mL) was added and an extraction was performed with Et$_2$O. The combined organic layers were dried (MgSO$_4$) and concentrated after which the residue was purified by FC (30% EtOAc/hexanes) to give 318 mg of aldehyde 332 (0.845 mmol, 95%) as an oil. 332: $[\alpha]_D$=−45.4 (c 1.55, CHCl$_3$); IR 2962, 2935, 1728, 1585, 1470, 1274, 1117, 1086, 1037 cm$^{-1}$; $^1$H NMR (400 MHz, CDCl$_3$) δ 9.79 (1H, dd, J=1.6, 3.6 Hz), 7.23 (1H, app.t, J=8.0 Hz), 6.77 (1H, d, J=8.0 Hz), 6.75 (1H, d, J=8.0 Hz), 5.09 (1H, ddd, J=3.6, 8.8, 10.0 Hz), 5.49 (1H, br dd, J=11.6, 15.2 Hz), 5.34 (1H, br dd, J=10.0, 15.2 Hz), 4.92 (1H, d, J=7.2 Hz), 4.85 (1H, d, J=7.2 Hz), 4.20 (1H, dd, J=3.6, 9.2 Hz), 3.74 (3H, s), 3.71 (1H, dd, J=10.0, 16.4 Hz), 3.47 (3H, s), 3.31 (1H, br d, J=16.4 Hz), 2.77 (1H, ddd, J=3.6, 10.0, 16.4 Hz), 2.53 (1H, ddd, J=1.6, 3.6, 16.4 Hz), 2.31 (1H, br d, J=14.0 Hz), 2.10–2.21 (1H, m), 1.83 (1H, dd, J=8.8, 15.2 Hz), 1.71 (1H, app.td, J=11.6, 14.0 Hz), 1.45 (1H, dd, J=9.2, 15.2 Hz), 0.87 (3H, d, J=6.8 Hz); $^{13}$C NMR (75 MHz, CDCl$_3$) δ 200.5, 168.0, 156.6, 139.0, 131.5, 130.3, 128.7, 123.9, 122.7, 109.2, 97.2, 79.4, 69.8, 55.9, 55.5, 49.4, 37.5, 37.87, 35.9, 34.5, 13.6.

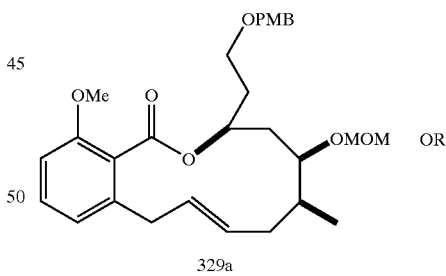

329a

OR

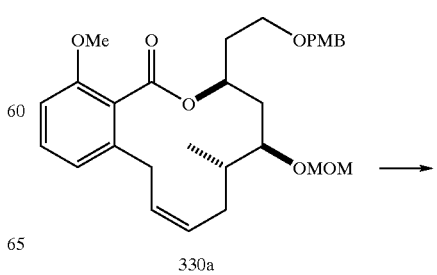

330a

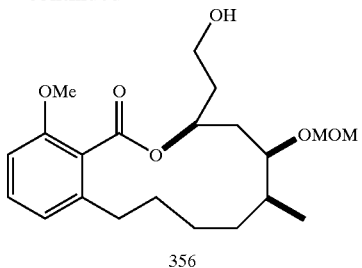

356

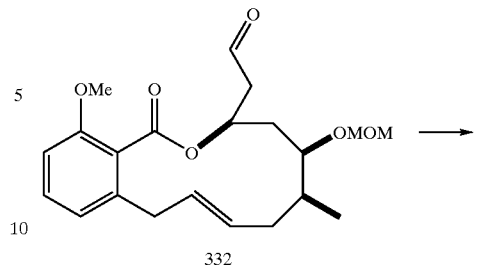

332

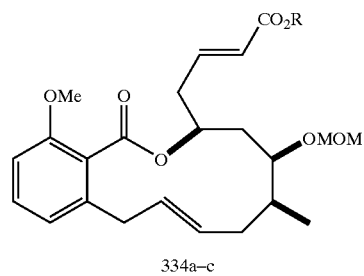

334a–c

A mixture of 329a (120 mg, 0.317 mmol) and 10% Pd/C (30 mg) in MeOH (5 mL) was stirred under an atmosphere of $H_2$ for 3 h at rt. Filtration, concentration and purification by FC (50% EtOAc in hexanes) delivered 99 mg of alcohol 356 (82%). Alternatively, a mixture of alkene 330a (111 mg, 0.223 mmol), ammonium formate (100 mg) and 10% Pd/C (100 mg) in MeOH (6 mL) was refluxed for 6 h. Filtration, concentration and purification of the residue by FC (50% EtOAc/hexanes) delivered 57 mg of alcohol 356 (0.15 mmol, 67%). 356: $[\alpha]_D$=−35.6 (c 1.0, $CHCl_3$); IR 3451, 2933, 1724, 1582, 1470, 1265 $cm^{-1}$; $^1H$ NMR (400 MHz, $CDCl_3$) δ 7.26 (1H, t, J=8.0 Hz), 6.79 (1H, d, J=7.6 Hz), 6.79 (1H, d, J=8.4 Hz), 5.52 (1H, app.q, J=8.0 Hz), 4.76 (2H, s), 5.83 (3H, s), 3.70–84 (3H, m), 3.44 (3H, s), 2.80–291 (1H, m), 2.42–2.51 (2H, m), 1.98–2.06 (1H, m), 1.87–1.95 (3H, m), 1.60–1.78 (3H, m), 1.42–1.56 (2H, m), 1.18–1.30 (2H, m), 0.91 (3H, d, J=6.8 Hz); $^{13}C$ NMR (75 MHz, $CDCl_3$) δ 168.7, 156.5, 141.5, 130.8, 123.6, 122.4, 109.0, 96.7, 71.6, 58.9, 56.07, 55.97, 39.0, 35.8, 34.1, 31.8, 26.1, 15.4; HRMS Calcd for $C_{21}H_{33}O_6$ ($MH^+$): 381.2277. Found: 381.2274.

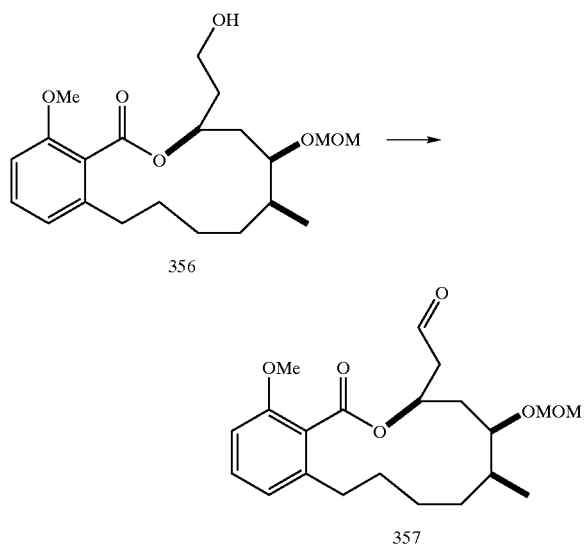

According to the procedure described for the synthesis of 332, alcohol 356 (52 mg, 0.137 mmol) was oxidized with Dess-Martin periodinane (231 mg, 0.547 mmol), delivering 42 mg of aldehyde 357 (81%).

To a suspension of NaH (60% in mineral oil, 74 mg, 1.84 mmol) in THF (15 mL) was added allyl diethylphosphonoacetate (0.436 mL, 2.0 mmol) at 0° C. After stirring for 20 min at the same temperature, a solution of aldehyde 332 (302 mg, 0.802 mmol) in THF (5 mL) was added and stirring was continued for 1 h at 0° C. Saturated aqueous $NaHCO_3$ (5 mL) and water (100 mL) was added and an extraction was performed with $Et_2O$ (3×). After concentration of the organic layers, drying ($MgSO_4$) and concentration in vacuo, the residue was purified by FC (20% EtOAc/hexanes) to yield 343 mg of allyl ester 334b (0.75 mmol, 93%). Esters 334a-c were prepared using the same procedure with trimethylsilyl dimethylphosphonoacetate, t-butyl dimethylphosphonoacetate and trimethyl phosphonoacetate respectively. 334b: $[\alpha]_D$=−95.0 (c 2.49, $CHCl_3$); IR $^1H$ NMR (400 MHz, $CDCl_3$) δ 7.23 (1H, app.t, J=8.0 Hz), 7.14 (1H, ddd, J=6.0, 8.0, 15.6 Hz), 6.81 (1H, d, J=8.4 Hz), 6.75 (1H, d, J=7.2 Hz), 5.95 (1H, d, J=15.6 Hz), 5.90–6.00 (1H, m), 5.32–5.52 (3H, m), 5.33 (1H, td, J=1.2, 17.0 Hz), 5.24 (1H, td, J=1.2, 10.4 Hz), 4.89 (1H, d, J=6.8 Hz), 4.81 (1H, d, J=6.8 Hz), 4.64 (2H, dd, J=1.2, 5.6 Hz), 4.16 (1H, dd, J=3.6, 9.6 Hz), 3.85 (3H, s), 3.71 (1H, dd, J=9.6, 16.4 Hz), 3.45 (3H, s), 3.32 (1H, br d, J=16.4 Hz), 2.65 (1H, ddd, J=6.0, 7.6, 15.6 Hz), 2.47 (1H, ddd, J=4.0, 8.0, 15.6 Hz), 2.27–2.36 (1H, m), 2.08–2.19 (1H, m), 1.76 (1H, dd, J=8.8, 15.6), 1.70 (1H, app.dt, J=11.6, 14.0 Hz), 1.44 (1H, dd, J=9.6, 15.6 Hz), 0.86 (3H, d, J=6.4 Hz); HRMS (FAB) Calcd for $C_{26}H_{35}O_7$ ($MH^+$): 459.2383. Found: 459.2386. ent-334c (t-butyl): $[\alpha:]_D$=+68.6 (c 0.35, $CHCl_3$); IR 2933, 1713, 1653, 1587, 1473, 1277, 1250, 1153, 1117, 1040 $cm^{-1}$; $^1H$ NMR (400 MHz, $CDCl_3$) δ 7.23 (1H, dd, J=7.6, 8.4 Hz), 6.99 (1H, ddd, J=6.0, 8.4, 15.6 Hz), 6.81 (1H, d, J=8.4 Hz), 6.75 (1H, d, J=7.6 Hz), 5.95 (1H, dt, J=1.6, 15.6 Hz), 5.30–5.52 (3H, m), 4.89 (1H, d, J=6.8 Hz), 4.81 (1H, d, J=6.8 Hz), 4.66 (1H, dd, J=3.6, 8.8 Hz), 3.86 (3H, s), 3.71 (1H, dd, J=9.6, 16.4 Hz), 3.45 (3H, s), 3.32 (1H, br d, J=16.4 Hz), 2.61 (1H, dddd, J=1.6, 6.0, 8.8, 15.2 Hz), 2.43 (1H, dddd, J=1.6, 4.4, 8.0, 15.2 Hz), 2.26–2.34 (1H, m), 2.08–2.20 (1H, m), 1.75 (1H, dd, J=8.4, 15.2), 1.70 (1H, ddd, J=11.6, 11.6, 14.4 Hz), 1.49 (9H, s), 1.43 (1H, dd, J=9.2, 15.2 Hz), 0.86 (3H, d, J=6.8 Hz); $^{13}C$ NMR (75 MHz, $CDCl_3$) δ 168.5, 166.0, 157.0, 143.5, 139.2, 131.5, 130.3, 128.8, 125.5, 124.5, 122.8, 109.5, 97.3, 80.4, 79.6, 73.4, 55.9, 55.8, 39.2, 37.93, 37.88, 35.9, 34.4, 28.4, 13.5. HRMS Calcd for $C_{27}H_{38}O_7Li$ (MLi+): 481.2778. Found: 481.2774. 334a (Mixture of E/Z isomers, ~3.5–4:1): IR 2954, 1725, 1585, 1584, 1469, 1440, 1275, 1249, 1117, 1041 cm$^{-1}$; $^1$H NMR (400 MHz, CDCl$_3$, peaks corresponding to major isomer) δ 7.24 (1H, app.t, J=7.6 Hz), 7.12 (1H, ddd, J=5.6, 8.4, 15.6 Hz), 6.82 (1H, d, J=8.4 Hz), 6.75 (1H, d, J=7.6 Hz), 5.92 (1H, br d, J=15.6 Hz), 5.48 (1H, br dd, J=10.8, 15.2 Hz), 5.38 (1H, ddd, J=4.0, 8.8, 8.8 Hz), 5.36 (1H, br dd, J=9.2, 15.2 Hz), 4.89 (1H, d, J=6.8 Hz), 4.81 (1H, d, J=6.8 Hz), 4.16 (1H, dd, J=3.6, 8.8 Hz), 3.86 (3H, s), 3.74 (3H, s), 3.71 (1H, dd, J=10.8, 16.4 Hz), 3.45 (3H, s), 3.32 (1H, dddd, J=2.4, 2.4, 4.8, 16.4 Hz), 2.64 (1H, dddd, J=1.6, 5.6, 8.8, 15.2 Hz), 2.46 (1H, dddd, J=1.2, 4.0, 8.4, 15.2 Hz), 2.31 (1H, br d, J=14.0 Hz), 2.10–2.19 (1H, m), 1.76 (1H, dd, J=8.8, 15.6 Hz), 1.71 (1H, app.td, J=11.6, 14.0 Hz), 1.45 (1H, dd, J=9.6, 15.2 Hz), 0.86 (3H, d, J=7.2 Hz).

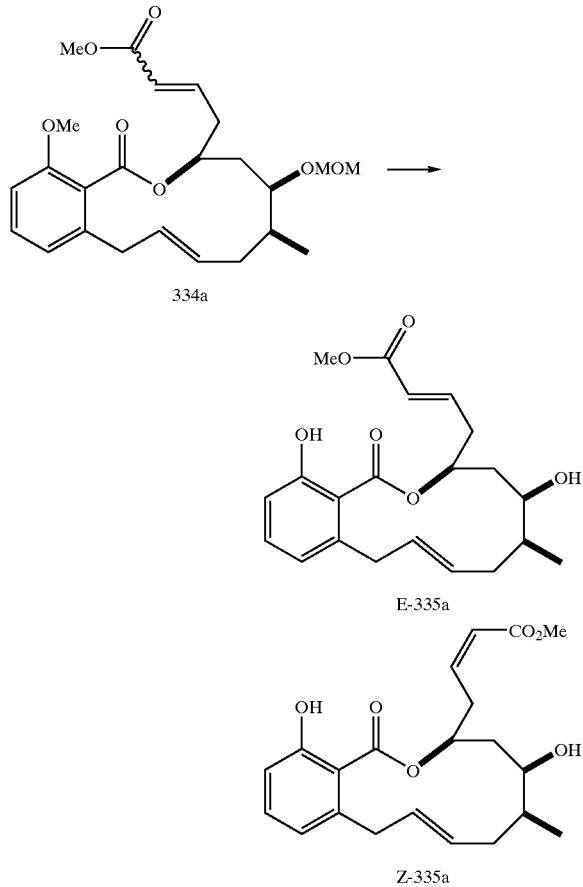

According to the procedure described below for the deprotection of allyl ester 334b, the mixture of methyl esters 334a (250 mg, 0.505 mmol) were deprotected with BBr$_3$ (2.5 equiv.) to give after separation by FC (35% EtOAc/hexanes) 30 mg of the less polar Z-isomer Z-335a (0.08 mmol, 16%) and 121 mg of the more polar E-isomer E-335a (0.323 mmol, 64%). E-335a: [α]$_D$=+8.7 (c 1.2, CHCl$_3$) [ent-E-335a =–7.0 (c 1.1, CHCl$_3$]; IR 3404, 3162, 2949, 2914, 1729, 1691, 1589, 1468, 1426, 1297, 1268, 1249, 1127, 1031, 966 cm$^{-1}$; $^1$H NMR (400 MHz, CDCl$_3$) δ 7.31 (1H, app.t, J=8.4 Hz), 6.98 (1H, app.dt, J=7.6, 15.6 Hz), 6.90 (1H, dd, J=0.8, 8.0 Hz), 6.71 (1H, d, J=7.6 Hz), 5.94 (1H, br d, J=15.6 Hz), 5.64 (1H, app.dt, J=5.6, 10.8 Hz), 5.49 (1H, br d, J=16 Hz), 5.02–5.13 (1H, m), 3.74 (3H, s), 3.70–3.78 (1H, m), 3.61 (1H, br d, J=8.0 Hz), 3.38 (1H, br d, J=16.4 Hz), 2.56–2.68 (2H, m), 2.32–2.40 (1H, m), 2.03 (1H, dd, J=11.2, 15.2 Hz), 1.79–1.96 (2H, m), 1.50 (1H, s), 1.37 (1H, ddd, J=1.2, 8.4, 14.8 Hz), 0.92 (3H, d, J=6.8 Hz); $^{13}$C NMR (75 MHz, CDCl$_3$) δ 171.4, 166.7, 163.3, 144.4, 142.7, 134.5, 133.4, 126.3, 123.9, 122.2, 117.0, 112.9, 74.1, 70.6, 51.4, 39.3, 38.6, 37.5, 35.8, 34.7, 13.9. HRMS Calcd for C$_{21}$H$_{26}$O$_6$Li (MLi+): 381.1889. Found: 381.1889. Ent-Z-335a: [α:]$_D$=–40.8 (c 1.2, CHCl$_3$); IR 3200–3600, 2955, 2926, 1722, 1652, 1606, 1588, 1464, 1441, 1293, 1248, 1214, 1176, 1119, 1064, 1028, 760 cm$^{-1}$; $^1$H NMR (400 MHz, CDCl$_3$) δ 7.31 (1H, app.t, J=8.0 Hz), 6.90 (1H, d,J=8.0 Hz), 6.70 (1H, d, J=7.2 Hz), 6.30 (1H, app.dt, J=7.2, 11.2 Hz), 5.92 (1H, d, J=11.2 Hz), 5.66 (1H, app.dt, J=6.0, 11.2 Hz), 5.51 (1H, br d, J=16 Hz), 5.02–5.12 (1H, m), 3.78 (1H, dd, J=6.4, 16.8), 3.69 (3H, s), 3.59 (1H, dd, J=3.2, 8.8 Hz), 3.36 (1H, d, J=16.8 Hz), 3.15–3.24 (1H, m), 3.00–3.08 (1H, m), 2.32–2.40 (1H, m), 2.08 (1H, dd, J=10.8, 14.8 Hz), 1.79–1.96 (2H, m), 1.40 (1H, dd, J=7.6, 14.8 Hz), 0.93 (3H, d, J=6.8 Hz). HRMS Calcd for C$_{21}$H$_{26}$O$_6$Li (MLi+): 381.1889. Found: 381.1891.

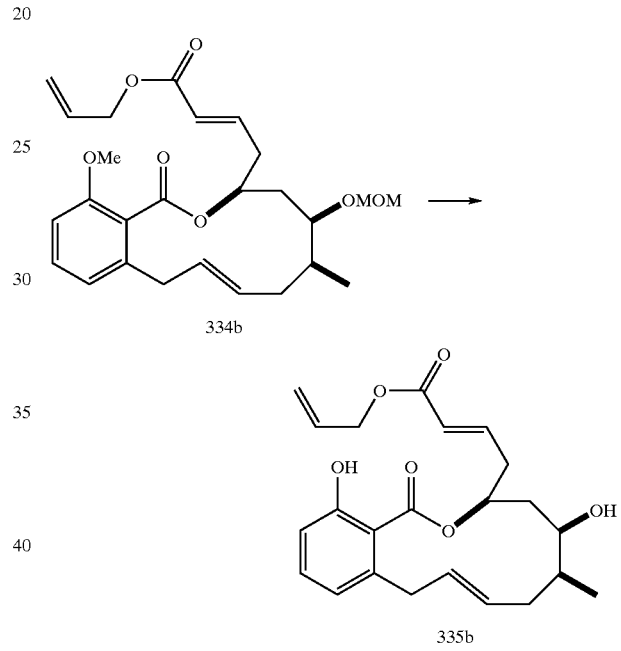

To a solution of allyl ester 334b (343 mg, 0.748 mmol) in CH$_2$Cl$_2$ (40 mL) was added at –78° C. BBr$_3$ (0.29 mL, 1.87 mmol). After stirring for 20 min, a saturated aqueous solution of NaHCO$_3$ (10 mL) and H$_2$O (100 mL) was added followed by extraction with EtOAc (3×), drying (MgSO$_4$) and concentration. The residue was purified by FC (25% EtOAc/hexanes) to yield 243 mg of diol 335b (0.607 mmol, 81%). 335b: [α]$_D$=4.3 (c 0.88, CHCl$_3$); IR 3407, 3172, 2959, 1731, 1690, 1656, 1590 cm$^{-1}$; $^1$H NMR (400 MHz, CDCl$_3$) δ 11.0 (1H, s), 7.31 (1H, dd, J=7.6, 8.4 Hz), 7.01 (1H, app.dt, J=7.2, 15.6 Hz), 6.89 (1H, dd, J=0.8, 8.4 Hz), 6.71 (1H, dd, J=0.8, 7.6 Hz), 5.97 (1H, d, J=15.6 Hz), 5.95 (1H, ddt, J=5.6, 10.4, 15.6 Hz), 5.64 (1H, app.dt, J=5.2, 11.2 Hz), 5.44–5.52 (1H, m), 5.33 (1H, app.qd, J=1.2, 15.6 Hz), 5.24 (1H, app.qd, J=1.2, 10.4 Hz), 5.02–5.13 (1H, m), 4.65 (1H, app.td, J=1.2, 5.6 Hz), 3.74 (1H, dd, J=5.6, 16.4 Hz), 3.62 (1H, dd, J=3.2, 8.8 Hz), 3.38 (1H, br d, J=16.4 Hz), 2.56–2.69 (2H, m), 2.31–2.40 (1H, m), 2.03 (1H, dd, J=11.2, 15.2), 1.79–1.97 (2H, m), 1.52–1.72 (1H, m), 1.44 (1H, ddd, J=1.2, 8.4, 14.8 Hz), 0.93 (3H, d, J=6.8 Hz); $^{13}$C NMR (75 MHz, CDCl$_3$) δ 171.1, 165.9, 163.1, 143.7, 142.5, 134.5, 133.2, 132.3, 126.5, 124.5, 123.9, 118.5, 116.9, 113.1, 73.2, 70.5, 65.3, 39.3, 38.6, 38.0, 37.5, 35.6, 13.9; MS (CI) m/z (%): 401 (28), 383 (30), 343 (37), 325 (100); HRMS (FAB) Calcd for $C_{23}H_{29}O_6$ (MH$^+$): 401.1964. Found: 401.1973.

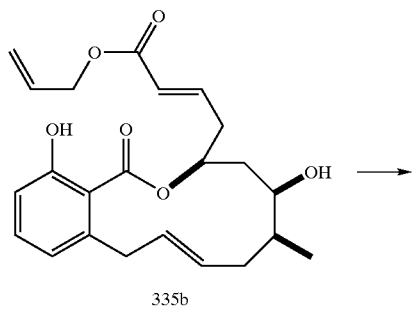

335b

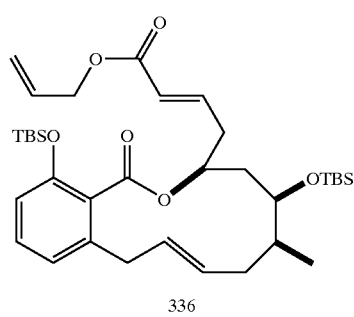

336

To a solution of 335b (208 mg, 0.52 mmol), imidazole (250 mg, 3.63 mmol) and DMAP (25 mg) in DMF (10 mL) was added tert.butyldimethylsilyl chloride (479 mg, 3.12 mmol). After stirring for 10 h at rt, the mixture was poured into water (100 mL), extracted with Et$_2$O (3×), and the combined organics washed with brine, dried over MgSO$_4$ and concentrated in vacuo. FC (2% EtOAc/hexanes) yields 301 mg of silylether 336 (0.48 mmol, 92%). 336: $[\alpha]_D$=−1.0 (c 0.5, CHCl$_3$); IR $^1$H NMR (400 MHz, CDCl$_3$) δ 7.12 (1H, app.t, J=8.0 Hz), 6.93 (1H, app.dt, J=7.2, 15.6 Hz), 6.75 (1H, d, J=7.6 Hz), 6.72 (1H, d, J=8.0 Hz), 5.95 (1H, ddt, J=6.0, 10.4, 17.2 Hz), 5.94 (1H, d, J=15.6 Hz), 5.29–5.46 (3H, m), 5.33 (1H, app.qd, J=1.6, 17.2 Hz), 5.24 (1H, app.qd, J=1.6, 10.4 Hz), 4.64 (2H, dd, J=1.6, 5.6 Hz), 4.26 (1H, dd, J=3.2, 8.8 Hz), 3.65 (1H, dd, J=8.8, 16.4 Hz), 3.32 (1H, br d, J=16.4 Hz), 2.55–2.60 (2H. m), 2.22–2.30 (1H, m), 1.76–1.85 (1H, m), 1.65–1.75 (1H, m), 1.67 (1H, dd, J=8.8, 15.6 Hz), 1.41 (1H, dd, J=8.8, 15.6 Hz), 0.96 (9H, s), 0.90 (9H, s), 0.83 (3H, d, J=6.4 Hz), 0.22 (3H, s), 0.20 (3H, s), 0.15 (3H, s), 0.12 (3H, s); HRMS (FAB) Calcd for $C_{35}H_{57}O_6Si_2$ (MH$^+$): 629.3694. Found: 629.3687.

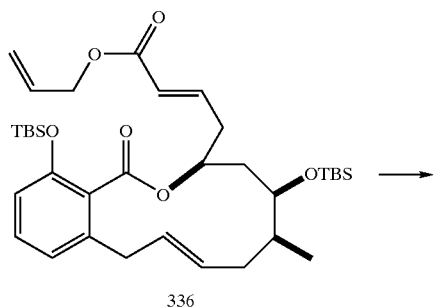

336

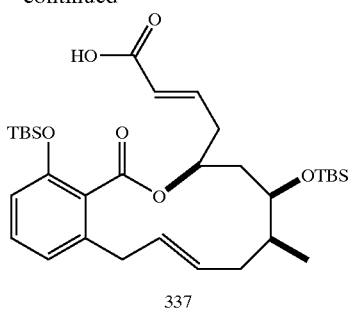

337

To a solution of morpholine (0.41 mL, 4.78 mmol) and allyl ester 336 (301 mg, 0.478 mmol) in THF (10 mL) was added Pd(PPh$_3$)$_4$ (28 mg, 0.024 mmol). The mixture was stirred at rt in the dark for 4 h and brine (80 mL) was added. The aqueous phase was extracted with EtOAc (4×) and the combined organic layers were dried (MgSO$_4$) and concentrated in vacuo. The residue was purified by FC (20% EtOAc/hexanes) to give 270 mg of acid 337 (0.458 mmol, 96%). 337: $[\alpha]_D$=+2.0 (c 1.84, CHCl$_3$); IR 2956, 2930, 2858, 1728, 1700, 1652, 1582, 1457 cm$^{-1}$; $^1$H NMR (400 MHz, CDCl$_3$) δ 7.13 (1H, app.t, J=8.0 Hz), 7.02 (1H, app.dt, J=7.2, 15.6 Hz), 6.75 (1H, d, J=7.6 Hz), 6.72 (1H, d, J=8.0 Hz), 5.93 (1H, d, J=15.6 Hz), 5.30–5.46 (3H, m), 4.26 (1H, dd, J=3.2, 8.8 Hz), 3.66 (1H, dd, J=8.8, 16.0 Hz), 3.32 (1H, br d, J=16.0 Hz), 2.60 (2H, app.t, J=6.8 Hz), 2.21–2.30 (1H, m), 1.75–1.86 (1H, m), 1.35–1.45 (1H, m), 0.96 (9H, s), 0.91 (9H, s), 0.83 (3H, d, J=6.4 Hz), 0.22 (3H, s), 0.20 (3H, s), 0.15 (3H, s), 0.12 (3H, s); $^{13}$C NMR (75 MHz, CDCl$_3$) δ 171.5, 168.4, 152.9, 146.5, 138.9, 131.6, 129.8, 128.5, 127.5, 123.8, 123.4, 118.0, 72.5, 72.2, 38.7, 38.3, 38.2, 37.3, 36.5, 26.1, 25.9, 18.5, 18.2, 13.2, −3.9, −4.19, −4.24, −4.3; MS (ES) m/z (%): 589 (10), 531 (21), 457 (18), 367 (40), 115 (78), 73 (100); HRMS (FAB) Calcd for $C_{32}H_{53}O_6Si_2$ (MH$^+$): 589.3381. Found: 589.3391.

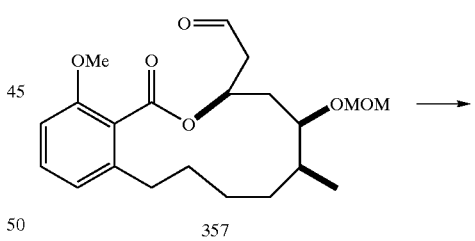

357

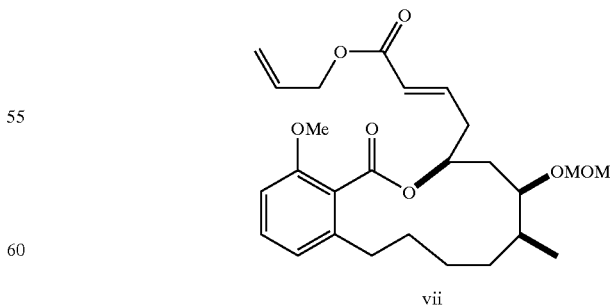

vii

According to the procedure described for the synthesis of allyl ester 334b, aldehyde 357 (22mg, 0.058 mmol) gave 25 mg of allyl ester vii (0.054 mmol, 93%). Allyl ester vii:

[α]$_D$=−54.2 (c 1.1, CHCl$_3$); IR 2933, 1724, 1471 cm$^{-1}$; $^1$H NMR (400 MHz, CDCl$_3$) δ 7.25 (1H, t, J=8.0 Hz), 7.08 (1H, ddd, J=6.8, 7.6, 16.0 Hz), 6.77 (2H (1H+1H), d, J=8.0 Hz), 6.72 (1H, d, J=8.0 Hz), 5.85–6.0 (1H, m), 5.96 (1H, d, J=16.0 Hz), 5.36–5.45 (1H, m), 5.33 (1H, br.d, J=17.2 Hz), 5.24 (1H, br.d, J=10.4 Hz), 4.80 (1H, d, J=6.8 Hz), 4.75 (1H, d, J=6.8 Hz), 4.64 (2H, br.d, J=5.2 Hz), 3.83 (3H, s), 3.75–3.81 (1H, m), 3.43 (3H, s), 2.86 (1H, ddd, J=5.2, 12.8, 12.8 Hz), 2.75 (1H, dddd, J=1.6, 6.4, 8.4, 14.8 Hz), 2.56 (1H, dddd, J=1.2, 4.4, 7.6, 14.8 Hz), 2.47 (2H, ddd, J=5.2, 12.4, 12.8 Hz), 1.90–2.06 (2H, m), 1.60–1.74 (3H, m), 1.39–1.56 (2H, m), 1.14–1.32 (2H, m), 0.89 (3H, d, J=6.4 Hz); $^{13}$C NMR (75 MHz, CDCl$_3$) δ 167.9, 166.0, 156.7, 144.5, 141.4, 132.4, 130.7, 123.8, 123.6, 122.1, 118.3, 108.9, 97.1, 72.4, 65.1, 55.9, 38.6, 35.4, 33.6, 31.9, 26.4, 15.2; HRMS (FAB) Calcd for C$_{26}$H$_{36}$O$_7$Li (MLi$^+$): 467.2621. Found: 467.2621.

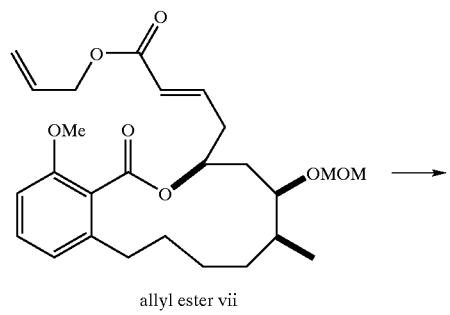

allyl ester vii

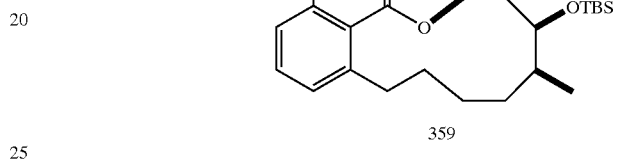

358

According to the procedure described for the synthesis of 335b, deprotection of allyl ester vii (25 mg, 0.054 mmol) with BBr$_3$ (2.5 equiv.) gave 21 mg of 358 (0.052 mmol, 97%). 358: [α]$_D$=−21.2 (c 0.61, CHCl$_3$); IR 3448, 2935, 1722, 1652, 1606, 1449 cm$^{-1}$; $^1$H NMR (400 MHz, CDCl$_3$) δ 10.95 (1H, s), 7.29 (1H, t, J=8.0 Hz), 6.93 (1H, ddd, J=7.6, 8.0, 15.2 Hz), 6.84 (1H, d, J=8.0 Hz), 6.72 (1H, d, J=8.0 Hz), 5.94 (1H, ddt, J=5.6, 10.4, 17.2 Hz), 5.91 (1H, br.d (1r), J=15.2 Hz), 5.32 (1H, ddt, J=1.2, 1.6, 17.2 Hz), 5.24 10.4 Hz), 5.22–5.30 (1H, m), 4.64 (2H, br.d, J=5.6 Hz), 3.89–3.95 (1H, m), 3.68–3.76 (1H, m), 2.64 (2H, ddd, J=1.2, 8.0, 8.0 Hz), 2.16–2.27 (2H, m), 1.66–1.80 (3H, m), 1.50–1.64 (4H, m), 1.32–1.44 (1H, m), 1.15–1.26 (1H, m), 0.96 (3H, d, J=6.6 Hz); $^{13}$C NMR (75 MHz, CDCl$_3$) δ 171.8, 165.7, 163.0, 146.7, 142.9, 134.7, 132.3, 124.9, 122.8, 118.5, 116.1, 111.7, 74.8, 73.6, 65.4, 38.3, 36.8, 33.7, 31.6, 25.3, 25.0, 16.3; HRMS (FAB) Calcd for C$_{23}$H$_{30}$O$_6$Li (MLi$^+$): 409.2202. Found: 409.2202.

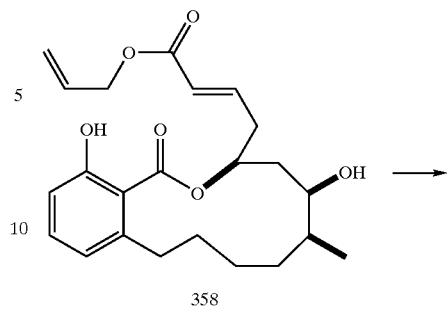

358

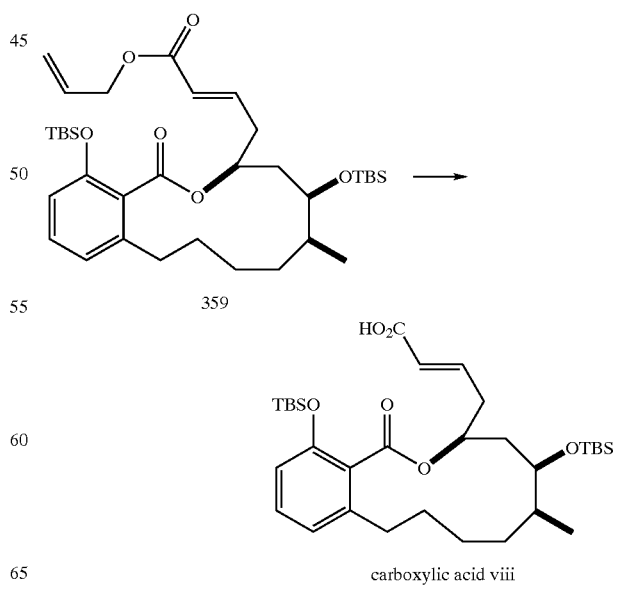

359

According to the procedure described for the synthesis of bis-silyl ether 336, silylation of 358 (20 mg, 0.050 mmol) provided 21 mg of bis-silyl ether 359 (0.033 mmol, 67%). 359: $^1$H NMR (400 MHz, CDCl$_3$) δ 7.14 (1H, dd, J=7.6, 8.0 Hz), 6.94 (1H, ddd, J=6.8, 7.6, 15.6 Hz), 6.75 (1H, d, J=7.6 Hz), 6.69 (1H, d, J=8.0 Hz), 5.95 (1H, br.d (1r), J=15.6 Hz), 5.94 (1H, ddt, J=5.6, 10.4, 17.2 Hz), 5.33 (1H, ddt (1r), J=1.2, 1.6, 17.2 Hz), 5.30–5.38 (1H, m), 5.24 (1H, ddt (1r), J=0.8, 1.2, 10.4 Hz), 4.64 (2H, ddd (1r), J=0.8, 1.6, 5.6 Hz), 3.79–3.86 (1H, m), 2.98–3.10 (1H, m), 2.51–2.64 (2H, m), 2.20–2.30 (1H, m), 1.96–2.06 (1H, m), 1.50–1.67 (5H, m), 1.23–1.48 (3H, m), 0.97 (9H, s), 0.89 (9H, s), 0.88 (3H, d, J=6.8 Hz), 0.25 (3H, s), 0.22 (3H, s), 0.09 (3H, s), 0.05 (3H, s); $^{13}$C NMR (75 MHz, CDCl$_3$) δ 171. HRMS Calcd for C$_{35}$H$_{58}$O$_6$Si$_2$Li (MLi$^+$): 637.3932. Found: 637.3925.

carboxylic acid viii

According to the procedure described for the synthesis of carboxylic acid 337, allyl ester 359 (21 mg, 0.033 mmol) was deprotected to provide 18 mg of carboxylic acid viii (0.030 mmol, 92%). viii: $[\alpha]_D$=−24.7 (c 0.85, CHCl$_3$); IR 2930, 2858, 1728, 1701, 1657, 1464, 1253 cm$^{-1}$; $^1$H NMR (400 MHz, CDCl$_3$) δ 7.15 (1H, dd, J=7.6, 8.0 Hz), 7.03 (1H, ddd, J=6.8, 7.6, 16.0 Hz), 6.75 (1H, d, J=7.6 Hz), 6.70 (1H, d, J=8.0 Hz), 5.94 (1H, br.d (1r), J=16.0 Hz), 5.32–5.41 (1H, m), 3.80–3.88 (1H, m), 2.98–3.12 (1H, m), 2.55–2.68 (2H, m), 2.20–2.30 (1H, m), 1.96–2.08 (1H, m), 1.50–1.70 (5H, m), 1.20–1.48 (3H, m), 0.97 (9H, s), 0.89 (9H, s), 0.88 (3H, d, J=6.8 Hz), 0.25 (3H, s), 0.22 (3H, s), 0.11 (3H, s), 0.05 (3H, s); $^{13}$C NMR (75 MHz, CDCl$_3$) δ 171.1, 167.2, 153.5, 146.2, 142.4, 130.6, 125.5, 124.1, 122.7, 117.0, 77.4, 71.0, 39.1, 37.7, 33.2, 30.6, 26.1, 25.9, 18.4, 18.3, 16.3, −3.9, −4.11, −4.13, −4.4; MS (EI) m/z (%): 533 (M$^+$−57, 8), 459 (7), 367 (100), 365 (66), 309 (12), 115 (64), 75 (24), 73 (52), 57 (83). HRMS Calcd for C$_{32}$H$_{54}$O$_6$Si$_2$Li (MLi$^+$): 597.3619. Found: 597.3617.

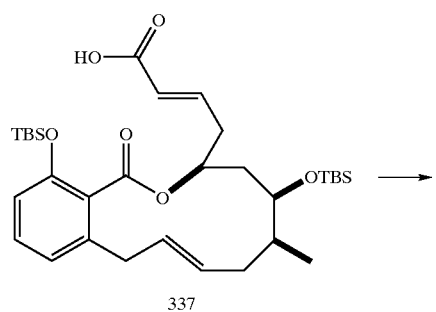

337

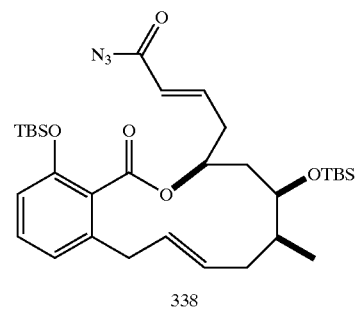

338

To a stirred solution of acid 337 (52 mg, 0.0883 mmol) and (PhO)$_2$P(O)N$_3$ (77.3 µL; 0.353 mmol) in benzene (4 mL) was added Et$_3$N (58 µL) at RT. After stirring for 14 h at RT, the solvent was removed and the residue was purified by FC (silicagel, 2.5% EtOAc in hexanes). The corresponding acyl azide 338 was obtained in 92% yield (50 mg). 338: $^1$H NMR (400 MHz, CDCl$_3$) δ 7.13 (1H, dd, J=7.6, 8.0 Hz), 7.00 (1H, app.dt, J=7.2, 15.6 Hz), 6.75 (1H, d, J=7.6 Hz), 6.72 (1H, d, J=8.0 Hz), 5.92 (1H, d, J=15.6 Hz), 5.29–5.46 (3H, m), 4.26 (1H, dd, J=3.6, 8.4 Hz), 3.65 (1H, dd, J=9.2, 16.4 Hz), 3.33 (1H, br d, J=16.4 Hz), 2.54–2.65 (2H, m), 2.27 (1H, br.d, J=14.0 Hz), 1.75–1.86 (1H, m), 1.65–1.74 (1H, m), 1.67 8.8, 15.2 Hz), 1.37 (1H, dd, J=8.8, 15.2 Hz), 0.96 (9H, s), 0.92 (9H, s), 0.83 (3H, d, J=6.4 Hz), 0.22 (3H, s), 0.20 (3H, s), 0.14 (3H, s), 0.12 (3H, s).

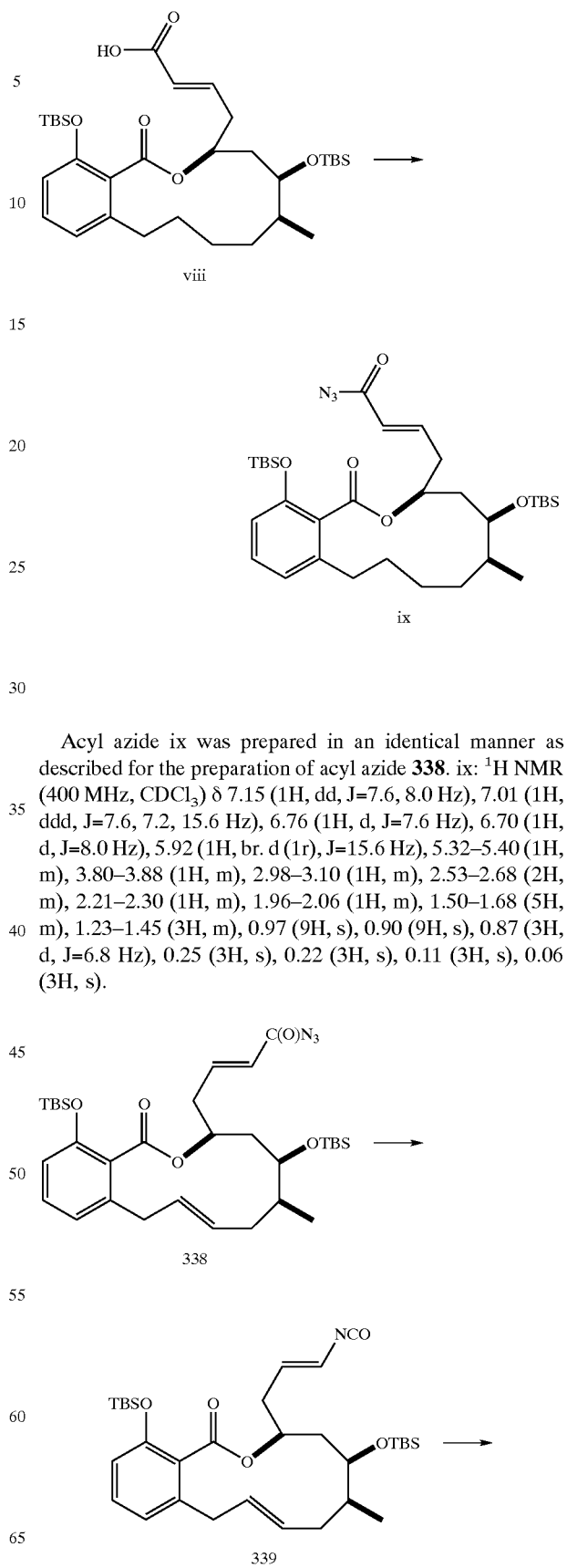

Acyl azide ix was prepared in an identical manner as described for the preparation of acyl azide 338. ix: $^1$H NMR (400 MHz, CDCl$_3$) δ 7.15 (1H, dd, J=7.6, 8.0 Hz), 7.01 (1H, ddd, J=7.6, 7.2, 15.6 Hz), 6.76 (1H, d, J=7.6 Hz), 6.70 (1H, d, J=8.0 Hz), 5.92 (1H, br. d (1r), J=15.6 Hz), 5.32–5.40 (1H, m), 3.80–3.88 (1H, m), 2.98–3.10 (1H, m), 2.53–2.68 (2H, m), 2.21–2.30 (1H, m), 1.96–2.06 (1H, m), 1.50–1.68 (5H, m), 1.23–1.45 (3H, m), 0.97 (9H, s), 0.90 (9H, s), 0.87 (3H, d, J=6.8 Hz), 0.25 (3H, s), 0.22 (3H, s), 0.11 (3H, s), 0.06 (3H, s).

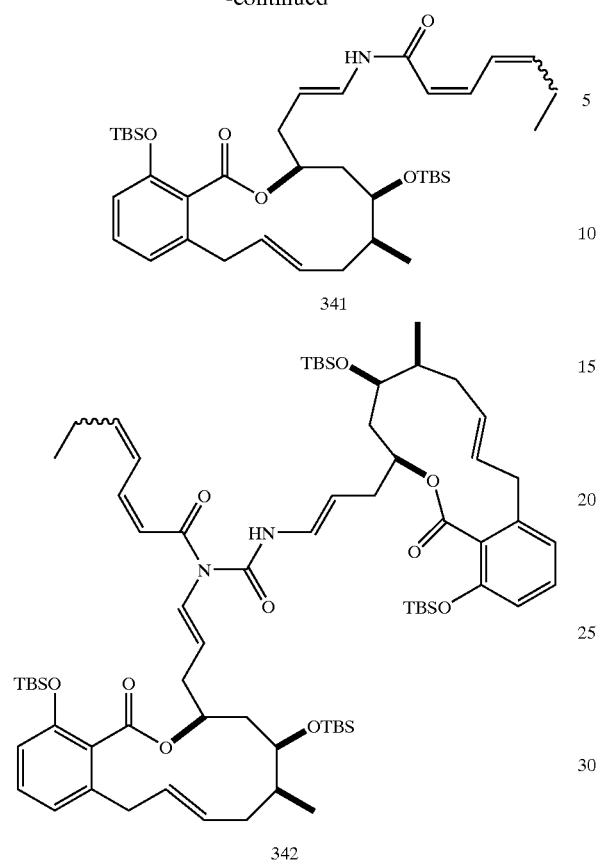

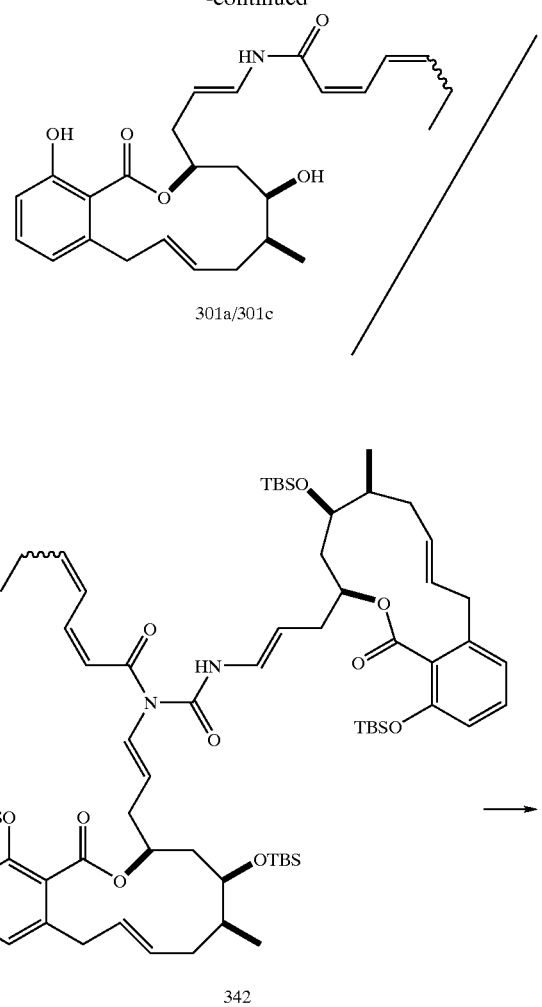

Acyl azide 338 (12 mg; 0.0195 mmol) in benzene (1 mL) was stirred at 75° C. for 6 h, after which the solvent was removed and the residue (isocyanate 339) dissolved in diethyl ether (1 mL). In a separate flask, a 0.15 M solution of 1-lithio-1,3-hexadiene (1:1 mixture of 1Z,3Z and 1Z,3E isomers) was prepared by the addition of t-BuLi (2.05 equiv with respect to the bromide) to a solution of the corresponding bromide in THF at −78° C. After stirring for 45 min at −78° C. and warming to RT, the organolithium (0.15 M in THF; 143 μL; 0.0215 mmol) was added dropwise to the ethereal solution of isocyanate 339 at −78° C. The mixture was allowed to reach 0° C. over a 1 h period followed by the addition of pH 7.0 phosphate buffer. Extraction with diethyl ether (3×), drying (Na$_2$SO$_4$), concentration and rapid purification by FC (silicagel, 6% EtOAc in hexanes containing 0.2% Et$_3$N) gave 3.7 mg of a less polar product 342 and 5.9 mg of a more polar product 341.

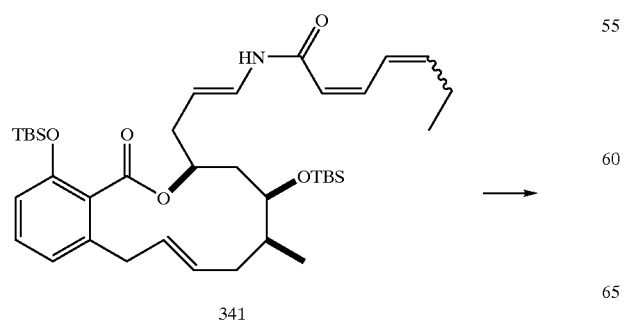

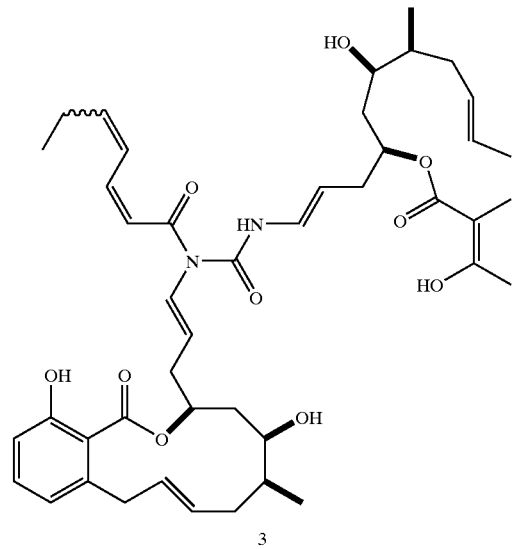

The less polar product 342 was treated with 250 μL of a solution prepared from 0.5 g commercial HF-pyridine in 1.25 mL pyridine and 6.75 mL THF. The more polar product 341 was similarly treated with 410 μL of the same solution. After stirring for 48 h at RT, the reactions were quenched with a phosphate buffer (pH 7.0; 10 mL), extracted with EtOAc (4×), dried (Na$_2$SO$_4$) and concentrated. The product derived from deprotection of 341 was purified by normal-phased semi-preparative HPLC (5 μ Luna silicagel; 250×10 mm column; 25% acetone in hexanes, t$_R$=25 min) yielding 1.7 mg of a 1:1 mixture of salicylihalamide A (301a) and the corresponding geometrical isomer 301c (20% from acyl azide 338). The product derived from deprotection of 342 provided two fractions after HPLC purification (35% acetone in hexanes): 1.5 mg of 343 (t$_R$=25.7 min; 10% yield from acyl azide 338) and 1.5 mg of 344 (t$_R$=26.7 min; 10% yield from acyl azide 338). The combined overall yield for 301a,c and 343–344 from acyl azide 338 is 40%. 343: $^1$H NMR (400 MHz, CD$_3$OD) δ 7.14 (1H, app.t, J=8.0 Hz), 7.13 (1H, app.t, J=8.0 Hz), 7.06 (1H, app.t, J=11.2 Hz), 6.75 (1H, d, J=8.0 Hz), 6.72 (1H, d, J=14.0 Hz), 6.71 (1H, d, J=8.0 Hz), 6.68 (1H, d, J=7.6 Hz), 6.67 (1H, d, J=7.6 Hz), 6.61 (1H, app.t, J=12.0 Hz), 6.44 (1H, d, J=14.0 Hz), 6.09 (1H, d, J=11.6 Hz), 5.81–5.90 (2H, m), 5.51 (1H, ddd, J=6.4, 8.4, 14.8 Hz), 5.23–5.48 (6H, m), 4.18 (1H, dd, J=3.6, 9.6 Hz), 4.17 (1H, dd, J=3.6, 9.6 Hz), 3.62 (1H, dd, J=8.8, 15.6 Hz), 3.58 (1H, dd, J=8.8, 15.6 Hz), 3.37 (2H, br d, J=15.6 Hz), 2.42–2.61 (3H, m), 2.25–2.40 (3H, m), 2.15–2.24 (2H, m), 1.84–1.95 (2H, m), 1.68–1.87 (4H, m), 1.30–1.43 (2H, m), 0.97 (3H, t, J=7.2 Hz), 0.87 (6H, d, J=6.8 Hz); MS (ES) m/z (%): 819.33 ([M+Na]$^+$, 35), 797.34 ([M+H]$^+$, 100); HRMS (FAB) Calcd for C$_{46}$H$_{57}$N$_2$O$_{10}$ (MH$^+$): 797.4013. Found: 797.4015. 344: $^1$H NMR (400 MHz, CD$_3$OD) δ 7.21 (1H, dd, J=11.2, 15.2 Hz), 7.14 (1H, app.t, J=8.0 Hz), 7.13 (1H, app.t, J=7.6 Hz), 6.75 (1H, d, J=7.6 Hz), 6.74 (1H, d, J=13.6 Hz), 6.71 (1H, d, J=8.0 Hz), 6.68 (1H, d, J=7.2 Hz), 6.67 (1H, d, J=7.6 Hz), 6.45 (1H, d, J=13.6 Hz), 6.29 (1H, app.t, J=11.2 Hz), 6.07 (1H, dt, J=6.8, 15.2 Hz), 5.99 (1H, d, J=11.6 Hz), 5.84 (1H, app.dt, J=6.8, 14.0 Hz), 5.51 (1H, ddd, J=6.4, 8.0, 14.4 Hz), 5.23–5.47 (6H, m), 4.18 (1H, dd, J=4.4, 8.8 Hz), 4.17 (1H, dd, J=4.4, 8.8 Hz), 3.61 (1H, dd, J=8.8, 16.8 Hz), 3.58 (1H, dd, J=8.4, 16.4 Hz), 3.37 (2H, br d, J=16.4 Hz), 2.42–2.55 (3H, m), 2.25–2.40 (3H, m), 2.15–2.24 (2H, m), 1.84–1.95 (2H, m), 1.69–1.87 (4H, m), 1.32–1.43 (2H, m), 1.04 (3H, t, J=7.2 Hz), 0.87 (6H, d, J=6.8 Hz); MS (ES) m/z (%): 819.30 ([M+Na]$^+$, 60), 797.34 ([M+H]$^+$, 100); HRMS (FAB) Calcd for C$_{46}$H$_{57}$N$_2$O$_{10}$ (MH$^+$): 797.4013. Found: 797.4021.

38 ⟶ 39 ⟶

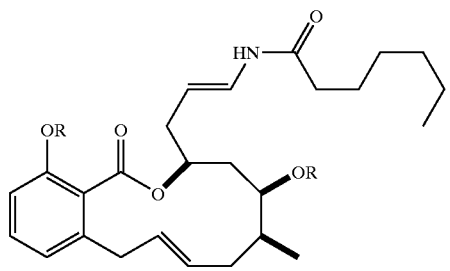

xi R = TBS
346 R = H

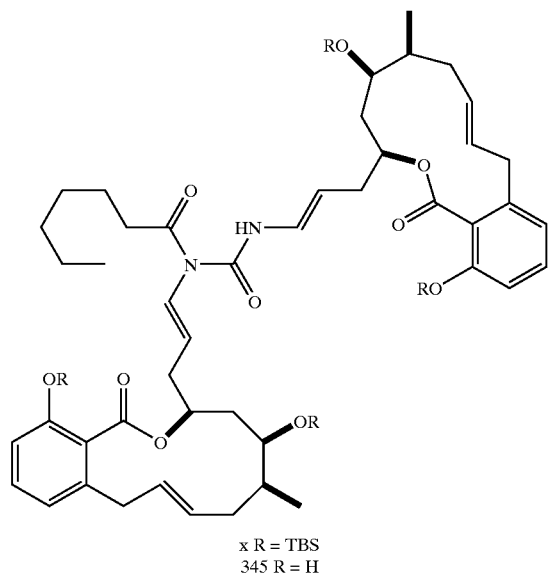

x R = TBS
345 R = H

Following the procedure described above, acyl azide 338 (9.0 mg; 0.0146 mmol) was converted to isocyanate 339, followed by the addition of n-hexyllithium (0.15 M in THF; prepared from the bromide as described above). Workup and rapid purification by FC (silicagel, 15% EtOAc in hexanes containing 0.2% Et$_3$N) gave 4.0 mg of a less polar product x and 4.2 mg of a more polar product xi. Deprotection and purification by semi-preparative HPLC as described above yielded 1.4 mg of 346 (22%) and 1.6 mg of the corresponding dimer 345 (14%), respectively. 346: $^1$H NMR (400 MHz, CD$_3$OD) δ 7.15 (1H, app.t, J=8.0 Hz), 6.76 (1H, d, J=14.0 Hz), 6.74 (1H, d, J=8.0 Hz), 6.67 (1H, d, J=7.2 Hz), 5.25–5.44 (4H, m), 4.13 (1H, dd, J=3.2, 8.8 Hz), 3.57 (1H, dd, J=8.0, 16.4 Hz), 3.37 (1H, br d, J=16.4 Hz), 2.25–2.46 (3H, m), 2.22 (2H, t, J=7.2 Hz), 1.84–1.95 (1H, m), 1.71–1.83 (2H, m), 1.57–1.66 (2H, m), 1.28–1.42 (7H, m), 0.91 (3H, t, J=7.2 Hz), 0.87 (3H, d, J=6.8 Hz); MS (ES) m/z (%): 466.24 ([M+Na]$^+$, 17), 444.26 ([M+H]$^+$, 100); HRMS (FAB) Calcd for C$_{26}$H$_{38}$NO$_5$ (MH$^+$): 444.2750. Found: 444.2759. 345: $^1$H NMR (400 MHz, CD$_3$OD) δ 7.14 (1H, app.t, J=7.6 Hz), 7.12 (1H, app.t, J=7.2 Hz), 6.75 (1H, d, J=8.4 Hz), 6.73 (1H, d, J=14.4 Hz), 6.72 (1H, d, J=8.8 Hz), 6.67 (2H, d, J=7.2 Hz), 6.35 (1H, d, J=14.0 Hz), 6.00 (1H, app.dt, J=7.6, 14.4 Hz), 5.50 (1H, ddd, J=6.4, 8.4, 14.4 Hz), 5.25–5.46 (6H, m), 4.19 (1H, dd, J=3.2, 9.2 Hz), 4.16 (1H, dd, J=3.2, 8.8 Hz), 3.60 (1H, dd, J=8.0, 16.0 Hz), 3.59 (1H, dd, J=7.6, 16.0 Hz), 3.37 (2H, br d, J=16.0 Hz), 2.63 (1H, app.dt, J=7.6, 16.8 Hz), 2.40–2.56 (4H, m), 2.24–2.39 (3H, m), 1.70–1.95 (6H, m), 1.47–1.57 (2H, m), 1.21–1.43 (8H, m), 0.87 (3H, d, J=6.8 Hz), 0.86 (3H, d, J=6.8 Hz), 0.86 (3H, t, J=7.2 Hz); MS (ES) m/z (%): 823.33 ([M+Na]$^+$, 50), 801.37 ([M+H]$^+$, 100); HRMS (FAB) Calcd for C$_{46}$H$_{61}$N$_2$O$_{10}$ (MH$^+$): 801.4326. Found: 801.4334.

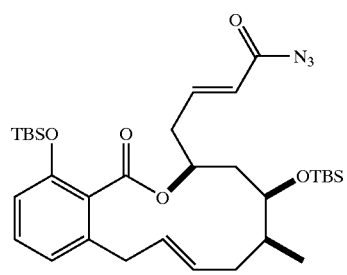

338

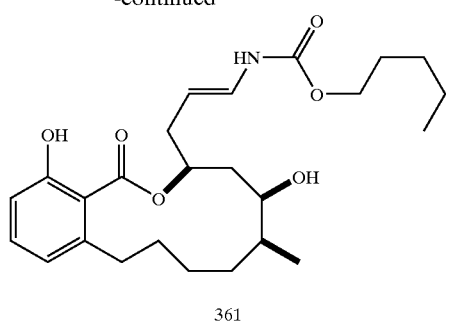

361

According to the procedure described for the synthesis of carbamate 351, acyl azide ix (15 mg, 0.02435 mmol) gave 4.7 mg of carbamate 361. 361: $[\alpha]_D$=−13.2 (c 0.24, MeOH); IR 3387, 2933, 1727, 1710, 1680, 1603, 1293, 1243, 1113 cm$^{-1}$; $^1$H NMR (400 MHz, CD$_3$OD) δ 7.25 (1H, app.t, J=7.6 Hz), 6.75 (1H, d, J=8.4 Hz), 6.73 (1H, d, J=7.6 Hz), 6.44 (1H, d, J=14.0 Hz), 5.14–5.22 (1H, m), 5.05 (1H, app.dt, J=7.6, 14.0 Hz), 4.04 (2H, t, J=6.4 Hz), 3.82–3.88 (1H, m), 3.66 (1H, ddd, 3.6, 12.4, 12.4 Hz), 2.39 (2H, app.t, J=6.6 Hz), 2.21 (1H, ddd, J=6.4, 12.4, 12.4 Hz), 2.10–2.20 (1H, m), 1.40–1.80 (9H, m), 1.30–1.40 (5H, m), 0.95 (3H, d, J=6.8 Hz), 0.92 (3H, t, J=6.4 Hz); $^{13}$C NMR (75 MHz, CD$_3$OD) δ 172.5, 162.3, 156.6, 147.0, 134.8, 128.5, 123.4, 116.3, 115.2, 105.5, 76.3, 66.4, 37.4, 34.4, 32.7, 29.9, 29.3, 23.5, 16.6, 14.5; MS (ES) m/z 448.20 ([M+H]$^+$, 100), 470.19 ([M+Na]$^+$, 32). HRMS Calcd for C$_{25}$H$_{37}$NO$_6$Li (MLi$^+$): 454.2781. Found: 454.2779.

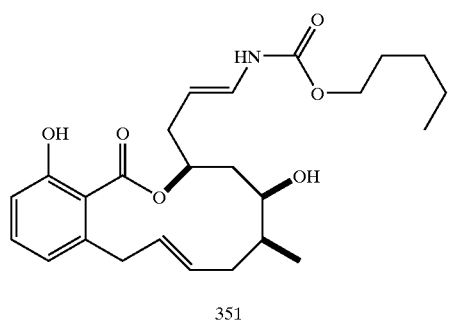

351

A solution of acyl azide 338 (10.0 mg; 0.0163 mmol) and 1-pentanol (11 μL; 0.1019 mmol) in benzene (1 mL) was stirred for 8 h at 80° C. After removal of the solvent, the residue was treated with 780 μL of a solution prepared from 0.5 g commercial HF-pyridine in 1.25 mL pyridine and 6.75 mL THF. After stirring for 24 h at RT, the reaction were quenched with a phosphate buffer (pH 7.0; 10 mL), extracted with EtOAc (4×), dried (Na$_2$SO$_4$) and concentrated. Purification by FC (silicagel; 25% acetone in hexanes) yielded 3.4 mg of carbamate 351 (0.00763 mmol; 47%). 351: $[\alpha]_D$=−18.8 (c 0.17, MeOH); $^1$H NMR (400 MHz, CD$_3$OD) δ 7.14 (1H, app.t, J=8.0 Hz), 6.73 (1H, d, J=8.0 Hz), 6.67 (1H, d, J=7.2 Hz), 6.49 (1H, d, J=14.4 Hz), 5.26–5.44 (3H, m), 5.18 (1H, app.dt, J=7.2, 14.4 Hz), 4.13 (1H, dd, J=3.6, 9.2 Hz), 4.07 (2H, t, 6.4 Hz), 3.57 (1H, dd, J=8.4, 16.4 Hz), 3.36 (1H, br d, J=16.4 Hz), 2.25–2.44 (3H, m), 1.84–1.95 (1H, m), 1.71–1.82 (2H, m), 1.60–1.69 (2H, m), 1.33–1.41 (5H, m), 0.93 (3H, t, J=7.6 Hz), 0.87 (3H, d, J=6.4 Hz); $^{13}$C NMR (75 MHz, CD$_3$OD) δ 171.2, 157.2, 156.6, 140.8, 131.83, 131.76, 127.8, 123.2, 122.6, 115.4, 106.9, 76.4, 72.1, 66.4, 39.1, 38.9, 38.7, 37.5, 36.6, 29.9, 29.3, 23.5, 14.5, 13.7; MS (ES) m/z (%): 468.20 ([M+Na]$^+$, 26), 446.23 ([M+H]$^+$, 100); HRMS (FAB) Calcd for C$_{25}$H$_{36}$NO$_6$ (MH$^+$): 446.2543. Found: 446.2528.

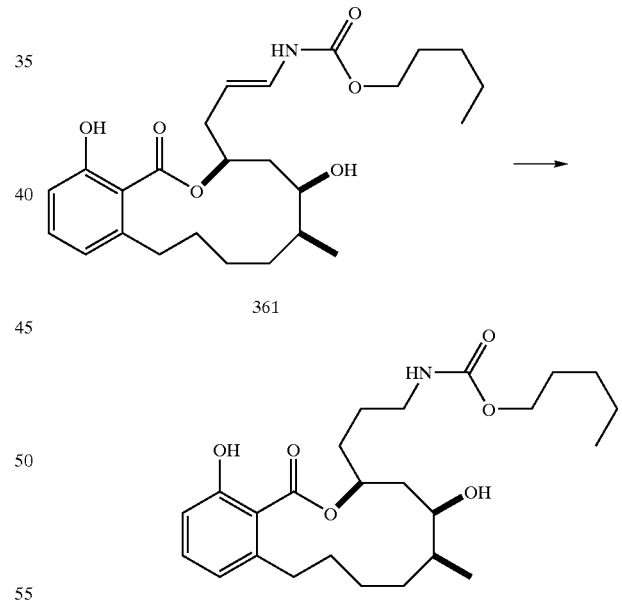

361

362

To a solution of carbamate 361 (1 mg, 0.00268 mmol) in MeOH (1 mL) was added 10% Pd/C (1 mg) and the resulting suspension was stirred under an atmosphere of hydrogen gas (balloon) at rt for 16 h. The catalyst was filtered and the filtrate concentrated and purified by HPLC (20% acetone/hexanes) to yield 0.3 mg of carbamate 362 (0.000667 mmol, 25%). 362: $^1$H NMR (400 MHz, CD$_3$OD) δ 7.24 (1H, app.t, J=8.0 Hz), 6.75 (1H, d, J=8.4 Hz), 6.73 (1H, d, J=7.2 Hz), 5.24–5.32 (1H, m), 3.99 (2H, t, J=6.8 Hz), 3.86–3.92 (1H,

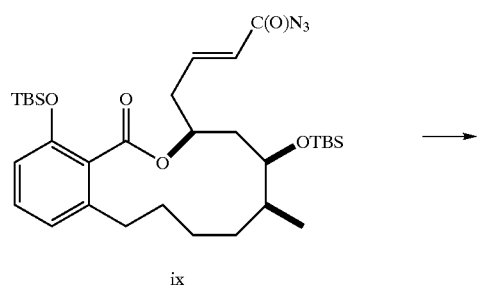

ix m), 3.55 (1H, ddd, 3.6, 12.4, 12.4 Hz), 3.11 (2H, app.t, J=6.8 Hz), 2.11–2.30 (2H, m), 1.45–1.77 (13H, m), 1.28–1.38 (5H, m), 0.94 (3H, d, J=6.8 Hz), 0.91 (3H, t, J=7.6 Hz); MS (ES) m/z 450.24 ([M+H]$^+$, 100), 472.24 ([M+Na]$^+$, 67). HRMS Calcd for $C_{25}H_{39}NO_6Li$ (MLi$^+$): 456.2937. Found: 456.2935.

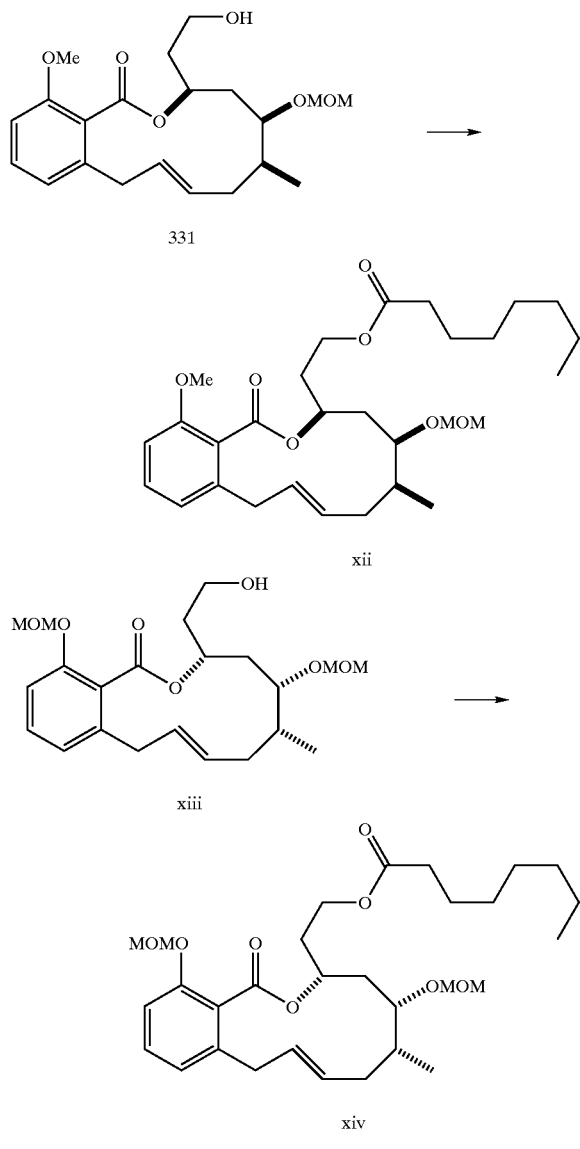

To a solution of 331 (6.4 mg, 0.0169 mmol), octanoic acid (5.3 μL, 0.034 mmol) and PPh$_3$ (8.8 mg, 0.034 mmol) in Et$_2$O (1 mL) was added diethylazodicarboxylate (DEAD, 5.5 μL, 0.034 mmol). After stirring for 1.5 h at rt, H$_2$O (5 mL) was added and an extraction was performed with Et$_2$O (3×). The combined organic layers were dried (MgSO$_4$) and concentrated in vacuo. The residue was purified by FC (10% EtOAc/hexanes) to give 6.7 mg of octanoate ester xii (0.0133 mmol, 79%). xii: $^1$H NMR (400 MHz, CDCl$_3$) δ 7.23 (1H, app.t, J=8.4 Hz), 6.80 (1H, d,J=8.4 Hz), 6.75 (1H, d,J=7.6 Hz), 5.42–5.53 (2H, m), 5.35 (1H, app.ddt, J=2.4, 9.6, 15.2 Hz), 4.90 (1H, d, J=6.8 Hz), 4.82 (1H, d, J=6.8 ), 4.27 (1H, ddd, J=4.8, 7.6, 11.2 Hz), 4.22 (1H, ddd, J=6.4, 8.8, 11.2 Hz), 4.18 (1H, dd, J=3.6, 9.2 Hz), 3.18 (3H, s), 3.72 (1H, dd, J=9.6, 16.4 Hz), 3.47 (3H, s), 3.32 (1H, dddd, J=2.0, 2.0, 4.4, 16.4 Hz), 2.27–2.36 (1H, m), 2.29 (2H, t, J=7.2 Hz), 2.07–2.18 (1H, m), 1.87–2.06 (2H, m), 1.78 (1H, dd, J=8.8, 15.6 Hz), 1.71 (1H, app.dt, J=11.6, 14.4 Hz), 1.53–1.67 (2H, m), 1.43 (1H, dd, J=9.2, 15.2 Hz), 1.22–1.34 (8H, m), 0.87 (3H, d, J=6.8 Hz), 0.87 (3H, t, J=6.8 Hz); $^{13}$C NMR (75 MHz, CDCl$_3$) δ 174.2, 168.5, 156.7, 139.2, 131.6, 130.3, 128.7, 124.5, 122.9, 109.3, 97.1, 79.4, 71.5, 61.1, 55.8, 55.6, 38.0, 37.9, 36.1, 35.4, 34.6, 34.2, 31.9, 29.3, 29.1, 25.2, 22.8, 14.3, 13.5. HRMS Calcd for $C_{29}H_{44}O_7Li$ (MLi$^+$): 511.3247. Found: 511.3251. The bis-MOM derivative xiv was prepared similarly from alcohol xiii. xiv: [α]$_D$=+47.6 (c 0.63, CHCl$_3$); IR 2927, 1733, 1587, 1463, 1273, 1157, 1040 cm$^{-1}$; $^1$H NMR (400 MHz, CDCl$_3$) δ 7.21 (1H, dd, J=8.4, 7.6 Hz), 7.09 (1H, d, J=8.4 Hz), 6.80 (1H, d, J=7.6 Hz), 5.42–5.54 (2H, m), 5.34 (1H, br.dd, J=9.6, 14.8 Hz), 5.22 (1H, d, J=6.8 Hz), 5.17 (1H, d, J=6.8), 4.89 (1H, d, J=6.8 Hz), 4.82 (1H, d, J=6.8), 4.21–4.33 (2H, m), 4.16 (1H, dd, J=3.6, 9.6 Hz), 3.72 (1H, dd, J=9.6, 16.4 Hz), 3.47 (3H, s), 3.43 (3H, s), 3.33 (1H, br.d, J=16.4 Hz), 2.28–2.36 (1H, m), 2.28 (2H, t, J=7.6 Hz), 2.09–2.20 (1H, m), 1.88–2.08 (2H, m), 1.81 (1H, dd, J=8.4, 16.0 Hz), 1.71 (1H, ddd, J=11.2, 11.2, 14.0 Hz), 1.52–1.64 (2H, m), 1.44 (1H, dd, J=9.6, 16.0 Hz), 1.20–1.34 (8H, m), 0.87 (3H, d, J=6.8 Hz), 0.87 (3H, t, J=6.4 Hz); $^{13}$C NMR (75 MHz, CDCl$_3$) δ 174.2, 168.3, 154.5, 139.3, 131.6, 130.3, 128.7, 125.3, 124.0, 113.0, 97.1, 94.6, 79.6, 71.6, 61.1, 56.2, 55.8, 37.95, 37.92, 35.9, 35.4, 34.5, 34.2, 31.9, 29.3, 29.1, 25.2, 22.8, 14.3, 13.5. HRMS Calcd for $C_{30}H_{46}O_8Li$ (MLi$^+$): 541.3353. Found: 541.3361.

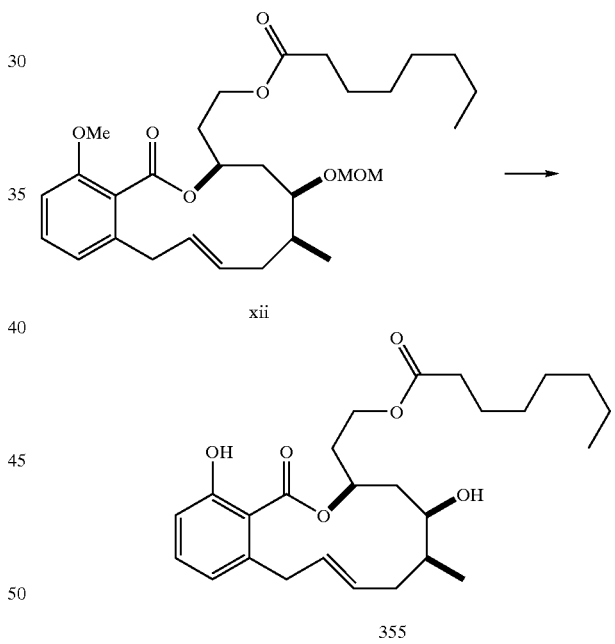

According to the procedure described for the deprotection of 334, deprotection of octanoate xii (9 mg, 0.0178 mmol) with BBr$_3$ (2.5 equiv.) yielded 5 mg of octanoate 355 (0.011 mmol, 63%). 355: [α]$_D$=–3.72 (c 0.2, CHCl$_3$); IR 3412, 3152, 2918, 2850, 1738, 1686, 1591, 1467 cm$^{-1}$; $^1$H NMR (400 MHz, CDCl$_3$) δ 11.0 (1H, br s), 7.30 7.6, 8.4 Hz), 6.90 (1H, dd, J=0.8, 8.4 Hz), 6.71 (1H, dd, J=0.8, 7.6 Hz), 5.62 (1H, app.ddt, J=0.8, 6.0, 12.0 Hz), 5.49 (1H, br d, J=15.6 Hz), 5.03–5.13 (1H, m), 4.24 (1H, app.dt, J=6.0, 6.4, 11.6 Hz), 4.18 (1H, app.dt, J=6.0, 11.6 Hz), 3.76 (1H, dd, J=6.0, 17.2 Hz), 3.64 (1H, dd, J=3.6, 8.8 Hz), 3.39 (1H, br d, J=17.2 Hz), 2.30–2:40 (1H, m), 2.27 (2H, t, J=7.2 Hz), 1.99–2.09 (3H, m), 1.78–1.97 (2H, m), 1.54–1.64 (2H, m), 1.39 (1H, ddd, J=0.8, 8.8, 15.2 Hz), 1.20–1.34 (8H, m), 0.93 (3H, d, J=6.8 Hz), 0.88 (3H, t, J=7.2 Hz); $^{13}$C NMR (75 MHz, CDCl$_3$) δ 174.2, 171.2, 162.8, 142.4, 134.3, 133.1, 126.6, 123.8, 117.0, 113.4, 72.3, 70.6, 60.8, 39.3, 38.6, 37.5, 34.7, 34.5, 31.9, 29.9, 29.3, 29.1, 25.1, 22.8, 14.3, 13.9; MS (CI) m/z (%): 447 (30), 429 (70), 303 (36), 285 (75), 145 (100); HRMS (FAB) Calcd for C$_{26}$H$_{38}$O$_6$ (MH$^+$): 446.2668. Found: 446.2658.

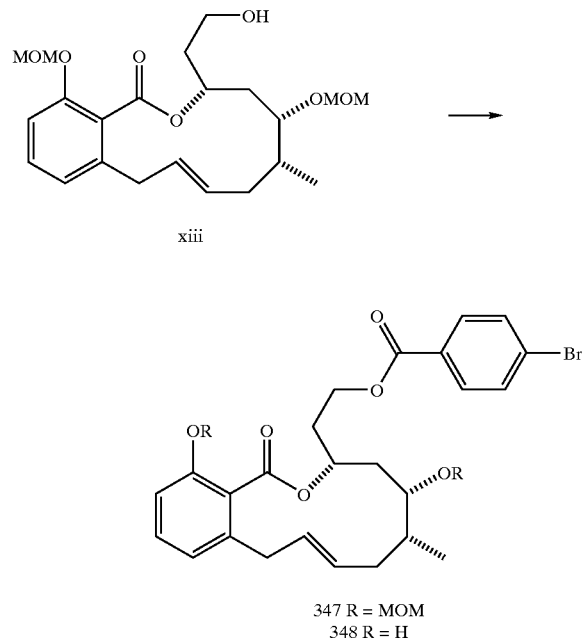

To a solution of xiii (25 mg, 0.061 mmol), p-bromo benzoic acid (49 mg, 0.245 mmol) and PPh$_3$ (65 mg, 0.245 mmol) in Et$_2$O (6 mL) was added diethylazodicarboxylate (DEAD, 40 μL, 0.245 mmol). After stirring for 2.5 h at rt, H$_2$O (10 mL) was added and an extraction was performed with Et$_2$O (3×). The combined organic layers were dried (MgSO$_4$) and concentrated in vacuo. The residue was purified by FC (10% EtOAc/hexanes) to give 32 mg of p-bromo benzoate 347 (0.054 mmol, 88%). 347: [α]$_D$=+29.0 (c 0.78, CHCl$_3$); IR 2953, 2933, 1720, 1590, 1460, 1273, 1037 cm$^{-1}$; $^1$H NMR (400 MHz, CDCl$_3$]) δ 7.90 (2H, d, J=8.8 Hz), 7.56 (2H, d, J=8.8 Hz), 7.21 (1H, dd, J=7.2, 8.8 Hz), 7.07 (1H, d, J=8.8 Hz), 6.81 (1H, d, J=7.2 Hz), 5.58–6.64 (1H, m), 5.50 (1H, br.dd, J=11.2, 15.2 Hz), 5.36 (1H, br.dd, J=9.2, 15.2 Hz), 5.22 (1H, d, J=6.8 Hz), 5.14 (1H, d, J=6.8 Hz), 4.87 (1H, d, J=6.8 Hz), 4.81 (1H, d, J=6.8 Hz), 4.48–4.55 (2H, m), 4.18 (1H, dd, J=3.2, 9.6 Hz), 3.72 (1H, dd, J=9.6, 16.4 Hz), 3.43 (3H, s), 3.37 (3H, s), 3.34 (1H, br.d, J=16.4 Hz), 2.30–2.35 (1H, m), 2.05–2.19 (3H, m), 1.84 (1H, dd, J=8.4, 15.6 Hz), 1.72 (1H, ddd, J=11.6, 11.6, 14.0 Hz), 1.48 (1H, dd, J=9.6, 15.6 Hz), 0.87 (3H, d, J=7.2 Hz); $^{13}$C NMR (75 MHz, CDCl$_3$) δ 168.3, 166.1, 154.5, 139.2, 131.9, 131.8, 131.5, 131.3, 130.3, 129.4, 128.8, 128.3, 125.2, 124.0, 113.0, 97.0, 94.6, 79.6, 71.4, 61.9, 56.2, 55.8, 38.0 (2 peaks), 35.8, 35.3, 34.1, 13.5. HRMS Calcd for C$_{29}$H$_{35}$BrO$_8$Li (MLi$^+$): 597.1675. Found: 597.1682. 348: [α]$_D$=+16.2 (c 0.45, CHCl$_3$); IR 3380, 2920, 2847, 1717, 1700, 1557, 1460, 1293, 1070 cm$^{-1}$; $^1$H NMR (400 MHz, acetone[D$_6$]) δ 9.23 (1H, s), 7.93 (2H, d (1r), J=8.8 (2.0 Hz), 7.68 (2H, d (1r), J=8.8 (2.0) Hz), 7.16 (1H, dd, J=7.6, 8.0 Hz), 6.83 (1H, d, J=8.0 Hz), 6.71 (1H, d, J=7.6 Hz), 5.63 (1H, ddd, J=4.8, 8.8, 8.8 Hz), 5.29–5.42 (2H, m), 4.50–4.58 (2H, m), 4.13 (1H, ddd, J=4.0, 4.4, 8.8 Hz), 3.62 (1H, dd, J=0.4, 4.8 Hz), 3.56 (1H, dd, J=7.2, 16.0 Hz), 3.40 (1H, br.d, J=16.0 Hz), 2.25–2.32 (1H, m), 2.09–2.18 (2H, m), 1.86–1.94 (2H, m), 1.74–1.94 (1H, m), 1.39 (1H, dd, J=8.8, 15.2 Hz), 0.87 (3H, d, J=6.8 Hz); $^{13}$C NMR (75 MHz, CDCl$_3$) δ 171.4, 166.1, 163.0, 142.4, 134.4, 133.2, 131.9, 131.3, 129.0, 128.4, 126.5, 123.8, 117.0, 113.2, 72.3, 70.5, 61.8, 39.4, 38.6, 37.5, 36.2, 34.6, 13.9; MS (El) m/z (%): 506 (16), 505 (55), 504 (45), 503 (50), 502 (32), 488 (18), 487 (40), 486 (58), 485 (100), 484 (16). HRMS Calcd for C$_{25}$H$_{27}$BrO$_6$Li (MLi$^+$): 509.1151. Found: 509.1153.

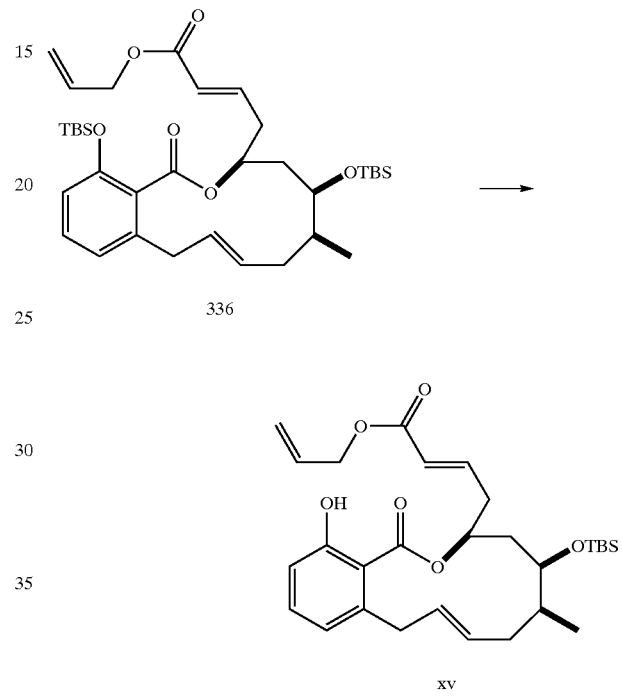

To a solution of 336 (35 mg, 0.0556 mmol) in THF at 0° C. was added Bu$_4$NF (1 M in THF, 56 μL, 0.056 mmol). After stirring for 10 min, aq. NH$_4$Cl was added and the mixture was extracted with Et$_2$O. The organic layer was washed with brine, dried (MgSO$_4$), filtered and concentrated. The residue was purified by FC (silicagel, 25% EtOAc in hexanes) to give 24 mg of phenol xv (84%) as a colorless oil. xv: [α]$_D$=−8.0 (c 1.37, CHCl$_3$); IR 2955, 2929, 2856, 1725, 1652, 1463, 1451, 1361, 1293, 1249, 1166, 1063, 972, 836 cm$^{-1}$; $^1$H-NMR (300 MHz, CDCl$_3$) δ 10.97 (1H, br.s, aryl-OH), 7.32 (1H, dd, J=7.5, 8.5 Hz), 7.00 (1H, ddd, J=7.5, 7.5, 15.6 Hz), 6.90 (1H, dd, J=1.2, 8.4 Hz), 6.72 (1H, dd, J=1.2, 7.5 Hz), 5.89–6.02 (2H, m), 5.42–5.52 (2H, m), 5.34 (1H, ddt, J=1.5, 1.5, 17.4 Hz), 5.25 (1H, ddt, J=1.5, 1.5, 10.5 Hz), 5.02–5.14 (1H, m), 4.66 (2H, dt, J=1.5, 5.7 Hz), 3.70 (1H, dd, J=6.3, 16.2 Hz), 3.60 (1H, dd, J=3.0, 8.4 Hz), 3.40 (1H, br.d, J=16.5 Hz), 2.58–2.64 (2H, m), 2.26–2.39 (1H, m), 2.01 (1H, dd, J=10.7, 15.0 Hz), 1.77–1.90 (2H, m), 1.38 (1H, ddd, J=1.2, 8.1, 15.0), 0.88 (9H, s), 0.87 (3H, d, J=6.9 Hz), 0.04 (3H, s), −0.03 (3H, s); $^{13}$C-NMR (100 MHz, CDCl$_3$) δ 170.8, 165.8, 162.8, 143.8, 142.5, 134.2, 132.8, 132.4, 126.9, 124.4, 123.8, 118.4, 116.8, 113.4, 73.8, 71.5, 65.3, 39.3, 38.5, 38.2, 37.5, 36.4, 26.0 (3C), 18.1, 14.0, −4.4, −4.7. HRMS Calcd for C$_{29}$H$_{42}$O$_6$SiLi (MLi$^+$): 521.2911. Found: 521.2912.

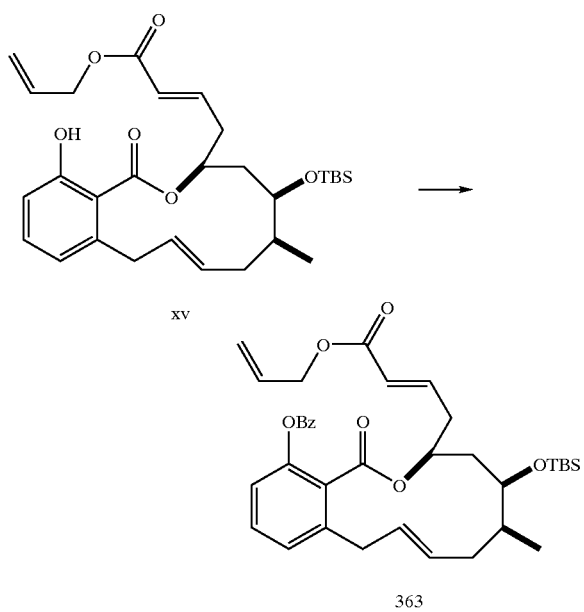

xv

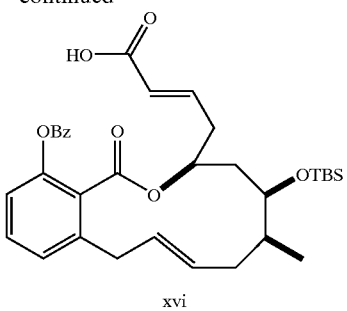

xvi

To a solution of phenol xv (23.5 mg, 0.0457 mmol) in CH$_2$Cl$_2$ (0.5 mL) was added pyridine (42 μL), benzoyl chloride (31 μL, 0.262 mmol) at 0° C. The mixture was stirred at 0° C. for 80 min, followed by the addition of water (5 mL) and AcOH (150 μL). The resulting mixture was extracted with ether (3×10 mL), dried over MgSO$_4$, filtered and concentrated. Purification by FC (silicagel, 25% EtOAc in hexanes) provided 22 mg of benzoate 363 (78%) as a colorless oil. 363 [α]$_D$=+4.0 (c 1.0, CHCl$_3$); IR 2928, 1745, 1726, 1452, 1268, 1228, 1176, 1067, 836, 775, 707 cm$^{-1}$; $^1$H-NMR (300 MHz, CDCl$_3$) δ 8.16–8.20 (2H, m), 7.62–7.69 (1H, m), 7.49–7.55 (2H, m), 7.37 (1H, dd, J=7.8, 8.1 Hz), 7.14 (1H, d, J=7.8 Hz), 7.11 (1H, d, J=8.1 Hz), 6.65 (1H, ddd, J=6.9, 7.6, 15.6 Hz), 5.95 (1H, dddd, J=5.7, 5.7, 10.5, 17.1 Hz), 5.50 (1H, br.d, J=15.9 Hz), 5.30–5.50 (2H, m), 5.33 (1H, ddt, J=1.5, 1.5, 17.1 Hz), 5.24 (1H, ddt, J=1.5, 1.5, 10.5 Hz), 5.14–5.22 (1H, m), 4.61 (2H, ddd, J=1.5, 1.5, 5.4 Hz), 4.23 (1H, dd, J=3.6, 8.7 Hz), 3.80 (1H, dd, J=9.3, 16.2 Hz), 3.41 (1H, br.d, J=16.2 Hz), 2.22–2.33 (1H, m), 2.08 (1H, dddd, J=1.8, 6.9, 8.4, 15.0 Hz), 1.74–1.93 (2H, m), 1.58–1.73 (2H, m), 1.32 (1H, dd, J=8.7, 15.0 Hz), 0.88 (9H, s), 0.80 (3H, d, J=6.6 Hz), 0.18 (3H, s), 0.12 (3H, s); $^{13}$C-NMR (75 MHz, CDCl$_3$) δ 166.6, 165.7, 164.6, 148.2, 143.3, 140.3, 134.2, 132.5, 132.1, 130.4 (2C), 130.3, 129.3, 129.0 (2C), 128.2, 128.1, 124.1, 121.4, 118.3, 73.4, 72.6, 65.2, 38.2, 37.9, 37.4, 36.4, 26.1 (3C), 18.1, 13.2, −4.1, −4.2. HRMS Calcd for C$_{36}$H$_{47}$O$_7$Si (MH$^+$): 619.3091. Found: 619.3061.

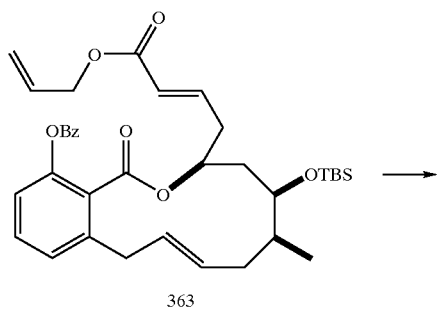

363

To a solution of allyl ester 363 (20 mg, 0.0323 mmol) in THF (3 mL) was added Pd(PPh$_3$)$_4$ (8 mg, 0.00646 mmol) and morpholine (28 μL, 0.323 mmol). After 3 h at RT, the solvent was removed and the residue was purified by FC (25% EtOAc in hexanes containing 5% ACOH). Carboxylic acid xvi (16 mg, 85%) was obtained as a colorless oil. xvi: [α]$_D$=+6.2 (c 0.8, CHCl$_3$); IR 2928, 1746, 1699, 1452, 1269, 1228, 1068, 972, 775, 707 cm$^{-1}$; $^1$H-NMR (300 MHz, CDCl$_3$) δ 8.18 (2H, dd, J=1.8, 7.5 Hz), 7.67 (1H, app.t, J=7.5 Hz), 7.52 (2H, app.t, J=7.8 Hz), 7.38 (1H, app.t, J=8.1 Hz), 7.14 (1H, d, J=7.5 Hz), 7.13 (1H, d, J=7.5 Hz), 6.74 (1H, ddd, J=7.8, 8.7, 15.3 Hz), 5.28–5.50 (3H, m), 5.20 (1H, ddd, J=3.3, 8.1, 11.1 Hz), 4.23 (1H, dd, J=3.6, 8.4 Hz), 3.81 (1H, dd, J=9.0, 16.2 Hz), 3.41 (1H, br.d, J=16.5 Hz), 2.29 (1H, br.d, J=14.4 Hz), 2.02–2.12 (1H, m), 1.60–1.94 (4H, m), 1.31 (1H, dd, J=9.0, 15.3 Hz), 0.88 (9H, s), 0.80 (3H, d, J=6.6 Hz), 0.19 (3H, s), 0.11 (3H, s); $^{13}$C-NMR (75 MHz, CDCl$_3$) δ 170.7, 166.6, 164.6, 148.2, 145.8, 140.4, 134.3, 132.1, 130.4 (2C), 130.3, 129.3, 129.0 (2C), 128.2, 128.0, 123.5, 121.5, 73.2, 72.7, 38.3, 37.9, 37.3, 36.5, 26.0 (3C), 18.1, 13.6, −4.1, −4.2. HRMS Calcd for C$_{33}$H$_{43}$O$_7$Si (MH$^+$): 579.2778. Found: 579.2776.

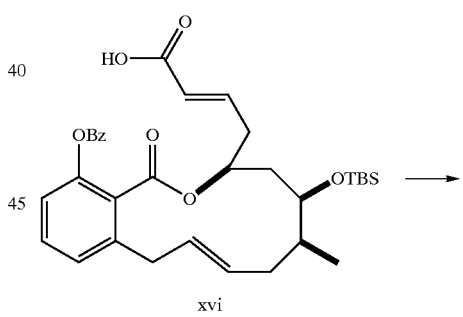

xvi

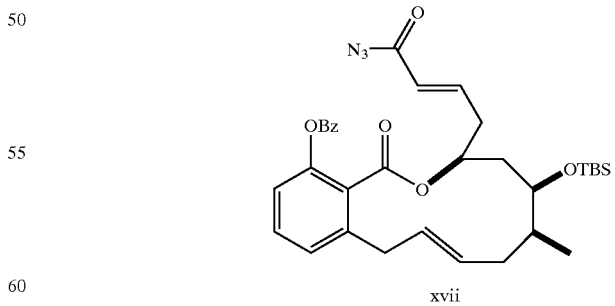

xvii

To a stirred solution of acid xvi (15.5 mg, 0.0268 mmol) and (PhO)$_2$P(O)N$_3$ (23 μL, 0.1071 mmol) in benzene (3 mL) was added Et$_3$N (19 μL, 0.134 mmol) at RT. After stirring for 16 h at RT, the solvent was removed and the residue was purified by FC (17% EtOAc in hexanes). The acyl azide xvii was obtained in 78% yield (12.5 mg). xvii: $^1$H-NMR (400 MHz, CDCl$_3$) δ 8.18 (2H, dd, J=1.2, 7.2 Hz), 7.67 (1H, m), 7.52 (2H, app.t, J=8.0 Hz), 7.38 (1H, app.t, J=8.0 Hz), 7.14 (1H, d, J=7.6 Hz), 7.12 (1H, d, J=7.6 Hz), 6.72 (1H, ddd, J=6.8, 8.0, 14.8 Hz), 5.46 (1H, br.d, J=15.6 Hz), 5.44 (1H, dddd, J=2.4, 2.4, 10.8, 15.2 Hz), 5.33 (1H, dddd, J=2.0, 2.0, 9.2, 15.2 Hz), 5.19 (1H, ddd, J=3.2, 7.6, 7.6 Hz), 4.23 (1H, dd, J=4.0, 9.2 Hz), 3.81 (1H, dd, J=9.2, 16.4 Hz), 3.41 (1H, br.d, J=16.4 Hz), 2.29 (1H, br.d, J=13.6 Hz), 2.01–2.09 (1H, m), 1.76–1.94 (2H, m), 1.59–1.71 (2H, m), 1.25–1.31 (1H, m), 0.89 (9H, s), 0.80 (3H, d, J=6.4 Hz), 0.19 (3H, s), 0.12 (3H, s).

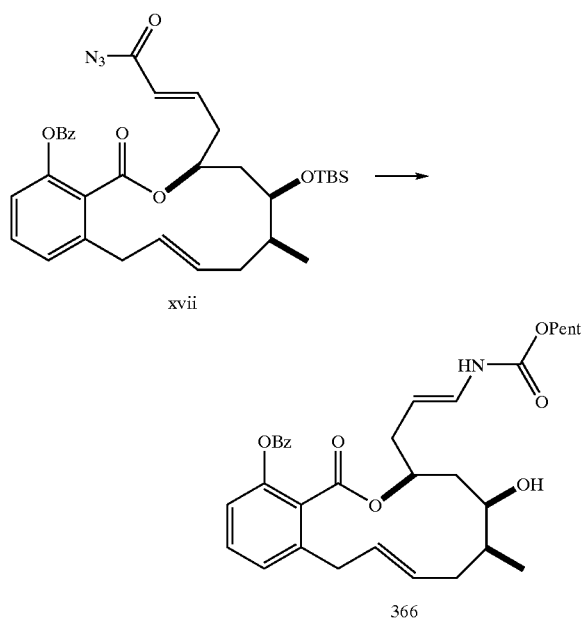

xvii

A solution of acylazide xvii (4 mg, 0.00663 mmol) and 1-pentanol (4.3 μL, 0.0398 mmol) in benzene (1 mL) was stirred for 6 h at 80° C. After removal of the solvent, the residue was treated with 370 μL of a solution of HF-pyridine in THF. After stirring for 4 days at RT, the reaction was quenched with a phosphate buffer (pH 7.0, 10 mL), extracted with EtOAc (3×15 mL), dried over MgSO$_4$ and concentrated. Purification by FC (silicagel, 33% EtOAc in hexanes) gave 1.5 mg of compound 366 (41%). 366: [α]$_D$=−48 (c 0.075, MeOH); IR 3439, 2960, 2929, 1713, 1678, 1452, 1350, 1272, 1230, 974 cm$^{-1}$; $^1$H-NMR (400 MHz, CDCl$_3$) δ 8.14–8.18 (2H, m), 7.72 (1H, apt.tt, J=1.6, 7.6 Hz), 7.58 (2H, app.t, J=7.6 Hz), 7.43 (1H, app.t, J=8.0 Hz), 7.19 (1H, d, J=8.0 Hz), 7.18 (1H, d, J=8.0 Hz), 6.14 (1H, d, J=14.4 Hz), 5.44–5.51 (1H, m), 5.27–5.34 (1H, m), 5.12–5.18 (1H, m), 4.78 (1H, dd, J=7.6, 14.8), 4.18 (1H, dd, J=3.6, 9.2 Hz), 4.05 (2H, app.t, J=6.4 Hz), 3.72 (1H, dd, J=9.2, 16.0 Hz), 3.46 (1H, br.d, J=16.0 Hz), 2.26 (1H, br), 1.71–1.90 (4H, m), 1.57–1.66 (3H, m), 1.26–1.38 (5H, m), 0.82 (3H, d, J=6.8 Hz); $^{13}$C-NMR (75 MHz, CDCl$_3$) δ 168.5, 166.1, 156.5, 149.5, 141.3, 135.6, 133.5, 131.3 (2C), 130.5, 130.2 (2C), 129.8, 129.4, 129.3, 128.1, 126.6, 122.6, 105.2, 76.5, 72.2, 66.4, 39.0, 38.7, 38.5, 37.2, 36.1, 29.9, 29.3, 23.5, 14.5, 13.6. MS (ES) m/z 550.27 ([M+H]$^+$, 100). HRMS Calcd for C$_{32}$H$_{39}$NO$_7$Li (MLi$^+$): 556.2887. Found: 556.2871.

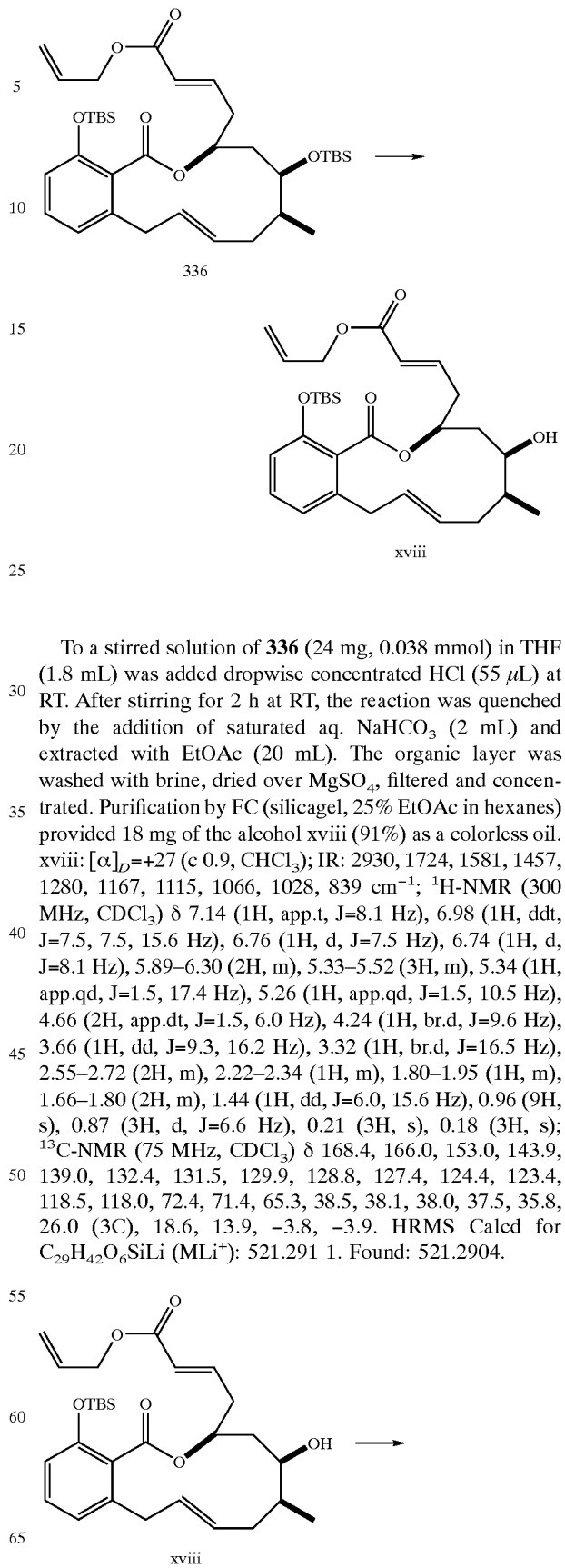

To a stirred solution of 336 (24 mg, 0.038 mmol) in THF (1.8 mL) was added dropwise concentrated HCl (55 μL) at RT. After stirring for 2 h at RT, the reaction was quenched by the addition of saturated aq. NaHCO$_3$ (2 mL) and extracted with EtOAc (20 mL). The organic layer was washed with brine, dried over MgSO$_4$, filtered and concentrated. Purification by FC (silicagel, 25% EtOAc in hexanes) provided 18 mg of the alcohol xviii (91%) as a colorless oil. xviii: [α]$_D$=+27 (c 0.9, CHCl$_3$); IR: 2930, 1724, 1581, 1457, 1280, 1167, 1115, 1066, 1028, 839 cm$^{-1}$; $^1$H-NMR (300 MHz, CDCl$_3$) δ 7.14 (1H, app.t, J=8.1 Hz), 6.98 (1H, ddt, J=7.5, 7.5, 15.6 Hz), 6.76 (1H, d, J=7.5 Hz), 6.74 (1H, d, J=8.1 Hz), 5.89–6.30 (2H, m), 5.33–5.52 (3H, m), 5.34 (1H, app.qd, J=1.5, 17.4 Hz), 5.26 (1H, app.qd, J=1.5, 10.5 Hz), 4.66 (2H, app.dt, J=1.5, 6.0 Hz), 4.24 (1H, br.d, J=9.6 Hz), 3.66 (1H, dd, J=9.3, 16.2 Hz), 3.32 (1H, br.d, J=16.5 Hz), 2.55–2.72 (2H, m), 2.22–2.34 (1H, m), 1.80–1.95 (1H, m), 1.66–1.80 (2H, m), 1.44 (1H, dd, J=6.0, 15.6 Hz), 0.96 (9H, s), 0.87 (3H, d, J=6.6 Hz), 0.21 (3H, s), 0.18 (3H, s); $^{13}$C-NMR (75 MHz, CDCl$_3$) δ 168.4, 166.0, 153.0, 143.9, 139.0, 132.4, 131.5, 129.9, 128.8, 127.4, 124.4, 123.4, 118.5, 118.0, 72.4, 71.4, 65.3, 38.5, 38.1, 38.0, 37.5, 35.8, 26.0 (3C), 18.6, 13.9, −3.8, −3.9. HRMS Calcd for C$_{29}$H$_{42}$O$_6$SiLi (MLi$^+$): 521.291 1. Found: 521.2904.

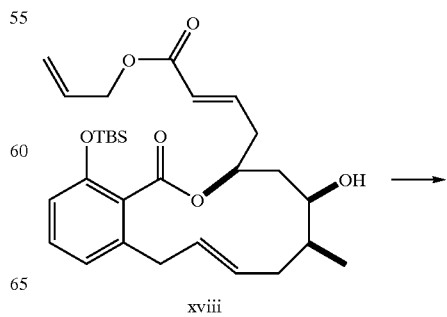

xviii

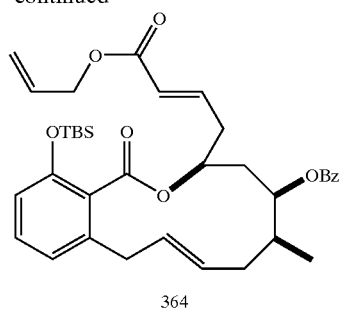

364

To a solution of xviii (14 mg, 0.027 mmol) in pyridine (0.5 mL) was added benzoyl chloride (10 μL, 0.085 mmol) at 0° C. The reaction mixture was allowed to warm to RT and stirring was continued overnight. Aq. HCl (2N, 10 mL) was added and an extraction was performed with Et$_2$O (3×10 mL). The combined organic layers were washed with water and brine, dried (MgSO$_4$), filtered and concentrated. Purification by FC (silicagel, 5% EtOAc in hexanes) provided 10 mg of the benzoate 364 (50%) as a colorless oil. 364: [α]$_D$=−20.8 (c 0.5, CHCl$_3$ ); IR 2930, 1722, 1457, 1270, 1111, 1066, 839, 712; $^1$H-NMR (400 MHz, CDCl$_3$) δ 8.07 (2H, dd, J=2.0, 7.2 Hz), 7.57 (1H, ddd, J=0.8, 7.2, 7.2 Hz), 7.45 (2H, app.t, J=8.0 Hz), 7.16 (1H, app.t, J=8.0 Hz), 7.00 (1H, ddd, J=7.2, 7.2, 15.6 Hz), 6.78 (1H, d, J=7.6 Hz), 6.75 (1H, d, J=8.0 Hz), 5.90–6.2 (2H, m), 5.64–5.74 (1H, m), 5.57–5.62 (1H, m), 5.36–5.45 (1H, m), 5.35 (1H, br.d, J=17.2 Hz), 5.26–5.33 (1H, m), 5.26 (1H, br.d, J=11.2 Hz), 4.67 (2H, br.d, J=6.0 Hz), 3.79 (1H, dd, J=9.6, 16.0 Hz), 3.34 (1H, br.d, J=16.0 Hz), 2.60–2.70 (2H, m), 2.32–2.42 (2H, m), 1.78–1.92 (2H, m), 1.30 (1H, m), 0.94 (9H, s), 0.91 (3H, d, J=6.4 Hz), 0.18 (3H, s), 0.15 (3H, s); $^{13}$C-NMR (75 MHz, CDCl$_3$) δ 167.7, 166.1, 165.9, 153.0, 143.8, 139.5, 132.9, 132.4, 130.9, 130.8, 130.0, 129.9 (2C), 129.4, 128.6 (2C), 127.2, 124.4, 123.4, 118.5, 118.0, 76.4, 71.4, 65.3, 38.2, 37.9, 33.3, 33.1, 31.8, 26.0 (3C), 18.6, 14.3, −3.8, −3.9. HRMS Calcd for C$_{36}$H$_{46}$O$_7$SiLi (MLi$^+$): 625.3173. Found: 625.3172.

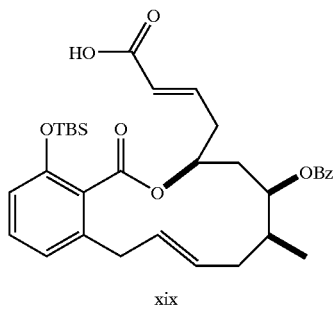

364

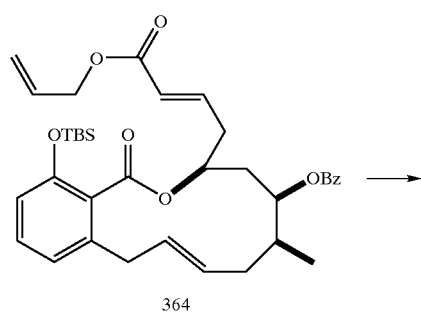

xix

Same procedure as described for the allyl ester deprotection of compound 363. Carboxylic acid xix: [α]$_D$$^{23}$ −14.2 (c 0.45, CHCl$_3$); IR 2928, 1716, 1457, 1271, 1112, 838; $^1$H-NMR (400 MHz, CDCl$_3$) δ 8.08 (2H, d, J=7.6 Hz), 7.54 (1H, app.t, J=7.2 Hz), 7.44 (2H, app.t, J=8.0 Hz), 7.16 (1H, app.t, J=8.0 Hz), 7.09 (1H, ddd, J=7.2,7.2, 15.6 Hz), 6.78 (1H, d, J=7.6 Hz), 6.77 (1H, d, J=8.0 Hz), 6.01 (1H, d, J=15.6 Hz), 5.66–5.75 (1H, m), 5.60 (1H, br.d, J=10.0 Hz), 5.42 (1H, br.dd, J=9.2, 15.2 Hz), 5.29–5.35 (1H, m), 3.79 (1H, dd, J=8.8, 16.0 Hz), 3.35 (1H, br.d, J=16.0 Hz), 2.62–2.74 (2H, m), 2.33–2.44 (2H, m), 1.76–1.97 (3H, m), 0.94 (9H, s), 0.90 (3H, d, J=7.2 Hz), 0.19 (3H, s), 0.16 (3H, s); $^{13}$C-NMR (75 MHz, CDCl$_3$) δ170.7, 167.7, 166.1, 153.0, 146.2, 139.5, 133.0, 130.82, 130.78, 130.0, 129.9 (2C), 129.4, 128.6 (2C), 127.1, 123.9, 123.4, 118.0, <u>76.2</u>, 71.2, 38.3, 37.9, 33.21, 32.18, 31.8, 26.0 (3C), 18.6, 14.3, −3.8, −3.9. HRMS Calcd for C$_{33}$H$_{43}$O$_7$Si (MH$^+$): 579.2778. Found: 579.2764.

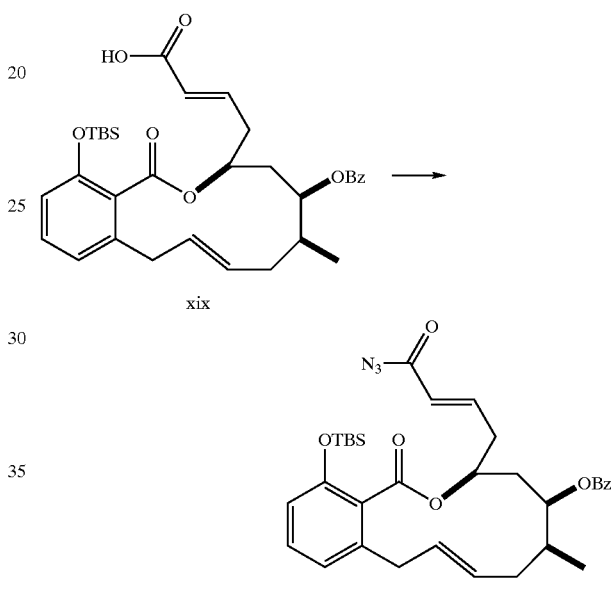

xix xx

Acyl azide xx was prepared according to the procedure described for the synthesis of acyl azide 336 in 96% yield. xx: $^1$H-NMR (300 MHz, CDCl$_3$) δ 8.08 (2H, br.d, J=7.2 Hz), 7.59 (1H, br.t, J=7.5 Hz), 7.46 (2H, app.t, J=8.1 Hz), 7.16 (1H, app.t, J=7.8 Hz), 7.04 (1H, app.dt, J=6.9, 15.9 Hz), 6.78 (1H, d, J=7.8 Hz), 6.75 (1H, d, J=8.4 Hz), 5.96 (1H, br.d, J=15.6 Hz), 5.62–5.74 (1H, m), 5.58 (1H, br.d, J=7.2 Hz), 5.40 (1H, br.dd, J=9.0, 15.0 Hz), 5.26–5.34 (1H, m), 3.78 (1H, dd, J=9.6, 16.2 Hz), 3.34 (1H, br.d, J=16.2 Hz), 2.58–2.74 (2H, m), 2.28–2.43 (2H, m), 1.75–1.96 (3H, m), 0.93 (9H, s), 0.90 (3H, d, J=6.3 Hz), 0.18 (3H, s), 0.14 (3H, s).

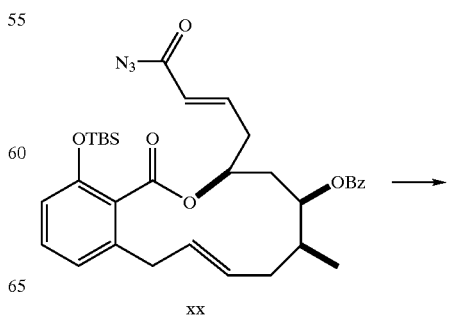

xx

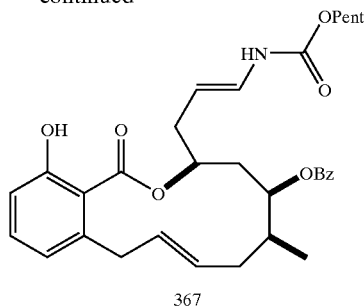

367

Compound 367 was prepared according to the procedure described for the preparation of compound 366 in 27% yield. 367: $[\alpha]_D=-17$ (c 0.12, MeOH); $^1$H-NMR (400 MHz, CDCl$_3$) δ 8.03 (2H, br.d, J=8.4 Hz), 7.60 (1H, br.t, J=7.2 Hz), 7.48 (2H, app.t, J=8.0 Hz), 7.16 (1H, dd, J=7.6,.8.4 Hz), 6.73 (1H, d, J=8.4 Hz), 6.70 (1H, d, J=7.6 Hz), 6.52 (1H, d, J=14.0 Hz), 5.53–5.63 (2H, m), 5.41 (1H, br.dd, J=7.6, 15.2 Hz), 5.08–5.20 (2H, m), 4.07 (2H, app.t, J=6.8 Hz), 3.68 (1H, dd, J=8.4, 16.0 Hz), 3.40 (1H, br.d, J=16.0 Hz), 2.22–2.44 (4H, m), 1.84–1.98 (3H, m), 1.58–1.70 (2H, m), 1.30–1.40 (4H, m), 0.94 (3H, d, J=6.8 Hz), 0.93 (3H, t, J=7.0 Hz); MS (ES) m/z 572.27 ([M+Na]$^+$, 18), 550.27 ([M+H]$^+$, 100). HRMS Calcd for C$_{32}$H$_{39}$NO$_7$Li (MLi$^+$): 556.2887. Found: 556.2881.

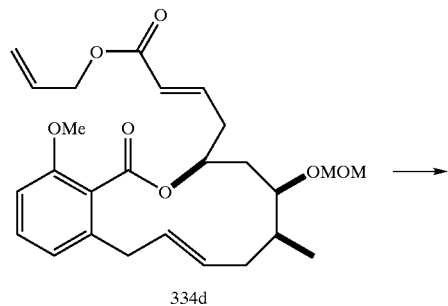

334d

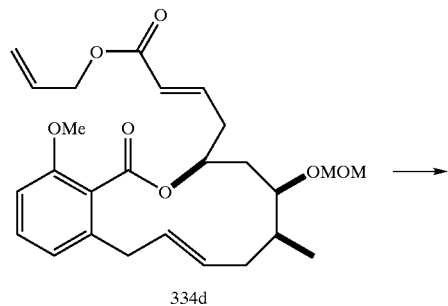

xxi

Compound xxi was prepared according to the procedure described for ompound 337 in 95% yield. xxi: $[\alpha]_D=-94$ (c 0.25, CHCl$_3$); IR 2956, 1725, 1490, 1273; $^1$H-NMR (300 MHz, CDCl$_3$) δ 7.18–7.30 (2H, m), 6.80 (1H, d, J=8.4 Hz), 6.77 (1H, d, J=7.5 Hz), 5.92 (1H, d, J=15.6 Hz), 5.30–5.56 (3H, m), 4.90 (1H, d, J=6.9 Hz), 4.82 (1H, d, J=6.9 Hz), 4.17 (1H, dd, J=3.6, 9.3 Hz), 3.84 (3H, s), 3.71 (1H, dd, J=9.3, 16.5 Hz), 3.45 (3H, s), 3.32 (1H, br.d, J=16.5 Hz), 2.62–2.74 (1H, m), 2.44–2.56 (1H, m), 2.26–2.38 (1H, m), 1.63–1.83 (2H, m), 1.44 (1H, dd, J=9.0, 16.2 Hz), 1.20–1.30 (1H, m), 0.87 (3H, d, J=6.6 Hz); $^{13}$C-NMR (75 MHz, CDCl$_3$) δ 171.6, 168.4, 157.0, 147.9, 139.2, 131.6, 130.4, 128.8, 124.3, 123.0, 122.9, 109.5, 97.2, 79.6, 73.1, 55.9, 39.4, 37.9, 35.9, 34.3, 29.9, 13.5. HRMS Calcd for C$_{23}$H$_{31}$O$_7$ (MH$^+$): 419.2070. Found: 419.2055.

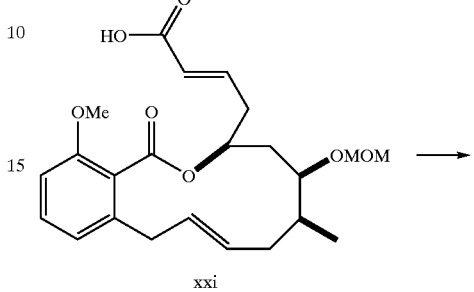

xxi

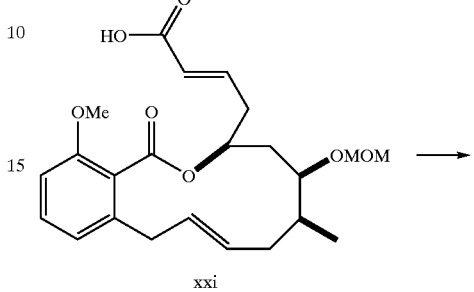

xxii

Acyl azide xxii was prepared according to the procedure described for acyl azide 338 in 68% yield. xxii: $[\alpha]_D=-112.4$ (c 0.45, CHCl$_3$); IR 2926, 2141, 1726, 1696, 1584, 1468, 1273, 1174, 1084, 1040 cm$^{-1}$; $^1$H-NMR (300 MHz, CDCl$_3$) δ 7.25 (1H, app.t, J=7.8 Hz), 7.21 (1H, ddd, J=6.0, 8.7, 15.3 Hz), 6.83 (1H, d, J=8.1 Hz), 6.76 (1H, d, J=7.8 Hz), 5.92 (1H, d, J=15.3 Hz), 5.28–5.58 (3H, m), 4.89 (1H, d, J=6.6 Hz), 4.81 (1H, d, J=6.6 Hz), 4.15 (1H, dd, J=3.6, 9.3 Hz), 3.87 (3H, s), 3.71 (1H, dd, J=9.0, 16.5 Hz), 3.45 (3H, s), 3.32 (1H, br.d, J=16.5 Hz), 2.61–2.72 (1H, m), 2.42–2.54 (1H, m), 2.26–2.38 (1H, m), 2.08–2.22 (1H, m), 1.58–1.80 (1H, m), 1.42 (1H, dd, J=9.3, 14.7 Hz), 0.86 (3H, d, J=6.9 Hz); $^{13}$C-NMR (75 MHz, CDCl$_3$) δ 171.8, 168.3, 156.9, 147.8, 139.3, 131.5, 130.4, 128.8, 124.9, 124.3, 123.0, 109.6, 97.2, 79.6, 72.9, 55.97, 55.87, 39.5, 37.93, 37.87, 35.9, 34.3, 13.5. HRMS Calcd for C$_{23}$H$_{29}$NO$_6$Li [MLi-N$_2$]$^+$: 422.2155. Found: 422.2151.

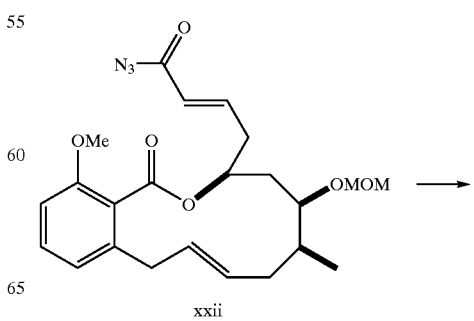

xxii

-continued

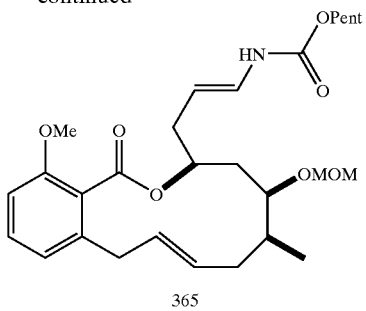

365

A solution of the acyl azide xxii (8 mg, 0.01804 mmol) and 1-pentanol (12 μL, 0.1082 mmol) in benzene (1 mL) was stirred for 7 h at 80° C. After removal of the solvent, the residue was purified by flash chromatography (silicagel, 25% EtOAc in hexanes) to yield 5 mg of compound 365 (55%). 365: $[\alpha]_D$=−70.8 (c 0.25, CHCl$_3$); IR 2926, 1723, 1467, 1275, 1042 cm$^{-1}$; $^{13}$C-NMR (75 MHz, CDCl$_3$) δ 170.6, 158.4, 140.1, 132.5, 131.4, 130.2, 127.9, 126.1, 123.7, 110.8, 106.7, 97.8, 80.7, 76.2, 67.1, 66.4, 56.6, 56.0, 38.8, 38.6, 37.8, 35.7, 35.6, 30.0, 29.3, 23.5, 14.5, 13.8. HRMS Calcd for C$_{28}$H$_{41}$NO$_7$Li (MLi$^+$): 510.3043. Found: 510.3049.

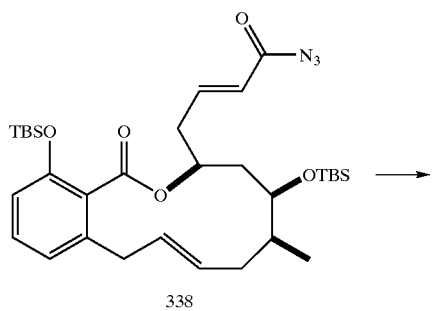

338

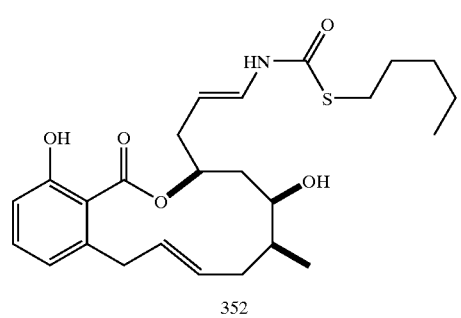

352

A solution of the acyl azide 338 (5 mg, 0.0081 mmol) and 1-pentanethiol (6 μL, 0.0486 mmol) in benzene (1 mL) was stirred for 5 h at 80° C. After removal of the solvent, the residue was treated with 370 μL of a solution HF-pyridine in THF (prepared by mixing 2 g commercial HF.Pyr, 10 mL pyridine and 27 mL THF). After stirring for 4 days at RT, the reaction was quenched with a phosphate buffer (pH 7.0; 10 mL), extracted with EtOAc (3×15 mL), dried over MgSO$_4$ and concentrated. Purification by FC (33% EtOAc in hexanes) gave 3 mg of compound 352 (80%). 352: $[\alpha]_D$=−20.0 (c 0.25, MeOH); IR 3208, 2928, 2855, 1663, 1604, 1451, 1294, 1248, 1184, 948, 825 cm$^{-1}$; $^1$H-NMR (300 MHz, acetone-d$_6$) δ 9.69 (1H, br.s, aryl-OH), 9.08 (1H, br.d, J=12.0 Hz, N—H), 7.21 (1H, dd, J=7.5, 7.8 Hz), 6.83 (1H, dd, J=0.9, 7.8 Hz), 6.70–6.78 (1H, m), 6.72 (1H, d, J=7.5 Hz), 5.22–5.40 (4H, m), 3.94 (1H, dd, J=3.9, 9.0 Hz), 3.57 (1H, d, J=5.1 Hz), 3.46–3.52 (2H, m), 2.89 (2H, t, J=7.2 Hz), 2.20–2.32 (1H, m), 1.74–1.94 (3H, m), 1.53–1.64 (2H, m), 1.28–1.38 (5H, m), 0.88 (3H, t, J=6.9 Hz), 0.87 (3H, d, J=6.6 Hz); $^{13}$C-NMR (75 MHz, CD$_3$OD) δ 171.2, 157.2, 140.8, 131.8, 130.9, 126.7, 123.2, 122.6, 115.4, 108.6, 76.2, 72.1, 39.1, 38.9, 38.7, 37.4, 36.6, 32.1, 31.4, 30.4, 23.4, 14.5, 13.7; MS (ES) m/z 484.33 ([M+Na]$^+$, 8), 462.25 ([M+H]$^+$, 100). HRMS Calcd for C$_{25}$H$_{35}$NO$_5$SLi (MLi$^+$): 468.2396. Found: 468.2400.

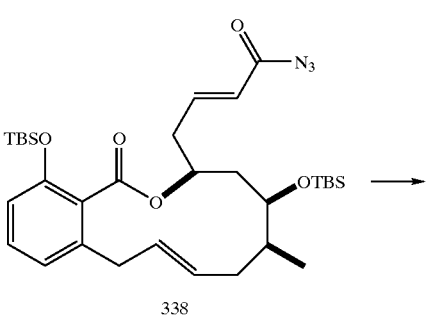

338

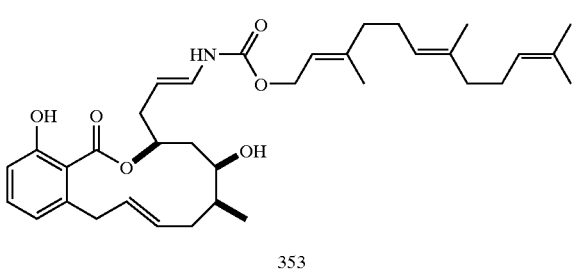

353

Compound 353 obtained from 338 in 53% yield. 353: $[\alpha]_D$=−15.8 (c 0.019, MeOH); IR 2928, 2853, 1724, 1453, 1376, 1293 cm$^{-1}$; $^1$H-NMR (300 MHz, CD$_3$COCD$_3$) δ 9.67 (1H, s, aryl-OH), 8.20 (1H, br.d, J=10.8 Hz, N—H), 7.22 (1H, app.t, J=8.1 Hz), 6.83 (1H, dd, J=0.9, 8.1 Hz), 6.72 (1H, br.d, J=7.6 Hz), 6.54 (1H, dd, J=10.8, 14.4 Hz), 5.06–5.41 (7H, m), 4.57 (2H, d, J=6.9 Hz), 3.93 (1H, ddd, J=3.6, 4.5, 8.1 Hz), 3.47–3.52 (2H, m), 2.22–2.42 (4H, m), 1.70–1.2.18 (1OH, m), 1.71 (3H, s), 1.65 (3H, s), 1.60 (3H, s), 1.59 (3H, s), 1.28–1.42 (1H, m), 0.87 (3H, d, J=6.6 Hz). MS (ES) m/z 580.37 ([M+H]$^+$, 54). HRMS Calcd for C$_{35}$H$_{49}$NO$_6$Li (MLi$^+$): 586.3720. Found: 856.3690.

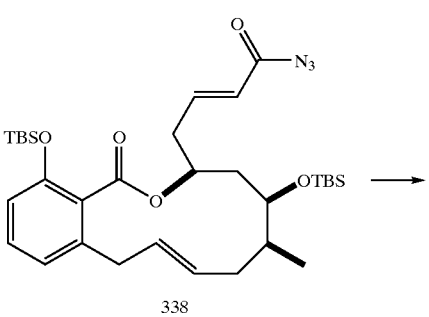

338

-continued

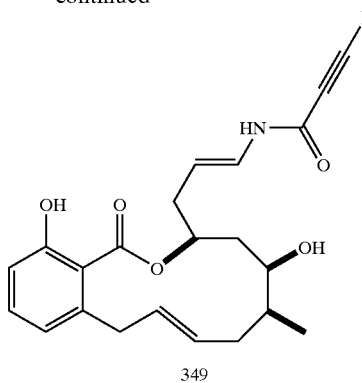

349

Acyl azide 338 (7 mg, 0.0114 mmol) in benzene (1 mL) was stirred at 80° C. for 6 h, after which the solvent was removed and the residue dissolved in THF. In a separate flask, a 0.19 M solution of 1-lithio-phenylacetylene was prepared by deprotonation of phenylacetylene (in THF) with $^n$-BuLi (0.88 equiv.) at −78° C. To this solution (0.2 mL, 0.19 M) in THF was added the isocyanate in THF (0.5 mL) at −78° C. After stirring at −78° C. for 50 min, saturated NH$_4$Cl (3 mL) and water (0.6 mL) were added and the resulting mixture was diluted with Et$_2$O (45 mL), the layers separated, and the organic layer washed with brine, dried over MgSO$_4$, filtered and concentrated. Filtration over silicagel (14% EtOAc in hexanes) provided a crude product (6 mg) which was treated with 370 µL of a solution HF pyridine in THF at RT. After stirring for 48 h at RT, the reaction was quenched with a phosphate buffer (pH 7.0; 10 mL), extracted with EtOAc (3×15 mL), dried over MgSO$_4$ and concentrated. Purification by FC (silicagel, 33% EtOAc in hexanes) gave 2 mg of compound 349 (56%). 349: [α]$_D$=−42 (c 0.1, MeOH ); IR 2927, 1652, 1605, 1500, 1451, 1294, 1218, 1123; $^1$H-NMR (400 MHz, CD$_3$OD) δ 7.58 (2H, app. dt, J=1.6, 6.8 Hz), 7.40–7.52 (3H, m), 7.14 (1H, app.t, J=8.0 Hz), 6.82 14.0 Hz), 6.74 (1H, d, J=8.4 Hz), 6.66 (1H, d, J=7.2 Hz), 5.51 (1H, ddd, J=7.6, 7.6, 14.4 Hz), 5.26–5.44 (3H, m), 4.14 (1H, dd, J=3.6, 9.2 Hz), 3.58 (1H, dd, J=8.4, 16.4 Hz), 3.38 (1H, br), 2.36–2.50 (2H, m), 2.29 (1H, br. d, J=14.4 Hz), 1.84–1.94 (1H, m), 1.72–1.84 (3H, m), 0.88 (3H, d, J=6.8 Hz); MS (ES) m/z (%): 460.22 ([M+H]$^+$, 100) HRMS (FAB) Calcd for C28H29NO5Li (MLi+): 466.2206. Found: 466:2204.

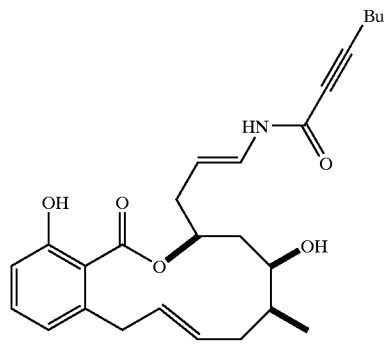

350

Compound 350 is prepared as described for the synthesis of 349 (42% yield). 350: [α]$_D^{23}$ −24.0 (c0.1, MeOH); IR 2929, 1653, 1498, 1451, 1248, 1111; $^1$H-NMR (400 MHz, CD$_3$OD) δ 7.13 (1H, dd, J=7.6, 8.0 Hz), 6.75 (1H, d, J=10.4 Hz), 6.73 (1H, d, J=8.0 Hz), 6.66 (1H, d, J=7.6 Hz), 5.43 (1H, ddd, J=7.2, 7.6, 14.0 Hz), 5.26–5.38 (3H, m), 4.12 (1H, dd, J=3.6, 8.8 Hz), 3.57 (1H, dd, J=8.8, 16.8 Hz), 3.37 (1H, m), 2.24–2.44 (4H, m), 1.70–1.92 (3H, m), 1.32–1.62 (6H, m), 0.94 (3H, t, J=7.6 Hz), 0.87 (3H, d, J=6.8 Hz); MS (ES) m/z (%):440.28 ([M+H]$^+$, 100), 462.21 ([M+Na]$^+$, 10). HRMS (FAB) Calcd for C$_{26}$H$_{33}$NO$_5$Li (MLi$^+$): 446.2519. Found: 446.2513.

All of the compositions and/or methods disclosed and claimed herein can be made and executed without undue experimentation in light of the present disclosure. While the compositions and methods of the invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A compound of formula:

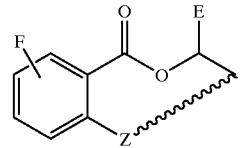

wherein E is selected from the group consisting of:

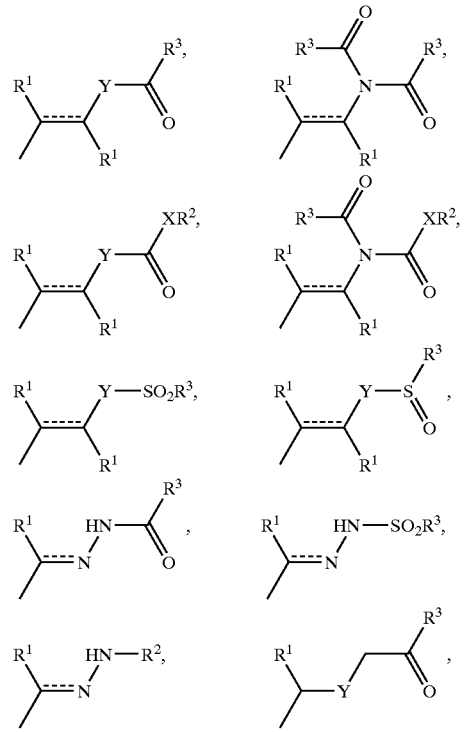

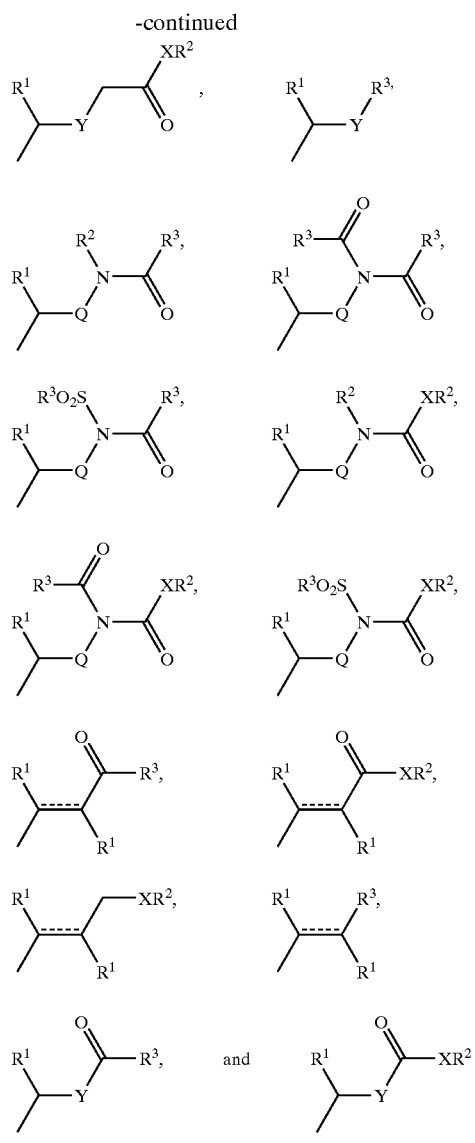

X=O, S, NR$^2$;

Y=CH$_2$, O, S, NR$^2$;

Q=O, NH;

F=ortho, meta, para substituents such as halogen, CN, OR$^2$, OC(O)R$^3$, NO$_2$, OSO$_2$R$^3$, NR$^2$R$^2$, NR$^2$C(O)R$^3$, NR$^2$SO$_2$R$^3$, R$^3$;

R$^1$=H, Me;

R$^2$=R$^1$, straight chain saturated alkyl, straight chain unsaturated alkyl, branched chain alkyl, branched chain unsaturated alkyl, cycloalkyl, aryl, heteroaryl, heterocycle, CH$_2$aryl, CH$_2$heteroaryl, CH$_2$heterocycle, CHR$^1$CHR$^1$aryl, CHR$^1$CHR$^1$heteroaryl, CHR$^1$CHR$^1$heterocycle;

R$^3$=R$^2$ or CR$^1$=CR$^1$aryl, CR$^1$=CR$^1$heteroaryl, CR$^1$=CR$^1$heterocycle, C≡Caryl, C≡Cheteroaryl, C≡Cheterocycle; and Z is a contiguous linker whose presence completes an 11 to 15 membered ring.

2. The compound of claim 1 wherein E is selected from the group consisting of:

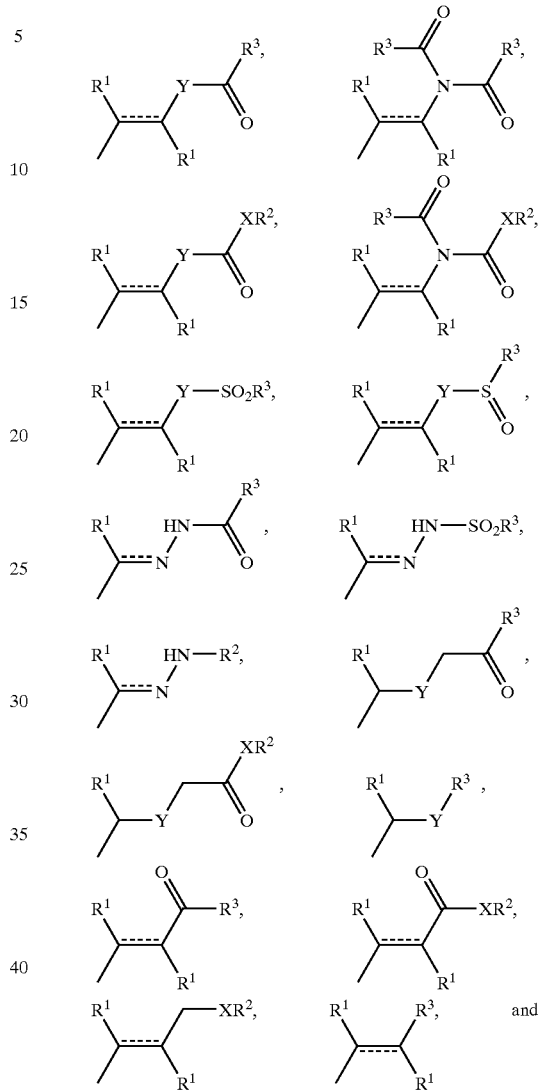

X=O, S, NR$^2$;

Y=CH$_2$, O, S, NR$^2$;

F=ortho, meta, para substituents such as halogen, CN, OR$^2$, OC(O)R$^3$, NO$_2$, OSO$_2$R$^3$, NR$^2$R$^2$, NR$^2$C(O)R$^3$, NR$^2$SO$_2$R$^3$, R$^3$;

R$^1$=H, Me;

R$^2$=R$^1$, straight chain saturated alkyl, straight chain unsaturated alkyl, branched chain alkyl, branched chain unsaturated alkyl, cycloalkyl, aryl, heteroaryl, heterocycle, CH$_2$aryl, CH$_2$heteroaryl, CH$_2$heterocycle, CHR$^1$CHR$^1$aryl, CHR$^1$CHR$^1$heteroaryl, CHR$^1$CHR$^1$heterocycle;

R$^3$=R$^2$ or CR$^1$=CR$^1$aryl, CR$^1$=CR$^1$heteroaryl, CR$^1$=CR$^1$heterocycle, C≡Caryl, C≡Cheteroaryl, C≡Cheterocycle; and Z is a contiguous linker whose presence completes an 11 to 15 membered ring.

3. A compound of formula:

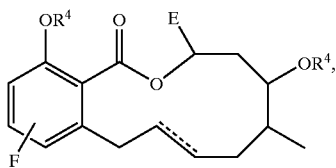

wherein E is selected from the group consisting of:

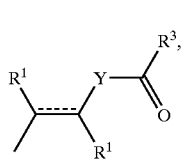 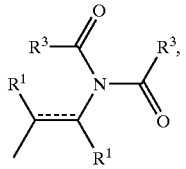
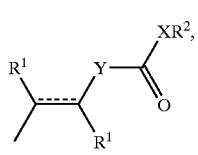 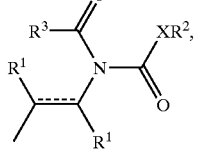
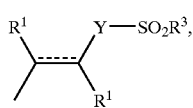 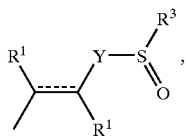
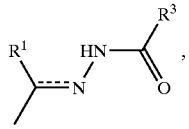 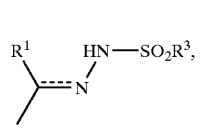
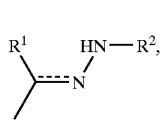 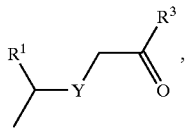
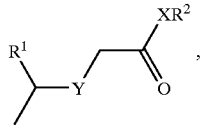 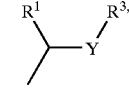
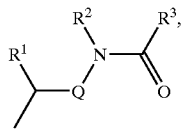 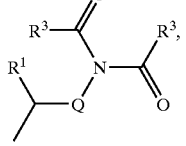
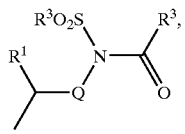 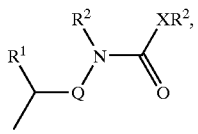
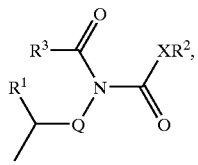 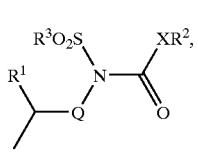

-continued

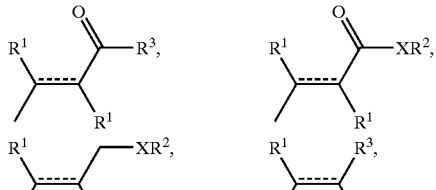

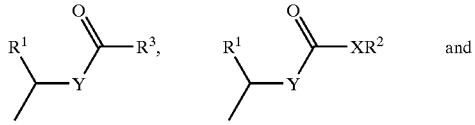 and

X=O, S, $NR^2$;

Y=$CH_2$, O, S, $NR^2$;

Q=O, NH;

F=ortho, meta, para substituents such as halogen, CN, $OR^2$, $OC(O)R^3$, $NO_2$, $OSO_2R^1$, $NR^2R^2$, $NR^2C(O)R^3$, $NR^2SO_2R^3$, $R^3$;

$R^1$H, Me;

$R^2$=$R^1$, straight chain saturated alkyl, straight chain unsaturated alkyl, branched chain alkyl, branched chain unsaturated alkyl, cycloalkyl, aryl, heteroaryl, heterocycle, $CH_2$aryl, $CH_2$heteroaryl, $CH_2$heterocycle, $CHR^1CHR^1$aryl, $CHR^1CHR^1$heteroaryl, $CHR^1CHR^1$heterocycle;

$R^3$=$R^2$ or $CR^1$=$CR^1$aryl, $CR^1$=$CR^1$heteroaryl, $CR^1$=$CR^1$heterocycle, C≡Caryl, C≡Cheteroaryl, C≡Cheterocycle; and $R^4$=$R^1$, $C(O)R^3$, $SO_2R^3$, $R^2$.

4. The compound of claim 3 wherein E is selected from the group consisting of:

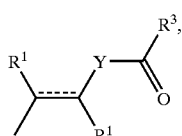 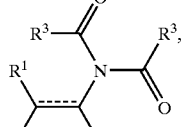
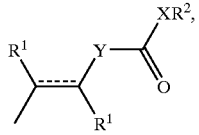 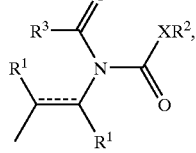
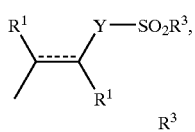 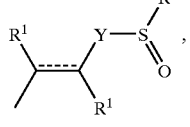
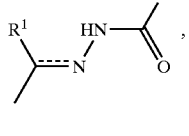 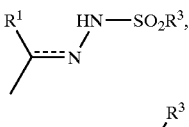
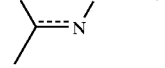 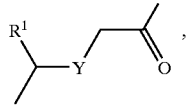

-continued

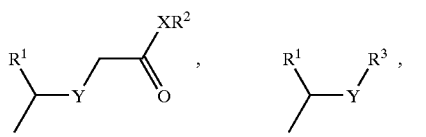

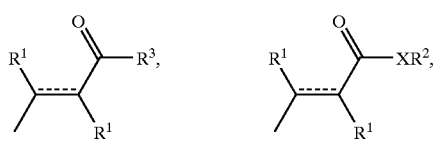

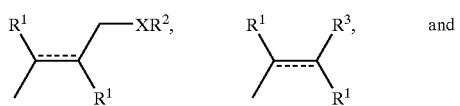

X=O, S, NR$^2$;

Y=CH$_2$, O, S, NR$^2$;

F=ortho, meta, para substituents such as halogen, CN, OR$^2$, OC(O)R$^3$, NO$_2$, OSO$_2$R$^3$, NR$^2$R$^2$, NR$^2$C(O)R$^3$, NR$^2$SO$_2$R$^3$, R$^3$;

R$^1$=H, Me;

R$^2$=R$^1$, straight chain saturated alkyl, straight chain unsaturated alkyl, branched chain alkyl, branched chain unsaturated alkyl, cycloalkyl, aryl, heteroaryl, heterocycle, CH$_2$aryl, CH$_2$heteroaryl, CH$_2$heterocycle, CHR$^1$CHR$^1$aryl, CHR$^1$CHR$^1$heteroaryl, CHR$^1$CHR$^1$heterocycle;

R$^3$=R$^2$ or CR$^1$=CR$^1$aryl, CR$^1$=CR$^1$heteroaryl, CR$^1$=CR$^1$heterocycle, C≡Caryl, C≡Cheteroaryl, C≡Cheterocycle; and

R$^4$=R$^1$, C(O)R$^3$, SO$_2$R$^3$, R$^2$.

5. A compound of formula:

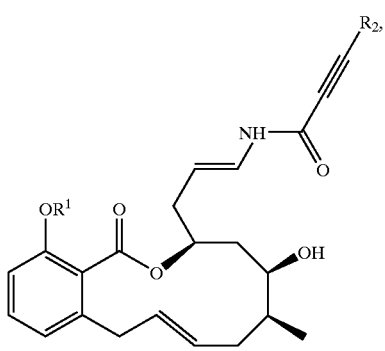

wherein R$^1$=H, Me, Ac; and

R$^2$=straight chain saturated alkyl, straight chain unsaturated alkyl, branched chain alkyl, branched chain unsaturated alkyl, cycloalkyl, aryl, heteroaryl, heterocycle, CH$_2$aryl.

6. A compound of formula:

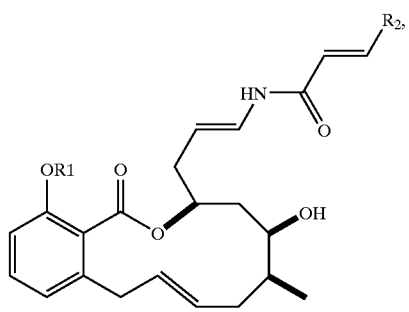

wherein R$^1$=H, Me, Ac; and

R$^2$=straight chain saturated alkyl, straight chain unsaturated alkyl, branched chain alkyl, branched chain unsaturated alkyl, cycloalkyl, aryl, heteroaryl, heterocycle, CH$_2$aryl.

7. A compound of formula:

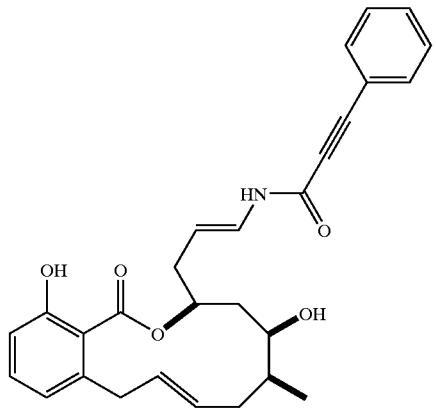

8. A compound of formula:

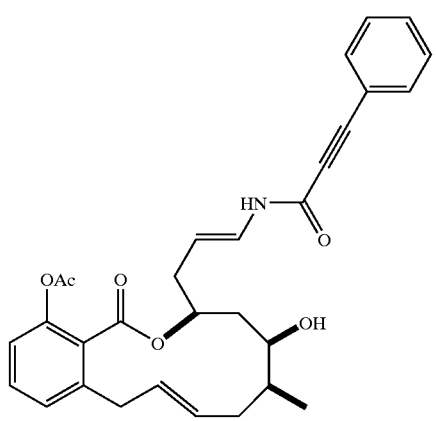

9. A compound of formula:
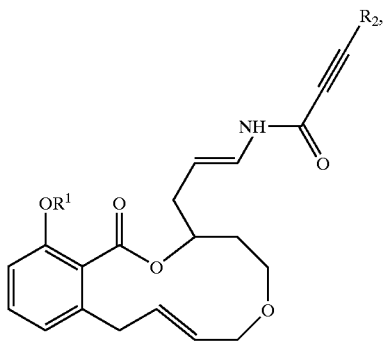
wherein R¹=H, Me, Ac; and
R²=straight chain saturated alkyl, straight chain unsaturated alkyl, branched chain alkyl, branched chain unsaturated alkyl, cycloalkyl, aryl, heteroaryl, heterocycle, CH₂aryl.
10. A compound of formula:
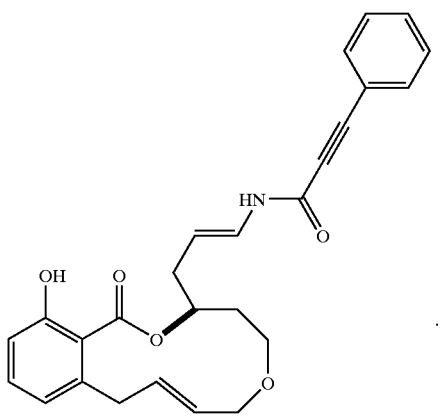
11. A compound of formula:
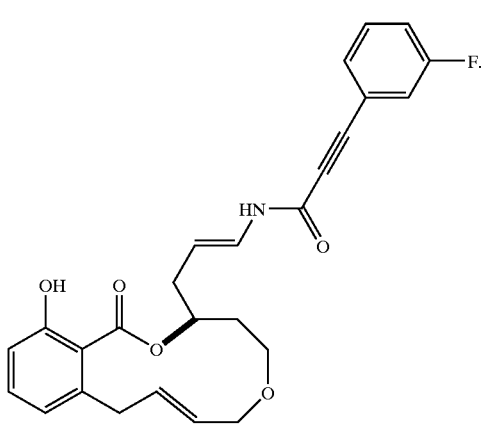
12. A compound of formula:
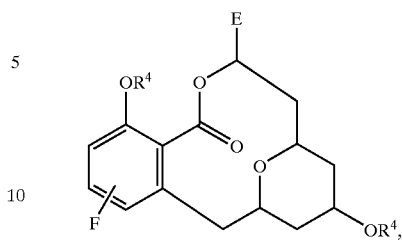
wherein E is selected from the group consisting of:
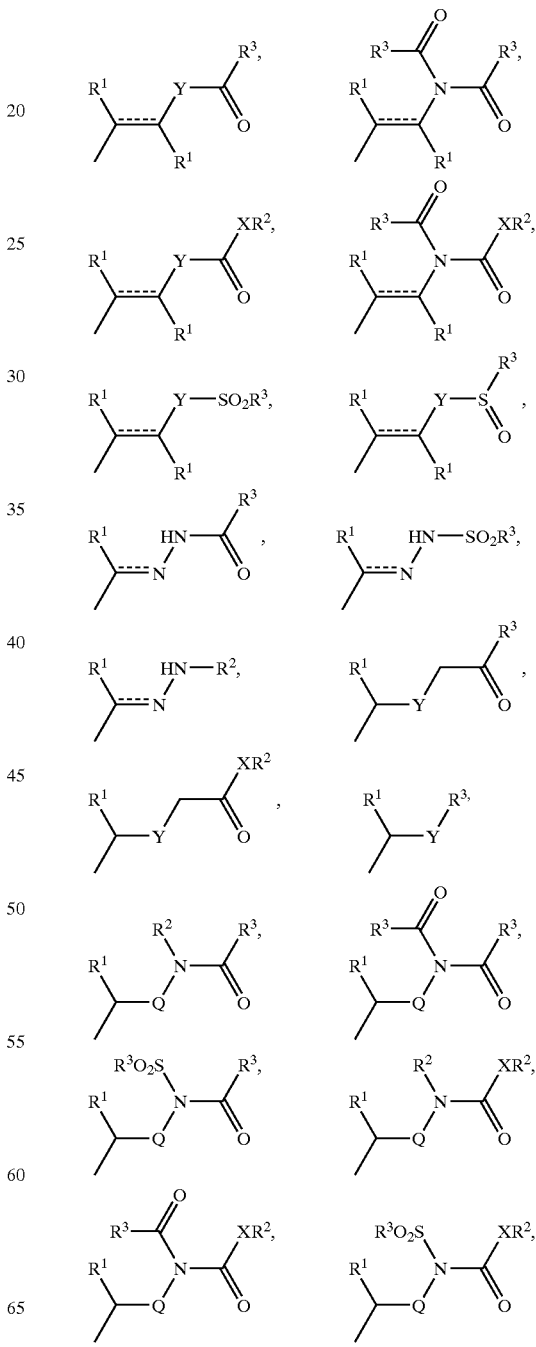

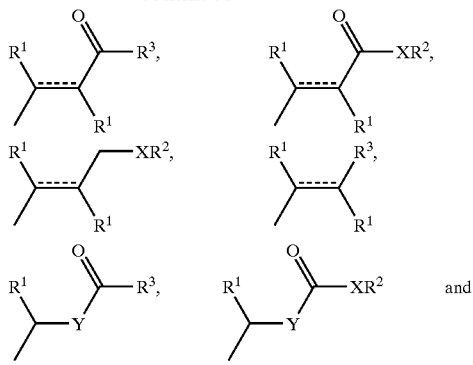

X=O, S, NR$^2$;
Y=CH$_2$, O, S, NR$^2$;
Q=O, NH;
F=ortho, meta, para substituents such as halogen, CN, OR$^2$, OC(O)R$^3$, NO$_2$, OSO$_2$R$^3$, NR$^2$R$^2$, NR$^2$C(O)R$^3$, NR$^2$SO$_2$R$^3$, R$^3$;
R$^1$=H, Me;
R$^2$=R$^1$, straight chain saturated alkyl, straight chain unsaturated alkyl, branched chain alkyl, branched chain unsaturated alkyl, cycloalkyl, aryl, heteroaryl, heterocycle, CH$_2$aryl, CH$_2$heteroaryl, CH$_2$heterocycle, CHR$^1$CHR$^1$aryl, CHR$^1$CHR$^1$heteroaryl, CHR$^1$CHR$^1$heterocycle;
R$^3$=R$^2$ or CR$^1$=CR$^1$aryl, CR$^1$=CR$^1$heteroaryl, CR$^1$=CR$^1$heterocycle, C≡Caryl, C≡Cheteroaryl, C≡Cheterocycle; and
R$^4$=R$^1$, C(O)R$^3$, SO$_2$R$^3$, R$^2$.

13. The compound of claim 12 wherein E is selected from the group consisting of:

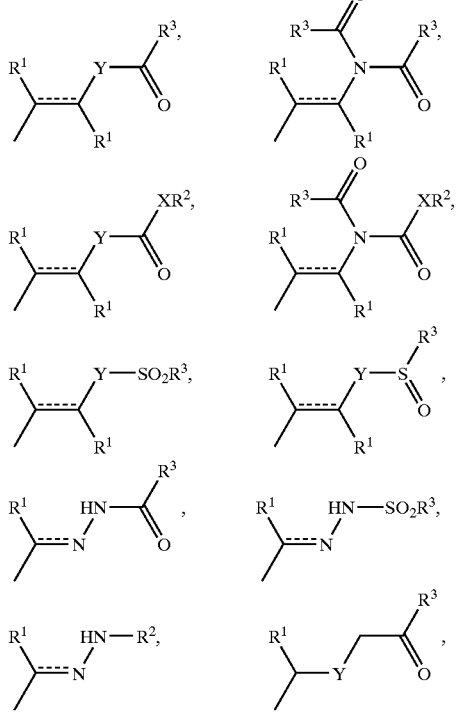

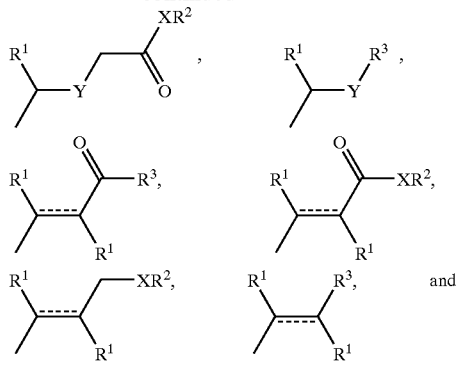

X=O, S, NR$^2$;
Y=CH$_2$, O, S, NR$^2$;
F=ortho, meta, para substituents such as halogen, CN, OR$^2$, OC(O)R$^3$, NO$_2$, OSO$_2$R$^3$, NR$^2$R$^2$, NR$^2$C(O)R$^3$, NR$^2$SO$_2$R$^3$, R$^3$;
R$^1$=H, Me;
R$^2$=R$^1$, straight chain saturated alkyl, straight chain unsaturated alkyl, branched chain alkyl, branched chain unsaturated alkyl, cycloalkyl, aryl, heteroaryl, heterocycle, CH$_2$aryl, CH$_2$heteroaryl, CH$_2$heterocycle, CHR$^1$CHR$^1$aryl, CHR$^1$CHR$^1$heteroaryl, CHR$^1$CHR$^1$heterocycle;
R$^3$=R$^2$ or CR$^1$=CR$^1$aryl, CR$^1$=CR$^1$heteroaryl, CR$^1$=CR$^1$heterocycle, C≡Caryl, C≡Cheteroaryl, C≡Cheterocycle; and
R$^4$=R$^1$, C(O)R$^3$, SO$_2$R$^3$, R$^2$.

14. A compound of formula:

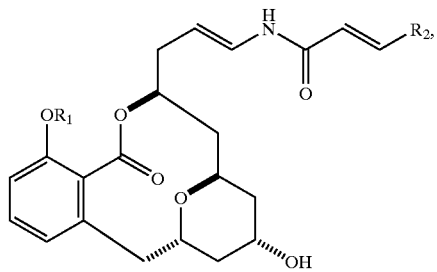

wherein R$^1$=H, Me, Ac; and
R$^2$=straight chain saturated alkyl, straight chain unsaturated alkyl, branched chain alkyl, branched chain unsaturated alkyl, cycloalkyl, aryl, heteroaryl, heterocycle, CH$_2$aryl.

15. A compound of formula:

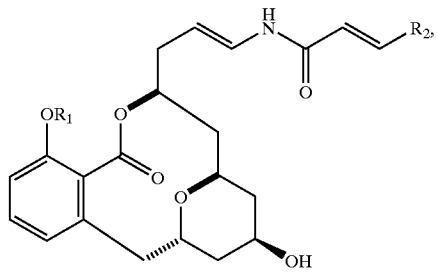

wherein R$^1$=H, Me, Ac; and
R$^2$=straight chain saturated alkyl, straight chain unsaturated alkyl, branched chain alkyl, branched chain unsaturated alkyl, cycloalkyl, aryl, heteroaryl, heterocycle, CH$_2$aryl.

16. A compound of formula:

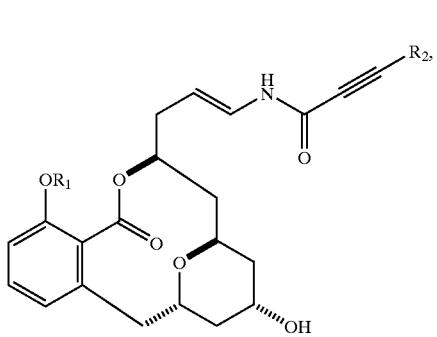

wherein $R^1$=H, Me, Ac; and
$R^2$=straight chain saturated alkyl, straight chain unsaturated alkyl, branched chain alkyl, branched chain unsaturated alkyl, cycloalkyl, aryl, heteroaryl, heterocycle, $CH_2$aryl.

17. A compound of formula:

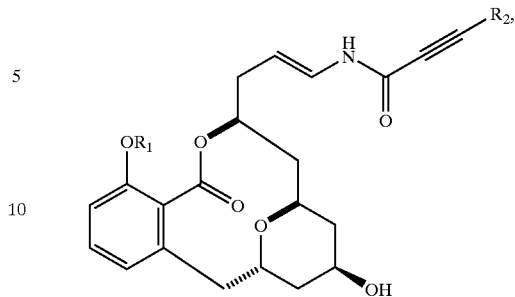

wherein $R^1$=H, Me, Ac; and
$R^2$=straight chain saturated alkyl, straight chain unsaturated alkyl, branched chain alkyl, branched chain unsaturated alkyl, cycloalkyl, aryl, heteroaryl, heterocycle, $CH_2$aryl.

* * * * *